US012703757B2

(12) United States Patent
Pichiorri et al.

(10) Patent No.: US 12,703,757 B2
(45) Date of Patent: Aug. 11, 2026

(54) ANTI-HVEM ANTIBODIES

(71) Applicant: CITY OF HOPE, Duarte, CA (US)

(72) Inventors: Flavia Pichiorri, La Canada, CA (US); Ada Dona, Pasadena, CA (US); Alfur Hung, Taichung City (TW); Miso Park, Duarte, CA (US); John C. Williams, Monrovia, CA (US)

(73) Assignee: City of Hope, Duarte, CA (US)

( * ) Notice: Subject to any disclaimer, the term of this patent is extended or adjusted under 35 U.S.C. 154(b) by 505 days.

(21) Appl. No.: 18/550,655

(22) PCT Filed: Mar. 16, 2022

(86) PCT No.: PCT/US2022/020643
§ 371 (c)(1),
(2) Date: Sep. 14, 2023

(87) PCT Pub. No.: WO2022/197866
PCT Pub. Date: Sep. 22, 2022

(65) Prior Publication Data

US 2024/0317873 A1 Sep. 26, 2024

Related U.S. Application Data

(60) Provisional application No. 63/161,842, filed on Mar. 16, 2021.

(51) Int. Cl.

| | |
|---|---|
| ***C07K 16/28*** | (2006.01) |
| ***A61K 39/00*** | (2006.01) |
| ***C07K 14/705*** | (2006.01) |

(52) U.S. Cl.
CPC .... *C07K 16/2878* (2013.01); *C07K 14/70578* (2013.01); *A61K 39/00* (2013.01); *A61K 2039/505* (2013.01); *C07K 2317/24* (2013.01); *C07K 2317/55* (2013.01); *C07K 2317/732* (2013.01); *C07K 2317/92* (2013.01); *C07K 2319/30* (2013.01)

(58) Field of Classification Search
CPC .................................................. C07K 16/2878
See application file for complete search history.

(56) References Cited

U.S. PATENT DOCUMENTS

2024/0317871 A1* 9/2024 Heiland ............ C07K 16/2878

* cited by examiner

*Primary Examiner* — Gary B Nickol
(74) *Attorney, Agent, or Firm* — Mintz Levin Cohn Ferris Glovsky and Popeo. P.C.

(57) ABSTRACT

Provided herein are, inter alia, antibodies (e.g. humanized antibodies, monoclonal antibodies, antibody fragments (e.g., scFvs) and antibody compositions (e.g., chimeric antigen receptors, bispecific antibodies), which bind herpesvirus entry mediator (HVEM) with high efficiency and specificity. The antibodies and antibody compositions provided herein include novel light and heavy chain domain CDRs and framework regions and are, inter alia, useful for diagnosing and treating cancer and other HVEM-related diseases.

19 Claims, 58 Drawing Sheets

Specification includes a Sequence Listing.

mcHVEM5Ab

Comparative sizes of tumor set from six mice in different groups

FIG. 19C
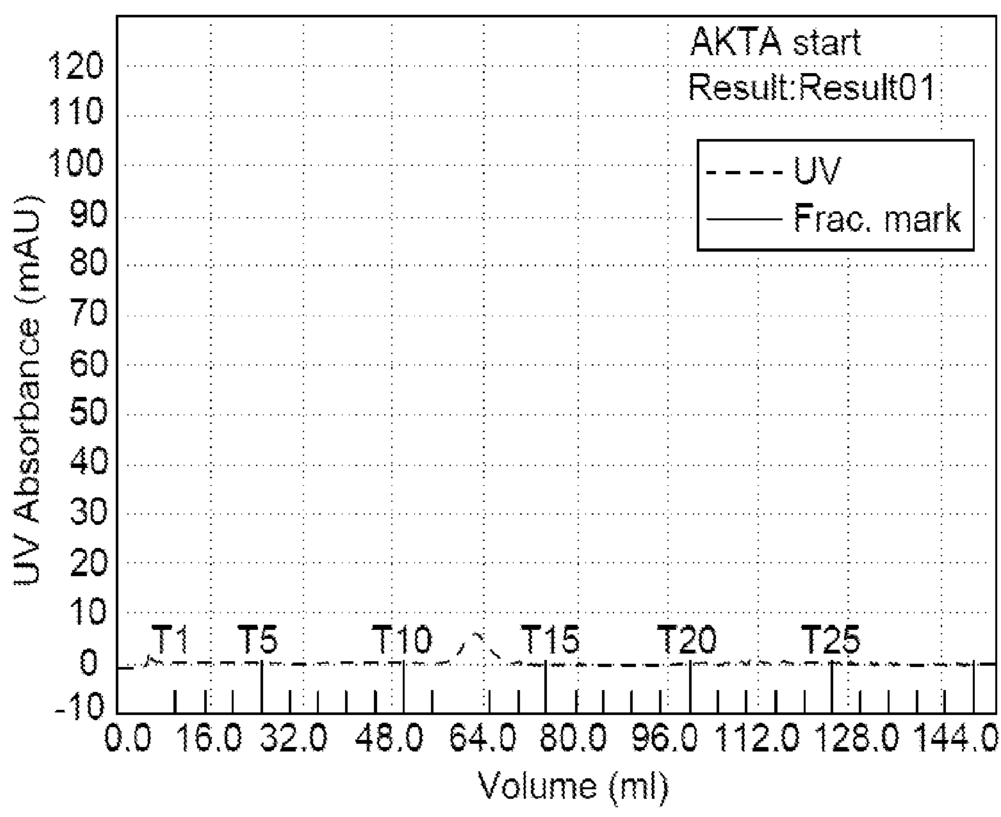

| | Yield (mg/L) |
|---|---|
| HVEM17Ab | 44.4 |
| HVEM22Ab | 6.6 |
| HVEM23Ab | 1.3 |

FIG. 22A
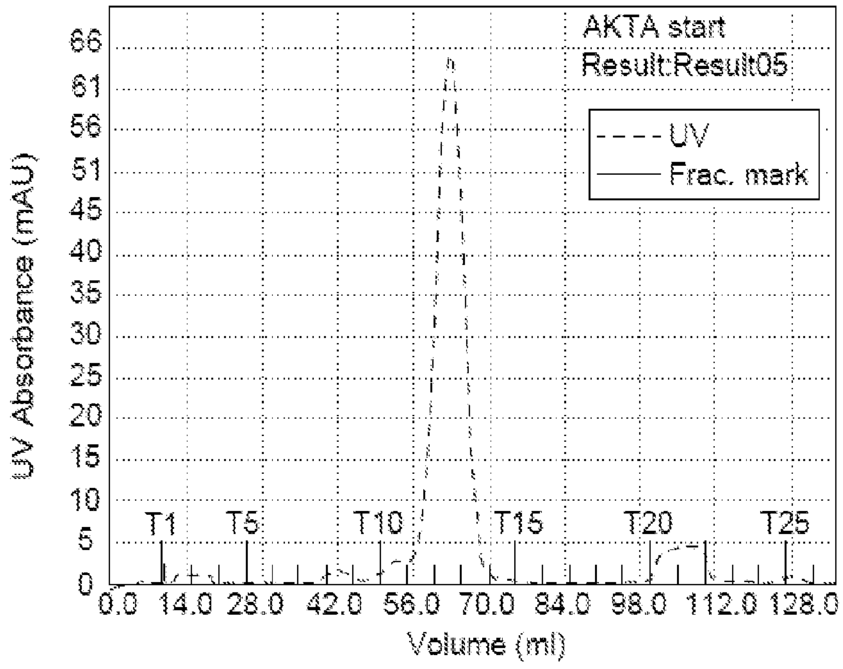
FIG. 22B
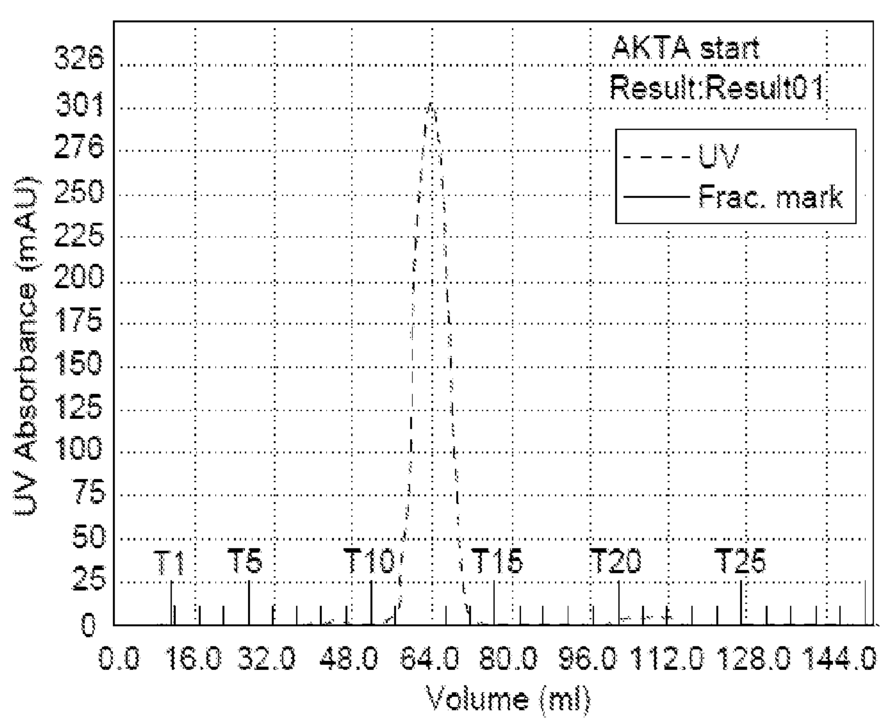

| | Yield (mg/L) |
|---|---|
| HVEM17 mIgG1 | 23 |
| HVEM17 mIgG2a | 113 |

1. HVEM17 mIgG1
2. HVEM17 mIgG2a

FIG. 25A
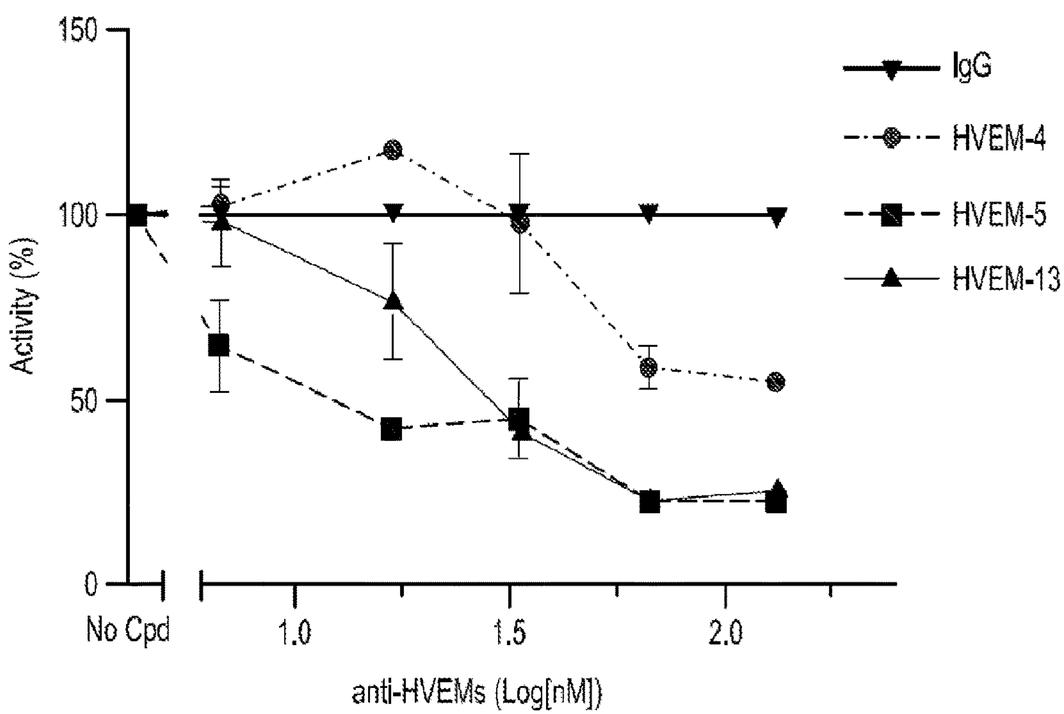
FIG. 25B
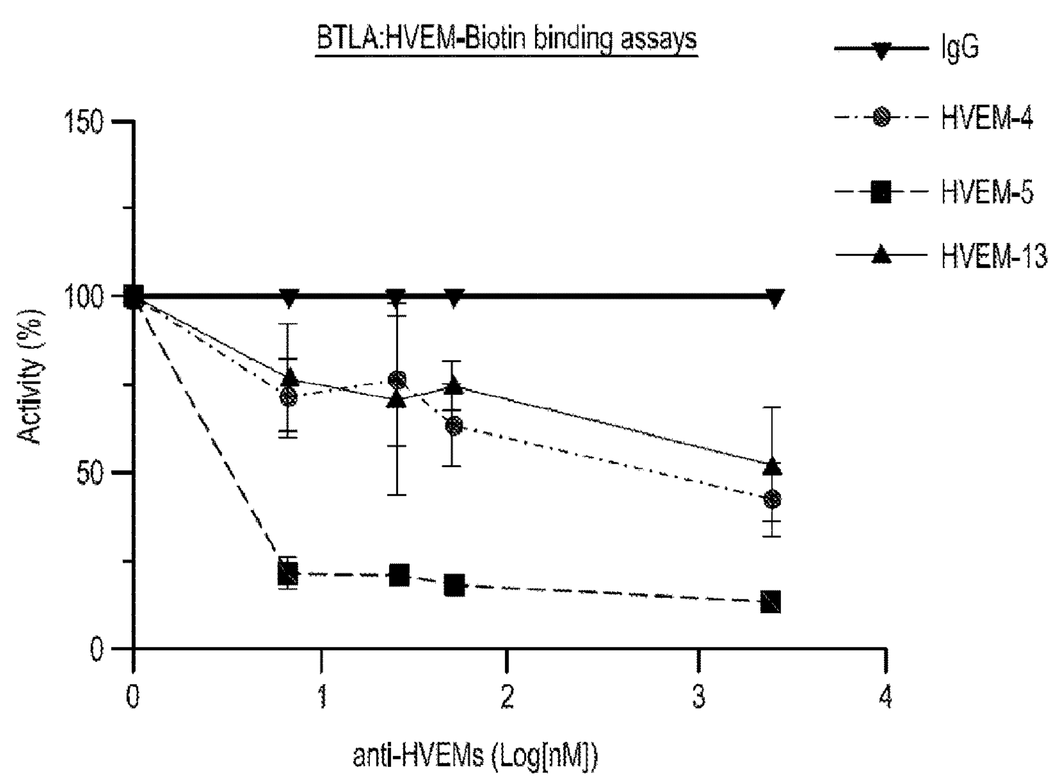

ANTI-HVEM ANTIBODIES

RELATED APPLICATION DATA

This application is a U.S. National Phase Application of PCT International Application No. PCT/US2022/020643, filed on Mar. 16, 2022, which is an International Application of and claims the benefit of priority under 35 U.S.C. § 119 (e) of U.S. Patent Application No. 63/161,842, filed on Mar. 16, 2021, both of which are hereby incorporated by reference in their entireties and for all purposes.

SEQUENCE LISTING

The material in the accompanying Sequence Listing is hereby incorporated by reference in its entirety. The accompanying file, named "048440-770N01US_SL_ST25.txt" was created on Sep. 13, 2023 and is 80,634 bytes. The file can be accessed using Microsoft Word on a computer that uses Windows OS.

BACKGROUND

The herpes virus entry Mediator (HVEM) is a member of the TNF receptor family and plays a critical role in immune regulation. It engages and coordinates with multiple partners (BLTA, LIGHT, LTa, and CD160) to regulate an immune response. The interaction between HVEM and BTLA plays a critical role in immune tolerance and immune responses and dendritic cells (DCs) were demonstrated to induce extrathymic T-cell tolerance in peripheral Treg cells through the BTLA-HVEM signaling pathway (Jones A et al., Immunity 2016). However, the possible biological significance of targeting BTLA and impairs BTLA/HVEM signaling pathway in human diseases remain unclear. Several clinical studies have shown that HVEM expression is upregulated in many types of cancers including colorectal cancers (Inoue T, et al., Anticancer Res. 2015), esophageal carcinomas (Migita K et al., Cancer. 2014), gastric cancers (Lan X, et al., OncoTargets Ther. 2017), hepatocarcinomas (Hokuto D et al., Eur J Cancer 2015), breast cancer (Tsang J Y S, et al. Ann Surg Oncol. 2017) melanoma or lymphomas (M'Hidi H et al., Am J Clin Pathol. 2009). Recent published data have also shown that HVEM has a broader expression than PD-L1 and constitutes a negative prognostic marker and potential treatment target for melanoma (Malissen N. et al. Oncoimmunology 2019).

BRIEF SUMMARY

In an aspect is provided an anti-Herpes Virus Entry Mediator (HVEM) antibody including a light chain variable domain and a heavy chain variable domain, wherein the light chain variable domain includes: a CDR L1 as set forth in SEQ ID NO:1, a CDR L2 as set forth in SEQ ID NO:2 and a CDR L3 as set forth in SEQ ID NO:3; and wherein the heavy chain variable domain includes: a CDR H1 as set forth in SEQ ID NO:4, a CDR H2 as set forth in SEQ ID NO:5, and a CDR H3 as set forth in SEQ ID NO:6.

In another aspect is provided a pharmaceutical composition including a therapeutically effective amount of an antibody as disclosed herein including embodiments thereof and a pharmaceutically acceptable excipient.

In another aspect is provided a method of treating cancer in a subject in need thereof, the method including administering to a subject a therapeutically effective amount of an antibody as disclosed herein including embodiments thereof, thereby treating cancer in the subject.

In another aspect is provided a recombinant protein including: (i) an antibody region including: (a) a light chain variable domain including a CDR L1 as set forth in SEQ ID NO:1, a CDR L2 as set forth in SEQ ID NO:2 and a CDR L3 as set forth in SEQ ID NO:3; and (b) a heavy chain variable domain including a CDR H1 as set forth in SEQ ID NO:4, a CDR H2 as set forth in SEQ ID NO:5, and a CDR H3 as set forth in SEQ ID NO: 6; and (ii) a transmembrane domain.

In another aspect is provided an isolated nucleic acid encoding a recombinant protein as disclosed herein including embodiments thereof.

In another aspect is provided a pharmaceutical composition including a therapeutically effective amount of a recombinant protein as disclosed herein and a pharmaceutically acceptable excipient.

In another aspect is provided a method of treating cancer in a subject in need thereof, the method including administering to a subject a therapeutically effective amount of a recombinant protein as disclosed herein including embodiments thereof, thereby treating cancer in the subject.

In another aspect is provided a bispecific recombinant protein including: (i) a first antibody region capable of binding an effector cell ligand; and (ii) a second antibody region, including: (a) a light chain variable domain including a CDR L1 as set forth in SEQ ID NO:1, a CDR L2 as set forth in SEQ ID NO:2 and a CDR L3 as set forth in SEQ ID NO:3; and (b) a heavy chain variable domain including a CDR H1 as set forth in SEQ ID NO:4, a CDR H2 as set forth in SEQ ID NO:5, and a CDR H3 as set forth in SEQ ID NO:6.

In another aspect is provided a pharmaceutical composition including a therapeutically effective amount of a bispecific recombinant protein as disclosed herein including embodiments thereof and a pharmaceutically acceptable excipient.

In another aspect is provided a method of treating cancer in a subject in need thereof, the method including administering to a subject a therapeutically effective amount of a bispecific recombinant protein as disclosed herein including embodiments thereof, thereby treating cancer in the subject.

In another aspect is provided an anti-Herpes Virus Entry Mediator (HVEM) antibody including a light chain variable domain and a heavy chain variable domain, wherein the light chain variable domain includes: a CDR L1 as set forth in SEQ ID NO:17, a CDR L2 as set forth in SEQ ID NO: 18 and a CDR L3 as set forth in SEQ ID NO:19; and wherein the heavy chain variable domain includes: a CDR H1 as set forth in SEQ ID NO: 20, a CDR H2 as set forth in SEQ ID NO:21, and a CDR H3 as set forth in SEQ ID NO:22.

In another aspect is provided an isolated nucleic acid encoding an antibody as disclosed herein including embodiments thereof.

In another aspect is provided a pharmaceutical composition including a therapeutically effective amount of an antibody as disclosed herein including embodiments thereof and a pharmaceutically acceptable excipient.

In another aspect is provided a method of treating cancer in a subject in need thereof, the method including administering to a subject a therapeutically effective amount of an antibody as disclosed herein including embodiments thereof, thereby treating cancer in the subject.

In another aspect is provided a recombinant protein including: (i) an antibody region including: (a) a light chain variable domain including a CDR L1 as set forth in SEQ ID NO: 17, a CDR L2 as set forth in SEQ ID NO:18 and a CDR L3 as set forth in SEQ ID NO: 19; and (b) a heavy chain variable domain including a CDR H1 as set forth in SEQ ID NO:20, a CDR H2 as set forth in SEQ ID NO:21, and a CDR H3 as set forth in SEQ ID NO:22; and (ii) a transmembrane domain.

In another aspect is provided an isolated nucleic acid encoding a recombinant protein as disclosed herein including embodiments thereof.

In another aspect is provided a pharmaceutical composition including a therapeutically effective amount of a recombinant protein as disclosed herein and a pharmaceutically acceptable excipient.

In another aspect is provided a method of treating cancer in a subject in need thereof, the method including administering to a subject a therapeutically effective amount of a recombinant protein as disclosed herein including embodiments thereof, thereby treating cancer in the subject.

In another aspect is provided a bispecific recombinant protein including: (i) a first antibody region capable of binding an effector cell ligand; and (ii) a second antibody region, including: (a) a light chain variable domain including a CDR L1 as set forth in SEQ ID NO:17, a CDR L2 as set forth in SEQ ID NO:18 and a CDR L3 as set forth in SEQ ID NO:19; and (b) a heavy chain variable domain including a CDR H1 as set forth in SEQ ID NO:20, a CDR H2 as set forth in SEQ ID NO:21, and a CDR H3 as set forth in SEQ ID NO:22.

In another aspect is provided a pharmaceutical composition including a therapeutically effective amount of a bispecific recombinant protein as disclosed herein including embodiments thereof and a pharmaceutically acceptable excipient.

In another aspect is provided a method of treating cancer in a subject in need thereof, the method including administering to a subject a therapeutically effective amount of a bispecific recombinant protein as disclosed herein including embodiments thereof, thereby treating cancer in the subject.

In another aspect is provided an anti-Herpes Virus Entry Mediator (HVEM) antibody including a light chain variable domain and a heavy chain variable domain, wherein the light chain variable domain includes: a CDR L1 as set forth in SEQ ID NO:33, a CDR L2 as set forth in SEQ ID NO:34 and a CDR L3 as set forth in SEQ ID NO:35; and wherein the heavy chain variable domain includes: a CDR H1 as set forth in SEQ ID NO:36, a CDR H2 as set forth in SEQ ID NO:37, and a CDR H3 as set forth in SEQ ID NO:38.

In another aspect is provided an isolated nucleic acid encoding an antibody as disclosed herein including embodiments thereof.

In another aspect is provided a pharmaceutical composition including a therapeutically effective amount of an antibody as disclosed herein including embodiments thereof and a pharmaceutically acceptable excipient.

In another aspect is provided a method of treating cancer in a subject in need thereof, the method including administering to a subject a therapeutically effective amount of an antibody as disclosed herein including embodiments thereof, thereby treating cancer in the subject.

In another aspect is provided a recombinant protein including: (i) an antibody region including: (a) a light chain variable domain including a CDR L1 as set forth in SEQ ID NO:33, a CDR L2 as set forth in SEQ ID NO:34 and a CDR L3 as set forth in SEQ ID NO:35; and (b) a heavy chain variable domain including a CDR H1 as set forth in SEQ ID NO:36, a CDR H2 as set forth in SEQ ID NO:37, and a CDR H3 as set forth in SEQ ID NO:38; and (ii) a transmembrane domain.

In another aspect is provided an isolated nucleic acid encoding a recombinant protein as disclosed herein including embodiments thereof.

In another aspect is provided a pharmaceutical composition including a therapeutically effective amount of a recombinant protein as disclosed herein and a pharmaceutically acceptable excipient.

In another aspect is provided a method of treating cancer in a subject in need thereof, the method including administering to a subject a therapeutically effective amount of a recombinant protein as disclosed herein including embodiments thereof, thereby treating cancer in the subject.

In another aspect is provided a bispecific recombinant protein including: (i) a first antibody region capable of binding an effector cell ligand; and (ii) a second antibody region, including: (a) a light chain variable domain including a CDR L1 as set forth in SEQ ID NO:33, a CDR L2 as set forth in SEQ ID NO:34 and a CDR L3 as set forth in SEQ ID NO:35; and (b) a heavy chain variable domain including a CDR H1 as set forth in SEQ ID NO:36, a CDR H2 as set forth in SEQ ID NO:37, and a CDR H3 as set forth in SEQ ID NO:38.

In another aspect is provided a pharmaceutical composition including a therapeutically effective amount of a bispecific recombinant protein as disclosed herein including embodiments thereof and a pharmaceutically acceptable excipient.

In another aspect is provided a method of treating cancer in a subject in need thereof, the method including administering to a subject a therapeutically effective amount of a bispecific recombinant protein as disclosed herein including embodiments thereof, thereby treating cancer in the subject.

In another aspect is provided an anti-Herpes Virus Entry Mediator (HVEM) antibody including a light chain variable domain and a heavy chain variable domain, wherein the light chain variable domain includes: a CDR L1 as set forth in SEQ ID NO:49, a CDR L2 as set forth in SEQ ID NO:50 and a CDR L3 as set forth in SEQ ID NO:51; and wherein the heavy chain variable domain includes: a CDR H1 as set forth in SEQ ID NO:52, a CDR H2 as set forth in SEQ ID NO:53, and a CDR H3 as set forth in SEQ ID NO:54.

In another aspect is provided an isolated nucleic acid encoding an antibody as disclosed herein including embodiments thereof.

In another aspect is provided a pharmaceutical composition including a therapeutically effective amount of an antibody as disclosed herein including embodiments thereof and a pharmaceutically acceptable excipient.

In another aspect is provided a method of treating cancer in a subject in need thereof, the method including administering to a subject a therapeutically effective amount of an antibody as disclosed herein including embodiments thereof, thereby treating cancer in the subject.

In another aspect is provided a recombinant protein including: (i) an antibody region including: (a) a light chain variable domain including a CDR L1 as set forth in SEQ ID NO:49, a CDR L2 as set forth in SEQ ID NO:50 and a CDR L3 as set forth in SEQ ID NO:51; and (b) a heavy chain variable domain including a CDR H1 as set forth in SEQ ID NO:52, a CDR H2 as set forth in SEQ ID NO:53, and a CDR H3 as set forth in SEQ ID NO:54; and (ii) a transmembrane domain.

In another aspect is provided an isolated nucleic acid encoding a recombinant protein as disclosed herein including embodiments thereof.

In another aspect is provided a pharmaceutical composition including a therapeutically effective amount of a recombinant protein as disclosed herein and a pharmaceutically acceptable excipient.

In another aspect is provided a bispecific recombinant protein including: (i) a first antibody region capable of binding an effector cell ligand; and (ii) a second antibody region, including: (a) a light chain variable domain including a CDR L1 as set forth in SEQ ID NO:49, a CDR L2 as set forth in SEQ ID NO:50 and a CDR L3 as set forth in SEQ ID NO:51; and (b) a heavy chain variable domain including a CDR H1 as set forth in SEQ ID NO:52, a CDR H2 as set forth in SEQ ID NO:53, and a CDR H3 as set forth in SEQ ID NO:54.

In another aspect is provided a pharmaceutical composition including a therapeutically effective amount of a bispecific recombinant protein as disclosed herein including embodiments thereof and a pharmaceutically acceptable excipient.

In another aspect is provided a method of treating cancer in a subject in need thereof, the method including administering to a subject a therapeutically effective amount of a bispecific recombinant protein as disclosed herein including embodiments thereof, thereby treating cancer in the subject.

In another aspect is provided an anti-Herpes Virus Entry Mediator (HVEM) antibody including a light chain variable domain and a heavy chain variable domain, wherein the light chain variable domain includes: a CDR L1 as set forth in SEQ ID NO:66, a CDR L2 as set forth in SEQ ID NO:67 and a CDR L3 as set forth in SEQ ID NO:68; and wherein the heavy chain variable domain includes: a CDR H1 as set forth in SEQ ID NO:69, a CDR H2 as set forth in SEQ ID NO:70, and a CDR H3 as set forth in SEQ ID NO:71.

In another aspect is provided an isolated nucleic acid encoding an antibody as disclosed herein including embodiments thereof.

In another aspect is provided a pharmaceutical composition including a therapeutically effective amount of an antibody as disclosed herein including embodiments thereof and a pharmaceutically acceptable excipient.

In another aspect is provided a method of treating cancer in a subject in need thereof, the method including administering to a subject a therapeutically effective amount of an antibody disclosed herein including embodiments thereof, thereby treating cancer in the subject.

In another aspect is provided a recombinant protein including: (i) an antibody region including: (a) a light chain variable domain including a CDR L1 as set forth in SEQ ID NO:66, a CDR L2 as set forth in SEQ ID NO:67 and a CDR L3 as set forth in SEQ ID NO:68; and (b) a heavy chain variable domain including a CDR H1 as set forth in SEQ ID NO:69, a CDR H2 as set forth in SEQ ID NO:70, and a CDR H3 as set forth in SEQ ID NO:71; and (ii) a transmembrane domain.

In another aspect is provided an isolated nucleic acid encoding a recombinant protein as disclosed herein including embodiments thereof.

In another aspect is provided a pharmaceutical composition including a therapeutically effective amount of a recombinant protein as described herein including embodiments thereof and a pharmaceutically acceptable excipient.

In another aspect is provided a method of treating cancer in a subject in need thereof, the method including administering to a subject a therapeutically effective amount of a recombinant protein as disclosed herein including embodiments thereof, thereby treating cancer in the subject.

In another aspect is provided a bispecific recombinant protein including: (i) a first antibody region capable of binding an effector cell ligand; and (ii) a second antibody region, including: (a) a light chain variable domain including a CDR L1 as set forth in SEQ ID NO:66, a CDR L2 as set forth in SEQ ID NO:67 and a CDR L3 as set forth in SEQ ID NO:68; and (b) a heavy chain variable domain including a CDR H1 as set forth in SEQ ID NO:69, a CDR H2 as set forth in SEQ ID NO:70, and a CDR H3 as set forth in SEQ ID NO:71.

In another aspect is provided a pharmaceutical composition including a therapeutically effective amount of a bispecific recombinant protein as disclosed herein including embodiments thereof and a pharmaceutically acceptable excipient.

In another aspect is provided a method of treating cancer in a subject in need thereof, the method including administering to a subject a therapeutically effective amount of a bispecific recombinant protein as disclosed herein including embodiments thereof, thereby treating cancer in the subject.

In another aspect is provided an anti-Herpes Virus Entry Mediator (HVEM) antibody including a light chain variable domain and a heavy chain variable domain, wherein the light chain variable domain includes: a CDR L1 as set forth in SEQ ID NO:84, a CDR L2 as set forth in SEQ ID NO:85 and a CDR L3 as set forth in SEQ ID NO:86; and wherein the heavy chain variable domain includes: a CDR H1 as set forth in SEQ ID NO:87, a CDR H2 as set forth in SEQ ID NO:88, and a CDR H3 as set forth in SEQ ID NO:89.

In another aspect is provided an isolated nucleic acid encoding an antibody as disclosed herein including embodiments thereof.

In another aspect is provided a pharmaceutical composition including a therapeutically effective amount of an antibody as disclosed herein including embodiments thereof and a pharmaceutically acceptable excipient.

In another aspect is provided a method of treating cancer in a subject in need thereof, the method including administering to a subject a therapeutically effective amount of an antibody as disclosed herein including embodiments thereof, thereby treating cancer in the subject.

In another aspect is provided a recombinant protein including: (i) an antibody region including: (a) a light chain variable domain including a CDR L1 as set forth in SEQ ID NO:84, a CDR L2 as set forth in SEQ ID NO:85 and a CDR L3 as set forth in SEQ ID NO:86; and (b) a heavy chain variable domain including a CDR H1 as set forth in SEQ ID NO:87, a CDR H2 as set forth in SEQ ID NO:88, and a CDR H3 as set forth in SEQ ID NO:89; and (ii) a transmembrane domain.

In another aspect is provided an isolated nucleic acid encoding a recombinant protein as disclosed herein including embodiments thereof.

In another aspect is provided a pharmaceutical composition including a therapeutically effective amount of a recombinant protein as disclosed herein including embodiments thereof and a pharmaceutically acceptable excipient.

In another aspect is provided a method of treating cancer in a subject in need thereof, the method including administering to a subject a therapeutically effective amount of a recombinant protein as disclosed herein including embodiments thereof, thereby treating cancer in the subject.

In another aspect is provided a bispecific recombinant protein including: (i) a first antibody region capable of binding an effector cell ligand; and (ii) a second antibody region, including: (a) a light chain variable domain including a CDR L1 as set forth in SEQ ID NO:84, a CDR L2 as set forth in SEQ ID NO:85 and a CDR L3 as set forth in SEQ ID NO:86; and (b) a heavy chain variable domain including a CDR H1 as set forth in SEQ ID NO:87, a CDR H2 as set forth in SEQ ID NO:88, and a CDR H3 as set forth in SEQ ID NO:89.

In another aspect is provided a pharmaceutical composition including a therapeutically effective amount of a bispecific recombinant protein as disclosed herein including embodiments thereof and a pharmaceutically acceptable excipient.

In another aspect is provided a method of treating cancer in a subject in need thereof, the method including administering to a subject a therapeutically effective amount of a bispecific recombinant protein as disclosed herein including embodiments thereof, thereby treating cancer in the subject.

In another aspect is provided an anti-Herpes Virus Entry Mediator (HVEM) antibody including a light chain variable domain and a heavy chain variable domain, wherein the light chain variable domain includes: a CDR L1 as set forth in SEQ ID NO:102, a CDR L2 as set forth in SEQ ID NO: 103 and a CDR L3 as set forth in SEQ ID NO:104; and wherein the heavy chain variable domain includes: a CDR H1 as set forth in SEQ ID NO: 105, a CDR H2 as set forth in SEQ ID NO:106, and a CDR H3 as set forth in SEQ ID NO:107.

In another aspect is provided an isolated nucleic acid encoding an antibody as disclosed herein including embodiments thereof.

In another aspect is provided a pharmaceutical composition including a therapeutically effective amount of an antibody as disclosed herein including embodiments thereof and a pharmaceutically acceptable excipient.

In another aspect is provided a method of treating cancer in a subject in need thereof, the method including administering to a subject a therapeutically effective amount of an antibody as disclosed herein including embodiments thereof, thereby treating cancer in the subject.

In another aspect is provided a recombinant protein including: (i) an antibody region including: (a) a light chain variable domain including a CDR L1 as set forth in SEQ ID NO:102, a CDR L2 as set forth in SEQ ID NO:103 and a CDR L3 as set forth in SEQ ID NO:104; and (b) a heavy chain variable domain including a CDR H1 as set forth in SEQ ID NO: 105, a CDR H2 as set forth in SEQ ID NO:106, and a CDR H3 as set forth in SEQ ID NO: 107; and (ii) a transmembrane domain.

In another aspect is provided an isolated nucleic acid encoding a recombinant protein as disclosed herein including embodiments thereof.

In another aspect is provided a pharmaceutical composition including a therapeutically effective amount of a recombinant protein as disclosed herein including embodiments thereof and a pharmaceutically acceptable excipient.

In another aspect is provided a method of treating cancer in a subject in need thereof, the method including administering to a subject a therapeutically effective amount of a recombinant protein as disclosed herein including embodiments thereof, thereby treating cancer in the subject.

In another aspect is provided a bispecific recombinant protein including: (i) a first antibody region capable of binding an effector cell ligand; and (ii) a second antibody region, including: (a) a light chain variable domain including a CDR L1 as set forth in SEQ ID NO:102, a CDR L2 as set forth in SEQ ID NO:103 and a CDR L3 as set forth in SEQ ID NO:104; and (b) a heavy chain variable domain including a CDR H1 as set forth in SEQ ID NO: 105, a CDR H2 as set forth in SEQ ID NO:106, and a CDR H3 as set forth in SEQ ID NO: 107.

In another aspect is provided a pharmaceutical composition including a therapeutically effective amount of a bispecific recombinant protein as disclosed herein including embodiments thereof and a pharmaceutically acceptable excipient.

In another aspected is provided a method of treating cancer in a subject in need thereof, the method including administering to a subject a therapeutically effective amount of a bispecific recombinant protein as disclosed herein including embodiments thereof, thereby treating cancer in the subject.

BRIEF DESCRIPTION OF THE DRAWINGS

FIG. 11A is a dot plot showing mean florescence intensity of HVEM in bone marrow (BM) plasma cells (MM cells) versus non-MM cells BM cellular fraction from 10 myeloma BM aspirates. FIG. 11B presents boxplots show the median and first and third quartiles of expression, with the whiskers extending to the most extreme data point within 1.5 times the interquartile range. Cancer types are sorted by median expression for HVEM and include data from the Genomic Data Commons. LAML, acute myeloid leukemia; DLBC, lymphoid neoplasm diffuse large B cell lymphoma; ALL, acute lymphoblastic leukemia; BLCA, bladder urothelial carcinoma; BRCA, breast invasive carcinoma; COAD, colon adenocarcinoma; HNSC, head and neck squamous cell carcinoma; KIRC, kidney renal clear cell carcinoma; LGG, brain lower grade glioma; LUAD, lung adenocarcinoma; LUSC, lung squamous cell carcinoma; PRAD, prostate adenocarcinoma; THCA, thyroid carcinoma; UCEC, uterine corpus endometrial carcinoma.

FIG. 12A shows representative line graph showing effector cell killing activity (%) obtained from 1 healthy donor (HD) in n=3 technical replicates against myeloma cells (MM.1S gfp+/Luc+) in presence of control IgG (C-IgG), Daratumumab (DARA), anti-HVEM13 (HVEM13) and a combination of both DARA+HVEM13. Effector cells (NK cells) were obtained from HD, and target cells (MM.1S GFP+/Luc+) were co-cultured at different effector:target ratios. (1:1, 3:1, 5:1, 8:1) for 4 hrs, then incubated with C-IgG (Cat. #1-001-A); Dara (Dara-mAb) (Cat. #NCD 57894-502-05) (10 μg/mL) and anti-HVEM13 (10 μg/mL). After incubation, the killing induction (%) was assessed by flow cytometry using 7-aminoactinomycin D (7-AAD) (Cat. #51-68981E BD Biosciences). Data are representative of the average of three technical replicate. Data are expressed as the mean±SEM (n=3). The effector:ratio 8:1 in MM.1S gfp+/luc+ cells for each treatment group was repeated in at least n=4 donors. FIG. 12B is a bar graph showing ADCC activity of HVEM13 and HVEM5 but no activity of HVEM4. Effector cells (NK cells) were obtained from n=1 HD, and target cells (MM.1S GFP+/Luc+) were co-cultured at 8:1 effector:target ratios for 4 hrs, then incubated with C-IgG; Dara (10 μg/mL) HVEM13 (10 μg/mL) and HVEM5 (10 μg/mL). FIG. 12C is a bar graph showing $1\times10^6$ MM1.S GFP+/Luc+, H929, LP-1, ARP-1 and XG-1 were stained for the surface expression of Anti-Human HVEM (mouse Anti-Human Alexa Fluor 647, CD270) and analyzed by flow cytometry. Bar Graph showing the surface expression in MFI of the 5 different cell lines. FIG. 12D is a dot blot reporting killing assay repeated in at least n=3 of 5 different cell lines (MM1.S GFP+/Luc+, H929, LP-1, ARP-1 and XG-1) using NK cells as effector cells co-cultured with different myeloma cells expressing different HVEM expression and treated with C-IgG or HVEM13 (10 μg/mL), at a ratio of 8:1 for 4 hrs. The graph reports the percentage of dead cells as 7-AAD-positive among target cells repeated in triplicate for each experimental point. The expression of surface HVEM seems to be correlated to anti-HVEM13 ADCC activity.

FIG. 13A is a bar graph showing Ki-67(+) CD8(+) cells fold change versus a control, for HVEM13 or Dara. FIG. 13B is a bar graph showing Ki-67(+) CD8(+) cells frequency (%) for aHVEM13 or a control. FIG. 13C is a bar graph showing Ki-67(+) CD4(+) cells frequency (%) for aHVEM13 or a control.

FIG. 14A is a bar graph showing IFN-gamma RNA expression levels in primary NK cells treated for 1-6-12 hours with C-IgG, HVEM4, HVEM13, Dara. Data are expressed in fold change and normalized using GADPH as housekeeping gene. Each point was repeated in triplicate. FIG. 14B is a dot plot and bar graph showing HVEM13 induction in T cell stimulatory molecules (CD80/CD86) on the surface of the monocytic fraction (CD14+) when PBMCs are treated for 24 hours with C-IgG, HVEM13, HVEM4 and Dara (10 ug/mL) alone or in combination. Data are representative of the average of three independent experiments using n=3 HD PBMCs isolated cells. Data are presented as mean±SD.

FIG. 15A is a box plot showing the effect of HVEM13 was tested in 18 NSG mice subcutaneously engrafted with $20\times10^6$ MM1s cells/mouse. When mice showed comparable tumor sizes, they were randomly separated into 3 group treatment groups and injected subcutaneously with HVEM13, Dara or control IgG daily with 1 mg/kg of HVEM13, H-IgG and DARA for 11 days. Tumor burden was measured as indicated in the figure on day 0-7-11. FIG. 15B is a picture showing tumor sizes after that the mice were humanely anesthetized. n=6 mice for each treatment.

FIG. 16A is a bar graph showing the binding of HVEM5, HVEM13 and HVEM4 or control human IgG, as assessed by mass cytometry analysis and reported in median of expression; in this experiment, the HVEM+ myeloma cells (MM.1S) were incubated for 1 hour with metal conjugated (−166 Er) HVEM5, HVEM13 and HVEM4 or control human IgG. FIG. 16B is a graph presenting surface plasmon resonance data showing high binding affinity of HVEM5. FIG. 16C is a bar graph showing specific lysis (%) of HVEM5, HVEM13 and HVEM4 or control human IgG (C-IgG). HVEM5 showed strong ADCC activity, comparable to the one observed with HVEM13, but absence of killing activity was observed when a non HVEM binding antibody (HVEM4) and control IgG were used. In this experiment, MM.1S cells were co-cultured for 4 hours with human NK cells at the effector target ratio 8:1.

FIG. 17A presents flow cytometry plots showing that HVEM-5 treatment increased surface expression of the early activation marker CD69 in mature monocytes (CD14+/HLDR+). FIGS. 17B-17C presents flow cytometry plots showing that HVEM-5 treatment induced increase in CD80/86 monocyte activation costimulatory molecules (FIG. 17B) and higher expression of the Fc-gamma receptor 1 (FcγRI) CD64 (FIG. 17C), which plays a central role in macrophage antibody-dependent cellular cytotoxicity and clearance of immune complexes. FIG. 17D is a bar graph showing that HVEM-5 treatment also eliminated the monocytic derived myeloid derived suppressor cell population (mo-MDSCs).

FIG. 18A shows that the effect of HVEM5 was tested in 8 NSG mice injected by intravenous injection with $5\times10^6$ MM.1S Gfp/Luc+ cells/mouse. When mice showed comparable tumor distribution by luminescence, they were randomly separated into 2 group treatment groups and injected by intravenous injection (IV) with $1\times10^6$ human PBMCs plus anti-HVEM5 (10 mg/kg) or control IgG (10 mg/kg) once a week for three weeks total treatment. Mice were imaged every week until control mice needed to be humanely anesthetized. n=4 mice for each treatment. FIGS. 18B-18C are graphs showing survival curve (FIG. 18B) and luminescence assessment (FIG. 18C) of the mice in the two treatment groups.

FIGS. 19A-19C present graphs showing size-exclusion chromatography of anti-HVEM antibody clones 17Ab (FIG. 19A), 22Ab (FIG. 19B) and 23Ab (FIG. 19C).

FIGS. 22A-22B present graphs showing size-exclusion chromatography of anti-HVEM antibody clones comprising murine IgG1 (FIG. 22A) or murine IgG2a (FIG. 22B) on SPR.

FIGS. 25A-25C present exemplary data showing that HVEM5 blocks binding of HVEM recombinant protein to recombinant BTLA. In vitro competition binding assays were performed using recombinant protein of HVEM with LIGHT/CD160/BTLA in presence of anti-HVEM antibodies. A Recombinant Proteins ELISA-based assay was performed using human, recombinant or His-tagged LIGHT or BTLA and anti-HVEM-4, 5, 13 or C-IgG. FIG. 25A presents in vitro binding assay data showing HVEM5 and HVEM13 interfere with HVEM recombinant protein binding to recombinant LIGHT. FIG. 25B presents in vitro binding assay data showing HVEM5 has increased inhition of HVEM recombinant protein binding to recombinant BTLA compared to HVEM13 and HVEM4. FIG. 25C presents in vitro binding assay internal control data using a biotin-labeled human HVEM.

FIG. 28A presents a representative dot plot showing that HVEM5, HVEM13, HVEM17, HVEM22 induce ADCC in MM cells. FIG. 28B presents a bar graph showing effector cell killing activity (%) obtained from 1 healthy donor (HD) in n=3 technical replicates against myeloma cells (MM.1S gfp+/Luc+) in presence of control IgG (C-IgG), or anti-HVEM antibody clones HVEM4, HVEM5, HVEM, 13, HVEM17, and HVEM22. Effector cells (tot PBMC cells) were obtained from HD, and target cells (MM.1S GFP+/Luc+) were co-cultured at an 8:1 effector:target ratio, for 12 hours, then incubated with C-IgG (Cat. #1-001-A); and anti-HVEM antibody (10 μg/mL). After incubation, the killing induction (%) was assessed by flow cytometry using 7-aminoactinomycin D (7-AAD) (Cat. #51-68981E BD Biosciences). Data are representative of the average of three technical replicates. Data are expressed as the mean±SEM (n=3).

FIG. 29A presents a representative dot plot showing that HVEM5, HVEM13, HVEM17, HVEM22 induce ADCC in MM cells. B) Bar graph showing effector cell killing activity (%) obtained from 1 healthy donor (HD) in n=3 technical replicates against myeloma cells (MM.1S gfp+/Luc+) in presence of control IgG (C-IgG), or anti-HVEM antibody clones HVEM4, HVEM5, HVEM, 13, HVEM17, and HVEM22. Effector cells (NK cells) were obtained from HD, and target cells (MM.1S GFP+/Luc+) were co-cultured at an 8:1 effector:target ratio, for 4 hours, then incubated with C-IgG (Cat. #1-001-A); and anti-HVEM antibody (10 μg/mL). After incubation, the killing induction (%) was assessed by flow cytometry using 7-aminoactinomycin D (7-AAD) (Cat. #51-68981E BD Biosciences). Data are representative of the average of three technical replicate. Data are expressed as the mean±SEM (n=3).

FIG. 30A presents t-SNE Heatmaps showing that HVEM-5 and HVEM-13 antibodies bind to cynomologus monkey total PBMC. FIG. 30B-30C present bar graphs showing HVEM-5 and HVEM-13 antibodies binding in NK (FIG. 30B) and CD14 cells (FIG. 30C) gated in the total Cynomolgus Monkey PBMCs population.

FIG. 31A presents t-SNE Heatmaps showing the binding of CD270 (144Nd) commercial Anti-HVEM, HVEM-17(166Er) and HVEM-22 (166Er) antibodies in total PBMCs from Cynomolgus Monkey PBMCs population. FIG. 31B presents bar graphs showing the binding of HVEM-17 and HVEM-22 antibodies to cynomolgus monkey gated cell populations (B,NK, Monocytes, CD4, CD8 T cells).

FIG. 32A presents CyTOF analyses conducted on a longitudinal Dara-Progressing patient to detect HVEM expression during anti-MM treatment. Metal-conjugated HVEM-5 was used to stain the PB from this patient. These t-SNE plots showing increased HVEM expression at progression following the treatment course. FIG. 32B presents FlowSom maps showing increased HVEM distribution in B cells, NK, Monocytes, CD8, CD4 subsets during the treatment.

FIGS. 33A-33B present line graphs of CyTOF analysis conducted on a longitudinal Dara-Progressing patient showing HVEM expression during anti-MM treatment. 166Er metal-conjugated HVEM-5 was used to stain the PB from this patient. FIGS. 33C-33E present bar graphs showing increased expression of immune checkpoint inhibitors TIGIT (FIG. 33C), TIM-3 (FIG. 33D), and PD-1 (FIG. 33E) in CD8 T cells from the same patient, following the treatment course.

DETAILED DESCRIPTION

Definitions

Figure 1:
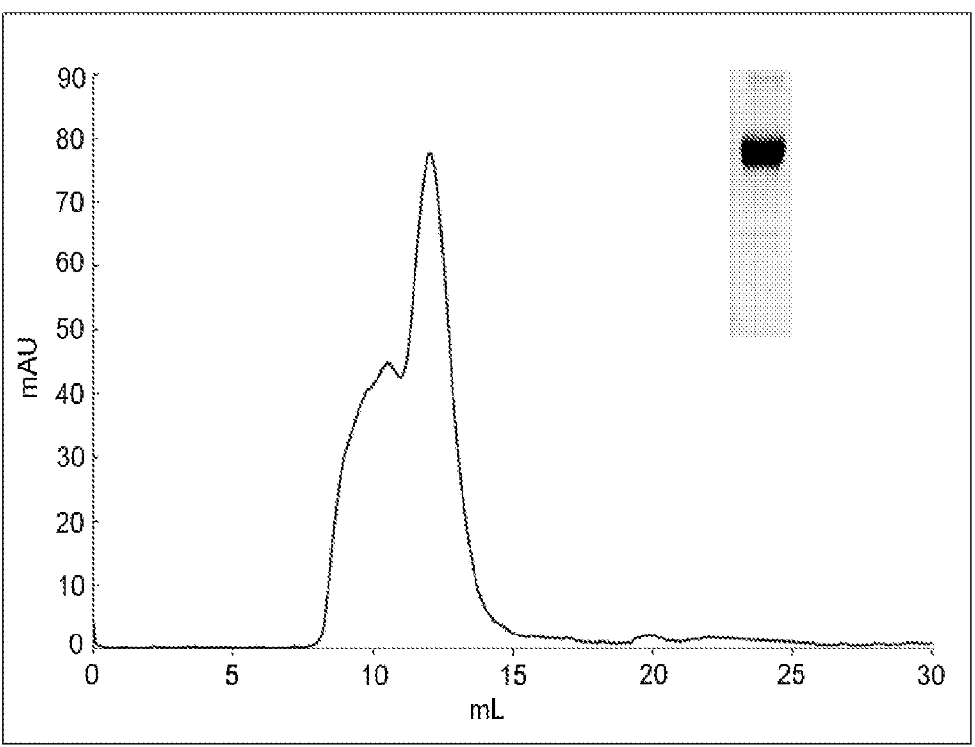
FIG. 1 is a graph showing reduced SDS-PAGE of HVEM fusion proteins with Mini-PROTEAN® TGX Stain-Free™ Precast Gels (Bio-Rad) and a Superdex 200 Increase 10/300 GL column (GE Healthcare) run with PBS.
Figure 2:
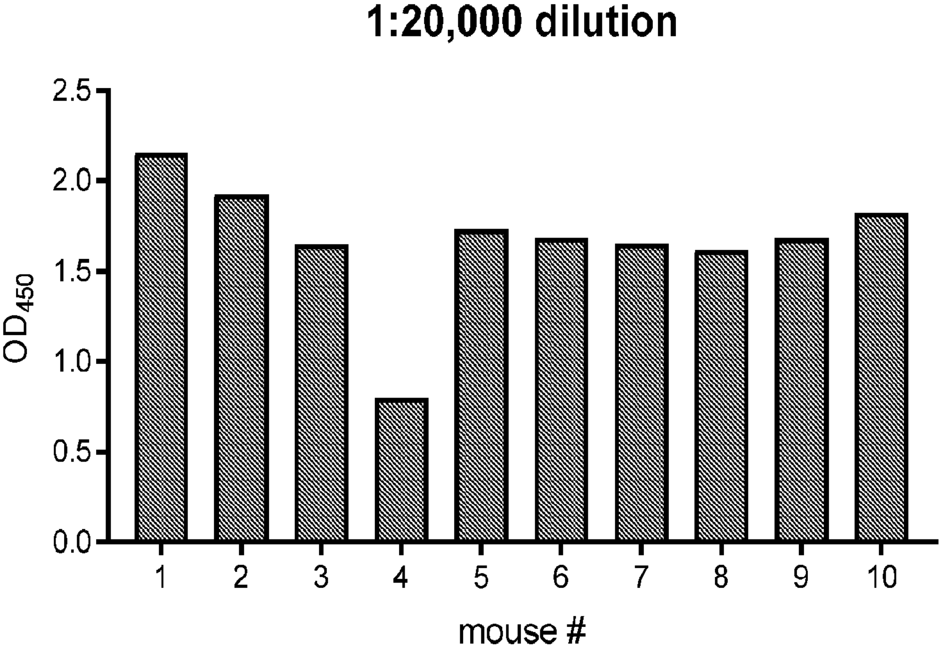
FIG. 2 is a bar graph showing antibody titer in 10 Balb/c mice immunized with recombinant HVEM proteins. Serum sample from each mouse was diluted 20,000 times in PBS, and antibody titer was evaluated on ELISA.

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

The abbreviations used herein have their conventional meaning within the chemical and biological arts. The chemical structures and formulae set forth herein are constructed according to the standard rules of chemical valency known in the chemical arts.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, NY 1994); Sambrook et al., MOLECULAR CLONING, A LABORATORY MANUAL, Cold Springs Harbor Press (Cold Springs Harbor, N Y 1989). Any methods, devices and materials similar or equivalent to those described herein can be used in the practice of this invention. The following definitions are provided to facilitate understanding of certain terms used frequently herein and are not meant to limit the scope of the present disclosure.

"Nucleic acid" refers to nucleotides (e.g., deoxyribonucleotides or ribonucleotides) and polymers thereof in either single-, double- or multiple-stranded form, or complements thereof; or nucleosides (e.g., deoxyribonucleosides or ribonucleosides). In embodiments, "nucleic acid" does not include nucleosides. The terms "polynucleotide," "oligonucleotide," "oligo" or the like refer, in the usual and customary sense, to a linear sequence of nucleotides. The term "nucleoside" refers, in the usual and customary sense, to a glycosylamine including a nucleobase and a five-carbon sugar (ribose or deoxyribose). Non limiting examples, of nucleosides include, cytidine, uridine, adenosine, guanosine, thymidine and inosine. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA. Examples of nucleic acid, e.g. polynucleotides contemplated herein include any types of RNA, e.g. mRNA, siRNA, miRNA, and guide RNA and any types of DNA, genomic DNA, plasmid DNA, and minicircle DNA, and any fragments thereof. The term "duplex" in the context of polynucleotides refers, in the usual and customary sense, to double strandedness. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

Nucleic acids, including e.g., nucleic acids with a phosphothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphodiester derivatives including, e.g., phosphoramidate, phosphorodiamidate, phosphorothioate (also known as phosphothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, OLIGONUCLEOTIDES AND ANALOGUES: A PRACTICAL APPROACH, Oxford University Press) as well as modifications to the nucleotide bases such as in 5-methyl cytidine or pseudouridine.; and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA) as known in the art), including those described in U.S. Pat. Nos. 5,235,033 and 5,034,506, and Chapters 6 and 7, ASC Symposium Series 580, CARBOHYDRATE MODIFICATIONS IN ANTISENSE RESEARCH, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

Nucleic acids can include nonspecific sequences. As used herein, the term "nonspecific sequence" refers to a nucleic acid sequence that contains a series of residues that are not designed to be complementary to or are only partially complementary to any other nucleic acid sequence. By way of example, a nonspecific nucleic acid sequence is a sequence of nucleic acid residues that does not function as an inhibitory nucleic acid when contacted with a cell or organism.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

The term "complement," as used herein, refers to a nucleotide (e.g., RNA or DNA) or a sequence of nucleotides capable of base pairing with a complementary nucleotide or sequence of nucleotides. As described herein and commonly known in the art the complementary (matching) nucleotide of adenosine is thymidine and the complementary (matching) nucleotide of guanosine is cytosine. Thus, a complement may include a sequence of nucleotides that base pair with corresponding complementary nucleotides of a second nucleic acid sequence. The nucleotides of a complement may partially or completely match the nucleotides of the second nucleic acid sequence. Where the nucleotides of the complement completely match each nucleotide of the second nucleic acid sequence, the complement forms base pairs with each nucleotide of the second nucleic acid sequence. Where the nucleotides of the complement partially match the nucleotides of the second nucleic acid sequence only some of the nucleotides of the complement form base pairs with nucleotides of the second nucleic acid sequence. Examples of complementary sequences include coding and a non-coding sequences, wherein the non-coding sequence contains complementary nucleotides to the coding sequence and thus forms the complement of the coding sequence. A further example of complementary sequences are sense and antisense sequences, wherein the sense sequence contains complementary nucleotides to the antisense sequence and thus forms the complement of the antisense sequence.

As described herein the complementarity of sequences may be partial, in which only some of the nucleic acids match according to base pairing, or complete, where all the nucleic acids match according to base pairing. Thus, two sequences that are complementary to each other, may have a specified percentage of nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues, wherein the polymer may In embodiments be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence. An amino acid residue in a protein "corresponds" to a given residue when it occupies the same essential structural position within the protein as the given residue. One skilled in the art will immediately recognize the identity and location of residues corresponding to a specific position in a protein (e.g., HVEM) in other proteins with different numbering systems. For example, by performing a simple sequence alignment with a protein (e.g., HVEM) the identity and location of residues corresponding to specific positions of the protein are identified in other protein sequences aligning to the protein. For example, a selected residue in a selected protein corresponds to glutamic acid at position 138 when the selected residue occupies the same essential spatial or other structural relationship as a glutamic acid at position 138. In some embodiments, where a selected protein is aligned for maximum homology with a protein, the position in the aligned selected protein aligning with glutamic acid 138 is the to correspond to glutamic acid 138. Instead of a primary sequence alignment, a three dimensional structural alignment can also be used, e.g., where the structure of the selected protein is aligned for maximum correspondence with the glutamic acid at position 138, and the overall structures compared. In this case, an amino acid that occupies the same essential position as glutamic acid 138 in the structural model is the to correspond to the glutamic acid 138 residue.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure.

The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, Proteins (1984)).

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

A "comparison window", as used herein, includes reference to a segment of any one of the number of contiguous positions selected from the group consisting of, e.g., a full length sequence or from 20 to 600, about 50 to about 200, or about 100 to about 150 amino acids or nucleotides in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith and Waterman (1970) Adv. Appl. Math. 2:482c, by the homology alignment algorithm of Needleman and Wunsch (1970)

J. Mol. Biol. 48:443, by the search for similarity method of Pearson and Lipman (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Ausubel et al., Current Protocols in Molecular Biology (1995 supplement)).

An example of an algorithm that is suitable for determining percent sequence identity and sequence similarity are the BLAST and BLAST 2.0 algorithms, which are described in Altschul et al. (1977) Nuc. Acids Res. 25:3389-3402, and Altschul et al. (1990) J. Mol. Biol. 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) or 10, M=5, N=−4 and a comparison of both strands. For amino acid sequences, the BLASTP program uses as defaults a word length of 3, and expectation (E) of 10, and the BLOSUM62 scoring matrix (see Henikoff and Henikoff (1989) Proc. Natl. Acad. Sci. USA 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

Antibodies are large, complex molecules (molecular weight of −150,000 or about 1320 amino acids) with intricate internal structure. A natural antibody molecule contains two identical pairs of polypeptide chains, each pair having one light chain and one heavy chain. Each light chain and heavy chain in turn consists of two regions: a variable ("V") region, involved in binding the target antigen, and a constant ("C") region that interacts with other components of the immune system. The light and heavy chain variable regions (also referred to herein as light chain variable (VL) domain and heavy chain variable (VH) domain, respectively) come together in 3-dimensional space to form a variable region that binds the antigen (for example, a receptor on the surface of a cell). In human, two types of light chain are known: kappa chain (VK or Vκ), encoded by the immunoglobulin kappa locus on chromosome 2, and the lambda chain (Vλ), encoded by the immunoglobulin lambda locus on chromosome 22. Within each light or heavy chain variable region, there are three short segments (averaging 10 amino acids in length) called the complementarity determining regions ("CDRs"). The six CDRs in an antibody variable domain (three from the light chain and three from the heavy chain) fold up together in 3-dimensional space to form the actual antibody binding site which docks onto the target antigen. The position and length of the CDRs have been precisely defined by Kabat, E. et al., Sequences of Proteins of Immunological Interest, U.S. Department of Health and Human Services, 1983, 1987. The part of a variable region not contained in the CDRs is called the framework ("FR"), which forms the environment for the CDRs.

An "antibody variant" as provided herein refers to a polypeptide capable of binding to an antigen and including one or more structural domains (e.g., light chain variable domain, heavy chain variable domain) of an antibody or fragment thereof. Non-limiting examples of antibody variants include single-domain antibodies or nanobodies, monospecific Fab2, bispecific Fab2, trispecific Fab3, monovalent IgGs, scFv, bispecific antibodies, bispecific diabodies, trispecific triabodies, scFv-Fc, minibodies, IgNAR, V-NAR, hcIgG, VhH, or peptibodies. A "peptibody" as provided herein refers to a peptide moiety attached (through a covalent or non-covalent linker) to the Fc domain of an antibody. Further non-limiting examples of antibody variants known in the art include antibodies produced by cartilaginous fish or camelids. A general description of antibodies from camelids and the variable regions thereof and methods for their production, isolation, and use may be found in references WO97/49805 and WO 97/49805 which are incorporated by reference herein in their entirety and for all purposes. Likewise, antibodies from cartilaginous fish and the variable regions thereof and methods for their production, isolation, and use may be found in WO2005/118629, which is incorporated by reference herein in its entirety and for all purposes.

The terms "CDR L1", "CDR L2" and "CDR L3" as provided herein refer to the complementarity determining regions (CDR) 1, 2, and 3 of the variable light (L) chain of an antibody. In embodiments, the variable light chain provided herein includes in N-terminal to C-terminal direction a CDR L1, a CDR L2 and a CDR L3. Likewise, the terms "CDR H1", "CDR H2" and "CDR H3" as provided herein refer to the complementarity determining regions (CDR) 1, 2, and 3 of the variable heavy (H) chain of an antibody. In embodiments, the variable heavy chain provided herein includes in N-terminal to C-terminal direction a CDR H1, a CDR H2 and a CDR H3.

The terms "FR L1", "FR L2", "FR L3" and "FR L4" as provided herein are used according to their common meaning in the art and refer to the framework regions (FR) 1, 2, 3 and 4 of the variable light (L) chain of an antibody. In embodiments, the variable light chain provided herein includes in N-terminal to C-terminal direction a FR L1, a FR L2, a FR L3 and a FR L4. Likewise, the terms "FR H1", "FR H2", "FR H3" and "FR H4" as provided herein are used according to their common meaning in the art and refer to the framework regions (FR) 1, 2, 3 and 4 of the variable heavy (H) chain of an antibody. In embodiments, the variable heavy chain provided herein includes in N-terminal to C-terminal direction a FR H1, a FR H2, a FR H3 and a FRH4.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL), variable light chain (VL) domain or light chain variable region and variable heavy chain (VH), variable heavy chain (VH) domain or heavy chain variable region refer to these light and heavy chain regions, respectively. The terms variable light chain (VL), variable light chain (VL) domain and light chain variable region as referred to herein may be used interchangeably. The terms variable heavy chain (VH), variable heavy chain (VH) domain and heavy chain variable region as referred to herein may be used interchangeably. The Fc (i.e. fragment crystallizable region) is the "base" or "tail" of an immunoglobulin and is typically composed of two heavy chains that contribute two or three constant domains depending on the class of the antibody. By binding to specific proteins, the Fc region ensures that each antibody generates an appropriate immune response for a given antigen. The Fc region also binds to various cell receptors, such as Fc receptors, and other immune molecules, such as complement proteins.

The term "antibody" is used according to its commonly known meaning in the art. Antibodies exist, e.g., as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to $V_H$-$C_{H1}$ by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)). The term "antibody" as referred to herein further includes antibody variants such as single domain antibodies. Thus, in embodiments an antibody includes a single monomeric variable antibody domain. Thus, in embodiments, the antibody, includes a variable light chain (VL) domain or a variable heavy chain (VH) domain. In embodiments, the antibody is a variable light chain (VL) domain or a variable heavy chain (VH) domain.

For preparation of monoclonal or polyclonal antibodies, any technique known in the art can be used (see, e.g., Kohler & Milstein, *Nature* 256:495-497 (1975); Kozbor et al., *Immunology Today* 4:72 (1983); Cole et al., pp. 77-96 in *Monoclonal Antibodies and Cancer Therapy* (1985)). "Monoclonal" antibodies (mAb) refer to antibodies derived from a single clone. Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)).

A single-chain variable fragment (scFv) is typically a fusion protein of the variable regions of the heavy (VH) and light chains (VL) of immunoglobulins, connected with a short linker peptide of 10 to about 25 amino acids. The linker may usually be rich in glycine for flexibility, as well as serine or threonine for solubility. The linker can either connect the N-terminus of the VH with the C-terminus of the VL, or vice versa.

The epitope of a mAb is the region of its antigen to which the mAb binds. Two antibodies bind to the same or overlapping epitope if each competitively inhibits (blocks) binding of the other to the antigen. That is, a 1×, 5×, 10×, 20× or 100× excess of one antibody inhibits binding of the other by at least 30% but preferably 50%, 75%, 90% or even 99% as measured in a competitive binding assay (see, e.g., Junghans et al., Cancer Res. 50:1495, 1990). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

For preparation of suitable antibodies of the invention and for use according to the invention, e.g., recombinant, monoclonal, or polyclonal antibodies, many techniques known in the art can be used (see, e.g., Kohler & Milstein, Nature 256:495-497 (1975); Kozbor et al., Immunology Today 4:72 (1983); Cole et al., pp. 77-96 in Monoclonal Antibodies and Cancer Therapy, Alan R. Liss, Inc. (1985); Coligan, Current Protocols in Immunology (1991); Harlow & Lane, Antibodies, A Laboratory Manual (1988); and Goding, Monoclonal Antibodies: Principles and Practice (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, Immunology (3rd ed. 1997)). Techniques for the production of single chain antibodies or recombinant antibodies (U.S. Pat. Nos.

4,946,778, 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); and Lonberg & Huszar, Intern. Rev. Immunol. 13:65-93 (1995)). Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)). Antibodies can also be made bispecific, i.e., able to recognize two different antigens (see, e.g., WO 93/08829, Traunecker et al., EMBO J. 10:3655-3659 (1991); and Suresh et al., Methods in Enzymology 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art (e.g., U.S. Pat. Nos. 4,816,567; 5,530,101; 5,859,205; 5,585,089; 5,693,761; 5,693,762; 5,777,085; 6,180,370; 6,210,671; and 6,329,511; WO 87/02671; EP Patent Application 0173494; Jones et al. (1986) Nature 321:522; and Verhoyen et al. (1988) Science 239:1534). Humanized antibodies are further described in, e.g., Winter and Milstein (1991) Nature 349:293. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Morrison et al., PNAS USA, 81:6851-6855 (1984), Jones et al., Nature 321:522-525 (1986); Riechmann et al., Nature 332:323-327 (1988); Morrison and Oi, Adv. Immunol., 44:65-92 (1988), Verhoeyen et al., Science 239:1534-1536 (1988) and Presta, Curr. Op. Struct. Biol. 2:593-596 (1992), Padlan, Molec. Immun., 28:489-498 (1991); Padlan, Molec. Immun., 31(3):169-217 (1994)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies. For example, polynucleotides comprising a first sequence coding for humanized immunoglobulin framework regions and a second sequence set coding for the desired immunoglobulin complementarity determining regions can be produced synthetically or by combining appropriate cDNA and genomic DNA segments. Human constant region DNA sequences can be isolated in accordance with well known procedures from a variety of human cells.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. The preferred antibodies of, and for use according to the invention include humanized and/or chimeric monoclonal antibodies.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only a subset of antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998) for a description of immunoassay formats and conditions that can be used to determine specific immunoreactivity).

A "ligand" refers to an agent, e.g., a polypeptide or other molecule, capable of binding to a receptor or antibody, antibody variant, antibody region or fragment thereof.

Techniques for conjugating therapeutic agents to antibodies are well known (see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery" in Controlled Drug Delivery ($2^{nd}$ Ed.), Robinson et al. (eds.), pp. 623-53 (Marcel Dekker, Inc. 1987); Thorpe, "Antibody Carriers Of Cytotoxic Agents In Cancer Therapy: A Review" in Monoclonal Antibodies '84: Biological And Clinical Applications, Pinchera et al. (eds.), pp. 475-506 (1985); and Thorpe et al., "The Preparation And Cytotoxic Properties Of Antibody-Toxin Conjugates", Immunol. Rev., 62:119-58 (1982)). As used herein, the term "antibody-drug conjugate" or "ADC" refers to a therapeutic agent conjugated or otherwise covalently bound to an antibody.

For specific proteins described herein, the named protein includes any of the protein's naturally occurring forms, variants or homologs that maintain the protein transcription factor activity (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In other embodiments, the protein is the protein as identified by its NCBI sequence reference. In other embodiments, the protein is the protein as identified by its NCBI sequence reference, homolog or functional fragment thereof.

The terms "HVEM protein" and "HVEM" as used herein include any of the recombinant or naturally-occurring forms of the herpesvirus entry mediator, also known as tumor necrosis factor receptor superfamily member 14 (TNFRSF14), or variants or homologs thereof that maintain HVEM activity (e.g. within at least 50%, 80%, 90%, 95%, 96%, 97%, 98%, 99% or 100% activity compared to HVEM). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring HVEM protein. In embodiments, the HVEM protein is substantially identical to the protein identified by the UniProt reference number Q92956 or a variant or homolog having substantial identity thereto.

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

The terms "plasmid", "vector" or "expression vector" refer to a nucleic acid molecule that encodes for genes and/or regulatory elements necessary for the expression of genes. Expression of a gene from a plasmid can occur in cis or in trans. If a gene is expressed in cis, the gene and the regulatory elements are encoded by the same plasmid. Expression in trans refers to the instance where the gene and the regulatory elements are encoded by separate plasmids.

The terms "transfection", "transduction", "transfecting" or "transducing" can be used interchangeably and are defined as a process of introducing a nucleic acid molecule or a protein to a cell. Nucleic acids are introduced to a cell using non-viral or viral-based methods. The nucleic acid molecules may be gene sequences encoding complete proteins or functional portions thereof. Non-viral methods of transfection include any appropriate transfection method that does not use viral DNA or viral particles as a delivery system to introduce the nucleic acid molecule into the cell. Exemplary non-viral transfection methods include calcium phosphate transfection, liposomal transfection, nucleofection, sonoporation, transfection through heat shock, magnetifection and electroporation. In some embodiments, the nucleic acid molecules are introduced into a cell using electroporation following standard procedures well known in the art. For viral-based methods of transfection any useful viral vector may be used in the methods described herein. Examples for viral vectors include, but are not limited to retroviral, adenoviral, lentiviral and adeno-associated viral vectors. In some embodiments, the nucleic acid molecules are introduced into a cell using a retroviral vector following standard procedures well known in the art. The terms "transfection" or "transduction" also refer to introducing proteins into a cell from the external environment. Typically, transduction or transfection of a protein relies on attachment of a peptide or protein capable of crossing the cell membrane to the protein of interest. See, e.g., Ford et al. (2001) *Gene Therapy* 8:1-4 and Prochiantz (2007) *Nat. Methods* 4:119-20.

A "label" or a "detectable moiety" is a composition detectable by spectroscopic, photochemical, biochemical, immunochemical, chemical, or other physical means. For example, useful labels include 32P, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any appropriate method known in the art for conjugating an antibody to the label may be employed, e.g., using methods described in Hermanson, Bioconjugate Techniques 1996, Academic Press, Inc., San Diego.

When the label or detectable moiety is a radioactive metal or paramagnetic ion, the agent may be reacted with another long-tailed reagent having a long tail with one or more chelating groups attached to the long tail for binding to these ions. The long tail may be a polymer such as a polylysine, polysaccharide, or other derivatized or derivatizable chain having pendant groups to which the metals or ions may be added for binding. Examples of chelating groups that may be used according to the disclosure include, but are not limited to, ethylenediaminetetraacetic acid (EDTA), diethylenetriaminepentaacetic acid (DTPA), DOTA, NOTA, NETA, TETA, porphyrins, polyamines, crown ethers, bis-thiosemicarbazones, polyoximes, and like groups. The chelate is normally linked to the PSMA antibody or functional antibody fragment by a group, which enables the formation of a bond to the molecule with minimal loss of immunoreactivity and minimal aggregation and/or internal cross-linking. The same chelates, when complexed with non-radioactive metals, such as manganese, iron and gadolinium are useful for MRI, when used along with the antibodies and carriers described herein. Macrocyclic chelates such as NOTA, DOTA, and TETA are of use with a variety of metals and radiometals including, but not limited to, radionuclides of gallium, yttrium and copper, respectively. Other ring-type chelates such as macrocyclic polyethers, which are of interest for stably binding nuclides, such as $^{223}$Ra for RAIT may be used. In certain embodiments, chelating moieties may be used to attach a PET imaging agent, such as an Al-$^{18}$F complex, to a targeting molecule for use in PET analysis.

"Contacting" is used in accordance with its plain ordinary meaning and refers to the process of allowing at least two distinct species (e.g. antibodies and antigens) to become sufficiently proximal to react, interact, or physically touch. It should be appreciated, however, that the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be, for example, a pharmaceutical composition as provided herein and a cell. In embodiments contacting includes, for example, allowing a pharmaceutical composition as described herein to interact with a cell.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include, but are not limited to, yeast cells and cells derived from plants and animals, for example mammalian, insect (e.g., spodoptera) and human cells.

The term "recombinant" when used with reference, e.g., to a cell, nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all. Transgenic cells and plants are those that express a heterologous gene or coding sequence, typically as a result of recombinant methods.

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The term "exogenous" refers to a molecule or substance (e.g., a compound, nucleic acid or protein) that originates from outside a given cell or organism. For example, an "exogenous promoter" as referred to herein is a promoter that does not originate from the cell or organism it is expressed by. Conversely, the term "endogenous" or "endogenous promoter" refers to a molecule or substance that is native to, or originates within, a given cell or organism.

As defined herein, the term "inhibition", "inhibit", "inhibiting" and the like in reference to cell proliferation (e.g., cancer cell proliferation) means negatively affecting (e.g., decreasing proliferation) or killing the cell. In some embodiments, inhibition refers to reduction of a disease or symptoms of disease (e.g., cancer, cancer cell proliferation). Thus, inhibition includes, at least in part, partially or totally blocking stimulation, decreasing, preventing, or delaying activation, or inactivating, desensitizing, or down-regulating signal transduction or enzymatic activity or the amount of a protein (e.g. HVEM protein). Similarly an "inhibitor" is a compound or protein that inhibits a receptor or another protein, e.g., by binding, partially or totally blocking, decreasing, preventing, delaying, inactivating, desensitizing, or down-regulating activity (e.g., a receptor activity or a protein activity).

As defined herein, the term "inhibition", "inhibit", "inhibiting" and the like in reference to a protein-inhibitor interaction means negatively affecting (e.g. decreasing) the activity or function of the protein (e.g. HVEM protein) relative to the activity or function of the protein in the absence of the inhibitor. In embodiments inhibition means negatively affecting (e.g. decreasing) the concentration or levels of HVEM relative to the concentration or level of the protein in the absence of the inhibitor. In embodiments inhibition refers to reduction of a disease or symptoms of disease. In embodiments, inhibition refers to a reduction in the activity of HVEM. Thus, inhibition includes, at least in part, partially or totally blocking stimulation, decreasing, preventing, or delaying activation, or inactivating, desensitizing, or down-regulating signal transduction or enzymatic activity or the amount of HVEM. In embodiments, inhibition refers to a reduction of activity of HVEM resulting from a direct interaction (e.g. an inhibitor binds to HVEM). In embodiments, inhibition refers to a reduction of activity of HVEM from an indirect interaction (e.g. an inhibitor binds to a protein that activates HVEM, thereby preventing target protein activation).

Thus, the terms "inhibitor," "repressor" or "antagonist" or "downregulator" interchangeably refer to a substance capable of detectably decreasing the expression or activity of a given gene or protein (e.g. HVEM protein). The antagonist can decrease HVEM expression or activity 10%, 20%, 30%, 40%, 50%, 60%, 70%, 80%, 90% or more in comparison to a control in the absence of the antagonist. In certain instances, HVEM expression or activity is 1.5-fold, 2-fold, 3-fold, 4-fold, 5-fold, 10-fold or lower than the expression or activity in the absence of the antagonist.

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

"Biological sample" or "sample" refer to materials obtained from or derived from a subject or patient. A biological sample includes sections of tissues such as biopsy and autopsy samples, and frozen sections taken for histological purposes. Such samples include bodily fluids such as blood and blood fractions or products (e.g., serum, plasma, platelets, red blood cells, and the like), sputum, tissue, cultured cells (e.g., primary cultures, explants, and transformed cells) stool, urine, synovial fluid, joint tissue, synovial tissue, synoviocytes, fibroblast-like synoviocytes, macrophage-like synoviocytes, immune cells, hematopoietic cells, fibroblasts, macrophages, T cells, etc. A biological sample is typically obtained from a eukaryotic organism, such as a mammal such as a primate e.g., chimpanzee or human; cow; dog; cat; a rodent, e.g., guinea pig, rat, mouse; rabbit; or a bird; reptile; or fish.

A "control" or "standard control" refers to a sample, measurement, or value that serves as a reference, usually a known reference, for comparison to a test sample, measurement, or value. For example, a test sample can be taken from a patient suspected of having a given disease (e.g. cancer) and compared to a known normal (non-diseased) individual (e.g. a standard control subject). A standard control can also represent an average measurement or value gathered from a population of similar individuals (e.g. standard control subjects) that do not have a given disease (i.e. standard control population), e.g., healthy individuals with a similar medical background, same age, weight, etc. A standard control value can also be obtained from the same individual, e.g. from an earlier-obtained sample from the patient prior to disease onset. For example, a control can be devised to compare therapeutic benefit based on pharmacological data (e.g., half-life) or therapeutic measures (e.g., comparison of side effects). Controls are also valuable for determining the significance of data. For example, if values for a given parameter are widely variant in controls, variation in test samples will not be considered as significant. One of skill will recognize that standard controls can be designed for assessment of any number of parameters (e.g. RNA levels, protein levels, specific cell types, specific bodily fluids, specific tissues, etc).

One of skill in the art will understand which standard controls are most appropriate in a given situation and be able to analyze data based on comparisons to standard control values. Standard controls are also valuable for determining the significance (e.g. statistical significance) of data. For example, if values for a given parameter are widely variant in standard controls, variation in test samples will not be considered as significant.

"Patient" or "subject in need thereof" refers to a living organism suffering from or prone to a disease or condition that can be treated by administration of a composition or pharmaceutical composition as provided herein. Non-limiting examples include humans, other mammals, bovines, rats, mice, dogs, monkeys, goat, sheep, cows, deer, and other non-mammalian animals. In some embodiments, a patient is human.

The terms "disease" or "condition" refer to a state of being or health status of a patient or subject capable of being treated with the compounds or methods provided herein. The disease may be a cancer. The cancer may refer to a solid tumor malignancy. Solid tumor malignancies include malignant tumors that may be devoid of fluids or cysts. For example, the solid tumor malignancy may include breast cancer, ovarian cancer, pancreatic cancer, cervical cancer, gastric cancer, renal cancer, head and neck cancer, bone cancer, skin cancer or prostate cancer. In some further instances, "cancer" refers to human cancers and carcinomas, sarcomas, adenocarcinomas, lymphomas, leukemias, including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including acute myeloid leukemia (AML), ALL, and CML), or multiple myeloma.

As used herein, the term "cancer" refers to all types of cancer, neoplasm or malignant tumors found in mammals (e.g., humans), including leukemia, carcinomas and sarcomas. Exemplary cancers that may be treated with a compound or method provided herein include breast cancer, colon cancer, kidney cancer, leukemia, lung cancer, melanoma, ovarian cancer, prostate cancer, pancreatic cancer, brain cancer, liver cancer, gastric cancer or a sarcoma.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute myeloid leukemia, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatinifori carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

As used herein, the terms "metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

The term "associated" or "associated with" in the context of a substance or substance activity or function associated with a disease (e.g. a protein associated disease, a cancer associated with HVEM activity, HVEM-associated cancer, HVEM-associated disease (e.g., cancer, inflammatory disease, autoimmune disease, or infectious disease)) means that the disease (e.g. cancer, inflammatory disease, autoimmune disease, or infectious disease) is caused by (in whole or in part), or a symptom of the disease is caused by (in whole or in part) the substance or substance activity or function. As used herein, what is described as being associated with a disease, if a causative agent, could be a target for treatment of the disease. For example, a cancer associated with HVEM activity or function or a HVEM-associated disease (e.g., cancer, inflammatory disease, autoimmune disease, or infectious disease), may be treated with a HVEM modulator or HVEM inhibitor, in the instance where increased HVEM activity or function (e.g. signaling pathway activity) causes the disease (e.g., cancer, inflammatory disease, autoimmune disease, or infectious disease). For example, an inflammatory disease associated with HVEM activity or function or an HVEM associated inflammatory disease, may be treated with an HVEM modulator or HVEM inhibitor, in the instance where increased HVEM activity or function (e.g. signaling pathway activity) causes the disease.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propagated to other signaling pathway components.

The term "aberrant" as used herein refers to different from normal. When used to describe enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g. by using a method as described herein), results in reduction of the disease or one or more disease symptoms.

A "therapeutic agent" as referred to herein, is a composition useful in treating or preventing a disease such as cancer (e.g., leukemia). In embodiments, the therapeutic agent is an anti-cancer agent. "Anti-cancer agent" is used in accordance with its plain ordinary meaning and refers to a composition (e.g. compound, drug, antagonist, inhibitor, modulator) having antineoplastic properties or the ability to inhibit the growth or proliferation of cells. In embodiments, an anti-cancer agent is a chemotherapeutic. In embodiments, an anti-cancer agent is an agent identified herein having utility in methods of treating cancer. In embodiments, an anti-cancer agent is an agent approved by the FDA or similar regulatory agency of a country other than the USA, for treating cancer.

An "anticancer agent" as used herein refers to a molecule (e.g. compound, peptide, protein, nucleic acid, 0103) used to treat cancer through destruction or inhibition of cancer cells or tissues. Anticancer agents may be selective for certain cancers or certain tissues. In embodiments, anticancer agents herein may include epigenetic inhibitors and multi-kinase inhibit "Anti-cancer agent" and "anticancer agent" are used in accordance with their plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflomithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras famesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rlL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, lnanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, lsoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In, $^{90}$Y, or$^{131}$, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™) panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

As used herein, "treating" or "treatment of" a condition, disease or disorder or symptoms associated with a condition, disease or disorder refers to an approach for obtaining beneficial or desired results, including clinical results. Beneficial or desired clinical results can include, but are not limited to, alleviation or amelioration of one or more symptoms or conditions, diminishment of extent of condition, disorder or disease, stabilization of the state of condition, disorder or disease, prevention of development of condition, disorder or disease, prevention of spread of condition, disorder or disease, delay or slowing of condition, disorder or disease progression, delay or slowing of condition, disorder or disease onset, amelioration or palliation of the condition, disorder or disease state, and remission, whether partial or total. "Treating" can also mean prolonging survival of a subject beyond that expected in the absence of treatment. "Treating" can also mean inhibiting the progression of the condition, disorder or disease, slowing the progression of the condition, disorder or disease temporarily, although in some instances, it involves halting the progression of the condition, disorder or disease permanently. As used herein the terms treatment, treat, or treating refers to a method of reducing the effects of one or more symptoms of a disease or condition characterized by expression of the protease or symptom of the disease or condition characterized by expression of the protease. Thus in the disclosed method, treatment can refer to a 10%, 20%, 30%, 40%, 50%, 60%, 70%, 80%, 90%, or 100% reduction in the severity of an established disease, condition, or symptom of the disease or condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition. Further, as used herein, references to decreasing, reducing, or inhibiting include a change of 10%, 20%, 30%, 40%, 50%, 60%, 70%, 80%, 90% or greater as compared to a control level and such terms can include but do not necessarily include complete elimination.

The terms "dose" and "dosage" are used interchangeably herein. A dose refers to the amount of active ingredient given to an individual at each administration. The dose will vary depending on a number of factors, including the range of normal doses for a given therapy, frequency of administration; size and tolerance of the individual; severity of the condition; risk of side effects; and the route of administration. One of skill will recognize that the dose can be modified depending on the above factors or based on therapeutic progress. The term "dosage form" refers to the particular format of the pharmaceutical or pharmaceutical composition, and depends on the route of administration. For example, a dosage form can be in a liquid form for nebulization, e.g., for inhalants, in a tablet or liquid, e.g., for oral delivery, or a saline solution, e.g., for injection.

By "therapeutically effective dose or amount" as used herein is meant a dose that produces effects for which it is administered (e.g. treating or preventing a disease). The exact dose and formulation will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Remington: The Science and Practice of Pharmacy, 20th Edition, Gennaro, Editor (2003), and Pickar, Dosage Calculations (1999)). For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a standard control. A therapeutically effective dose or amount may ameliorate one or more symptoms of a disease. A therapeutically effective dose or amount may prevent or delay the onset of a disease or one or more symptoms of a disease when the effect for which it is being administered is to treat a person who is at risk of developing the disease.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols.

The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., *Gao Pharm. Res.* 12:857-863, 1995); or, as microspheres for oral administration (see, e.g., Eyles, *J. Pharm. Pharmacol.* 49:669-674, 1997). In embodiments, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, Am. *J Hosp. Pharm.* 46:1576-1587, 1989). The compositions of the present invention can also be delivered as nanoparticles.

As used herein, the term "pharmaceutically acceptable" is used synonymously with "physiologically acceptable" and "pharmacologically acceptable". A pharmaceutical composition will generally comprise agents for buffering and preservation in storage, and can include buffers and carriers for appropriate delivery, depending on the route of administration.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "pharmaceutically acceptable salt" refers to salts derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

The pharmaceutical preparation is optionally in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The unit dosage form can be of a frozen dispersion.

The terms "1-ethyl-3-(–3-dimethyoaminopropyl) carbodiimide", "EDC", "EDAC" and "EDCI" as used herein refer to a water-soluble carbodiimide usually handled as the hydrochloride. It is generally used as a carboxyl activating agent for the coupling of primary amines to yield amide bonds. Additionally, EDC can also be used to activate phosphate groups in order to form phosphomonoesters and phosphodiesters. Common uses for this carbodiimide include peptide synthesis, protein crosslinking to nucleic acids, but also in the preparation of immunoconjugates. EDC is often used in combination with N-hydroxysuccinimide (NHS) for the immobilisation of large biomolecules. Recent work has also used EDC to assess the structure state of uracil nucleobases in RNA.

The terms "N-hydroxysulfosuccinimide", "sulfo-NHS" and "NHS" refer to a compound that enables control and modification of carbodiimide crosslinking reactions involving activation of carboxylates (—COOH) for conjugation with primary amines (—$NH_2$). Derivatives can be synthesized by mixing the NHS with a carboxyl-containing molecule and a dehydrating agent such as the carbodiimide EDC. The method is the basis for generating many types of protein labeling reagents, including amine-reactive fluorescent dyes, biotin affinity tags and pegylation compounds.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Anti-Hvem Antibodies

Provided herein are, inter alia, antibodies (e.g., humanized antibodies, monoclonal antibodies, antibody fragments (e.g., scFvs)) and antibody compositions (e.g., chimeric antigen receptors (CARs), bispecific antibodies), which bind Herpesvirus Entry Mediator (HVEM) with high efficiency and specificity. The antibodies and antibody compositions provided herein include, for example, novel light and heavy chain domain CDRs and framework regions and are, inter alia, useful for diagnosing and treating cancer and other HVEM-related diseases. In embodiments, the anti-HVEM antibodies provided herein are capable of binding a cancer cell and directing immune cells against the cancer cell without requiring activation of the immune effector cell (e.g., Nk cell).

In an aspect is provided an anti-Herpes Virus Entry Mediator (HVEM) antibody including a light chain variable domain and a heavy chain variable domain, wherein the light chain variable domain includes: a CDR L1 as set forth in SEQ ID NO:1, a CDR L2 as set forth in SEQ ID NO:2 and a CDR L3 as set forth in SEQ ID NO:3; and wherein the heavy chain variable domain includes: a CDR H1 as set forth in SEQ ID NO:4, a CDR H2 as set forth in SEQ ID NO:5, and a CDR H3 as set forth in SEQ ID NO:6. In embodiments, light chain variable domain includes a FR L1 as set forth in SEQ ID NO:7, a FR L2 as set forth in SEQ ID NO:8, a FR L3 as set forth in SEQ ID NO:9 and a FR L4 as set forth in SEQ ID NO:10. In embodiments, the heavy chain variable domain includes a FR H1 as set forth in SEQ ID NO:11, a FR H2 as set forth in SEQ ID NO: 12, a FR H3 as set forth in SEQ ID NO: 13 and a FR H4 as set forth in SEQ ID NO:14.

In embodiments, the light chain variable domain includes the sequence of SEQ ID NO: 15. In embodiments, the heavy chain variable domain includes the sequence of SEQ ID NO: 16. In embodiments, the light chain variable domain is the sequence of SEQ ID NO: 15. In embodiments, the heavy chain variable domain is the sequence of SEQ ID NO:16. In embodiments, the antibody includes a light chain including the sequence of SEQ ID NO: 15. In embodiments, the antibody includes a heavy chain including the sequence of SEQ ID NO:16. In embodiments, the light chain is the sequence of SEQ ID NO:15. In embodiments, the heavy chain is the sequence of SEQ ID NO:16. In embodiments, the light chain includes the sequence of SEQ ID NO:15 and the heavy chain includes the sequence of SEQ ID NO:16. In embodiments, the light chain is the sequence of SEQ ID NO:15 and the heavy chain is the sequence of SEQ ID NO:16. In embodiments, the HVEM antibody is referred to herein as clone 13.

In another aspect is provided an anti-Herpes Virus Entry Mediator (HVEM) antibody including a light chain variable domain and a heavy chain variable domain, wherein the light chain variable domain includes: a CDR L1 as set forth in SEQ ID NO:17, a CDR L2 as set forth in SEQ ID NO: 18 and a CDR L3 as set forth in SEQ ID NO:19; and wherein the heavy chain variable domain includes: a CDR H1 as set forth in SEQ ID NO:20, a CDR H2 as set forth in SEQ ID NO:21, and a CDR H3 as set forth in SEQ ID NO:22.

In embodiments, the light chain variable domain includes a FR L1 as set forth in SEQ ID NO:23, a FR L2 as set forth in SEQ ID NO:24, a FR L3 as set forth in SEQ ID NO:25 and a FR L4 as set forth in SEQ ID NO:26. In embodiments, the heavy chain variable domain includes a FR H1 as set forth in SEQ ID NO:27, a FR H2 as set forth in SEQ ID NO:28, a FR H3 as set forth in SEQ ID NO:29 and a FR H4 as set forth in SEQ ID NO:30.

In embodiments, the light chain variable domain includes the sequence of SEQ ID NO:31. In embodiments, the heavy chain variable domain includes the sequence of SEQ ID NO:32. In embodiments, the light chain variable domain is the sequence of SEQ ID NO:31. In embodiments, the heavy chain variable domain is the sequence of SEQ ID NO: 32. In embodiments, the antibody includes a light chain including the sequence of SEQ ID NO:31. In embodiments, the antibody includes a heavy chain including the sequence of SEQ ID NO:32. In embodiments, the light chain is the sequence of SEQ ID NO:31. In embodiments, the heavy chain is the sequence of SEQ ID NO:32. In embodiments, the light chain includes the sequence of SEQ ID NO:31 and the heavy chain includes the sequence of SEQ ID NO:32. In embodiments, the light chain is the sequence of SEQ ID NO:31 and the heavy chain is the sequence of SEQ ID NO:32. In embodiments, the HVEM antibody is referred to herein as clone 4.

In another aspect is provided an anti-Herpes Virus Entry Mediator (HVEM) antibody including a light chain variable domain and a heavy chain variable domain, wherein the light chain variable domain includes: a CDR L1 as set forth in SEQ ID NO:33, a CDR L2 as set forth in SEQ ID NO:34 and a CDR L3 as set forth in SEQ ID NO:35; and wherein the heavy chain variable domain includes: a CDR H1 as set forth in SEQ ID NO:36, a CDR H2 as set forth in SEQ ID NO:37, and a CDR H3 as set forth in SEQ ID NO:38. In embodiments, the light chain variable domain includes a FR L1 as set forth in SEQ ID NO:39, a FR L2 as set forth in SEQ ID NO:40, a FR L3 as set forth in SEQ ID NO:41 and a FR L4 as set forth in SEQ ID NO:42. In embodiments, the heavy chain variable domain includes a FR H1 as set forth in SEQ ID NO:43, a FR H2 as set forth in SEQ ID NO:44, a FR H3 as set forth in SEQ ID NO:45 and a FR H4 as set forth in SEQ ID NO:46.

In embodiments, the light chain variable domain includes the sequence of SEQ ID NO:47. In embodiments, the heavy chain variable domain includes the sequence of SEQ ID NO:48. In embodiments, the light chain variable domain is the sequence of SEQ ID NO:47. In embodiments, the heavy chain variable domain is the sequence of SEQ ID NO:48. In embodiments, the antibody includes a light chain including the sequence of SEQ ID NO:47. In embodiments, the antibody includes heavy chain including the sequence of SEQ ID NO:48. In embodiments, the light chain is the sequence of SEQ ID NO:47. In embodiments, the heavy chain is the sequence of SEQ ID NO:48. In embodiments, the light chain includes the sequence of SEQ ID NO:47 and the heavy chain includes the sequence of SEQ ID NO:48. In embodiments, the light chain is the sequence of SEQ ID NO:47 and the heavy chain is the sequence of SEQ ID NO:48. In embodiments, the HVEM antibody is referred to herein as clone 5.

In another aspect is provided an anti-Herpes Virus Entry Mediator (HVEM) antibody including a light chain variable domain and a heavy chain variable domain, wherein the light chain variable domain includes: a CDR L1 as set forth in SEQ ID NO:49, a CDR L2 as set forth in SEQ ID NO:50 and a CDR L3 as set forth in SEQ ID NO:51; and wherein the heavy chain variable domain includes: a CDR H1 as set forth in SEQ ID NO:52, a CDR H2 as set forth in SEQ ID NO:53, and a CDR H3 as set forth in SEQ ID NO:54. In embodiments, the light chain variable domain includes a FR L1 as set forth in SEQ ID NO:55, a FR L2 as set forth in SEQ ID NO:56, a FR L3 as set forth in SEQ ID NO:57 and a FR L4 as set forth in SEQ ID NO:58. In embodiments, the heavy chain variable domain includes a FR H1 as set forth in SEQ ID NO:59, a FR H2 as set forth in SEQ ID NO:60, a FR H3 as set forth in SEQ ID NO:61 and a FR H4 as set forth in SEQ ID NO:62.

In embodiments, the light chain variable domain includes the sequence of SEQ ID NO:63. In embodiments, the heavy chain variable domain includes the sequence of SEQ ID NO:64. In embodiments, the light chain variable domain is the sequence of SEQ ID NO:63. In embodiments, the heavy chain variable domain is the sequence of SEQ ID NO: 64. In embodiments, the antibody includes a light chain including the sequence of SEQ ID NO:63. In embodiments, the antibody includes a heavy chain including the sequence of SEQ ID NO:64. In embodiments, the light chain is the sequence of SEQ ID NO:63. In embodiments, the heavy chain is the sequence of SEQ ID NO:64. In embodiments, the light chain includes the sequence of SEQ ID NO:63 and the heavy chain includes the sequence of SEQ ID NO:64. In embodiments, the light chain is the sequence of SEQ ID NO:63 and the heavy chain is the sequence of SEQ ID NO: 64. In embodiments, the HVEM antibody is referred to herein as clone 11.

In another aspect is provided an anti-Herpes Virus Entry Mediator (HVEM) antibody including a light chain variable domain and a heavy chain variable domain, wherein the light chain variable domain includes: a CDR L1 as set forth in SEQ ID NO:66, a CDR L2 as set forth in SEQ ID NO:67 and a CDR L3 as set forth in SEQ ID NO:68; and wherein the heavy chain variable domain includes: a CDR H1 as set forth in SEQ ID NO:69, a CDR H2 as set forth in SEQ ID NO:70, and a CDR H3 as set forth in SEQ ID NO:71. In embodiments, the light chain variable domain includes a FR L1 as set forth in SEQ ID NO:72, a FR L2 as set forth in SEQ ID NO:73, a FR L3 as set forth in SEQ ID NO:74 and a FR L4 as set forth in SEQ ID NO:75. In embodiments, the heavy chain variable domain includes a FR H1 as set forth in SEQ ID NO: 76, a FR H2 as set forth in SEQ ID NO:77, a FR H3 as set forth in SEQ ID NO:78 and a FR H4 as set forth in SEQ ID NO:79.

In embodiments, the light chain variable domain includes the sequence of SEQ ID NO:80. In embodiments, the heavy chain variable domain includes the sequence of SEQ ID NO:81. In embodiments, the light chain variable domain is the sequence of SEQ ID NO: 80. In embodiments, the heavy chain variable domain is the sequence of SEQ ID NO: 81. In embodiments, the light chain variable domain includes the sequence of SEQ ID NO:80 and the heavy chain variable domain includes the sequence of SEQ ID NO:81. In embodiments, the light chain variable domain is the sequence of SEQ ID NO:80 and the heavy chain variable domain is the sequence of SEQ ID NO:81.

In embodiments, the antibody includes a light chain including the sequence of SEQ ID NO:82. In embodiments, the antibody includes a heavy chain including the sequence of SEQ ID NO:83. In embodiments, the light chain is the sequence of SEQ ID NO:82. In embodiments, the heavy chain is the sequence of SEQ ID NO:83. In embodiments, the light chain includes the sequence of SEQ ID NO:82 and the heavy chain includes the sequence of SEQ ID NO:83. In embodiments, the light chain is the sequence of SEQ ID NO:82 and the heavy chain is the sequence of SEQ ID NO:83. In embodiments, the HVEM antibody is referred to herein as clone 17.

In embodiments, the antibody includes a light chain including the sequence of SEQ ID NO:120. In embodiments, the antibody includes a heavy chain including the sequence of SEQ ID NO:121. In embodiments, the light chain is the sequence of SEQ ID NO:120. In embodiments, the heavy chain is the sequence of SEQ ID NO:121. In embodiments, the light chain includes the sequence of SEQ ID NO:120 and the heavy chain includes the sequence of SEQ ID NO:121. In embodiments, the light chain is the sequence of SEQ ID NO: 120 and the heavy chain is the sequence of SEQ ID NO:121. In embodiments, the HVEM antibody is referred to herein as clone 17 mIgG1.

In embodiments, the antibody includes a light chain including the sequence of SEQ ID NO:122. In embodiments, the antibody includes a heavy chain including the sequence of SEQ ID NO:123. In embodiments, the light chain is the sequence of SEQ ID NO:122. In embodiments, the heavy chain is the sequence of SEQ ID NO:123. In embodiments, the light chain includes the sequence of SEQ ID NO:122 and the heavy chain includes the sequence of SEQ ID NO:123. In embodiments, the light chain is the sequence of SEQ ID NO: 122 and the heavy chain is the sequence of SEQ ID NO:123. In embodiments, the HVEM antibody is referred to herein as clone 17 mIgG2A.

In another aspect is provided an anti-Herpes Virus Entry Mediator (HVEM) antibody including a light chain variable domain and a heavy chain variable domain, wherein the light chain variable domain includes: a CDR L1 as set forth in SEQ ID NO:84, a CDR L2 as set forth in SEQ ID NO:85 and a CDR L3 as set forth in SEQ ID NO:86; and wherein the heavy chain variable domain includes: a CDR H1 as set forth in SEQ ID NO:87, a CDR H2 as set forth in SEQ ID NO:88, and a CDR H3 as set forth in SEQ ID NO:89. In embodiments, the light chain variable domain includes a FR L1 as set forth in SEQ ID NO:90, a FR L2 as set forth in SEQ ID NO:91, a FR L3 as set forth in SEQ ID NO:92 and a FR L4 as set forth in SEQ ID NO:93. In embodiments, the heavy chain variable domain includes a FR H1 as set forth in SEQ ID NO:94, a FR H2 as set forth in SEQ ID NO:95, a FR H3 as set forth in SEQ ID NO:96 and a FR H4 as set forth in SEQ ID NO:97.

In embodiments, the light chain variable domain includes the sequence of SEQ ID NO:98. In embodiments, the heavy chain variable domain includes the sequence of SEQ ID NO:99. In embodiments, the light chain variable domain is the sequence of SEQ ID NO:98. In embodiments, the heavy chain variable domain is the sequence of SEQ ID NO: 99. In embodiments, the light chain variable domain includes the sequence of SEQ ID NO:98 and the heavy chain variable domain includes the sequence of SEQ ID NO:99. In embodiments, the light chain variable domain is the sequence of SEQ ID NO:98 and the heavy chain variable domain is the sequence of SEQ ID NO:99. In embodiments, the antibody includes a light chain including the sequence of SEQ ID NO: 100. In embodiments, the antibody includes a heavy chain including the sequence of SEQ ID NO:101. In embodiments, the light chain is the sequence of SEQ ID NO:100. In embodiments, the heavy chain is the sequence of SEQ ID NO:101. In embodiments, the light chain includes the sequence of SEQ ID NO:100 and the heavy chain includes the sequence of SEQ ID NO:101. In embodiments, the light chain is the sequence of SEQ ID NO:100 and the heavy chain is the sequence of SEQ ID NO:101. In embodiments, the HVEM antibody is referred to herein as clone 22.

In another aspect is provided an anti-Herpes Virus Entry Mediator (HVEM) antibody including a light chain variable domain and a heavy chain variable domain, wherein the light chain variable domain includes: a CDR L1 as set forth in SEQ ID NO:102, a CDR L2 as set forth in SEQ ID NO: 103 and a CDR L3 as set forth in SEQ ID NO:104; and wherein the heavy chain variable domain includes: a CDR H1 as set forth in SEQ ID NO: 105, a CDR H2 as set forth in SEQ ID NO:106, and a CDR H3 as set forth in SEQ ID NO:107. In embodiments, the light chain variable domain includes a FR L1 as set forth in SEQ ID NO:108, a FR L2 as set forth in SEQ ID NO:109, a FR L3 as set forth in SEQ ID NO:110 and a FR L4 as set forth in SEQ ID NO:111. In embodiments, the heavy chain variable domain includes a FR H1 as set forth in SEQ ID NO:112, a FR H2 as set forth in SEQ ID NO:113, a FR H3 as set forth in SEQ ID NO:114 and a FR H4 as set forth in SEQ ID NO:115.

In embodiments, the light chain variable domain includes the sequence of SEQ ID NO:116. In embodiments, the heavy chain variable domain includes the sequence of SEQ ID NO:117. In embodiments, the light chain variable domain is the sequence of SEQ ID NO: 116. In embodiments, the heavy chain variable domain is the sequence of SEQ ID NO:117. In embodiments, the light chain variable domain includes the sequence of SEQ ID NO: 116 and the heavy chain variable domain includes the sequence of SEQ ID NO:117. In embodiments, the light chain variable domain is the sequence of SEQ ID NO:116 and the heavy chain variable domain is the sequence of SEQ ID NO:117. In embodiments, the antibody includes a light chain including the sequence of SEQ ID NO: 118. In embodiments, the antibody includes a heavy chain including the sequence of SEQ ID NO:119. In embodiments, the light chain is the sequence of SEQ ID NO:118. In embodiments, the heavy chain is the sequence of SEQ ID NO:119. In embodiments, the light chain includes the sequence of SEQ ID NO:118 and the heavy chain includes the sequence of SEQ ID NO:119. In embodiments, the light chain is the sequence of SEQ ID NO:118 and the heavy chain is the sequence of SEQ ID NO:119. In embodiments, the HVEM antibody is referred to herein as clone 23.

The CDR sequences, framework sequences and/or heavy and light chain sequences provided herein may form part of an antibody, antibody fragment or antibody variant. In embodiments, the antibody is a humanized antibody. In embodiments, the antibody is a chimeric antibody. In embodiments, the antibody is a Fab' fragment. In embodiments, the antibody is a single chain antibody (scFv). In embodiments, the light chain variable domain and the heavy chain variable domain form part of a scFv. In embodiments, the antibody is an IgG. In embodiments, the antibody is an IgG1 or IgG2A. In embodiments, the antibody is an IgG1. In embodiments, the antibody is an IgG2A.

In embodiments, the antibody is capable of binding a Herpes Virus Entry Mediator (HVEM) protein. In embodiments, the antibody is bound to a Herpes Virus Entry Mediator (HVEM) protein. In embodiments, the HVEM protein forms part of a cell. In embodiments, the cell is a plasma cell. In embodiments, the cell is a cancer cell. In embodiments, the cell is a myeloma cell. In embodiments, the cell is a multiple myeloma cell. In embodiments, the cell is a melanoma cell. In embodiments, the cell is a lymphoma cell. In embodiments, the cell is a myeloma cell.

The ability of an antibody to bind a specific epitope (e.g., HVEM) can be described by the equilibrium dissociation constant ($K_D$). The equilibrium dissociation constant ($K_D$) as defined herein is the ratio of the dissociation rate (K-off) and the association rate (K-on) of an antibody to HVEM. It is described by the following formula: $K_D$=K-off/K-on. In embodiments, the antibody is capable of binding HVEM with an equilibrium dissociation constant ($K_D$) as shown in Table 3. In embodiments, the antibody is capable of binding HVEM with an equilibrium dissociation constant ($K_D$) of about 82 nM. In embodiments, the antibody is capable of binding HVEM with an equilibrium dissociation constant ($K_D$) of 82 nM. In embodiments, the antibody is capable of binding HVEM with an equilibrium dissociation constant ($K_D$) of about 180 nM. In embodiments, the antibody is capable of binding HVEM with an equilibrium dissociation constant ($K_D$) of 180 nM. In embodiments, the antibody is capable of binding HVEM with an equilibrium dissociation constant ($K_D$) of about 99 nM. In embodiments, the antibody is capable of binding HVEM with an equilibrium dissociation constant ($K_D$) of 99 nM.

In embodiments, the antibody is capable of binding HVEM with an equilibrium dissociation constant ($K_D$) of about 50-250 nM. In embodiments, the antibody is capable of binding HVEM with an equilibrium dissociation constant ($K_D$) of about 60-250 nM. In embodiments, the antibody is capable of binding HVEM with an equilibrium dissociation constant ($K_D$) of about 70-250 nM. In embodiments, the antibody is capable of binding HVEM with an equilibrium dissociation constant ($K_D$) of about 80-250 nM. In embodiments, the antibody is capable of binding HVEM with an equilibrium dissociation constant ($K_D$) of about 90-250 nM. In embodiments, the antibody is capable of binding HVEM with an equilibrium dissociation constant ($K_D$) of about 100-250 nM. In embodiments, the antibody is capable of binding HVEM with an equilibrium dissociation constant ($K_D$) of about 110-250 nM. In embodiments, the antibody is capable of binding HVEM with an equilibrium dissociation constant ($K_D$) of about 120-250 nM. In embodiments, the antibody is capable of binding HVEM with an equilibrium dissociation constant ($K_D$) of about 130-250 nM. In embodiments, the antibody is capable of binding HVEM with an equilibrium dissociation constant ($K_D$) of about 140-250 nM. In embodiments, the antibody is capable of binding HVEM with an equilibrium dissociation constant ($K_D$) of about 150-250 nM. In embodiments, the antibody is capable of binding HVEM with an equilibrium dissociation constant ($K_D$) of about 160-250 nM. In embodiments, the antibody is capable of binding HVEM with an equilibrium dissociation constant ($K_D$) of about 170-250 nM. In embodiments, the antibody is capable of binding HVEM with an equilibrium dissociation constant ($K_D$) of about 180-250 nM. In embodiments, the antibody is capable of binding HVEM with an equilibrium dissociation constant ($K_D$) of about 190-250 nM. In embodiments, the antibody is capable of binding HVEM with an equilibrium dissociation constant ($K_D$) of about 200-250 nM. In embodiments, the antibody is capable of binding HVEM with an equilibrium dissociation constant ($K_D$) of about 210-250 nM. In embodiments, the antibody is capable of binding HVEM with an equilibrium dissociation constant ($K_D$) of about 220-250 nM. In embodiments, the antibody is capable of binding HVEM with an equilibrium dissociation constant ($K_D$) of about 230-250 nM. In embodiments, the antibody is capable of binding HVEM with an equilibrium dissociation constant ($K_D$) of about 240-250 nM.

In embodiments, the antibody is capable of binding HVEM with an equilibrium dissociation constant (KD) of 50-250 nM. In embodiments, the antibody is capable of binding HVEM with an equilibrium dissociation constant (KD) of 60-250 nM. In embodiments, the antibody is capable of binding HVEM with an equilibrium dissociation constant (KD) of 70-250 nM. In embodiments, the antibody is capable of binding HVEM with an equilibrium dissociation constant (KD) of 80-250 nM. In embodiments, the antibody is capable of binding HVEM with an equilibrium dissociation constant (KD) of 90-250 nM. In embodiments, the antibody is capable of binding HVEM with an equilibrium dissociation constant (KD) of 100-250 nM. In embodiments, the antibody is capable of binding HVEM with an equilibrium dissociation constant (KD) of 110-250 nM. In embodiments, the antibody is capable of binding HVEM with an equilibrium dissociation constant (KD) of 120-250 nM. In embodiments, the antibody is capable of binding HVEM with an equilibrium dissociation constant (KD) of 130-250 nM. In embodiments, the antibody is capable of binding HVEM with an equilibrium dissociation constant (KD) of 140-250 nM. In embodiments, the antibody is capable of binding HVEM with an equilibrium dissociation constant (KD) of 150-250 nM. In embodiments, the antibody is capable of binding HVEM with an equilibrium dissociation constant (KD) of 160-250 nM. In embodiments, the antibody is capable of binding HVEM with an equilibrium dissociation constant (KD) of 170-250 nM. In embodiments, the antibody is capable of binding HVEM with an equilibrium dissociation constant (KD) of 180-250 nM. In embodiments, the antibody is capable of binding HVEM with an equilibrium dissociation constant (KD) of 190-250 nM. In embodiments, the antibody is capable of binding HVEM with an equilibrium dissociation constant (KD) of 200-250 nM. In embodiments, the antibody is capable of binding HVEM with an equilibrium dissociation constant (KD) of 210-250 nM. In embodiments, the antibody is capable of binding HVEM with an equilibrium dissociation constant (KD) of 220-250 nM. In embodiments, the antibody is capable of binding HVEM with an equilibrium dissociation constant (KD) of 230-250 nM. In embodiments, the antibody is capable of binding HVEM with an equilibrium dissociation constant (KD) of 240-250 nM.

In embodiments, the antibody is capable of binding HVEM with an equilibrium dissociation constant (KD) of about 50-240 nM. In embodiments, the antibody is capable of binding HVEM with an equilibrium dissociation constant (KD) of about 50-230 nM. In embodiments, the antibody is capable of binding HVEM with an equilibrium dissociation constant (KD) of about 50-220 nM. In embodiments, the antibody is capable of binding HVEM with an equilibrium dissociation constant (KD) of about 50-210 nM. In embodiments, the antibody is capable of binding HVEM with an equilibrium dissociation constant (KD) of about 50-200 nM. In embodiments, the antibody is capable of binding HVEM with an equilibrium dissociation constant (KD) of about 50-190 nM. In embodiments, the antibody is capable of binding HVEM with an equilibrium dissociation constant (KD) of about 50-180 nM. In embodiments, the antibody is capable of binding HVEM with an equilibrium dissociation constant (KD) of about 50-170 nM. In embodiments, the antibody is capable of binding HVEM with an equilibrium dissociation constant (KD) of about 50-160 nM. In embodiments, the antibody is capable of binding HVEM with an equilibrium dissociation constant (KD) of about 50-150 nM. In embodiments, the antibody is capable of binding HVEM with an equilibrium dissociation constant (KD) of about 50-140 nM. In embodiments, the antibody is capable of binding HVEM with an equilibrium dissociation constant (KD) of about 50-130 nM. In embodiments, the antibody is capable of binding HVEM with an equilibrium dissociation constant (KD) of about 50-120 nM. In embodiments, the antibody is capable of binding HVEM with an equilibrium dissociation constant (KD) of about 50-110 nM. In embodiments, the antibody is capable of binding HVEM with an equilibrium dissociation constant (KD) of about 50-100 nM. In embodiments, the antibody is capable of binding HVEM with an equilibrium dissociation constant (KD) of about 50-90 nM. In embodiments, the antibody is capable of binding HVEM with an equilibrium dissociation constant (KD) of about 50-80 nM. In embodiments, the antibody is capable of binding HVEM with an equilibrium dissociation constant (KD) of about 50-70 nM. In embodiments, the antibody is capable of binding HVEM with an equilibrium dissociation constant (KD) of about 50-60 nM.

In embodiments, the antibody is capable of binding HVEM with an equilibrium dissociation constant (KD) of 50-240 nM. In embodiments, the antibody is capable of binding HVEM with an equilibrium dissociation constant (KD) of 50-230 nM. In embodiments, the antibody is capable of binding HVEM with an equilibrium dissociation constant (KD) of 50-220 nM. In embodiments, the antibody is capable of binding HVEM with an equilibrium dissociation constant (KD) of 50-210 nM. In embodiments, the antibody is capable of binding HVEM with an equilibrium dissociation constant (KD) of 50-200 nM. In embodiments, the antibody is capable of binding HVEM with an equilibrium dissociation constant (KD) of 50-190 nM. In embodiments, the antibody is capable of binding HVEM with an equilibrium dissociation constant (KD) of 50-180 nM. In embodiments, the antibody is capable of binding HVEM with an equilibrium dissociation constant (KD) of 50-170 nM. In embodiments, the antibody is capable of binding HVEM with an equilibrium dissociation constant (KD) of 50-160 nM. In embodiments, the antibody is capable of binding HVEM with an equilibrium dissociation constant (KD) of 50-150 nM. In embodiments, the antibody is capable of binding HVEM with an equilibrium dissociation constant (KD) of 50-140 nM. In embodiments, the antibody is capable of binding HVEM with an equilibrium dissociation constant (KD) of 50-130 nM. In embodiments, the antibody is capable of binding HVEM with an equilibrium dissociation constant (KD) of 50-120 nM. In embodiments, the antibody is capable of binding HVEM with an equilibrium dissociation constant (KD) of 50-110 nM. In embodiments, the antibody is capable of binding HVEM with an equilibrium dissociation constant (KD) of 50-100 nM. In embodiments, the antibody is capable of binding HVEM with an equilibrium dissociation constant (KD) of 50-90 nM. In embodiments, the antibody is capable of binding HVEM with an equilibrium dissociation constant (KD) of 50-80 nM. In embodiments, the antibody is capable of binding HVEM with an equilibrium dissociation constant (KD) of 50-70 nM. In embodiments, the antibody is capable of binding HVEM with an equilibrium dissociation constant (KD) of 50-60 nM.

In embodiments, the antibody is capable of binding HVEM with an equilibrium dissociation constant (KD) of about 250 nM. In embodiments, the antibody is capable of binding HVEM with an equilibrium dissociation constant (KD) of about 240 nM. In embodiments, the antibody is capable of binding HVEM with an equilibrium dissociation constant (KD) of about 230 nM. In embodiments, the antibody is capable of binding HVEM with an equilibrium dissociation constant (KD) of about 220 nM. In embodiments, the antibody is capable of binding HVEM with an equilibrium dissociation constant ($K_D$) of about 210 nM. In embodiments, the antibody is capable of binding HVEM with an equilibrium dissociation constant ($K_D$) of about 200 nM. In embodiments, the antibody is capable of binding HVEM with an equilibrium dissociation constant ($K_D$) of about 190 nM. In embodiments, the antibody is capable of binding HVEM with an equilibrium dissociation constant ($K_D$) of about 180 nM. In embodiments, the antibody is capable of binding HVEM with an equilibrium dissociation constant ($K_D$) of about 170 nM. In embodiments, the antibody is capable of binding HVEM with an equilibrium dissociation constant ($K_D$) of about 160 nM. In embodiments, the antibody is capable of binding HVEM with an equilibrium dissociation constant ($K_D$) of about 150 nM. In embodiments, the antibody is capable of binding HVEM with an equilibrium dissociation constant ($K_D$) of about 140 nM. In embodiments, the antibody is capable of binding HVEM with an equilibrium dissociation constant ($K_D$) of about 130 nM. In embodiments, the antibody is capable of binding HVEM with an equilibrium dissociation constant ($K_D$) of about 120 nM. In embodiments, the antibody is capable of binding HVEM with an equilibrium dissociation constant ($K_D$) of about 110 nM. In embodiments, the antibody is capable of binding HVEM with an equilibrium dissociation constant ($K_D$) of about 100 nM. In embodiments, the antibody is capable of binding HVEM with an equilibrium dissociation constant ($K_D$) of about 90 nM. In embodiments, the antibody is capable of binding HVEM with an equilibrium dissociation constant ($K_D$) of about 80 nM. In embodiments, the antibody is capable of binding HVEM with an equilibrium dissociation constant ($K_D$) of about 70 nM. In embodiments, the antibody is capable of binding HVEM with an equilibrium dissociation constant ($K_D$) of about 60 nM.

In embodiments, the antibody is capable of binding HVEM with an equilibrium dissociation constant ($K_D$) of 250 nM. In embodiments, the antibody is capable of binding HVEM with an equilibrium dissociation constant ($K_D$) of 240 nM. In embodiments, the antibody is capable of binding HVEM with an equilibrium dissociation constant ($K_D$) of 230 nM. In embodiments, the antibody is capable of binding HVEM with an equilibrium dissociation constant ($K_D$) of 220 nM. In embodiments, the antibody is capable of binding HVEM with an equilibrium dissociation constant ($K_D$) of 210 nM. In embodiments, the antibody is capable of binding HVEM with an equilibrium dissociation constant ($K_D$) of 200 nM. In embodiments, the antibody is capable of binding HVEM with an equilibrium dissociation constant ($K_D$) of 190 nM. In embodiments, the antibody is capable of binding HVEM with an equilibrium dissociation constant ($K_D$) of 180 nM. In embodiments, the antibody is capable of binding HVEM with an equilibrium dissociation constant ($K_D$) of 170 nM. In embodiments, the antibody is capable of binding HVEM with an equilibrium dissociation constant ($K_D$) of 160 nM. In embodiments, the antibody is capable of binding HVEM with an equilibrium dissociation constant ($K_D$) of 150 nM. In embodiments, the antibody is capable of binding HVEM with an equilibrium dissociation constant ($K_D$) of 140 nM. In embodiments, the antibody is capable of binding HVEM with an equilibrium dissociation constant ($K_D$) of 130 nM. In embodiments, the antibody is capable of binding HVEM with an equilibrium dissociation constant ($K_D$) of 120 nM. In embodiments, the antibody is capable of binding HVEM with an equilibrium dissociation constant ($K_D$) of 110 nM. In embodiments, the antibody is capable of binding HVEM with an equilibrium dissociation constant ($K_D$) of 100 nM. In embodiments, the antibody is capable of binding HVEM with an equilibrium dissociation constant ($K_D$) of 90 nM. In embodiments, the antibody is capable of binding HVEM with an equilibrium dissociation constant ($K_D$) of 80 nM. In embodiments, the antibody is capable of binding HVEM with an equilibrium dissociation constant ($K_D$) of 70 nM. In embodiments, the antibody is capable of binding HVEM with an equilibrium dissociation constant ($K_D$) of 60 nM.

In an aspect is provided an anti-HVEM antibody, wherein the anti-HVEM antibody binds the same epitope as an antibody including: a light chain variable domain including a CDR L1 as set forth in SEQ ID NO:1, a CDR L2 as set forth in SEQ ID NO:2 and a CDR L3 as set forth in SEQ ID NO:3; and a heavy chain variable domain including a CDR H1 as set forth in SEQ ID NO:4, a CDR H2 as set forth in SEQ ID NO:5, and a CDR H3 as set forth in SEQ ID NO:6 In an aspect is provided an anti-HVEM antibody, wherein the anti-HVEM antibody binds the same epitope as an antibody including: a light chain including the sequence of SEQ ID NO:15 and a heavy chain including the sequence of SEQ ID NO:16.

In an aspect is provided an anti-HVEM antibody, wherein the anti-HVEM antibody binds the same epitope as an antibody including: a light chain variable domain including a CDR L1 as set forth in SEQ ID NO:66, a CDR L2 as set forth in SEQ ID NO:67 and a CDR L3 as set forth in SEQ ID NO:68; and a heavy chain variable domain including a CDR H1 as set forth in SEQ ID NO:69, a CDR H2 as set forth in SEQ ID NO:70, and a CDR H3 as set forth in SEQ ID NO:71. In an aspect is provided an anti-HVEM antibody, wherein the anti-HVEM antibody binds the same epitope as an antibody including: a light chain variable domain including the sequence as set forth in SEQ ID NO:80 and a heavy chain variable domain including the sequence as set forth in SEQ ID NO:81. In an aspect is provided an anti-HVEM antibody, wherein the anti-HVEM antibody binds the same epitope as an antibody including: a light chain including the sequence of SEQ ID NO:82 and a heavy chain including the sequence of SEQ ID NO:83.

In an aspect is provided an anti-HVEM antibody, wherein the anti-HVEM antibody binds the same epitope as an antibody including: a light chain variable domain including a a CDR L1 as set forth in SEQ ID NO:84, a CDR L2 as set forth in SEQ ID NO:85 and a CDR L3 as set forth in SEQ ID NO:86; and a heavy chain variable domain including a CDR H1 as set forth in SEQ ID NO:87, a CDR H2 as set forth in SEQ ID NO:88, and a CDR H3 as set forth in SEQ ID NO:89. In an aspect is provided an anti-HVEM antibody, wherein the anti-HVEM antibody binds the same epitope as an antibody including: a light chain variable domain including the sequence as set forth in SEQ ID NO:98 and a heavy chain variable domain including the sequence as set forth in SEQ ID NO:99. In an aspect is provided an anti-HVEM antibody, wherein the anti-HVEM antibody binds the same epitope as an antibody including: a light chain including the sequence of SEQ ID NO:100 and a heavy chain including the sequence of SEQ ID NO:101.

In an aspect is provided an anti-HVEM antibody, wherein the anti-HVEM antibody binds the same epitope as an antibody including: a light chain variable domain including a a CDR L1 as set forth in SEQ ID NO:102, a CDR L2 as set forth in SEQ ID NO:103 and a CDR L3 as set forth in SEQ ID NO:104; and a heavy chain variable domain including a CDR H1 as set forth in SEQ ID NO:105, a CDR H2 as set forth in SEQ ID NO:106, and a CDR H3 as set forth in SEQ ID NO: 107. In an aspect is provided an anti-HVEM antibody, wherein the anti-HVEM antibody binds the same epitope as an antibody including: a light chain variable domain including the sequence as set forth in SEQ ID NO: 116 and a heavy chain variable domain including the sequence as set forth in SEQ ID NO:117. In an aspect is provided an anti-HVEM antibody, wherein the anti-HVEM antibody binds the same epitope as an antibody including: a light chain including the sequence of SEQ ID NO: 118 and a heavy chain including the sequence of SEQ ID NO:119.

In an aspect is provided an anti-HVEM antibody, wherein the anti-HVEM antibody binds the same epitope as an antibody including: a light chain variable domain including a CDR L1 as set forth in SEQ ID NO:17, a CDR L2 as set forth in SEQ ID NO:18 and a CDR L3 as set forth in SEQ ID NO: 19; and a heavy chain variable domain including a CDR H1 as set forth in SEQ ID NO:20, a CDR H2 as set forth in SEQ ID NO:21, and a CDR H3 as set forth in SEQ ID NO:22. In an aspect is provided an anti-HVEM antibody, wherein the anti-HVEM antibody binds the same epitope as an antibody including: a light chain including the sequence of SEQ ID NO:31 and a heavy chain including the sequence of SEQ ID NO:32.

In an aspect is provided an anti-HVEM antibody, wherein the anti-HVEM antibody binds the same epitope as an antibody including: a light chain variable domain including a CDR L1 as set forth in SEQ ID NO:33, a CDR L2 as set forth in SEQ ID NO:34 and a CDR L3 as set forth in SEQ ID NO:35; and a heavy chain variable domain including a CDR H1 as set forth in SEQ ID NO:36, a CDR H2 as set forth in SEQ ID NO:37, and a CDR H3 as set forth in SEQ ID NO:38. In an aspect is provided an anti-HVEM antibody, wherein the anti-HVEM antibody binds the same epitope as an antibody including: a light chain including the sequence of SEQ ID NO:47 and a heavy chain including the sequence of SEQ ID NO:48.

In an aspect is provided an anti-HVEM antibody, wherein the anti-HVEM antibody binds the same epitope as an antibody including: a light chain variable domain including a CDR L1 as set forth in SEQ ID NO:49, a CDR L2 as set forth in SEQ ID NO:50 and a CDR L3 as set forth in SEQ ID NO:51; and a heavy chain variable domain including a CDR H1 as set forth in SEQ ID NO:52, a CDR H2 as set forth in SEQ ID NO:53, and a CDR H3 as set forth in SEQ ID NO:54. In an aspect is provided an anti-HVEM antibody, wherein the anti-HVEM antibody binds the same epitope as an antibody including: a light chain including the sequence of SEQ ID NO:63 and a heavy chain including the sequence of SEQ ID NO:64.

Recombinant Proteins

As described above, the heavy chain variable (VH) domain and the light chain variable (VL) domain provided herein including embodiments thereof, may each independently form part of an antibody, a fragment of an antibody, a chimeric antigen receptor or a bispecific antibody. Thus, provided herein are, inter alia, chimeric antigen receptors and bispecific antibodies, which include the light chain variable (VL) domain and/or the heavy chain variable (VH) domain as provided herein and are capable of binding human HVEM effectively and efficiently. The antibody region of the chimeric antigen receptor may include any of the light chain and heavy chain variable domains provided herein including embodiments thereof. The light chain variable (VL) domain and/or the heavy chain variable (VH) domain as provided herein may form part of a chimeric antigen receptor.

In another aspect is provided a recombinant protein (e.g., chimeric antigen receptor) including: (i) an antibody region including: (a) a light chain variable domain including a CDR L1 as set forth in SEQ ID NO:1, a CDR L2 as set forth in SEQ ID NO:2 and a CDR L3 as set forth in SEQ ID NO:3; and (b) a heavy chain variable domain including a CDR H1 as set forth in SEQ ID NO:4, a CDR H2 as set forth in SEQ ID NO:5, and a CDR H3 as set forth in SEQ ID NO:6; and (ii) a transmembrane domain. In embodiments, the recombinant protein includes the CDR L1, CDR L2, CDR L3, CDR H1, CDR H2 and CDR H3 of anti-HVEM clone 13.

In another aspect is provided a recombinant protein including: (i) an antibody region including: (a) a light chain variable domain including a CDR L1 as set forth in SEQ ID NO:17, a CDR L2 as set forth in SEQ ID NO:18 and a CDR L3 as set forth in SEQ ID NO:19; and (b) a heavy chain variable domain including a CDR H1 as set forth in SEQ ID NO:20, a CDR H2 as set forth in SEQ ID NO:21, and a CDR H3 as set forth in SEQ ID NO:22; and (ii) a transmembrane domain. In embodiments, the recombinant protein includes the CDR L1, CDR L2, CDR L3, CDR H1, CDR H2 and CDR H3 of anti-HVEM clone 4.

In another aspect is provided a recombinant protein including: (i) an antibody region including: (a) a light chain variable domain including a CDR L1 as set forth in SEQ ID NO:33, a CDR L2 as set forth in SEQ ID NO:34 and a CDR L3 as set forth in SEQ ID NO:35; and (b) a heavy chain variable domain including a CDR H1 as set forth in SEQ ID NO:36, a CDR H2 as set forth in SEQ ID NO:37, and a CDR H3 as set forth in SEQ ID NO:38; and (ii) a transmembrane domain. In embodiments, the recombinant protein includes the CDR L1, CDR L2, CDR L3, CDR H1, CDR H2 and CDR H3 of anti-HVEM clone 5.

In another aspect is provided a recombinant protein including: (i) an antibody region including: (a) a light chain variable domain including a CDR L1 as set forth in SEQ ID NO:49, a CDR L2 as set forth in SEQ ID NO:50 and a CDR L3 as set forth in SEQ ID NO:51; and (b) a heavy chain variable domain including a CDR H1 as set forth in SEQ ID NO:52, a CDR H2 as set forth in SEQ ID NO:53, and a CDR H3 as set forth in SEQ ID NO:54; and (ii) a transmembrane domain. In embodiments, the recombinant protein includes the CDR L1, CDR L2, CDR L3, CDR H1, CDR H2 and CDR H3 of anti-HVEM clone 11.

In another aspect is provided a recombinant protein including: (i) an antibody region including: (a) a light chain variable domain including a CDR L1 as set forth in SEQ ID NO:66, a CDR L2 as set forth in SEQ ID NO:67 and a CDR L3 as set forth in SEQ ID NO:68; and (b) a heavy chain variable domain including a CDR H1 as set forth in SEQ ID NO:69, a CDR H2 as set forth in SEQ ID NO:70, and a CDR H3 as set forth in SEQ ID NO:71; and (ii) a transmembrane domain. In embodiments, the recombinant protein includes the CDR L1, CDR L2, CDR L3, CDR H1, CDR H2, and CDR H3 of anti-HVEM clone 17.

In another aspect is provided a recombinant protein including: (i) an antibody region including: (a) a light chain variable domain including a CDR L1 as set forth in SEQ ID NO:84, a CDR L2 as set forth in SEQ ID NO:85 and a CDR L3 as set forth in SEQ ID NO:86; and (b) a heavy chain variable domain including a CDR H1 as set forth in SEQ ID NO:87, a CDR H2 as set forth in SEQ ID NO:88, and a CDR H3 as set forth in SEQ ID NO:89; and (ii) a transmembrane domain. In embodiments, the recombinant protein includes the CDR L1, CDR L2, CDR L3, CDR H1, CDR H2, and CDR H3 of anti-HVEM clone 22.

In another aspect is provided a recombinant protein including: (i) an antibody region including: (a) a light chain variable domain including a CDR L1 as set forth in SEQ ID NO:102, a CDR L2 as set forth in SEQ ID NO:103 and a CDR L3 as set forth in SEQ ID NO:104; and (b) a heavy chain variable domain including a CDR H1 as set forth in SEQ ID NO: 105, a CDR H2 as set forth in SEQ ID NO:106, and a CDR H3 as set forth in SEQ ID NO: 107; and (ii) a transmembrane domain. In embodiments, the recombinant protein includes the CDR L1, CDR L2, CDR L3, CDR H1, CDR H2, and CDR H3 of anti-HVEM clone 23.

An "antibody region" as provided herein refers to a monovalent or multivalent protein moiety that forms part of the recombinant protein (e.g., CAR, bispecific recombinant protein such as a bispecific antibody) provided herein including embodiments thereof. A person of ordinary skill in the art will therefore immediately recognize that the antibody region is a protein moiety capable of binding an antigen (epitope). Thus, the antibody region provided herein may include a domain of an antibody (e.g., a light chain variable (VL) domain, a heavy chain variable (VH) domain) or a fragment of an antibody (e.g., Fab). In embodiments, the antibody region is a protein conjugate. A "protein conjugate" as provided herein refers to a construct consisting of more than one polypeptide, wherein the polypeptides are bound together covalently or non-covalently. In embodiments, the polypeptides of a protein conjugate are encoded by one nucleic acid molecule. In embodiments, the polypeptides of a protein conjugate are encoded by different nucleic acid molecules. In embodiments, the polypeptides are connected through a linker. In embodiments, the polypeptides are connected through a chemical linker. In embodiments, the antibody region is an scFv. The antibody region may include a light chain variable (VL) domain and/or a heavy chain variable (VH) domain. In embodiments, the antibody region includes a light chain variable (VL) domain. In embodiments, the antibody region includes a heavy chain variable (VH) domain.

A "transmembrane domain" as provided herein refers to a polypeptide forming part of a biological membrane. The transmembrane domain provided herein is capable of spanning a biological membrane (e.g., a cellular membrane) from one side of the membrane through to the other side of the membrane. In embodiments, the transmembrane domain spans from the intracellular side to the extracellular side of a cellular membrane. Transmembrane domains may include non-polar, hydrophobic residues, which anchor the proteins provided herein including embodiments thereof in a biological membrane (e.g., cellular membrane of a T cell). Any transmembrane domain capable of anchoring the proteins provided herein including embodiments thereof are contemplated. Non-limiting examples of transmembrane domains include the transmembrane domains of CD28, CD8, CD4 or CD3-zeta. In embodiments, the transmembrane domain is a CD4 transmembrane domain.

In embodiments, the transmembrane domain is a CD28 transmembrane domain. The term "CD28 transmembrane domain" as provided herein includes any of the recombinant or naturally-occurring forms of the transmembrane domain of CD28, or variants or homologs thereof that maintain CD28 transmembrane domain activity (e.g. within at least 50%, 80%, 90%, 95%, 96%, 97%, 98%, 99% or 100% activity compared to the CD28 transmembrane domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD28 transmembrane domain polypeptide. In embodiments, CD28 is the protein as identified by the NCBI sequence reference GI:340545506, homolog or functional fragment thereof.

In embodiments, the transmembrane domain is a CD8 transmembrane domain. The term "CD8 transmembrane domain" as provided herein includes any of the recombinant or naturally-occurring forms of the transmembrane domain of CD8, or variants or homologs thereof that maintain CD8 transmembrane domain activity (e.g. within at least 50%, 80%, 90%, 95%, 96%, 97%, 98%, 99% or 100% activity compared to the CD8 transmembrane domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD8 transmembrane domain polypeptide. In embodiments, CD8 is the protein as identified by the NCBI sequence reference GI:225007534, homolog or functional fragment thereof.

In embodiments, the transmembrane domain is a CD4 transmembrane domain. The term "CD4 transmembrane domain" as provided herein includes any of the recombinant or naturally-occurring forms of the transmembrane domain of CD4, or variants or homologs thereof that maintain CD4 transmembrane domain activity (e.g. within at least 50%, 80%, 90%, 95%, 96%, 97%, 98%, 99% or 100% activity compared to the CD4 transmembrane domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD4 transmembrane domain polypeptide. In embodiments, CD4 is the protein as identified by the NCBI sequence reference GI:303522473, homolog or functional fragment thereof.

In embodiments, the transmembrane domain is a CD3-zeta (also known as CD247) transmembrane domain. The term "CD3-zeta transmembrane domain" as provided herein includes any of the recombinant or naturally-occurring forms of the transmembrane domain of CD3-zeta, or variants or homologs thereof that maintain CD3-zeta transmembrane domain activity (e.g. within at least 50%, 80%, 90%, 95%, 96%, 97%, 98%, 99% or 100% activity compared to the CD3-zeta transmembrane domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD3-zeta transmembrane domain polypeptide. In embodiments, CD3-zeta is the protein as identified by the NCBI sequence reference GI:166362721, homolog or functional fragment thereof.

In embodiments, the chimeric antigen receptor further includes an intracellular T-cell signaling domain. An "intracellular T-cell signaling domain" as provided herein includes amino acid sequences capable of providing primary signaling in response to binding of an antigen to the antibody region provided herein including embodiments thereof. In embodiments, the signaling of the intracellular T-cell signaling domain results in activation of the T cell expressing the same. In embodiments, the signaling of the intracellular T-cell signaling domain results in proliferation (cell division) of the T cell expressing the same. In embodiments, the signaling of the intracellular T-cell signaling domain results expression by said T cell of proteins known in the art to characteristic of activated T cell (e.g., CTLA-4, PD-1, CD28, CD69). In embodiments, the intracellular T-cell signaling domain is a CD3 (intracellular T-cell signaling domain.

In embodiments, the chimeric antigen receptor further includes an intracellular co-stimulatory T-cell signaling domain. An "intracellular co-stimulatory signaling domain" as provided herein includes amino acid sequences capable of providing co-stimulatory signaling in response to binding of an antigen to the antibody region provided herein including embodiments thereof. In embodiments, the signaling of the co-stimulatory signaling domain results in production of cytokines and proliferation of the T cell expressing the same. In embodiments, the intracellular co-stimulatory signaling domain is a CD28 intracellular co-stimulatory signaling domain, a 4-1BB intracellular co-stimulatory signaling domain, an ICOS intracellular co-stimulatory signaling domain, or an OX-40 intracellular co-stimulatory signaling domain. In embodiments, the intracellular co-stimulatory signaling domain is a CD28 intracellular co-stimulatory signaling domain. In embodiments, the intracellular co-stimulatory signaling domain is a 4-1BB intracellular co-stimulatory signaling domain. In embodiments, the intracellular co-stimulatory signaling domain is an ICOS intracellular co-stimulatory signaling domain. In embodiments, the intracellular co-stimulatory signaling domain is an OX-40 intracellular co-stimulatory signaling domain.

In embodiments, the antibody region includes an Fc domain. In embodiments, the antibody region includes a spacer region. In embodiments, the spacer region is between the transmembrane domain and the antibody region. A "spacer region" as provided herein is a polypeptide connecting the antibody region with the transmembrane domain. In embodiments, the spacer region connects the heavy chain constant region with the transmembrane domain. In embodiments, the spacer region includes an Fc region. In embodiments, the spacer region is an Fc region. Examples of spacer regions contemplated for the compositions provided herein include without limitation, immunoglobulin molecules or fragments thereof (e.g., IgG1, IgG2, IgG3, IgG4) and immunoglobulin molecules or fragments thereof (e.g., IgG1, IgG2, IgG3, IgG4) including mutations affecting Fc receptor binding. In embodiments, the spacer region is a hinge region.

The term "CTLA-4" as referred to herein includes any of the recombinant or naturally-occurring forms of the cytotoxic T-lymphocyte-associated protein 4 protein, also known as CD152 (cluster of differentiation 152), or variants or homologs thereof that maintain CTLA-4 activity (e.g. within at least 50%, 80%, 90%, 95%, 96%, 97%, 98%, 99% or 100% activity compared to CTLA-4). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CTLA-4 protein. In embodiments, the CTLA-4 protein is substantially identical to the protein identified by the UniProt reference number P16410 or a variant or homolog having substantial identity thereto.

The term "CD28" as referred to herein includes any of the recombinant or naturally-occurring forms of the Cluster of Differentiation 28 protein, or variants or homologs thereof that maintain CD28 activity (e.g. within at least 50%, 80%, 90%, 95%, 96%, 97%, 98%, 99% or 100% activity compared to CD28). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD28 protein. In embodiments, the CD28 protein is substantially identical to the protein identified by the UniProt reference number P10747 or a variant or homolog having substantial identity thereto.

The term "CD69" as referred to herein includes any of the recombinant or naturally-occurring forms of the Cluster of Differentiation 69 protein, or variants or homologs thereof that maintain CD69 activity (e.g. within at least 50%, 80%, 90%, 95%, 96%, 97%, 98%, 99% or 100% activity compared to CD69). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD69 protein. In embodiments, the CD69 protein is substantially identical to the protein identified by the UniProt reference number Q07108 or a variant or homolog having substantial identity thereto.

The term "4-1BB" as referred to herein includes any of the recombinant or naturally-occurring forms of the 4-1BB protein, also known as tumor necrosis factor receptor superfamily member 9 (TNFRSF9), Cluster of Differentiation 137 (CD137) and induced by lymphocyte activation (ILA), or variants or homologs thereof that maintain 4-1BB activity (e.g. within at least 50%, 80%, 90%, 95%, 96%, 97%, 98%, 99% or 100% activity compared to 4-1BB). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring EGFR protein. In embodiments, the 4-1BB protein is substantially identical to the protein identified by the UniProt reference number Q07011 or a variant or homolog having substantial identity thereto.

The chimeric antigen receptors provided herein may include any of the anti-HVEM antibodies or fragments thereof described herein.

Bispecific Recombinant Proteins

The light chain variable (VL) domain and the heavy chain variable (VH) domain as provided herein may form part of a bispecific recombinant protein (e.g., bispecific antibody). Thus, the second antibody region may include any of the light chain and/or heavy chain variable domains provided herein including embodiments thereof.

In another aspect is provided bispecific recombinant protein including: (i) a first antibody region capable of binding an effector cell ligand; and (ii) a second antibody region, including: (a) a light chain variable domain including a CDR L1 as set forth in SEQ ID NO:1, a CDR L2 as set forth in SEQ ID NO:2 and a CDR L3 as set forth in SEQ ID NO:3; and (b) a heavy chain variable domain including a CDR H1 as set forth in SEQ ID NO:4, a CDR H2 as set forth in SEQ ID NO:5, and a CDR H3 as set forth in SEQ ID NO:6. In embodiments, the bispecific recombinant protein (e.g., bispecific antibody) includes the CDR L1, CDR L2, CDR L3, CDR H1, CDR H2 and CDR H3 of anti-HVEM clone 13.

In another aspect is provided a bispecific recombinant protein including: (i) a first antibody region capable of binding an effector cell ligand; and (ii) a second antibody region, including: (a) a light chain variable domain including a CDR L1 as set forth in SEQ ID NO:17, a CDR L2 as set forth in SEQ ID NO:18 and a CDR L3 as set forth in SEQ ID NO:19; and (b) a heavy chain variable domain including a CDR H1 as set forth in SEQ ID NO:20, a CDR H2 as set forth in SEQ ID NO:21, and a CDR H3 as set forth in SEQ ID NO:22. In embodiments, the bispecific recombinant protein (e.g., bispecific antibody) includes the CDR L1, CDR L2, CDR L3, CDR H1, CDR H2 and CDR H3 of anti-HVEM clone 4.

In another aspect is provided a bispecific recombinant protein including: (i) a first antibody region capable of binding an effector cell ligand; and (ii) a second antibody region, including: (a) a light chain variable domain including a CDR L1 as set forth in SEQ ID NO:33, a CDR L2 as set forth in SEQ ID NO:34 and a CDR L3 as set forth in SEQ ID NO:35; and (b) a heavy chain variable domain including a CDR H1 as set forth in SEQ ID NO:36, a CDR H2 as set forth in SEQ ID NO:37, and a CDR H3 as set forth in SEQ ID NO:38. In embodiments, the bispecific recombinant protein (e.g., bispecific antibody) includes the CDR L1, CDR L2, CDR L3, CDR H1, CDR H2 and CDR H3 of anti-HVEM clone 5.

In another aspect is provided a bispecific recombinant protein including: (i) a first antibody region capable of binding an effector cell ligand; and (ii) a second antibody region, including: (a) a light chain variable domain including a CDR L1 as set forth in SEQ ID NO:49, a CDR L2 as set forth in SEQ ID NO:50 and a CDR L3 as set forth in SEQ ID NO:51; and (b) a heavy chain variable domain including a CDR H1 as set forth in SEQ ID NO:52, a CDR H2 as set forth in SEQ ID NO:53, and a CDR H3 as set forth in SEQ ID NO:54. In embodiments, the bispecific recombinant protein (e.g., bispecific antibody) includes the CDR L1, CDR L2, CDR L3, CDR H1, CDR H2 and CDR H3 of anti-HVEM clone 11.

In another aspect is provided a bispecific recombinant protein including: (i) a first antibody region capable of binding an effector cell ligand; and (ii) a second antibody region, including: (a) a light chain variable domain including a CDR L1 as set forth in SEQ ID NO:66, a CDR L2 as set forth in SEQ ID NO:67 and a CDR L3 as set forth in SEQ ID NO:68; and (b) a heavy chain variable domain including a CDR H1 as set forth in SEQ ID NO:69, a CDR H2 as set forth in SEQ ID NO:70, and a CDR H3 as set forth in SEQ ID NO:71. In embodiments, the bispecific recombinant protein (e.g., bispecific antibody) includes the CDR L1, CDR L2, CDR L3, CDR H1, CDR H2 and CDR H3 of anti-HVEM clone 17.

In another aspect is provided a bispecific recombinant protein including: (i) a first antibody region capable of binding an effector cell ligand; and (ii) a second antibody region, including: (a) a light chain variable domain including a CDR L1 as set forth in SEQ ID NO:84, a CDR L2 as set forth in SEQ ID NO:85 and a CDR L3 as set forth in SEQ ID NO:86; and (b) a heavy chain variable domain including a CDR H1 as set forth in SEQ ID NO:87, a CDR H2 as set forth in SEQ ID NO:88, and a CDR H3 as set forth in SEQ ID NO:89. In embodiments, the bispecific recombinant protein (e.g., bispecific antibody) includes the CDR L1, CDR L2, CDR L3, CDR H1, CDR H2 and CDR H3 of anti-HVEM clone 22.

In another aspect is provided a bispecific recombinant protein including: (i) a first antibody region capable of binding an effector cell ligand; and (ii) a second antibody region, including: (a) a light chain variable domain including a CDR L1 as set forth in SEQ ID NO:102, a CDR L2 as set forth in SEQ ID NO:103 and a CDR L3 as set forth in SEQ ID NO:104; and (b) a heavy chain variable domain including a CDR H1 as set forth in SEQ ID NO:105, a CDR H2 as set forth in SEQ ID NO:106, and a CDR H3 as set forth in SEQ ID NO: 107. In embodiments, the bispecific recombinant protein (e.g., bispecific antibody) includes the CDR L1, CDR L2, CDR L3, CDR H1, CDR H2 and CDR H3 of anti-HVEM clone 23.

The term "effector cell ligand" as provided herein refers to a cell surface molecule expressed on an effector cell of the immune system (e.g., a cytotoxic T cell, a helper T cell, a B cell, a natural killer cell). Upon binding of the first antibody region to the effector cell ligand expressed on the effector cell, the effector cell is activated and able to exert its function (e.g., selective killing or eradication of malignant, infected or otherwise unhealthy cells). In embodiments, the effector cell ligand is a CD3 protein. In embodiments, the effector cell ligand is a CD16 protein. In embodiments, the effector cell ligand is a CD32 protein. In embodiments, the effector cell ligand is a NKp46 protein. The first antibody region as provided herein may be an antibody, an antibody variant, a fragment of an antibody or a fragment of an antibody variant.

A "CD3 protein" as referred to herein includes any of the recombinant or naturally-occurring forms of the Cluster of Differentiation 3 (CD3) proteins or variants or homologs thereof that comprise the CD3 complex that mediates signal transduction and maintains CD3 complex activity (e.g. within at least 50%, 80%, 90%, 95%, 96%, 97%, 98%, 99% or 100% activity compared to the CD3 complex). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD3 proteins in the CD3 complex.

A "CD16 protein" as referred to herein includes any of the recombinant or naturally-occurring forms of the Cluster of Differentiation 16 (CD16) protein, also known as low affinity immunoglobulin gamma Fc region receptor III-A, or variants or homologs thereof that maintain CD16 activity (e.g. within at least 50%, 80%, 90%, 95%, 96%, 97%, 98%, 99% or 100% activity compared to CD16). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD16 protein. In embodiments, the CD16 protein is substantially identical to the protein identified by the UniProt reference number P08637 or a variant or homolog having substantial identity thereto.

A "CD32 protein" as referred to herein includes any of the recombinant or naturally-occurring forms of the Cluster of Differentiation 32 (CD32) protein, also known as low affinity immunoglobulin gamma Fc region receptor II-A, or variants or homologs thereof that maintain CD32 activity (e.g. within at least 50%, 80%, 90%, 95%, 96%, 97%, 98%, 99% or 100% activity compared to CD32). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD32 protein. In embodiments, the CD32 protein is substantially identical to the protein identified by the UniProt reference number P12318 or a variant or homolog having substantial identity thereto.

A "NKp46 protein" as referred to herein includes any of the recombinant or naturally-occurring forms of the NKp46 protein, also known as natural cytotoxicity triggering receptor 1, or variants or homologs thereof that maintain NKp46 activity (e.g. within at least 50%, 80%, 90%, 95%, 96%, 97%, 98%, 99% or 100% activity compared to NKp46). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring NKp46 protein. In embodiments, the NKp46 protein is substantially identical to the protein identified by the UniProt reference number 076036 or a variant or homolog having substantial identity thereto.

The bispecific antibody provided herein may include any of the HVEM antibodies or fragments thereof described herein.

In embodiments, the first antibody region is a first Fab' fragment or the second antibody region is a second Fab' fragment. In embodiments, the first antibody region is a single chain variable fragment (scFv) or the second antibody region is a second single chain variable fragment (scFv). In embodiments, the first antibody region is a first Fab' fragment and the second antibody region is a second Fab' fragment. In embodiments, the first antibody region is a single chain variable fragment (scFv) and the second antibody region is a second single chain variable fragment (scFv).

Nucleic Acid Compositions

The compositions provided herein include nucleic acid molecules encoding the anti-HVEM antibodies, recombinant proteins (e.g., CARs) and bispecific recombinant proteins (e.g., bispecific antibodies) or portions thereof provided herein including embodiments thereof. The antibodies, recombinant proteins (e.g., CARs) and bispecific recombinant proteins (e.g., bispecific antibodies) encoded by the isolated nucleic acid provided herein are described in detail throughout this application (including the description above and in the examples section). Thus, in an aspect, an isolated nucleic acid encoding an antibody as provided herein including embodiments thereof is provided.

In another aspect is provided an isolated nucleic acid encoding a recombinant protein (e.g., chimeric antigen receptor) as disclosed herein including embodiments thereof.

In another aspect is provided an isolated nucleic acid encoding a bispecific recombinant protein (e.g., bispecific antibody) as disclosed herein including embodiments thereof.

Pharmaceutical Compositions

The compositions provided herein include pharmaceutical compositions including the anti-HVEM antibodies, recombinant proteins (e.g., CARs) and bispecific recombinant proteins (e.g., bispecific antibodies) provided herein including embodiments thereof. Thus, in another aspect is provided a pharmaceutical composition including a therapeutically effective amount of an antibody as disclosed herein including embodiments thereof and a pharmaceutically acceptable excipient.

In another aspect is provided a pharmaceutical composition including a therapeutically effective amount of a recombinant protein (e.g., chimeric antigen receptor) as disclosed herein and a pharmaceutically acceptable excipient.

In another aspect is provided a pharmaceutical composition including a therapeutically effective amount of a bispecific recombinant protein (e.g., bispecific antibody) as disclosed herein including embodiments thereof and a pharmaceutically acceptable excipient.

Methods of Treatment

The compositions (e.g., the anti-HVEM antibodies, recombinant proteins (e.g., CARs) and bispecific recombinant proteins (e.g., bispecific antibodies)) provided herein, including embodiments thereof, are contemplated as providing effective treatments for diseases such as cancer (e.g., myeloid myeloma).

Thus, in an aspect is provided a method of treating cancer in a subject in need thereof, the method including administering to a subject a therapeutically effective amount of an antibody as disclosed herein including embodiments thereof, thereby treating cancer in the subject.

In another aspect is provided a method of treating cancer in a subject in need thereof, the method including administering to a subject a therapeutically effective amount of a recombinant protein (e.g., chimeric antigen receptor) as disclosed herein including embodiments thereof, thereby treating cancer in the subject.

In another aspect is provided a method of treating cancer in a subject in need thereof, the method including administering to a subject a therapeutically effective amount of a bispecific recombinant protein (e.g, bispecific antibody) as disclosed herein including embodiments thereof, thereby treating cancer in the subject.

In embodiments, the cancer is melanoma, lymphoma, carcinoma, myeloma, leukemia, glioma, breast cancer, prostate cancer, bladder cancer, uterine cancer, gastric, cancer, colorectal cancer, lung cancer, esophageal cancer, brain cancer, head and neck cancer, renal cancer, hepatic cancer, or thyroid cancer. In embodiments, the cancer is melanoma. In embodiments, the cancer is lymphoma. In embodiments, the cancer is carcinoma. In embodiments, the cancer is myeloma. In embodiments, the cancer is multiple myeloma. In embodiments, the cancer is leukemia. In embodiments, the cancer is glioma. In embodiments, the cancer is breast cancer. In embodiments, the cancer is prostate cancer. In embodiments, the cancer is bladder cancer. In embodiments, the cancer is uterine cancer. In embodiments, the cancer is gastric cancer. In embodiments, the cancer is colorectal cancer. In embodiments, the cancer is lung cancer. In embodiments, the cancer is esophageal cancer. In embodiments, the cancer is brain cancer. In embodiments, the cancer is head and neck cancer. In embodiments, the cancer is renal cancer. In embodiments, the cancer is hepatic cancer. In embodiments, the cancer is thyroid cancer.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

Example 1: Anti-HVEM Monoclonal Antibodies (mAbs)

We have shown that myeloma cells but not bone marrow and peripheral blood mononuclear cells could be highly infected by herpes viruses and based on these observations we found that the herpes virus entry receptor HVEM was ubiquitously highly expressed on the surface of multiple myeloma (MM) cells and its expression was comparable to the myeloma specific antigen BCMA. We also found that both in cell lines and primary samples, myeloma cells had the highest level of HVEM expression compared to all other types of cancers. Based on this data we decided to investigate if the use of a commercial mouse anti-human HVEM antibody could potentiate myeloma cell killing by effector cells isolated from the peripheral mononuclear cells of healthy donors. Our initial preliminary data showed that targeting HVEM could facilitate myeloma cell killing even if the commercial antibody had a mouse Fc, supporting that not only direct ADCC but also other immune based mechanisms may be responsible in potentiating the killing activity of human immune effector cells. Given these observations, we sought to develop tumor specific mAbs to treat MM. Herein, we have immunized mice, identified several HVEM mAbs, and demonstrated one, HVEM13, lead to high affinity of binding not only in silico but also directly on the surface of myeloma cells (see figures). Our preliminary data also showed that HVEM13, lead to potent cell death through ADCC in myeloma cells (see figures) and its effect was fully comparable to the clinical active FDA approved humanized antibody against the myeloma CD38 surface receptor (Daratumumab). Our preliminary data also showed that similarly to daratumumab HVEM13 did not need immune effector activation to direct the immune cells against MM cells in both total PBMCs and isolated NK cells (see figures).

Example 2: Preparation of HVEM Fusion Proteins

To construct recombinant HVEM fusion proteins, the extracellular domain of HVEM was fused with mouse IgG2a.Fc (SEQ ID NO: 65). Recombinant DNAs encoding the protein as synthesized and cloned into a mammalian expression vector by the manufacture (Twist Bioscience). The HVEM proteins were produced using an ExpiCHO expression system (Thermo Fisher Scientific). The procedures were followed according to the manufacturer's manual. In brief, CHO cells were seeded at 3-4×106 cells/mL in fresh medium one day before transfection. On the next day cells were adjusted to 6×106 cells/mL with fresh medium. For a 100-mL transfection, 80 mg of DNA was added into 4 mL of OptiPRO™ SFM and then mixed with 320 mL of ExpiFectamine™ diluted in 3.7 mL OptiPRO™ SFM. The mixture was slowly added into the cell culture with gentle swirling, and cells were then cultured at 37° C. for 16-22 h. ExpiCHO™ Enhancer (0.6 mL) and ExpiCHO™ Feed (24 mL) were added into the cell culture, and then cells were cultured at 32° C. for 10 days. Culture supernatants were harvested by centrifugation at 4000×g for 30 minutes and passed through 0.22-mm filters for protein purification with Protein A resins (GE Healthcare). Purification procedures were followed by the manufacturer's manuals. Purified proteins were revealed by using reduced SDS-PAGE with Mini-PROTEAN® TGX Stain-Free™ Precast Gels (Bio-Rad) and a Superdex 200 Increase 10/300 GL column (GE Healthcare) run with PBS (FIG. 1).

Example 3: Mouse Immunization

All animal experiments were conducted under the approval of Institutional Animal Care and Use Committee of City of Hope (IUCAC #19070). For mouse immunization, recombinant HVEM proteins were emulsified with complete Freund's adjuvants (Sigma Aldrich) and subcutaneously injected into 10 Balb/c mice (The Jackson Laboratory). Fifty micrograms of proteins were used for injecting each mouse. Three weeks later, mice received two subcutaneous injections with 50 mg of HVEM proteins emulsified with incomplete Freund's adjuvants (Sigma Aldrich) in a two-week interval. Three days before spleen harvests for plasma cell isolation, 10 mg of HVEM proteins were injected via tail veins.

Figure 3:
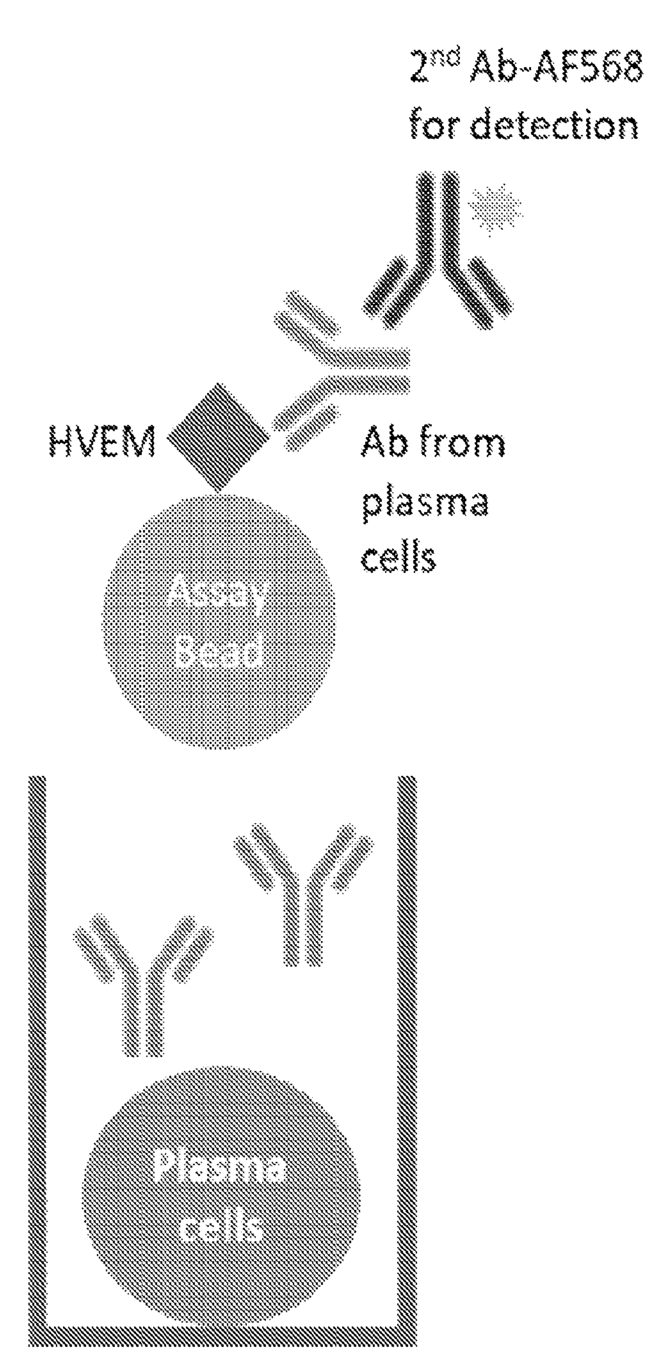
FIG. 3 is a schematic representation of a screen for new anti-hHVEM antibodies through single cell analysis on Beacon. New anti-hHVEM antibody was captured on the Assay Bead conjugated with recombinant HVEM on the top of the pen through HVEM binding. Antibody-captured Bead was detected by Alexa fluor-568 conjugated secondary antibody.

Example 4: Screening New Anti-hHVEM Antibody Through Single Cell Analysis on Beacon Plasma B cells: 2 months old mouse immunized with hHVEM, CD138 positive. Beacon: 14K Chip. See FIG. 3.

TABLE 1

| Chip ID | Cell Type | #Pens | Penned N = 1 (%) | Multiples (%) | Positive pen (%) | Positive pen with N = 1 (%) | VH/VL amplification | Sequence identified |
|---|---|---|---|---|---|---|---|---|
| D58293 | CD138+ B Cell (hHVEM) | 14115 | 6520 (46.2%) | 3516 (24.9%) | 18 (0.18) | 8 (0.08) | 13 | 5 |

Example 5: New Anti-hHVEM Murine Chimeric Antibody Production II

Figure 4:
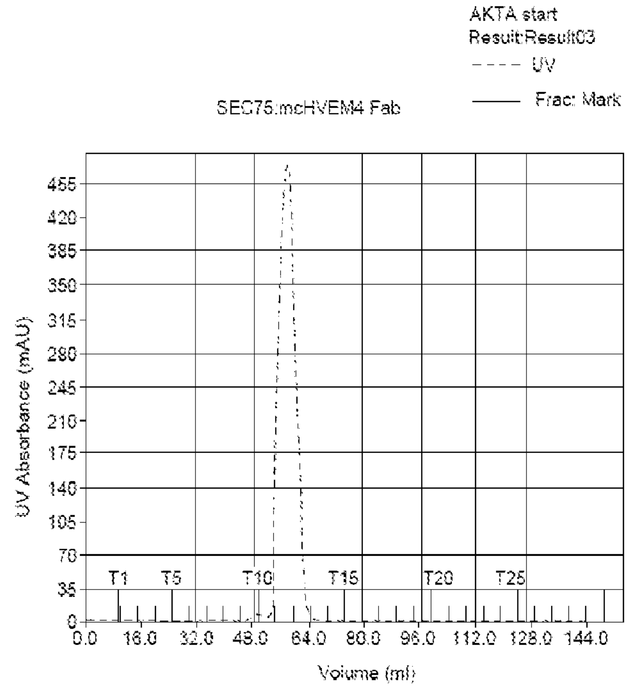
FIG. 4 presents graphs showing size-exclusion chromatogram of anti-hHVEM murine chimeric antibodies provided herein.
Figure 4:
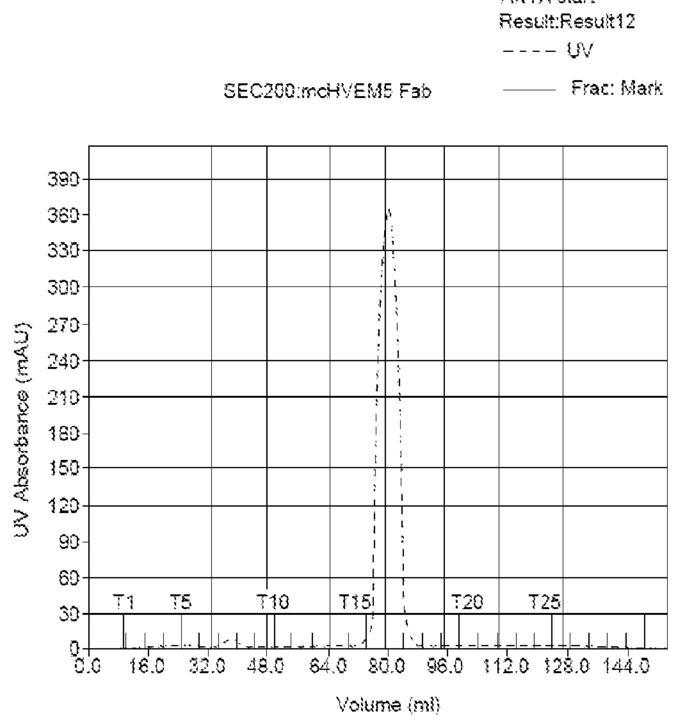
Figure 4:
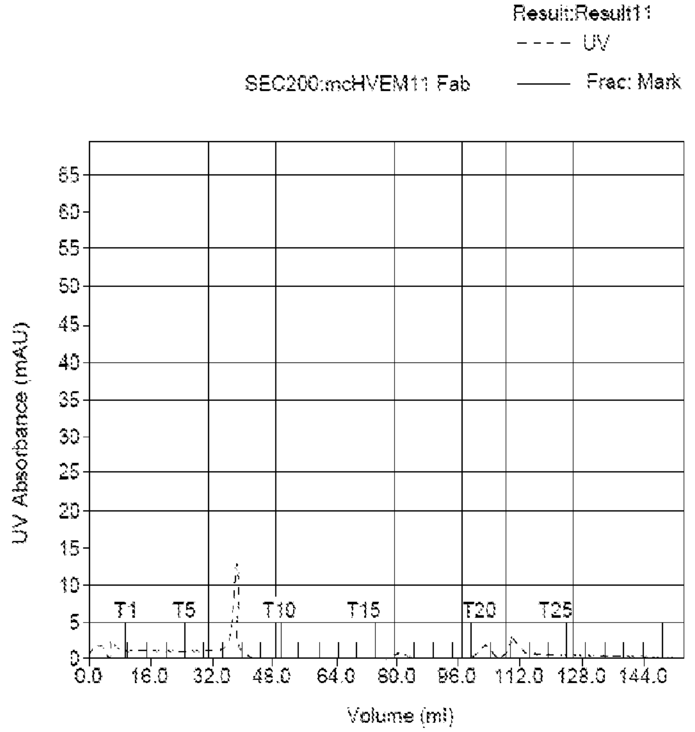
Figure 4:
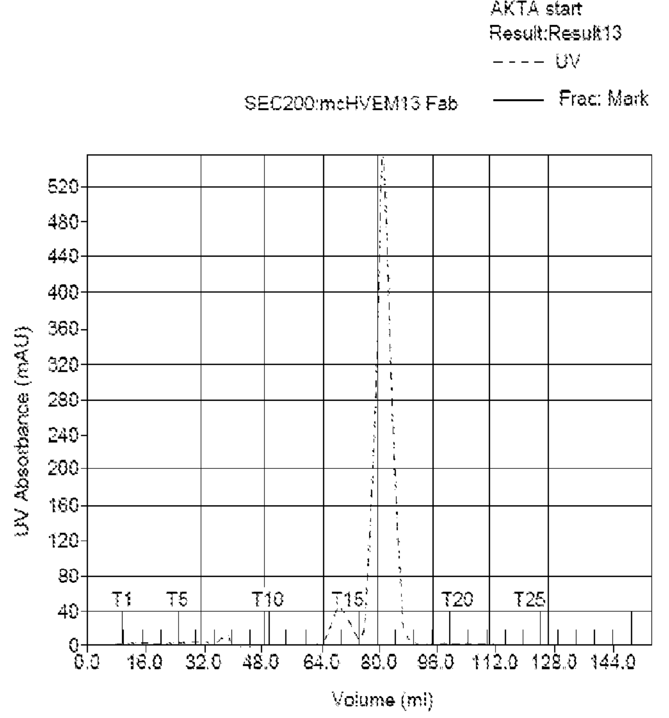
Figure 4:
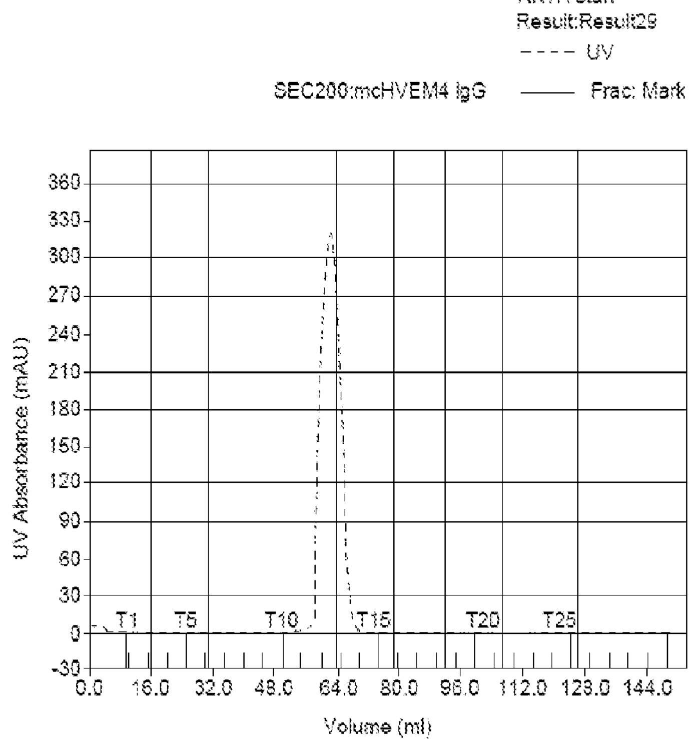
Figure 4:
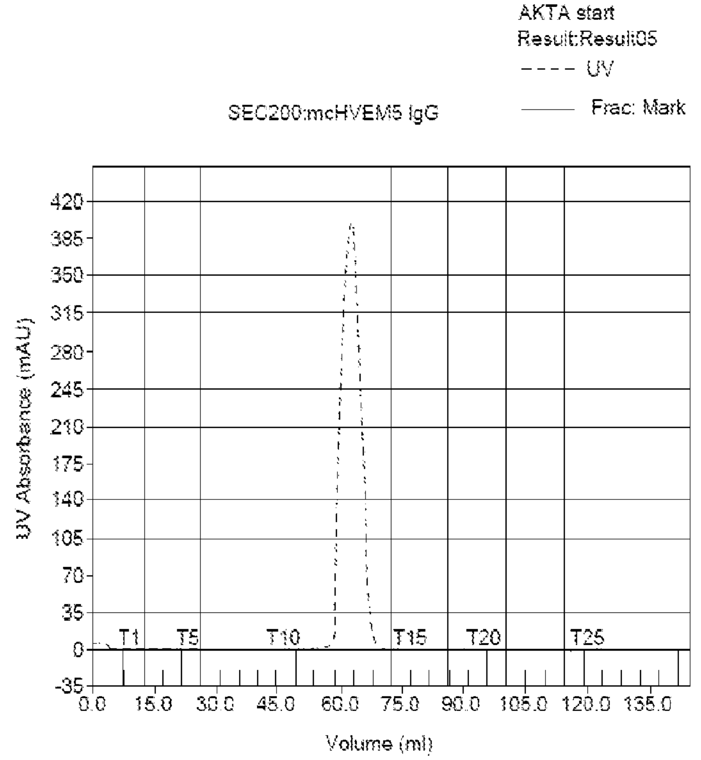
Figure 4:
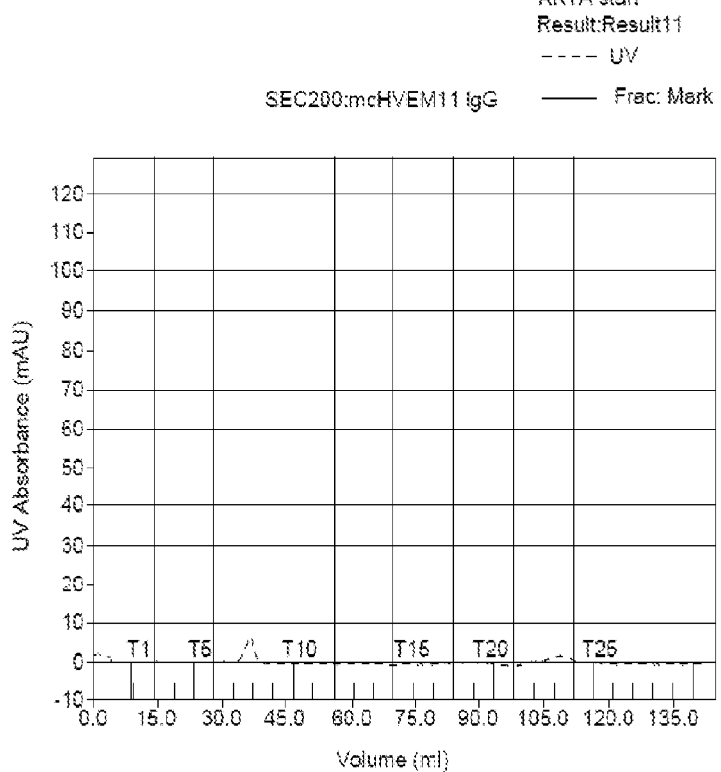
Figure 4:
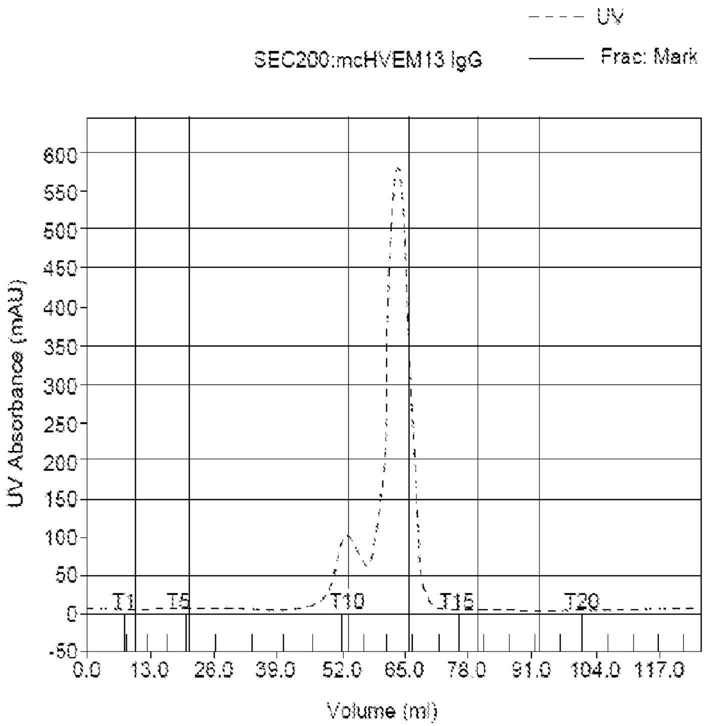
Figure 5:
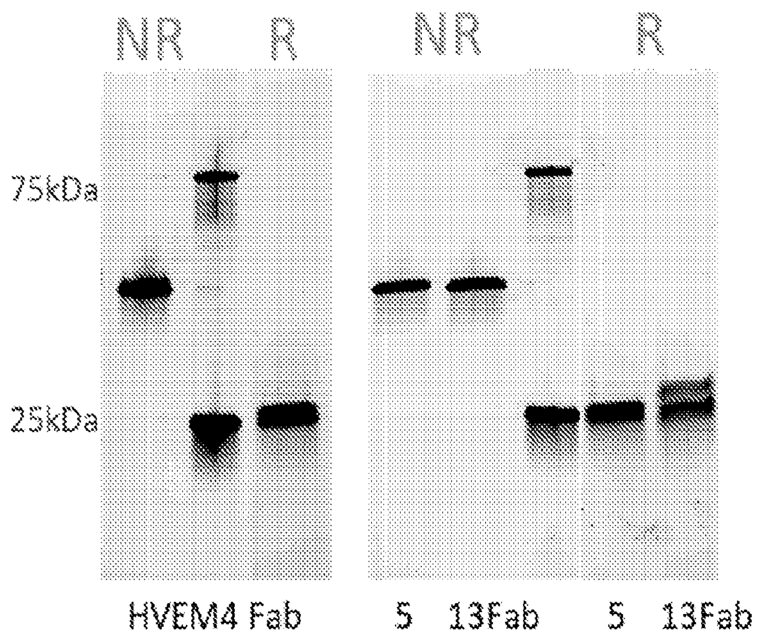
FIG. 5 is a picture of SDS-PAGE blot showing anti-hHVEM murine chimeric Fabs (NR-non-reduced and R-reduced) provided herein.
Figure 6:
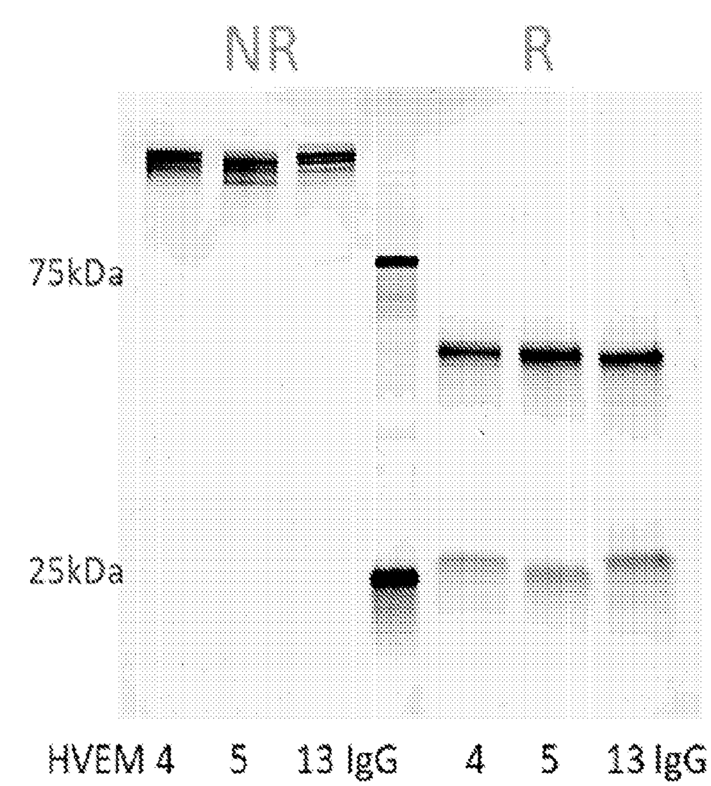
FIG. 6 is a picture of SDS-PAGE showing anti-hHVEM murine chimeric antibodies (NR-non-reduced and R-reduced) provided herein.

See FIGS. 4-6

TABLE 2

| Protein | Culture volume (L) | Total Protein (mg) | Yield (mg/L) |
|---|---|---|---|
| mcHVEM4 Fab | 0.05 | 7.3 | 145 |
| mcHVEM5 Fab | 0.05 | 7.2 | 144 |
| mcHVEM11 Fab | 0.05 | — | — |
| mcHVEM13 Fab | 0.05 | 10.8 | 216 |
| mcHVEM4 IgG | 0.05 | 5 | 100 |
| mcHVEM5 IgG | 0.05 | 6.4 | 128 |
| mcHVEM11 IgG | 0.05 | — | — |
| mcHVEM13 IgG | 0.05 | 9.45 | 189 |

Example 6: New Anti-hHVEM Fab Binding to HVEM on Surface Plasmon Resonance (SPR)

Figure 7:
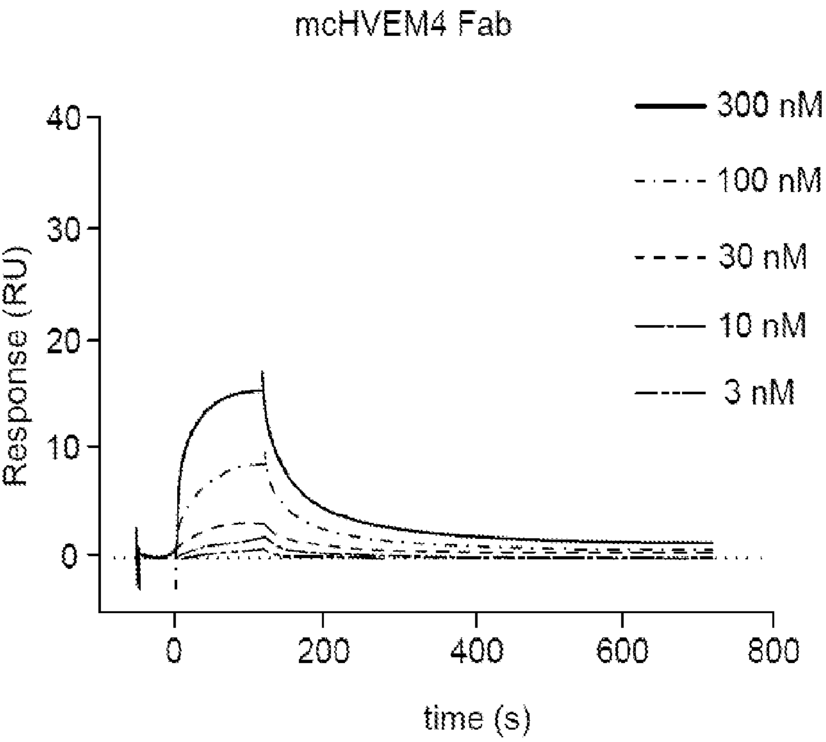
FIG. 7 presents graphs showing binding of anti-hHVEM Fab provided herein to HVEM on SPR.
Figure 7:
Figure 7:
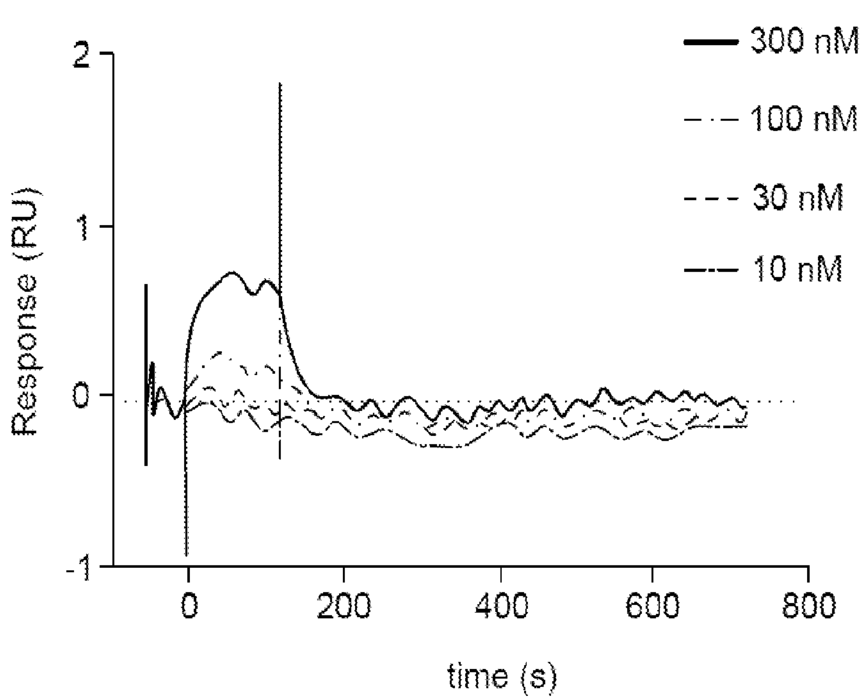
Figure 7:
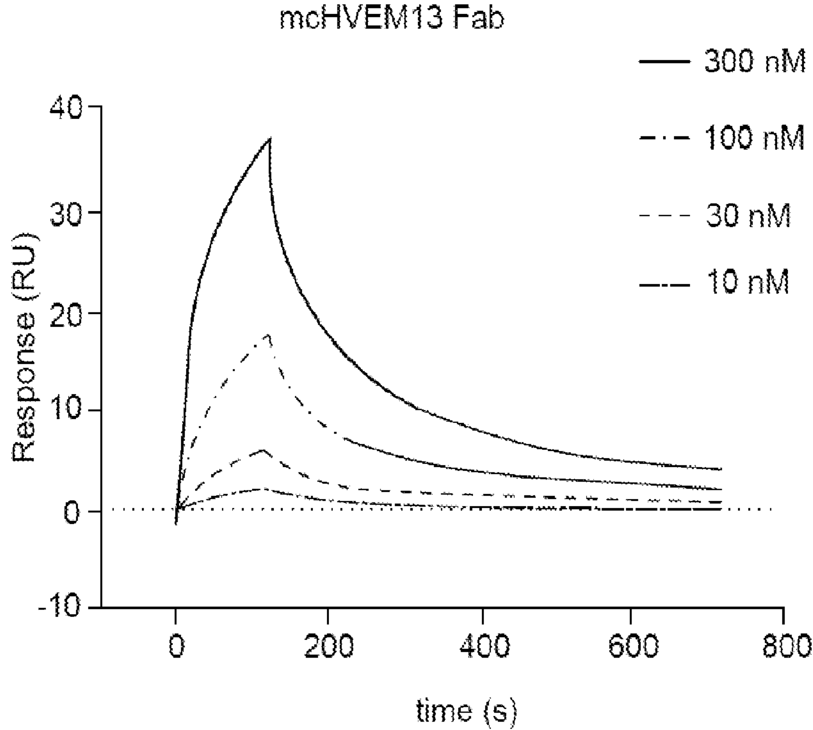
Figure 7:
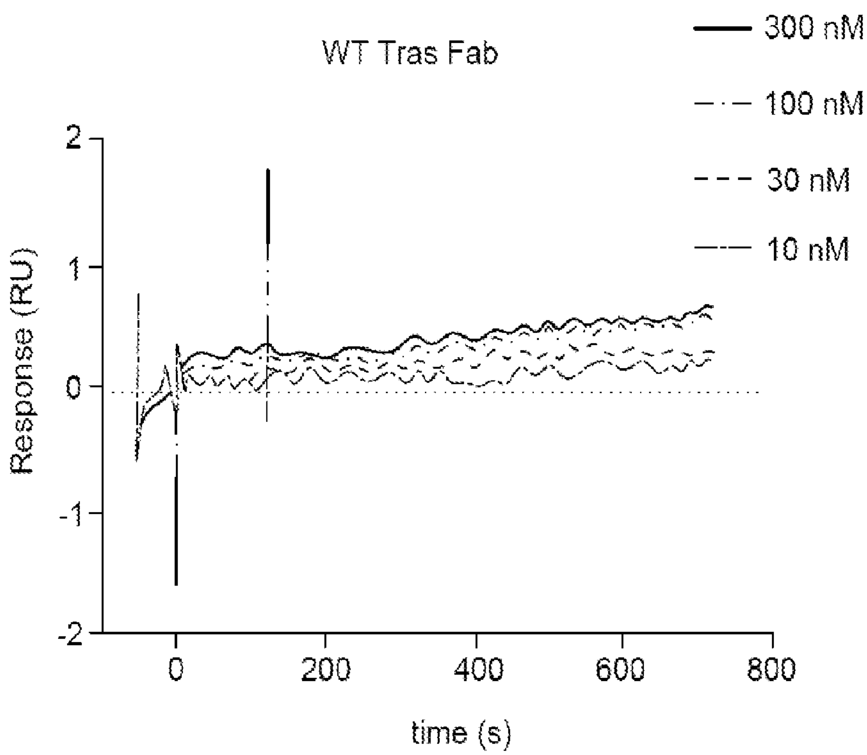
Figure 7:
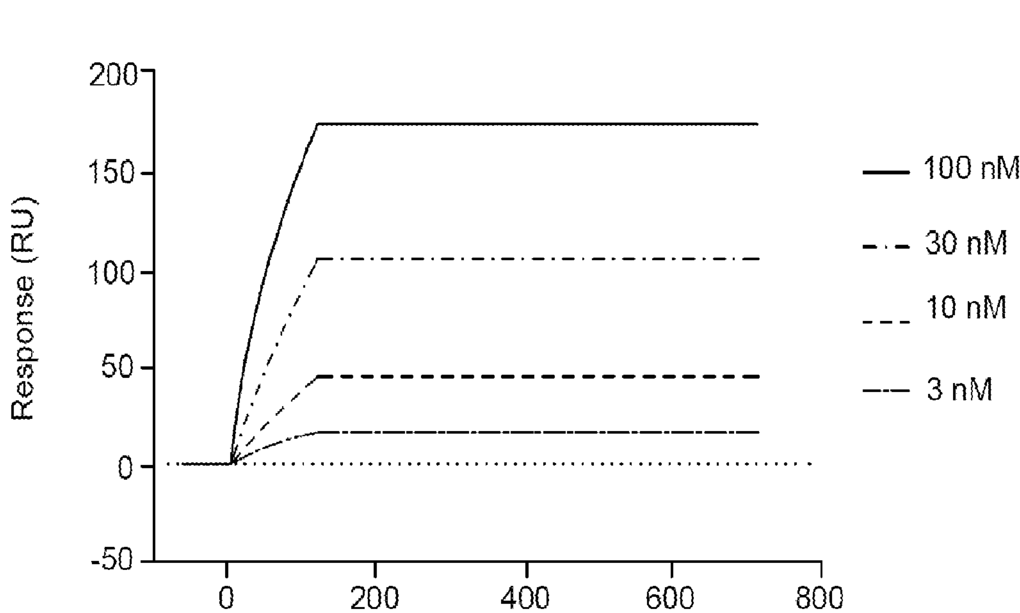

Binding on SPR. Immobilization HVEM (SinoBio, monomeric) on CM5 chip (1000 RU) through 1-ethyl-3-(-3-dimethyoaminopropyl) carbodiimide/N-hydroxysulfosuccinimide (EDC/NHS) coupling. Sample preparation: new mcHVEM4 Fab new mcHVEM5 Fab, new mcHVEM13 Fab, positive control (commercial anti-HVEM IgG) and negative control (Trastuzumab Fab) in HBS-EP+ running buffer at 300; 100; 30; 10; 3 nM at 25° C. See FIG. 7.

TABLE 3

| | ka (1/Ms) | kd (1/s) | KD (M) | $Chi^2$ ($RU^2$) | U-value |
|---|---|---|---|---|---|
| mcHVEM4 Fab (clone 4) | 8.96E+04 | 7.35E−03 | 8.20E−08 | 0.21 | 4 |
| mcHVEM5 Fab (clone 5) | 3.01E+05 | 0.05402 | 1.80E−07 | 0.0135 | 73 |
| mcHVEM13 Fab (clone 13) | 1.38E+06 | 0.1375 | 9.96E−08 | 0.426 | 73 |

Example 6: New Anti-hHVEM Fab Binding to HVEM on SPR

Figure 8:
FIG. 8 presents graphs showing binding of anti-hHVEM IgG to HVEM on SPR.
Figure 8:
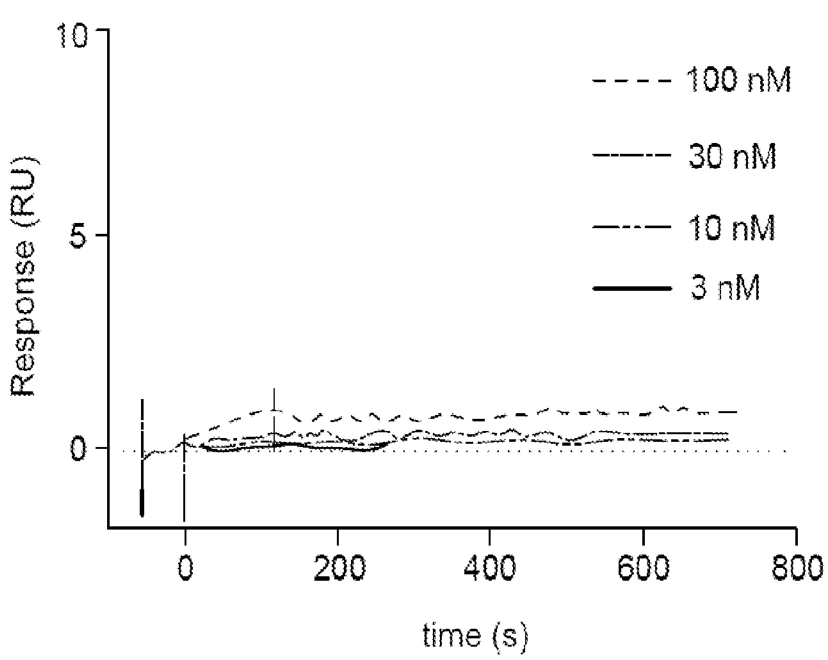
Figure 8:
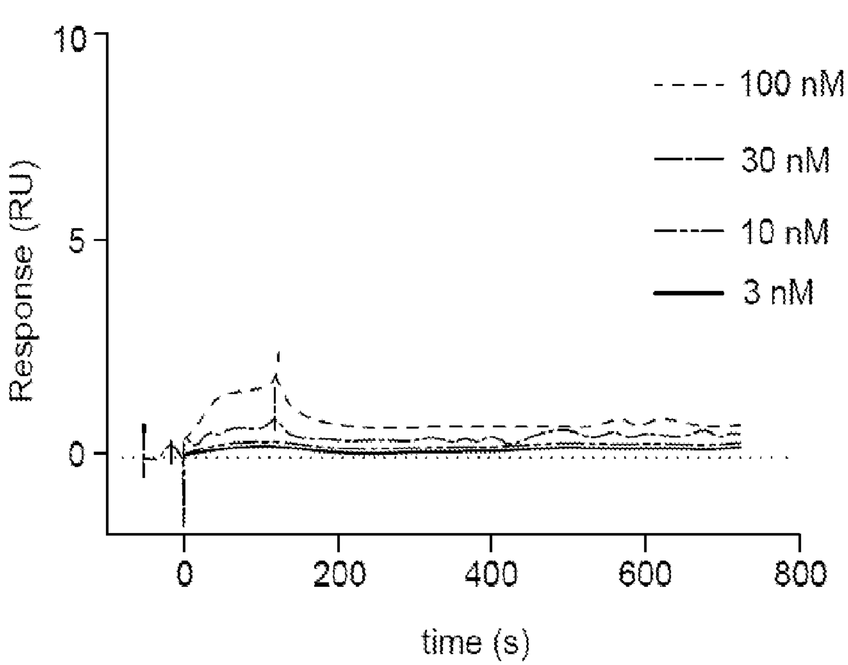
Figure 8:
Figure 8:
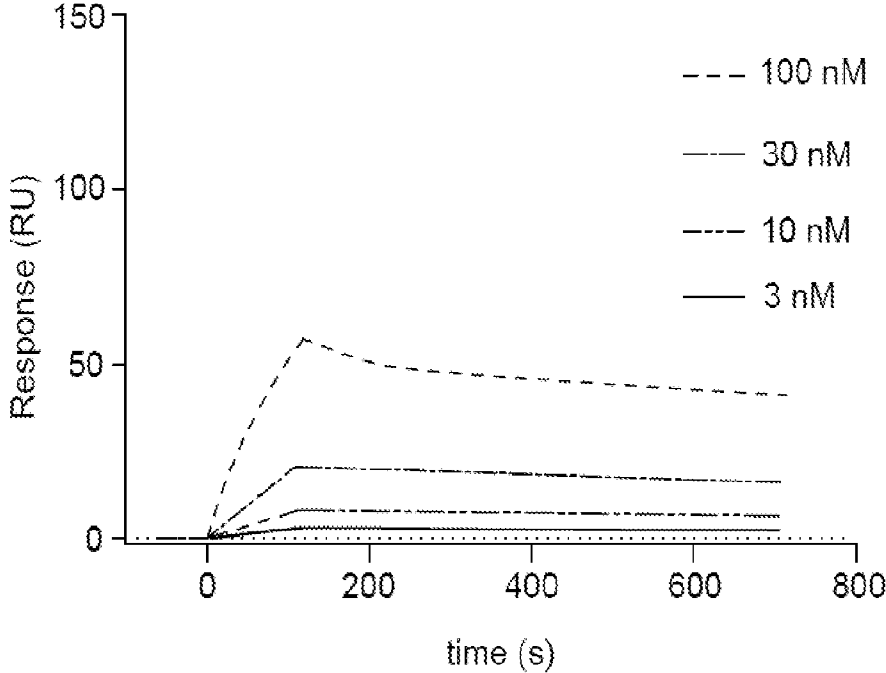
Figure 8:
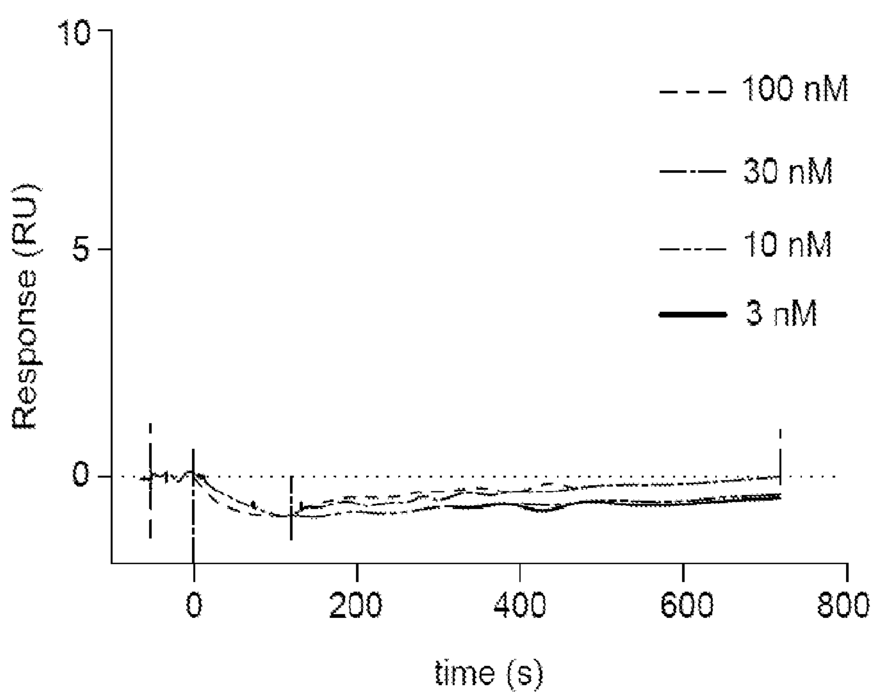
Figure 8:
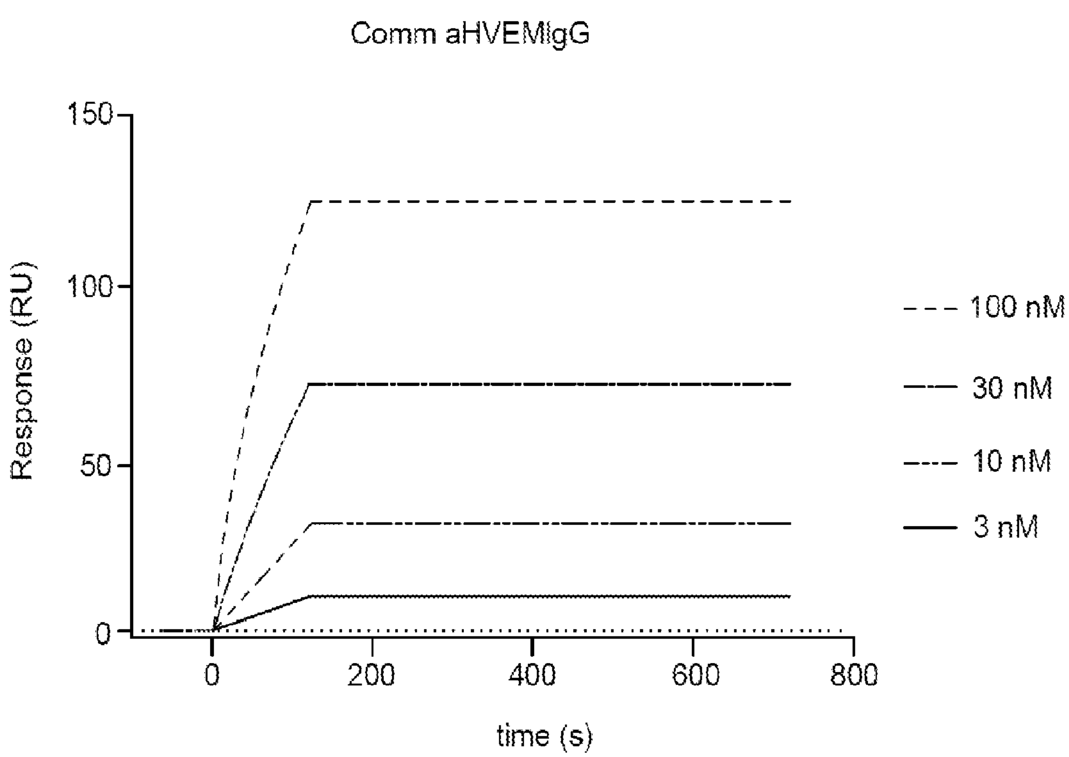

Binding on SPR. Immobilization HVEM (SinoBio, monomeric) on CM5 chip (1000 RU) through EDC/NHS coupling. Sample preparation: mcHVEM4 IgG, mcHVEM5 IgG, mcHVEM13 IgG, positive control (commercial anti-HVEM IgG) and negative control (Daratumumab) in HBS-EP+ running buffer at 100; 30; 10; 3 nM at 25° C. See FIG. 8.

Example 7: mcHVEM4, mcHVEM5 and mcHVEM13 Abs Binding Assay in Myeloma Cells

HVEM (Herpes Virus Entry Mediator), also known as tumor necrosis factor receptor superfamily member 14 (TNFRSF14), is a human cell surface receptor of the TNF-receptor superfamily).

MM cell lines MM.1S GFP+/Luc+, were kindly donated from Dr. Irene Ghobrial (Dana-Faber Cancer Institute, Boston, MA). MM cells were cultured in RPMI-1640 medium supplemented with 10% fetal bovine serum (Cat. #019K8420, Sigma), 100 IU/ml penicillin and 100 μg/ml streptomycin. Specifically, 0.5×106 cells/ml MM.1S GFP+/Luc+, were incubated for 30 minutes in culture media with 0, 1, 5, 10 and 20 μg/mL of each synthetized antibodies (aHVEM13, aHVEM4, aHVEM5 Abs). After incubation MM cells were collected by centrifugation (5 min. 1500 rpm) and washed with PBS 1×, collected by centrifugation again (1500 rpm for 5 minutes), resuspended in 1 ml PBS1× and stained with HVEM-(CD270) mouse Anti-Human Alexa Fluor 647, 1 (Clone: 94801, Cat. #564411 BD Biosciences) to evaluate the binding of the flow antibody in presence or absence of increased concentration of anti-HVEMs (aHVEM13, aHVEM4, aHVEM5 Abs). After 30 minutes of incubation each sample was washed and analyzed on LSRII (Becton Dickinson). Analysis was conducted using Kaluza Software (Beckman Coulter). Unstained cells were used as internal control for compensation.

aHVEM13: 1.57 mg/mL.
aHVEM4: 1.45 mg/mL
aHVEM5: 2 mg/mL

Figure 9:
FIG. 9 is a graph showing mcHVEM13 induced antibody dependent mediated cytotoxicity (ADCC) in myeloma cells.
Figure 9:
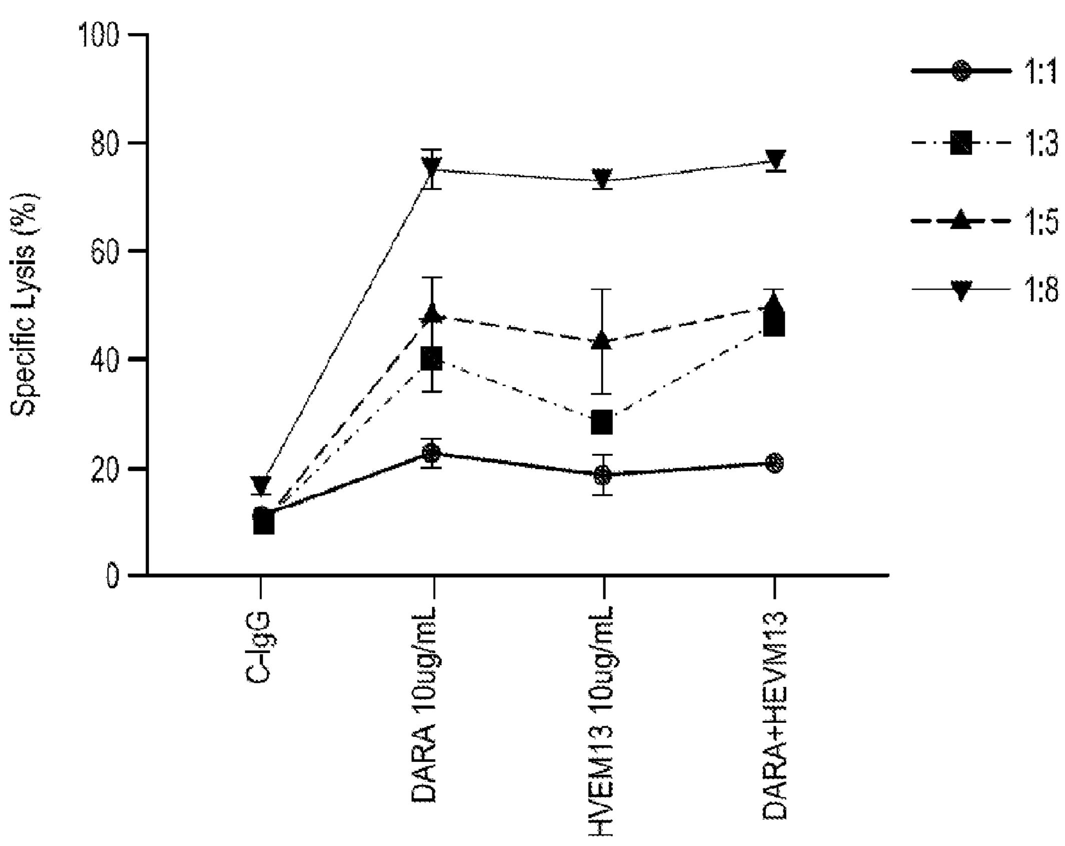
Figure 10:
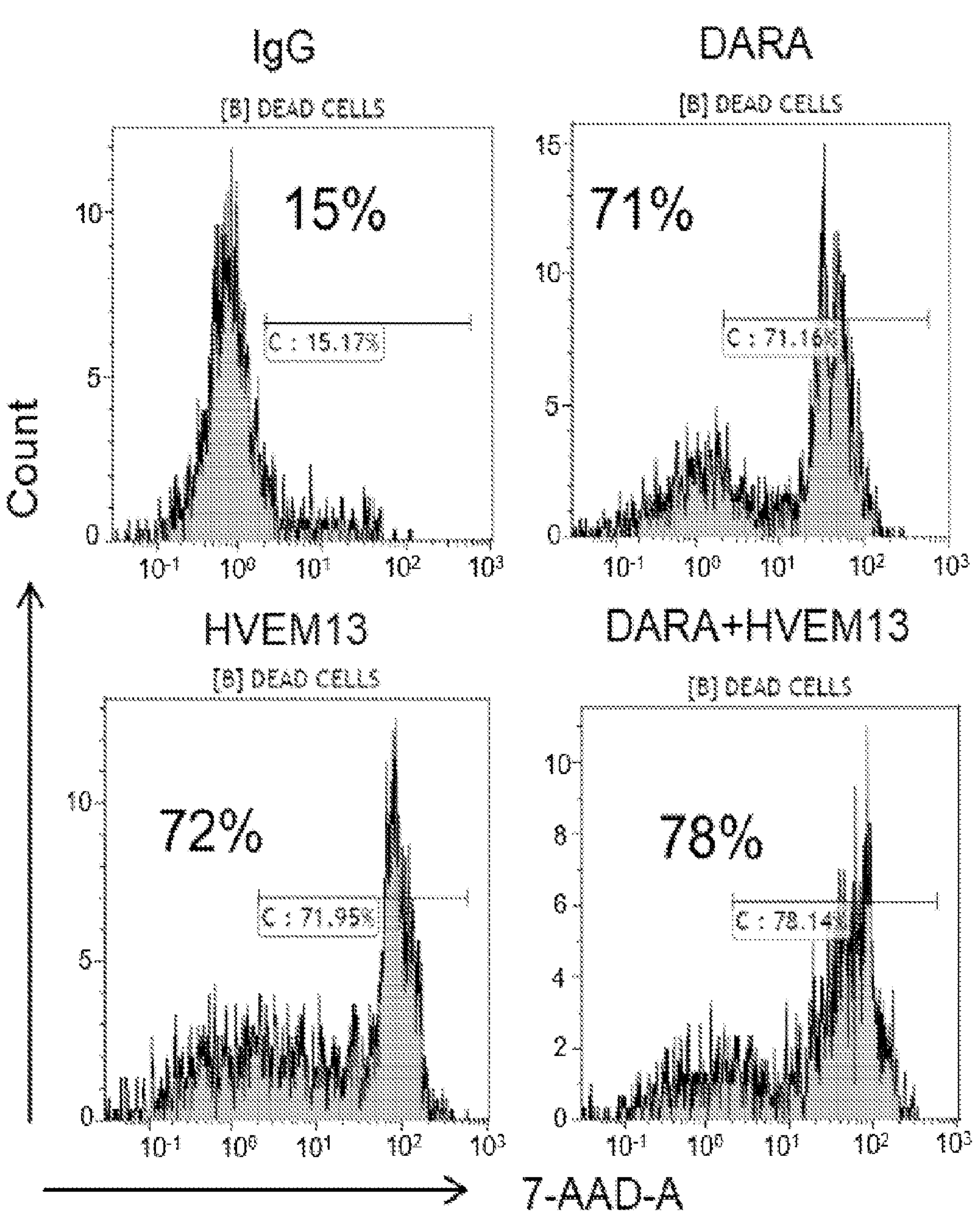
FIG. 10 presents flow cytometry plots showing mcHVEM13 induced antibody dependent mediated cytotoxicity in myeloma cells.
Figure 11A:
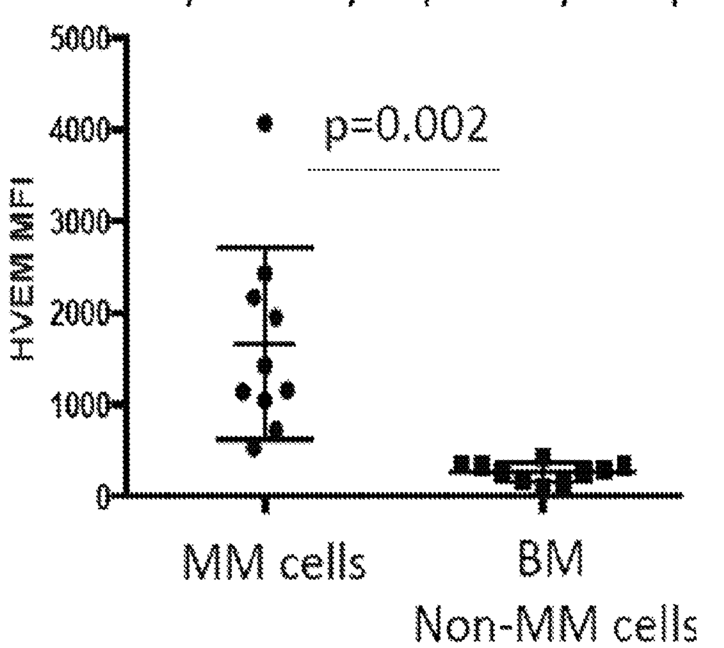
FIGS. 11A-11B present exemplary data showing that HVEM was highly expressed on the surface of myeloma cells.
Figure 11B:
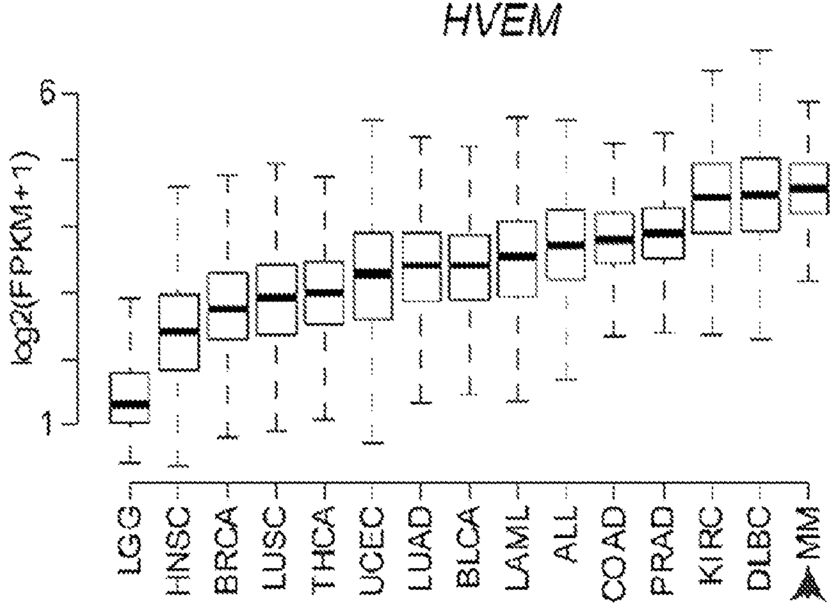
Figure 12A:
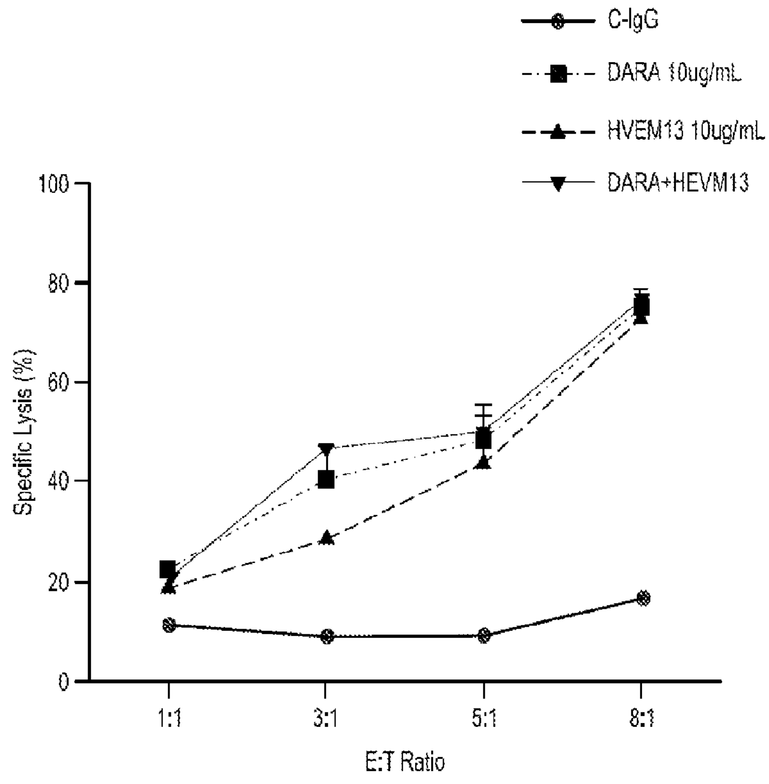
FIGS. 12A-12D present exemplary data showing that HVEM13 and HVEM5 induced ADCC in MM cells.
Figure 12B:
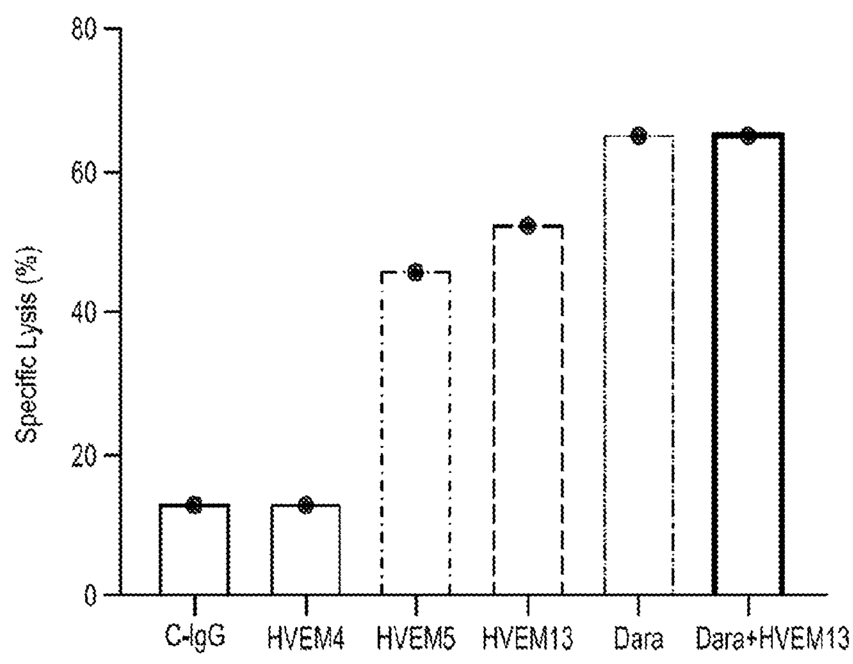
Figure 12C:
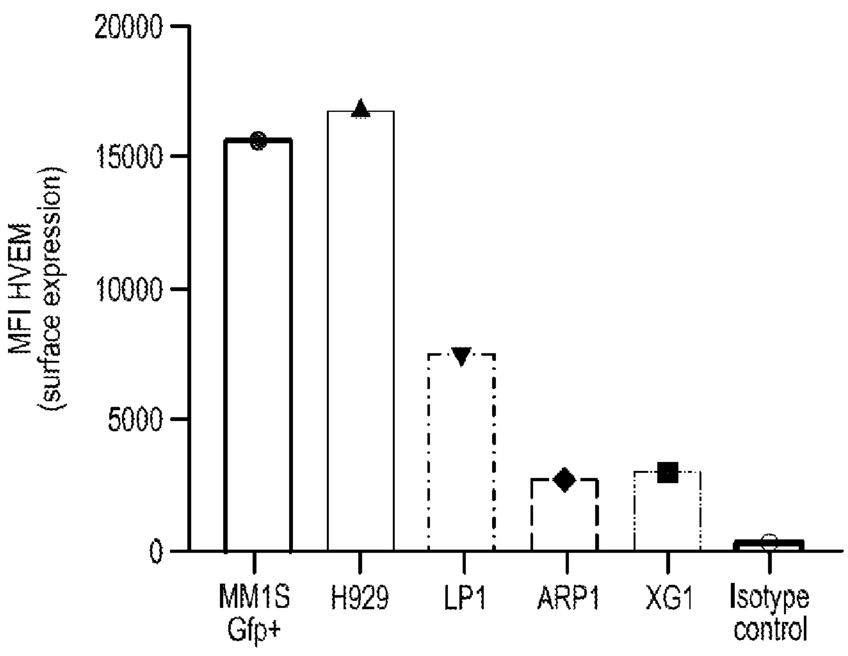
Figure 12D:
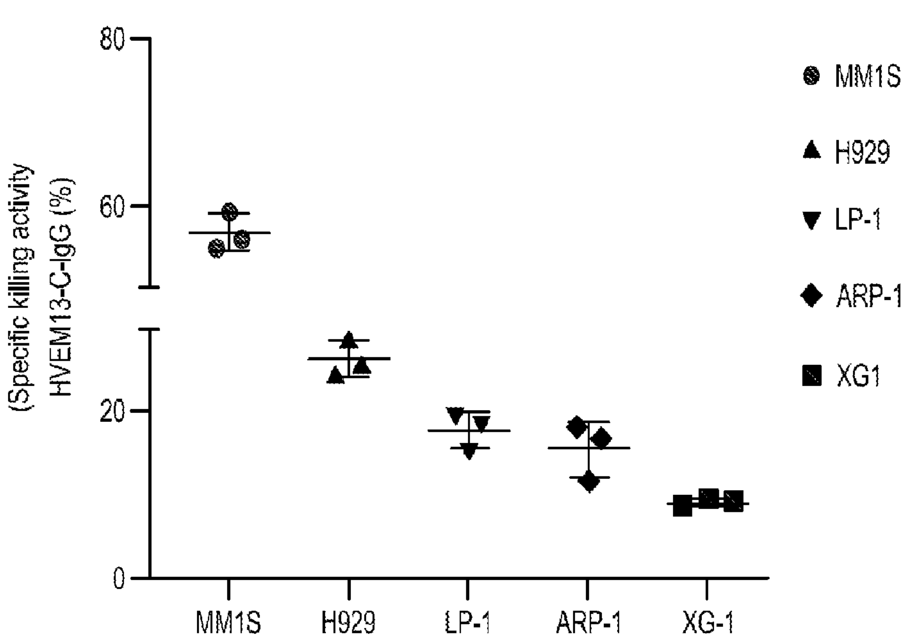
Figure 13A:
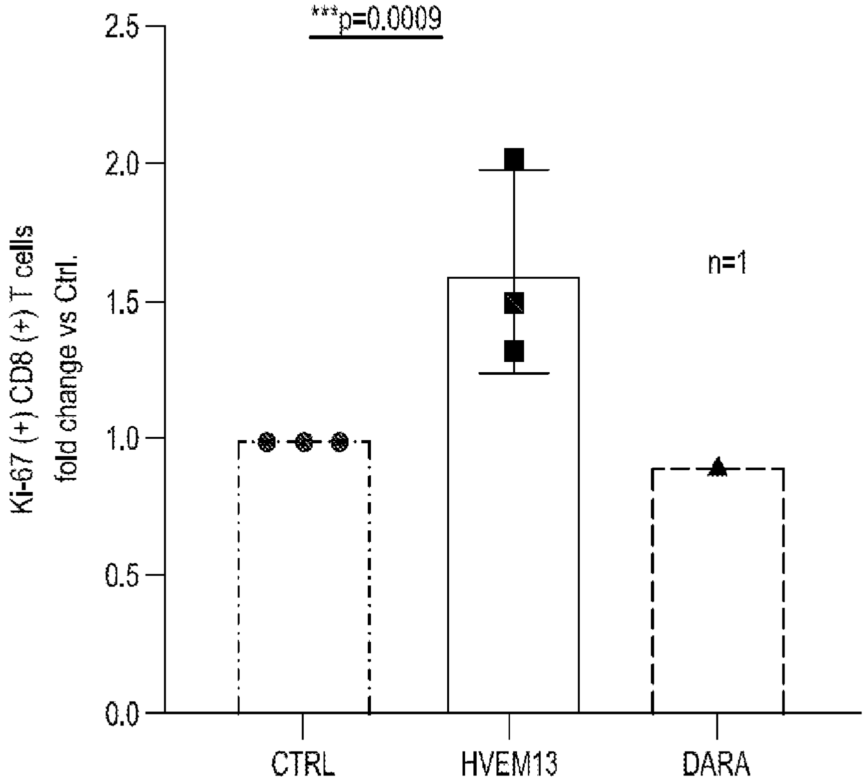
FIGS. 13A-13C present exemplary data showing that HVEM13 induced Human Cytotoxic-T cell expansion. Peripheral blood mononuclear cells obtained from n=3 different healthy donors were activated with CD3/CD28 Beads (Human T-Activator, Dynabeads) and IL-2 (30 U/mL) and treated with HVEM13 and Dara (10 ug/mL) for 7 days. Conditioned media (growing media plus Control human IgG (Ctrl) or anti-HVEM13, was added at the fourth day. The experiment was assessed by Flow Cytometry after intracellular staining for Ki-67 proliferation marker gated in CD3, CD4 and CD8 positive subpopulations. Data are representative of the average of three independent experiments using n=3 HD PBMCs isolated cells are shown in FIGS. 13A-13C. In these figures, data are presented as mean±SD. Paired t test Two-tailed used for the analysis.
Figure 13B:
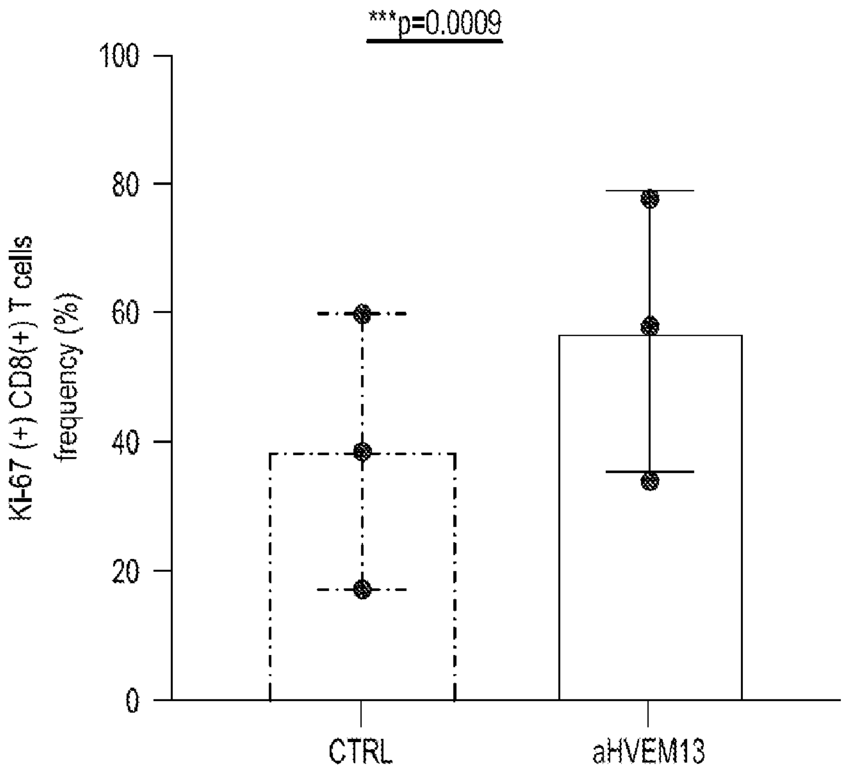
Figure 13C:
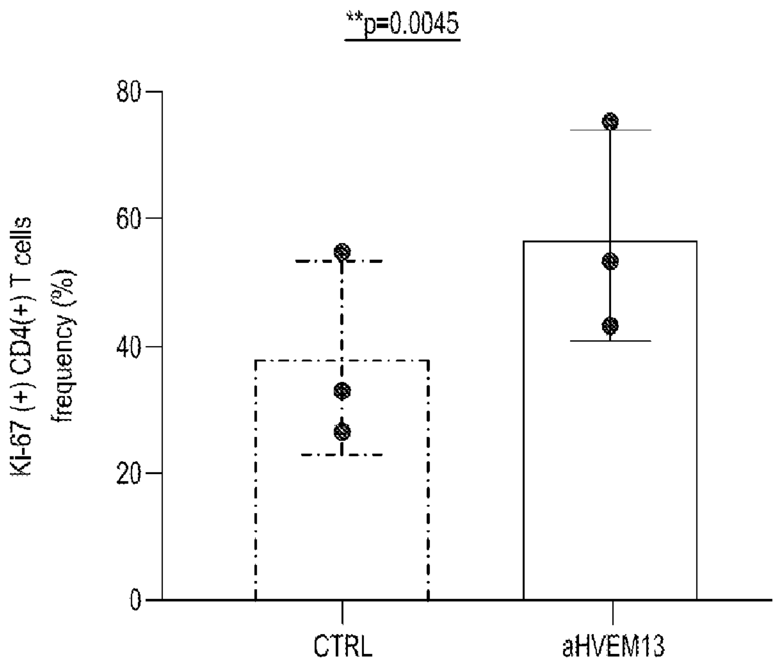
Figure 14A:
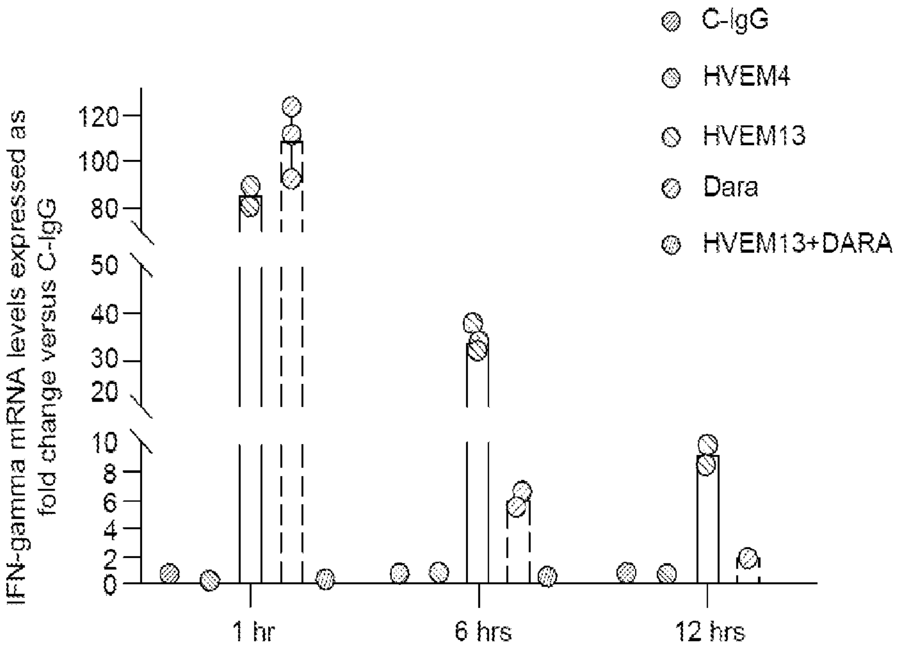
FIGS. 14A-14B present exemplary data showing that HVEM13 induced NK cell activation and costimulatory molecules (CD80/86) in human monocytes.
Figure 14B:
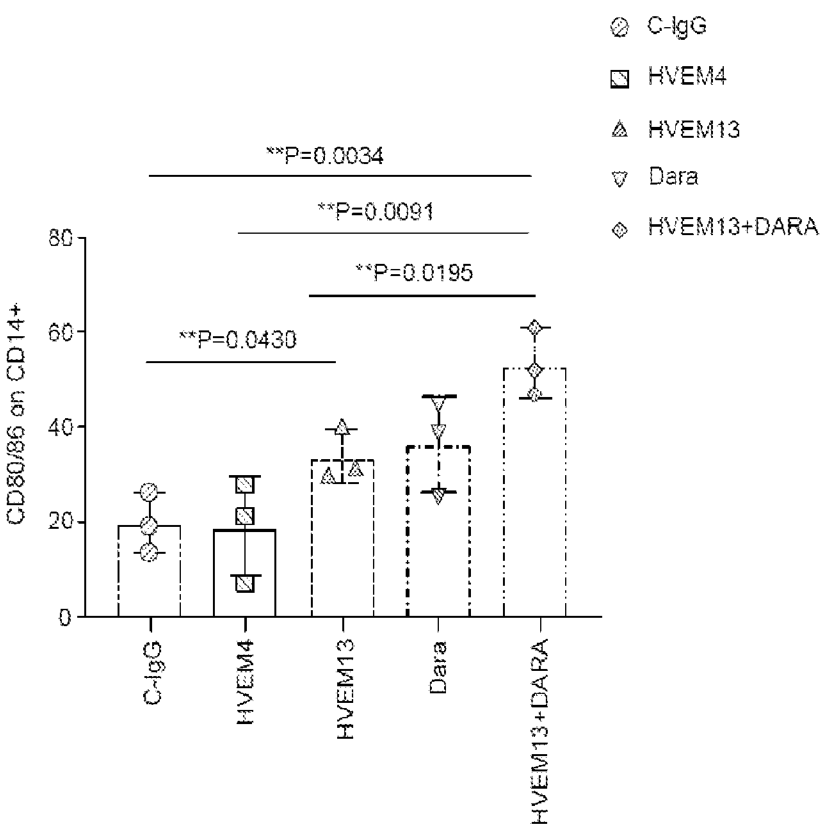
Figure 15A:
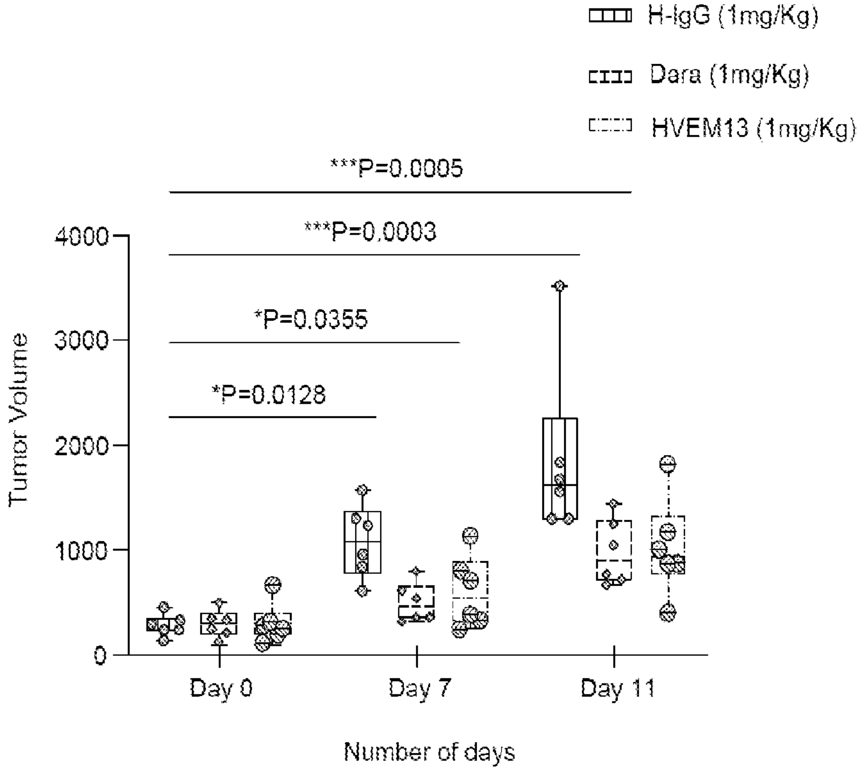
FIGS. 15A-15B present exemplary data showing that HVEM13 reduced myeloma tumor size in animal.
Figure 15B:
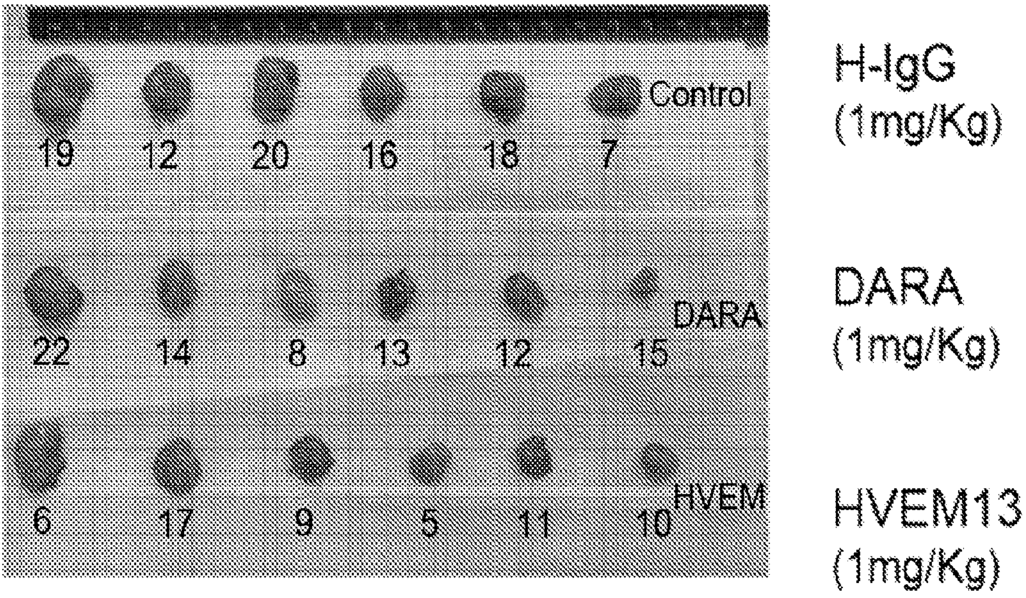
Figure 16A:
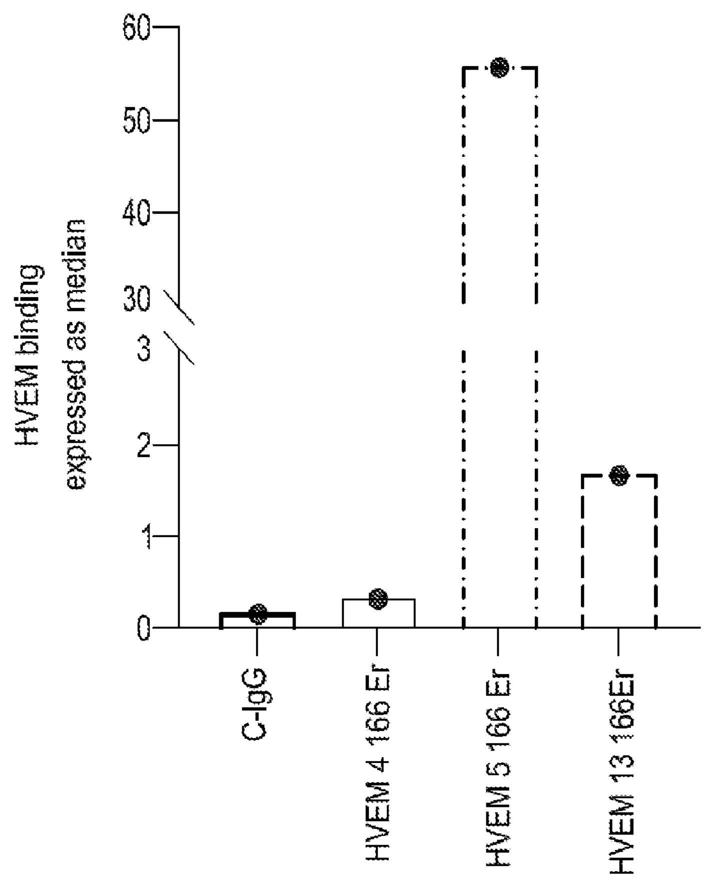
FIGS. 16A-16C present exemplary data showing that HVEM5 had high binding affinity in MM cells and in in vitro binding assays.
Figure 16B:
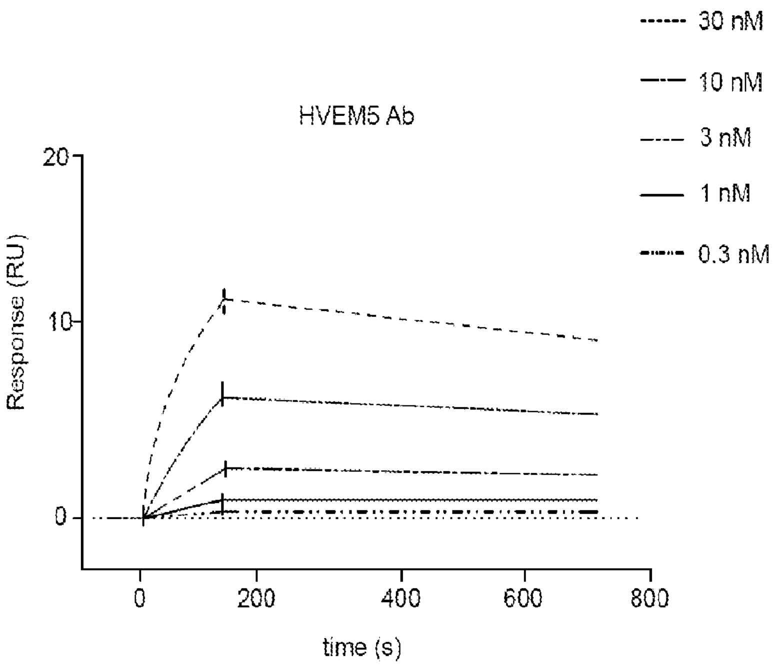
Figure 16C:
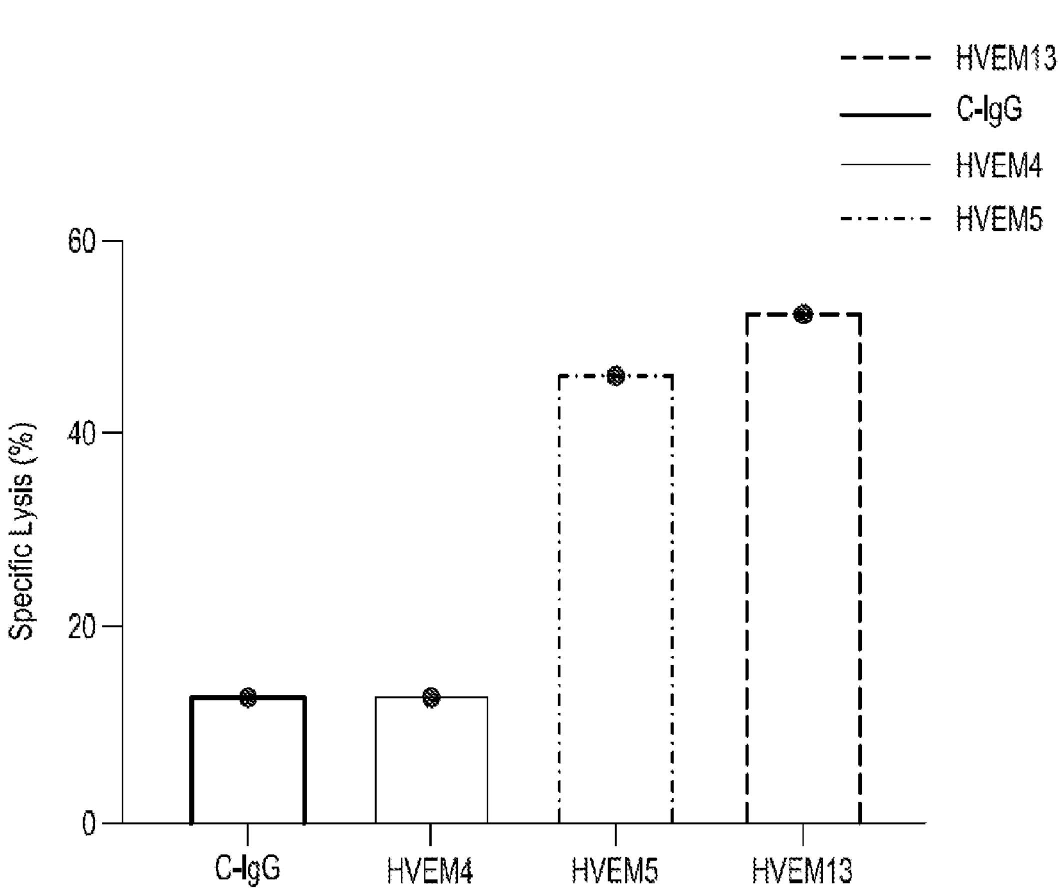
Figure 17A:
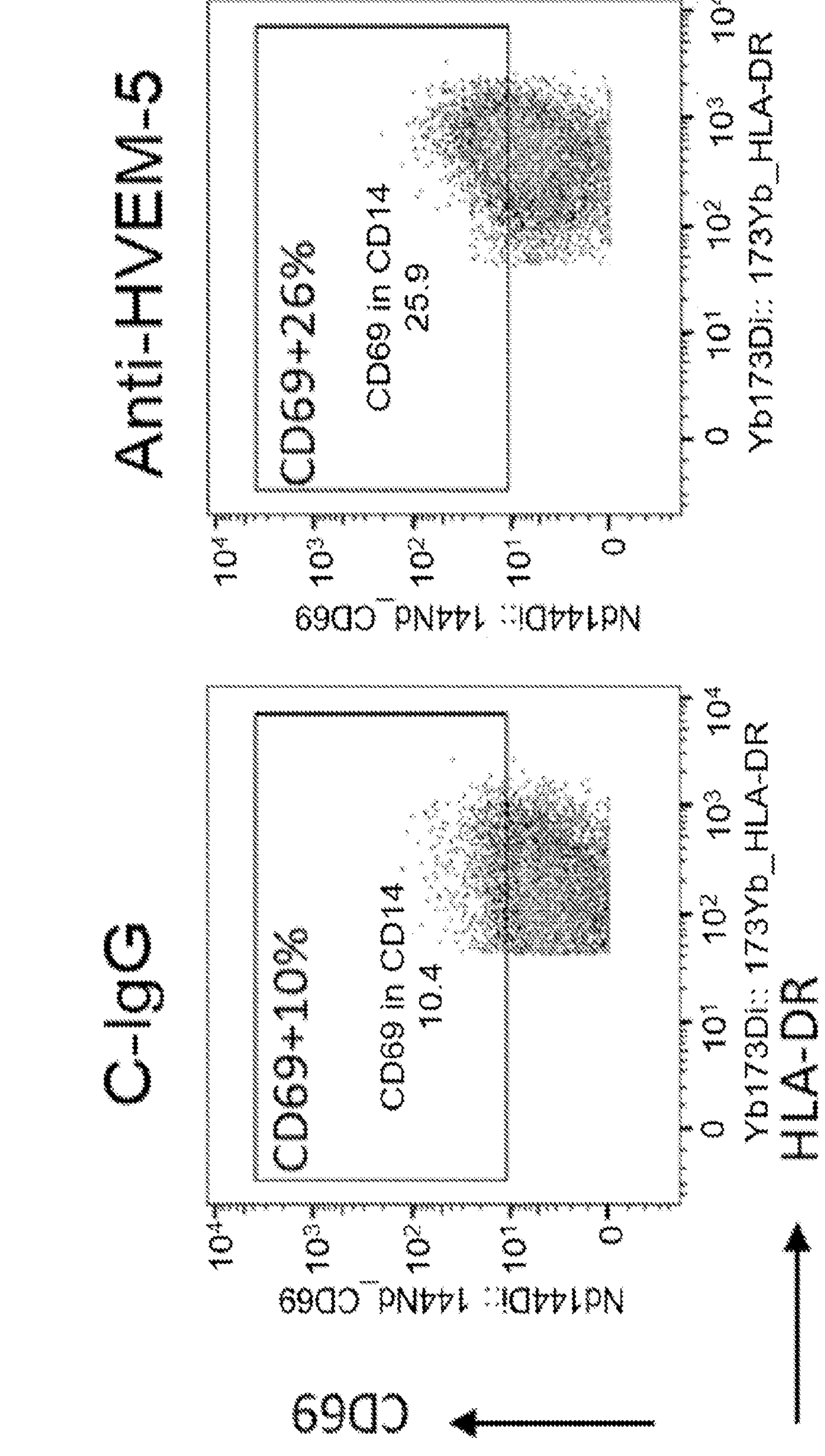
FIGS. 17A-17D present exemplary data showing that HVEM5 treatment induced antitumor macrophages differentiation and eliminated monocytes myeloid-derived suppressor cells (Mo-MDSCs) population ex-vivo. In the experiments presented in these figures, peripheral human mononuclear cells obtained from a healthy donor were treated for 24 hours with C-IgG or HVEM5. After treatment samples were stained with the 37 metal conjugated antibody panel and analyzed by mass flow cytometry.
Figure 17B:
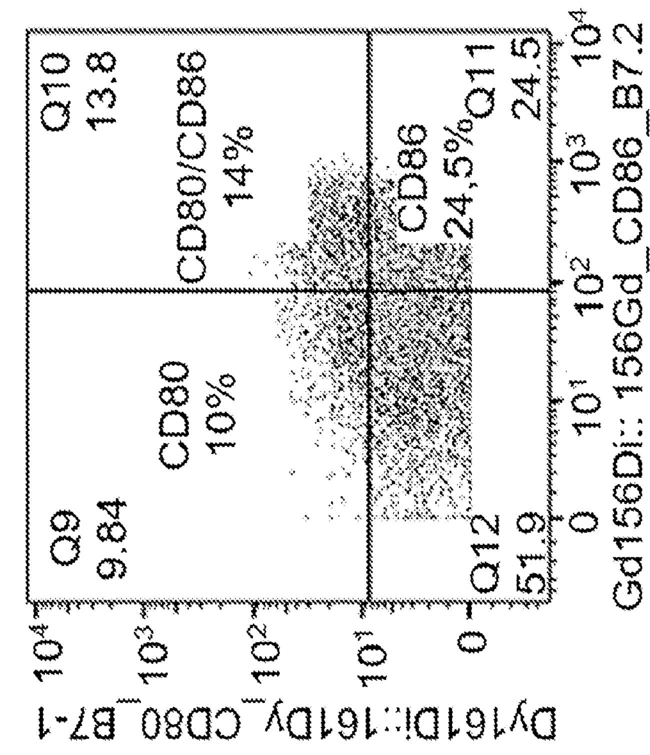
Figure 17B:
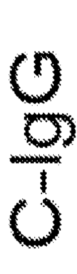
Figure 17B:
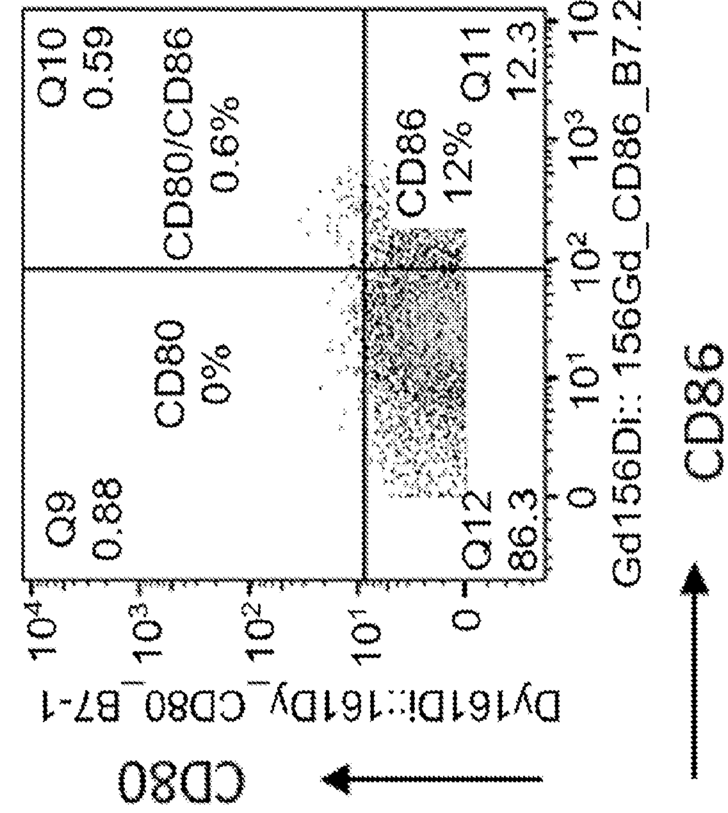
Figure 17C:
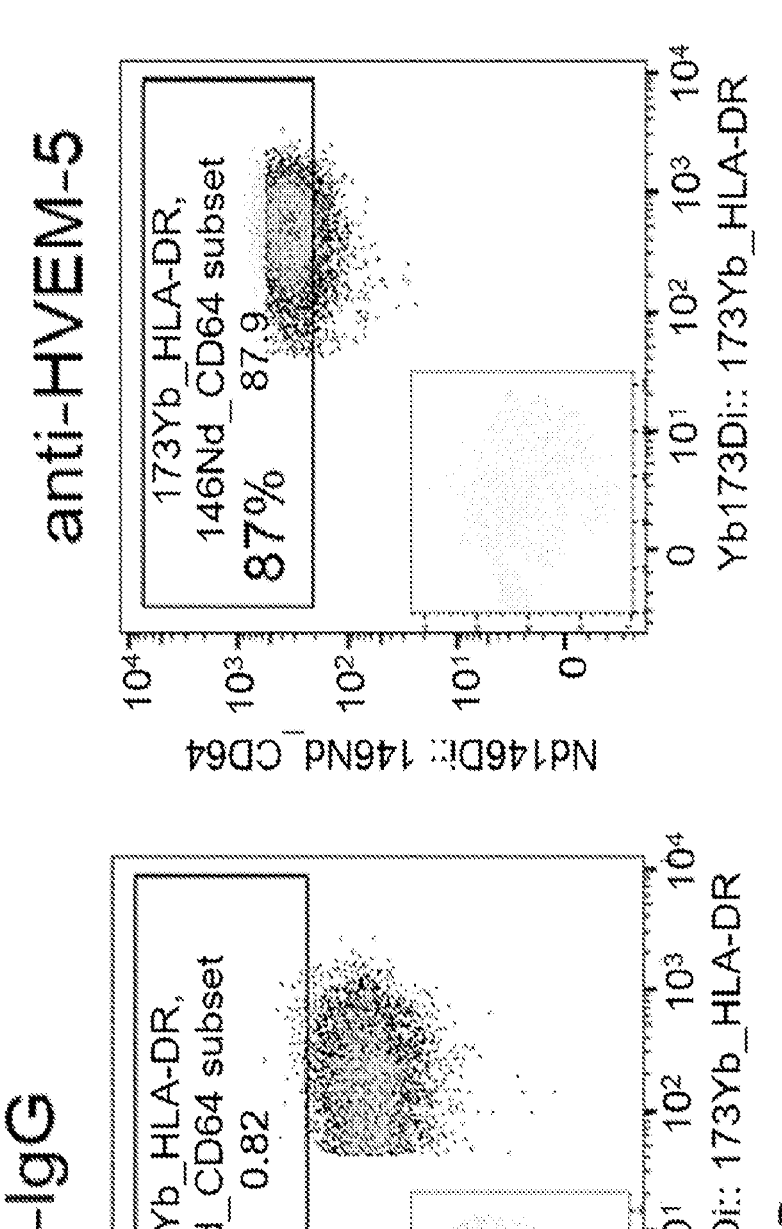
Figure 17D:
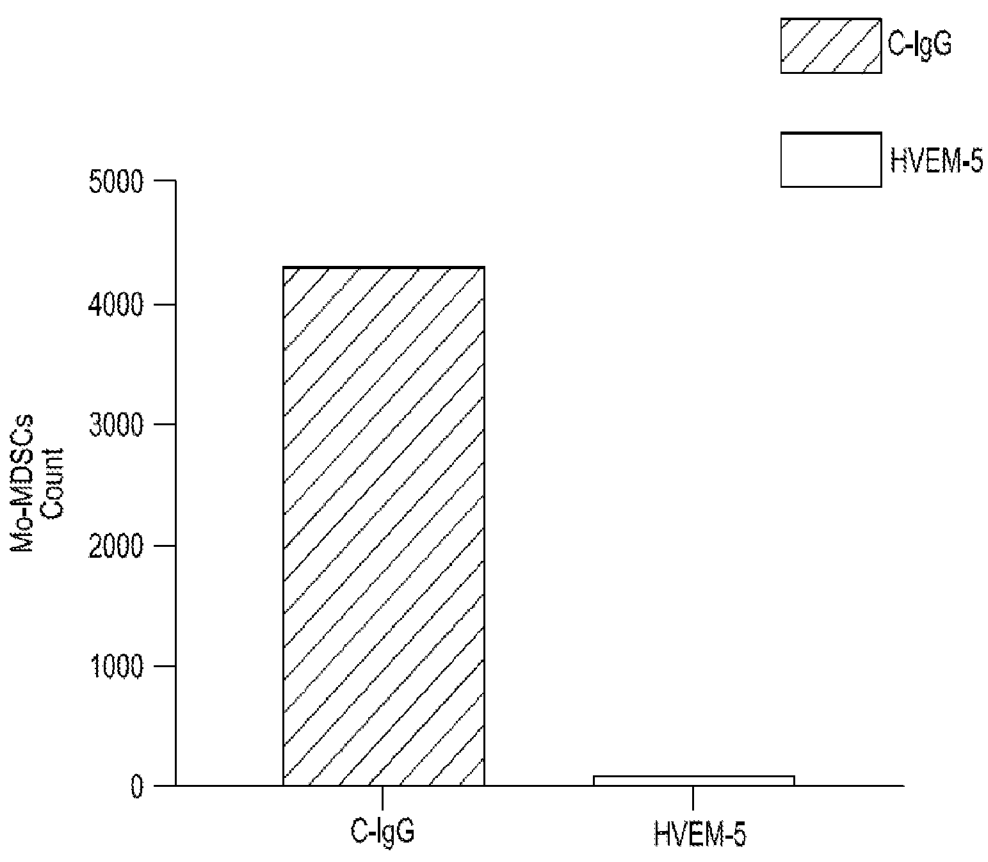
Figure 18A:
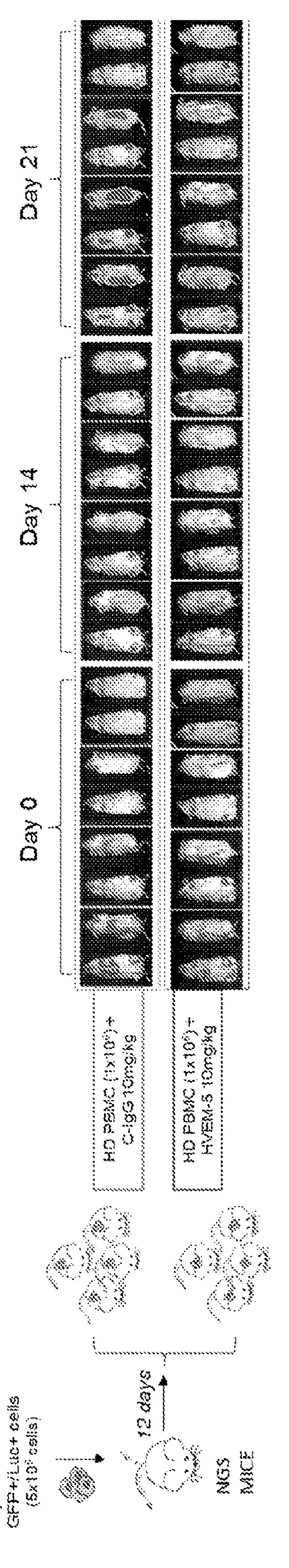
FIGS. 18A-18C present exemplary data showing that mice treated with HVEM5 in combination with human healthy donor PBMCs showed longer survival.
Figure 18B:
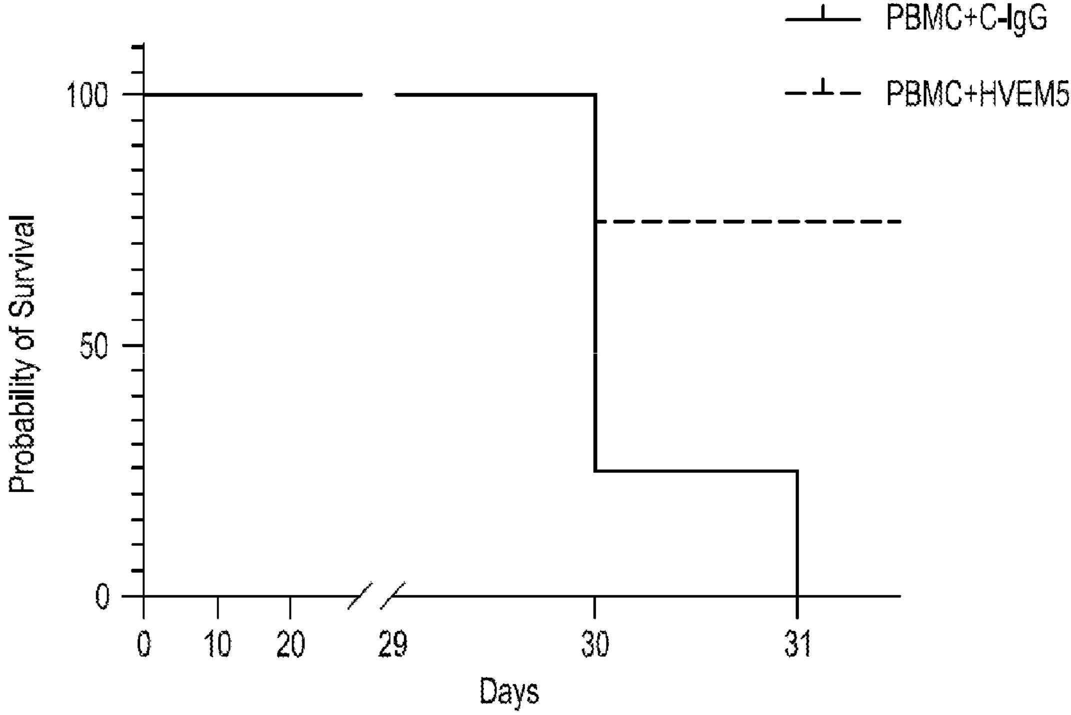
Figure 18C:
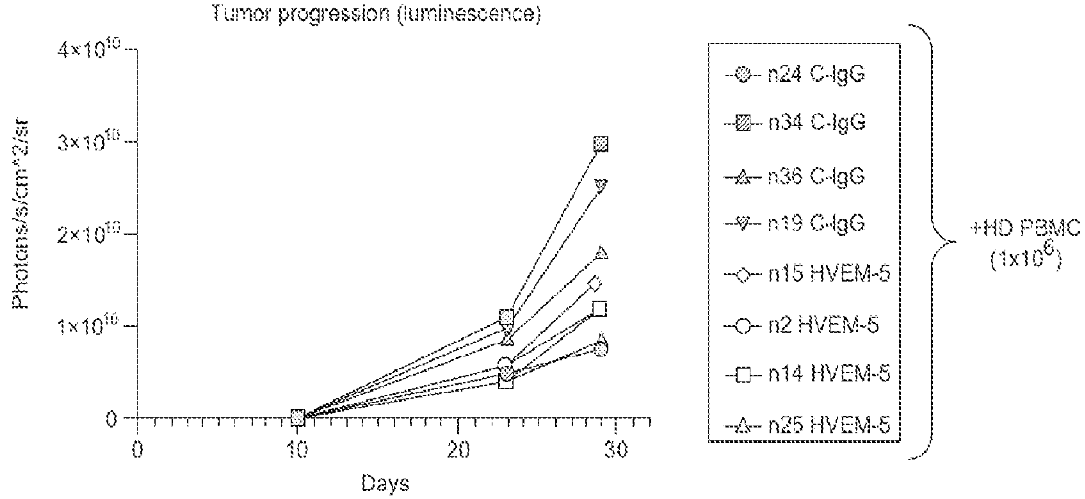
Figure 19A:
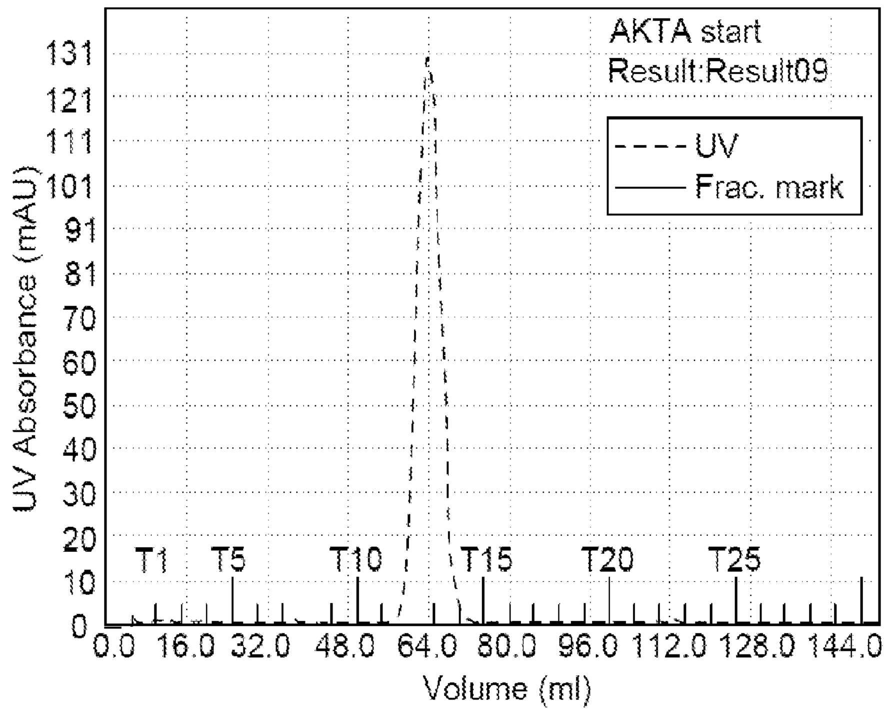
Figure 19B:
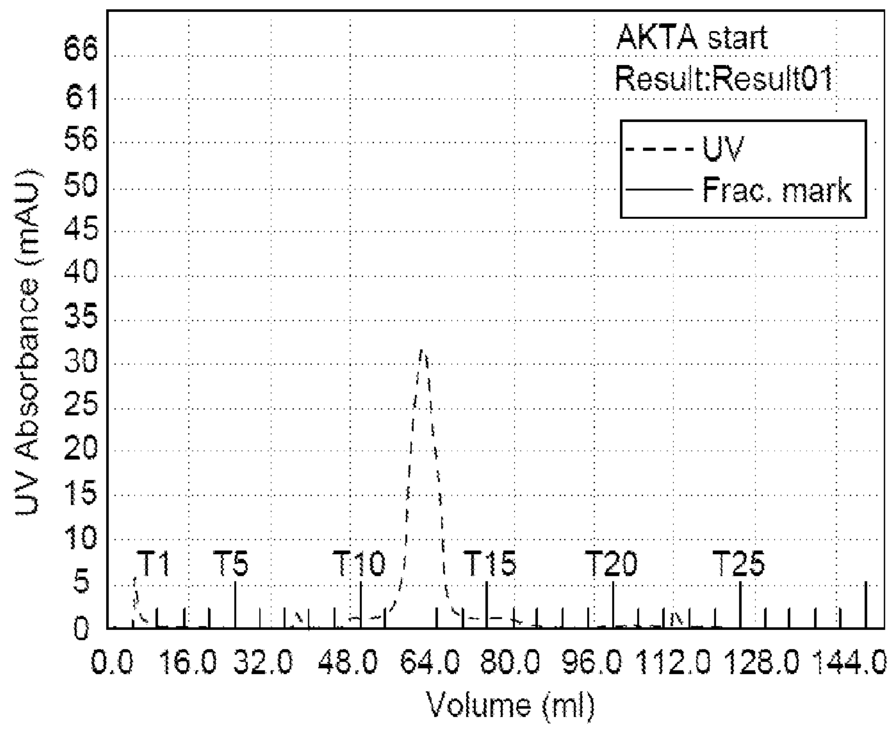
Figure 20:
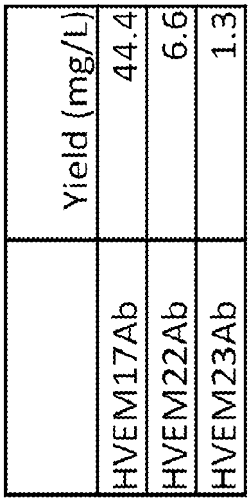
FIG. 20 presents a picture of a SDS-PAGE blot showing anti-HVEM antibody clones 17Ab, 22Ab and 23Ab (NR: non-reduced; R: reduced).
Figure 20:
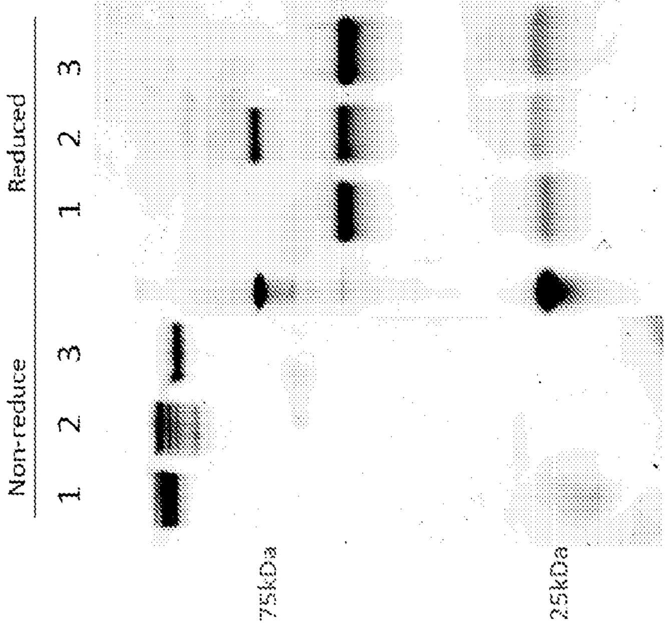
Figure 21A:
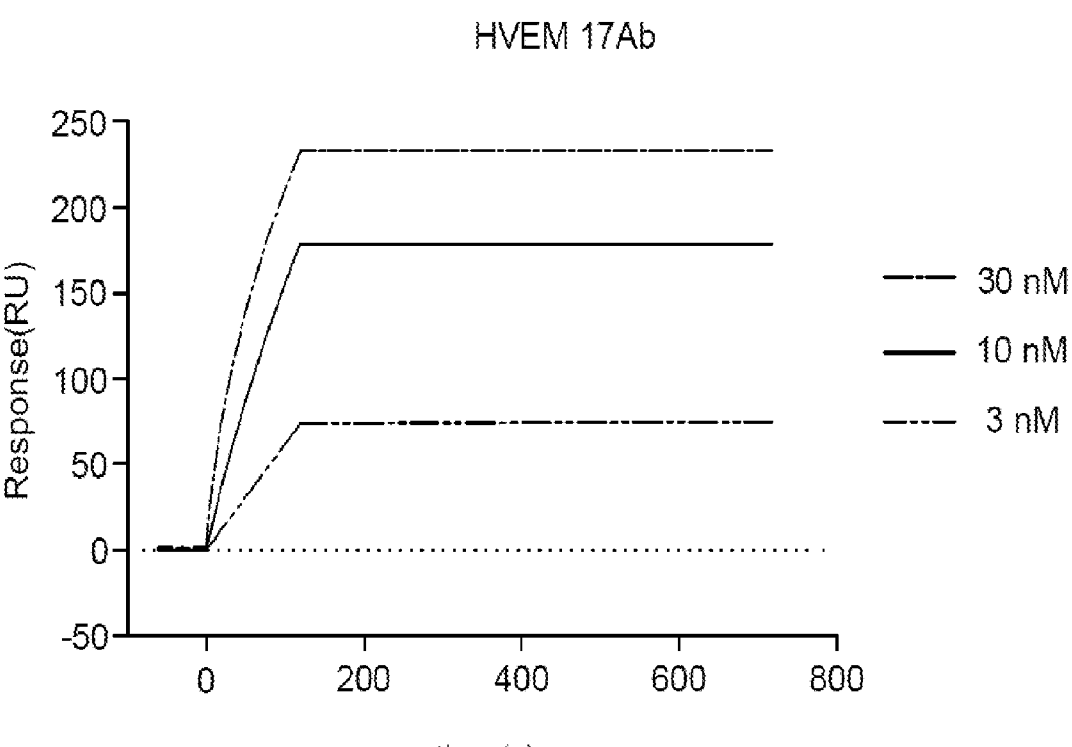
FIGS. 21A-21D present graphs showing binding of anti-HVEM antibody clones 17Ab (FIG. 21A), 22Ab (FIG. 21B), 23Ab (FIG. 21C) and 5Ab (FIG. 21D) on SPR.
Figure 21B:
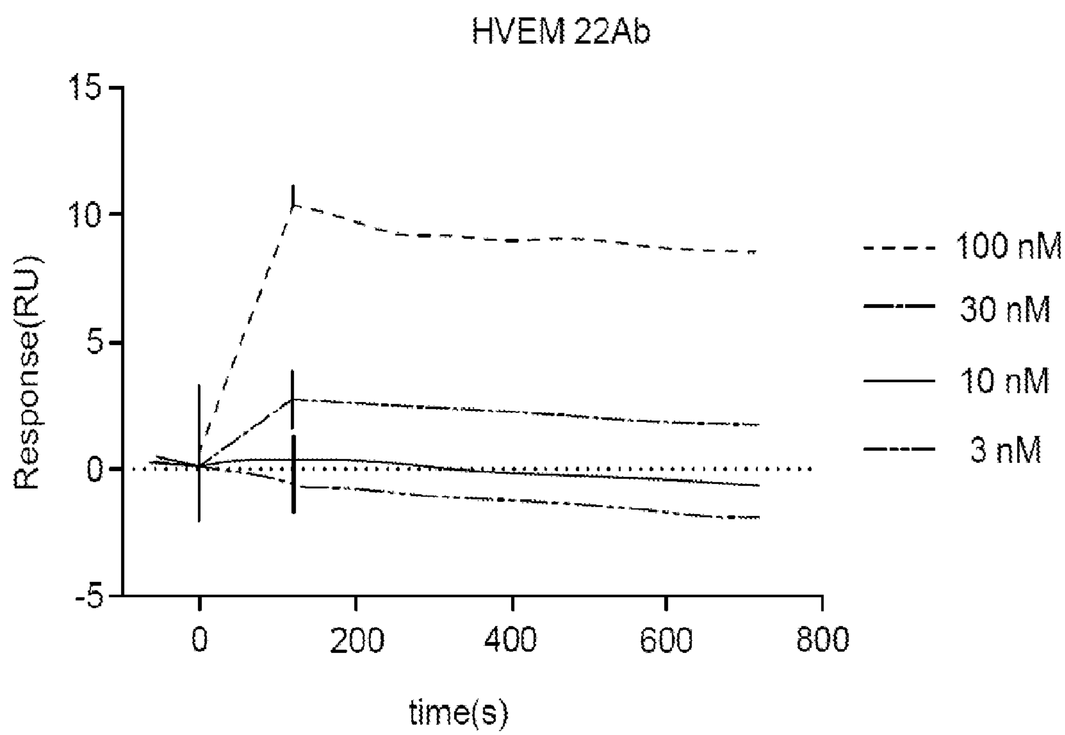
Figure 21C:
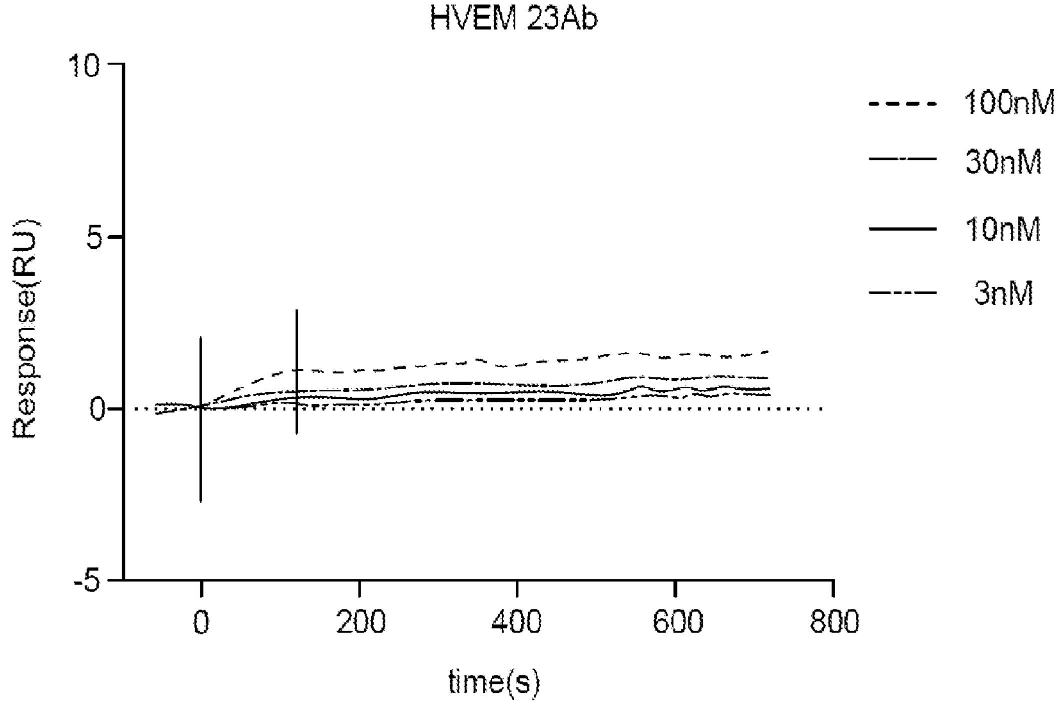
Figure 21D:
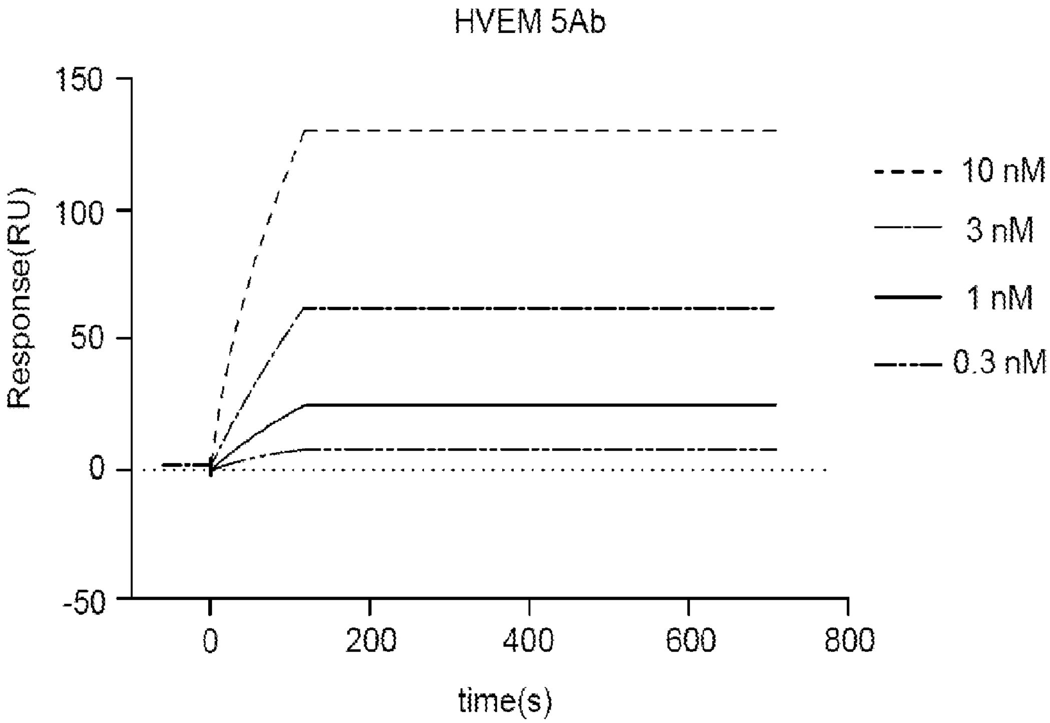
Figure 23:
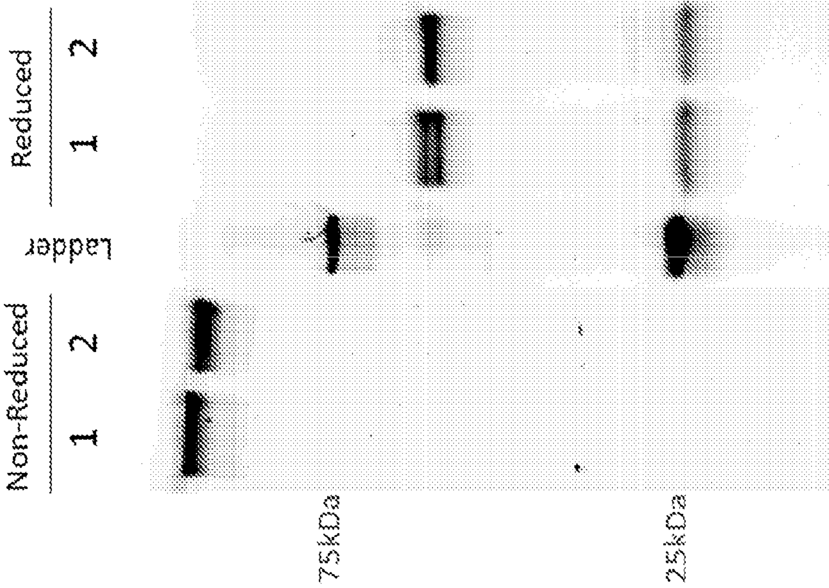
FIG. 23 is a picture of a SDS-PAGE blot showing anti-HVEM antibody clones comprising murine IgG1 or IgG2a (NR: non-reduced; R: reduced).
Figure 24A:
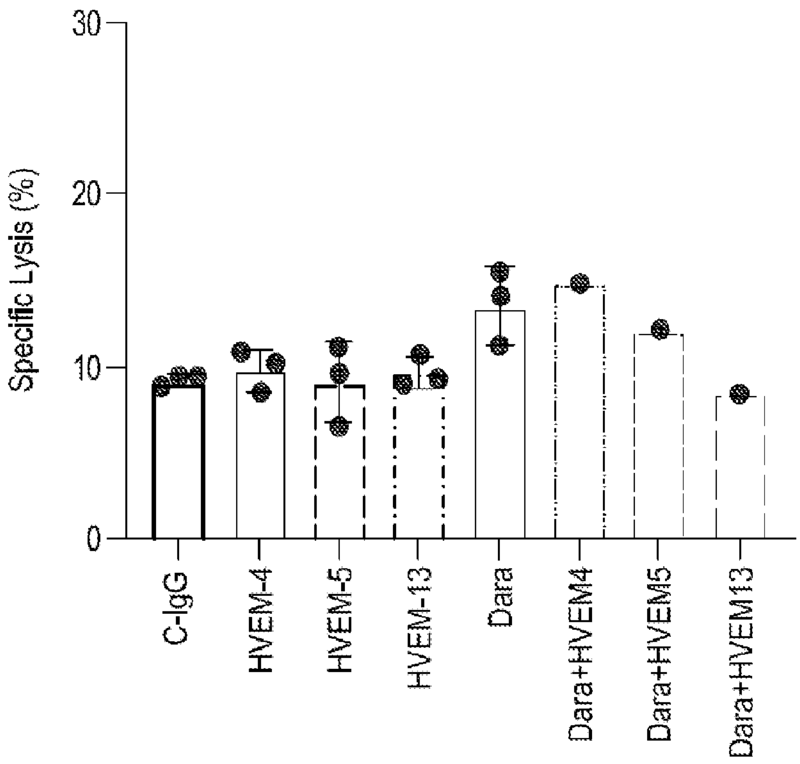
FIGS. 24A-24D present exemplary data showing that anti-HVEM antibody clones HVEM4, HVEM5, and HVEM13 do not induce ADCC in normal cells, fibroblasts, and bone marrow. ADCC assays were conducted using the following cells as effector cells: CSFE-labeled Normal Fibroblast BJ (ATCC® CRL-2522) (FIG. 24A), CSFE-labeled Normal Bone Marrow Stromal Cells (HS5) (FIG. 24B); CSFE-labeled Umbilical cord cell line (HEK-293) (FIG. 24C); and MM.1S gfp+/Luc+(internal control) (FIG. 24D). Bar graphs showing effector cell killing activity (%) obtained from 1 healthy donor (HD) in n=3 technical replicates in presence of control IgG (C-IgG), anti-HVEM4 (HVEM4), anti-HVEM5 (HVEM5), anti-HVEM13 (HVEM13), Daratumumab (DARA), and combinations thereof. Effector cells (NK cells) were obtained from HD, and target cells were co-cultured at 8:1 effector:target ratio, for 4 hrs, then incubated (10 μg/mL) for all antibodies. After incubation, the killing induction (%) was assessed by flow cytometry using 7-aminoactinomycin D (7-AAD) (Cat. #51-68981E BD Biosciences). Data are representative of the average of three technical replicates. Data are expressed as the mean±SEM (n=3).
Figure 24B:
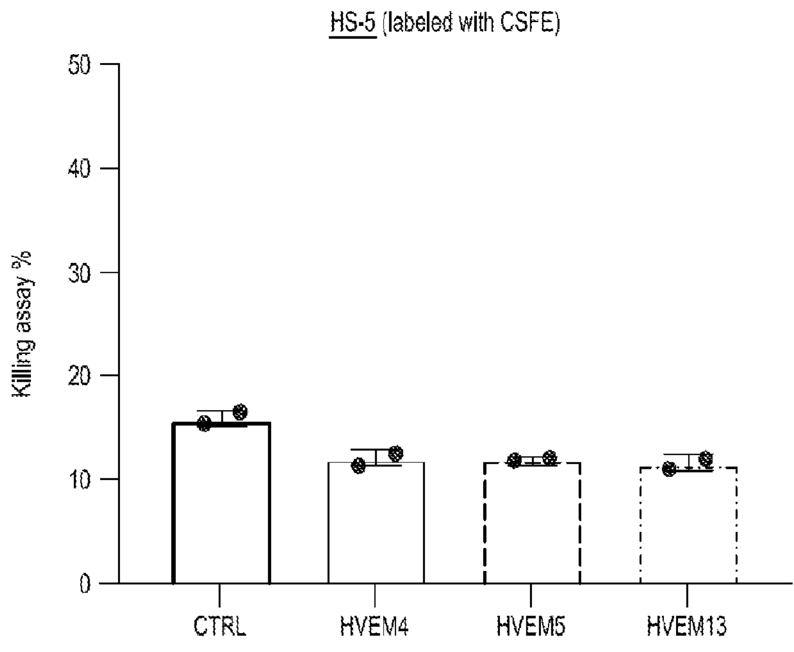
Figure 24C:
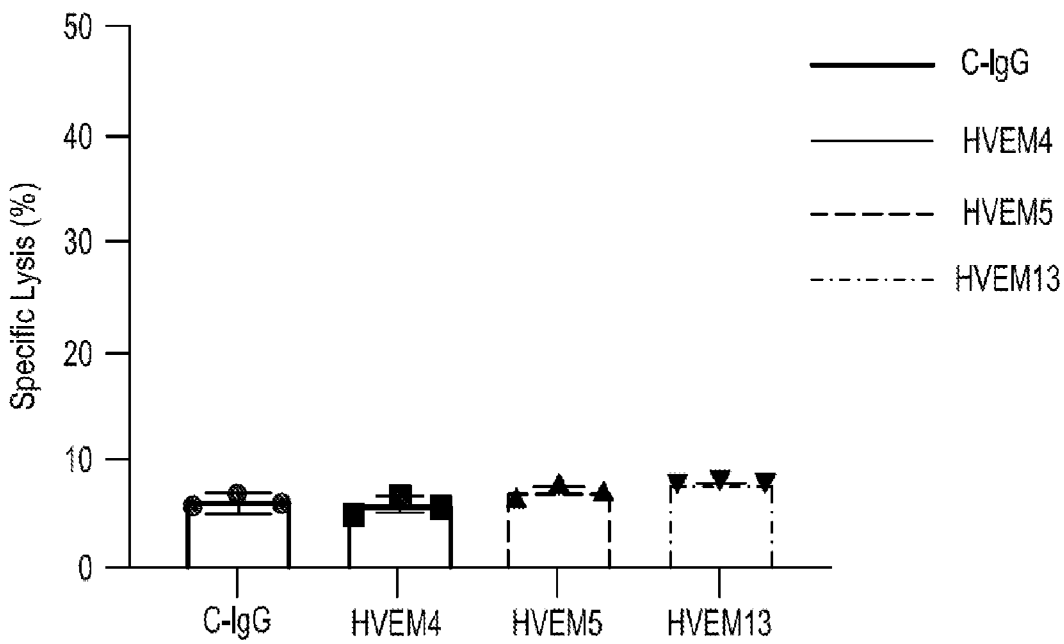
Figure 24D:
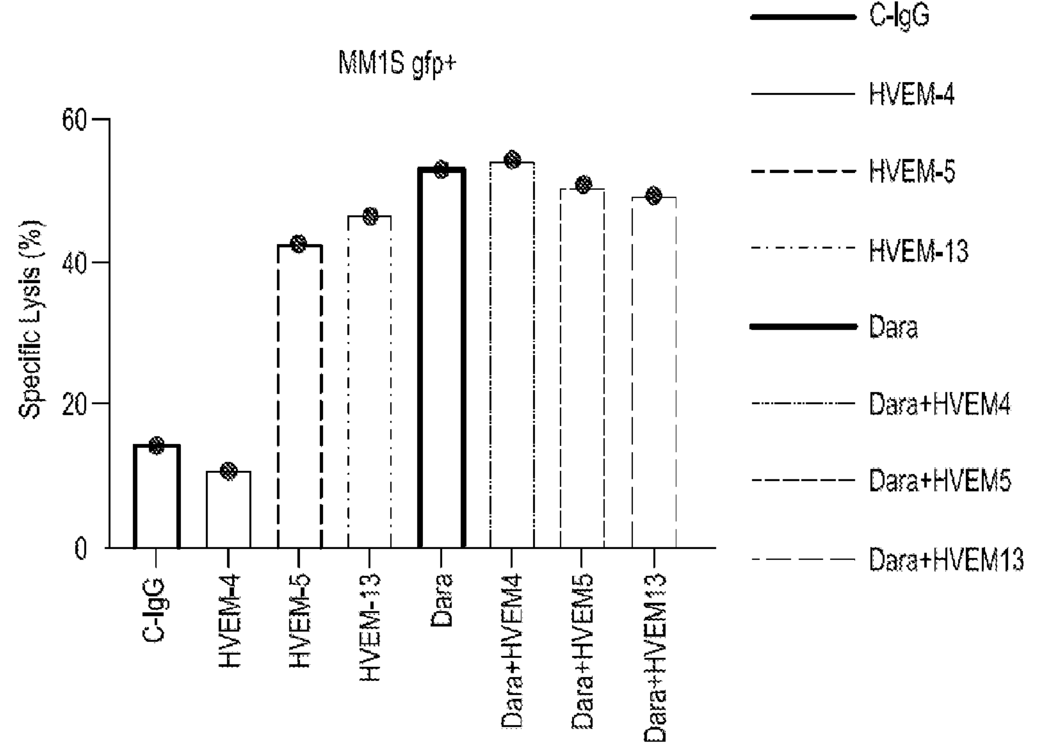
Figure 25C:
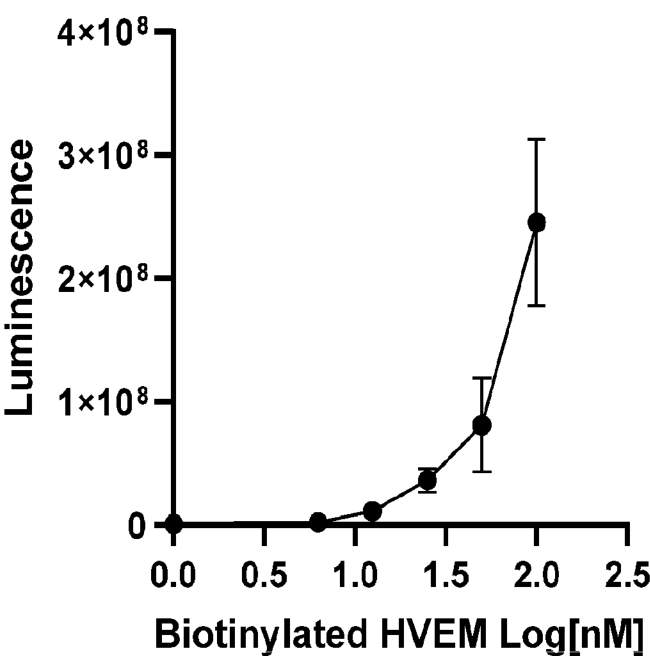
Figure 26A:
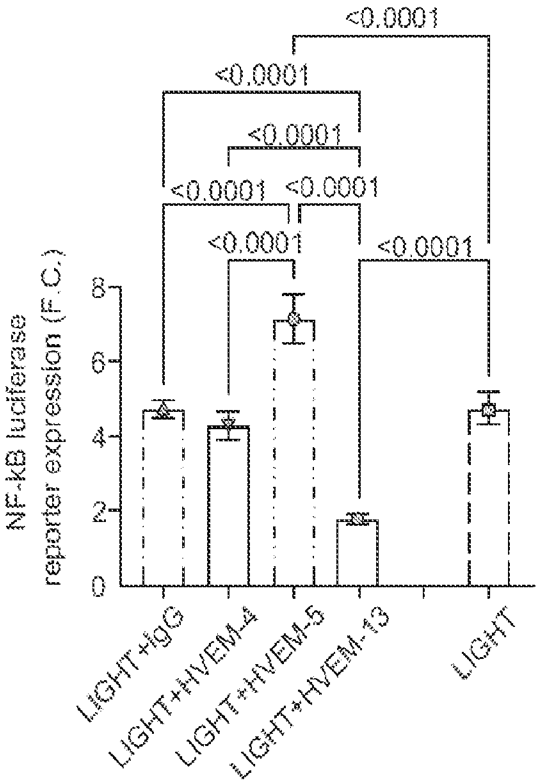
FIGS. 26A-26B present exemplary data from two separate experiments demonstrating that HVEM5 increases NF-κB LIGHT-induced activity while HVEM13 impairs LIGHT activity in T cells overexpressing HVEM. In vitro competition binding assays on cells were performed using HVEM and LIGHT/CD160/BTLA in the presence of anti-HVEM antibodies. Binding assays were performed on Jurkat cells carrying an NF-κB luciferase reporter and overexpressing human HVEM using human, recombinant and His-tagged LIGHT and HVEM4, HVEM5, or HVEM13 antibodies or C-IgG.
Figure 26B:
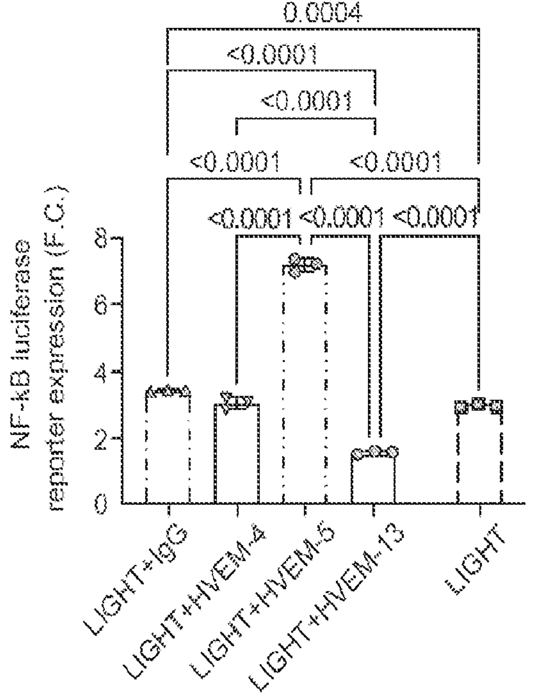
Figure 27A:
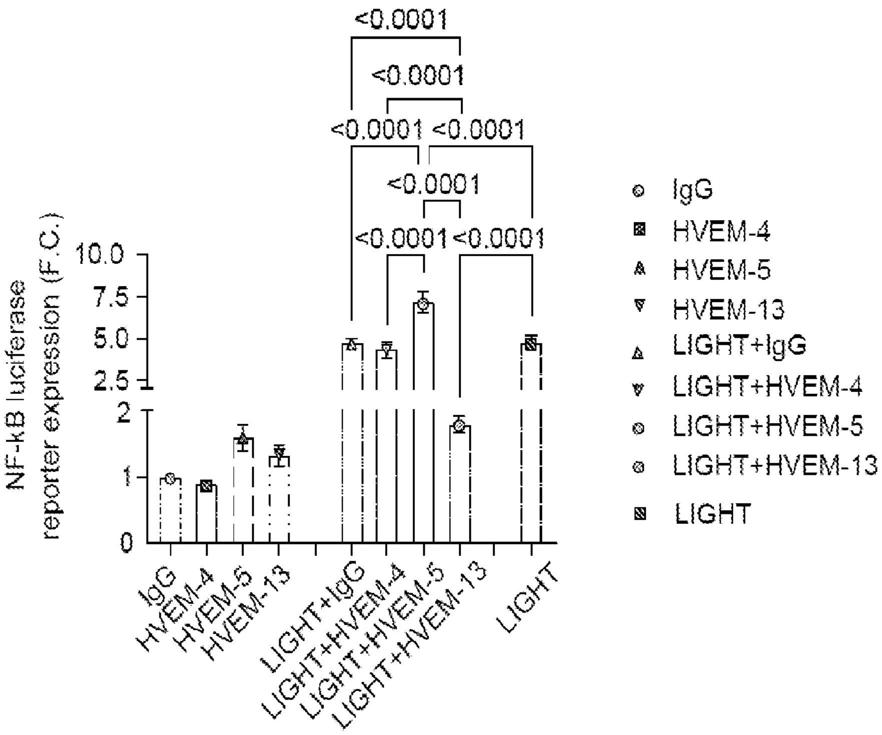
FIGS. 27A-27B present exemplary data from two different experiments demonstrating that HVEM5 acts as an agonist of LIGHT while HVEM13 acts as an antagonist of LIGHT. In vitro competition binding assays on cells were performed using HVEM and LIGHT/CD160/BTLA in the presence of anti-HVEM antibodies. LIGHT, either in soluble form or as an oligomer expressed on the cell surface, can activate NF-κB through binding to HVEM. Binding assays were performed on Jurkat cells carrying a luciferase gene under the control of 4 copies of NF-κB response elements and constitutive expression of human HVEM using human, recombinant and His-tagged LIGHT and HVEM4, HVEM5, or HVEM13 antibodies or C-IgG. Experiments were performed twice in technical triplicates.
Figure 27B:
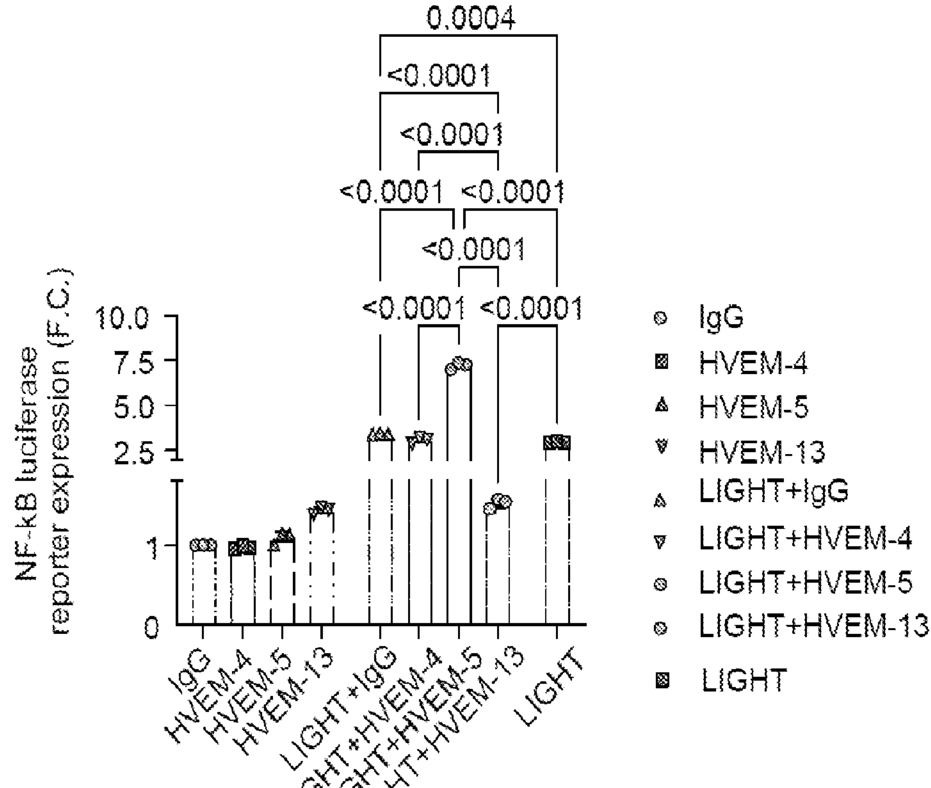
Figure 28A:
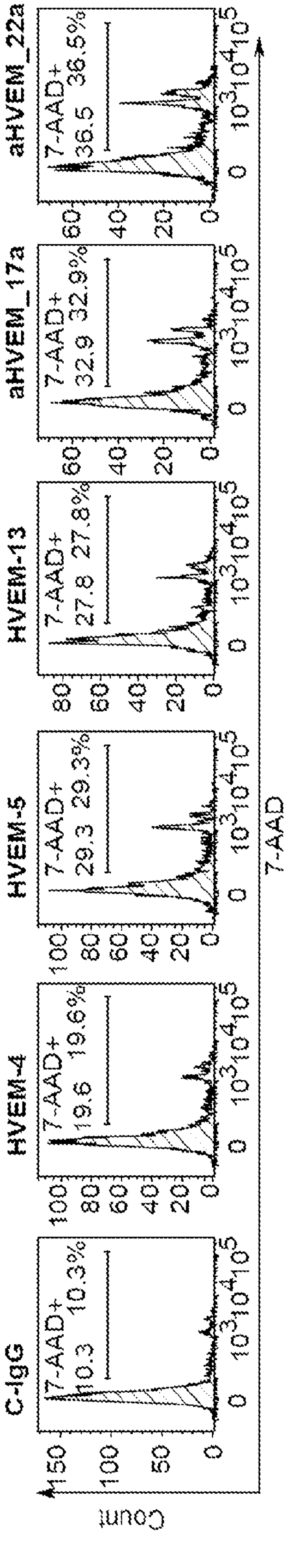
FIGS. 28A-28B present exemplary data showing that HVEM5, HVEM13, HVEM17 and HVEM22 induce ADCC in MM cells.
Figure 28B:
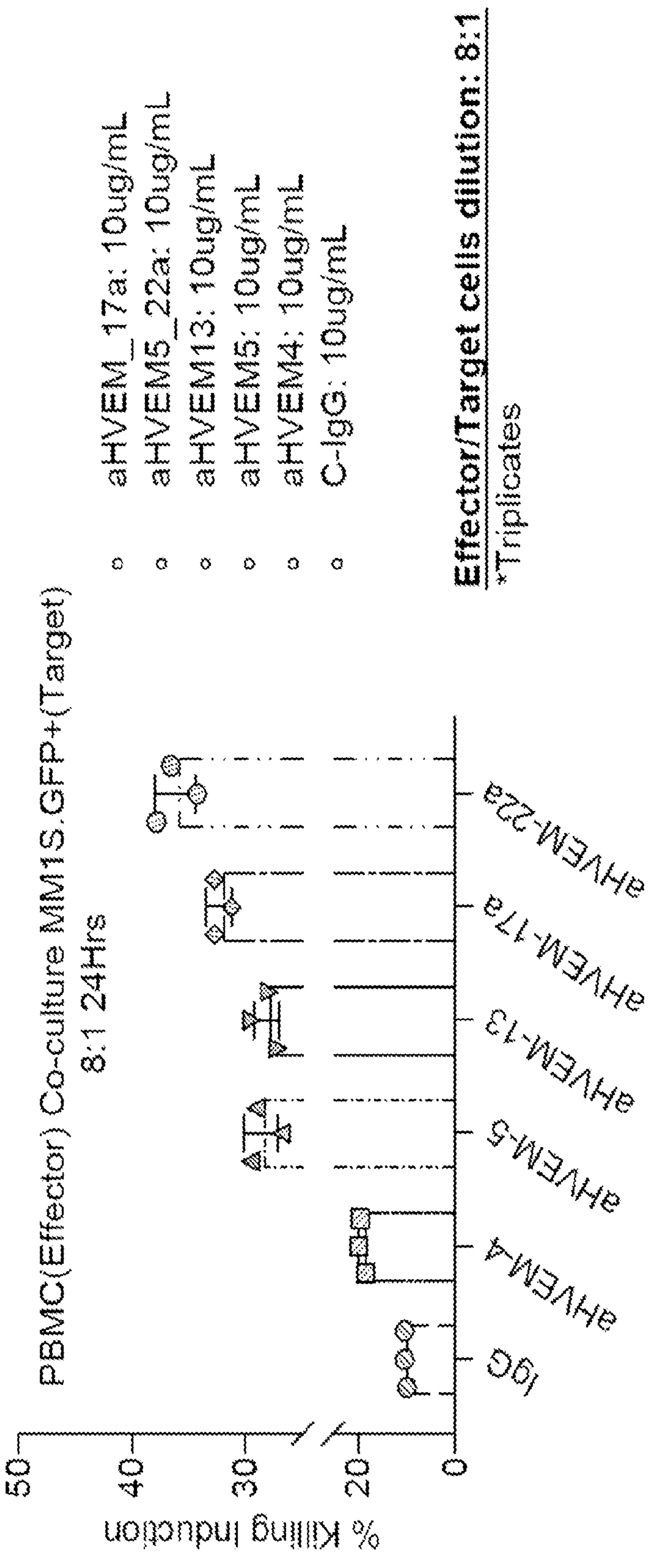
Figure 29A:
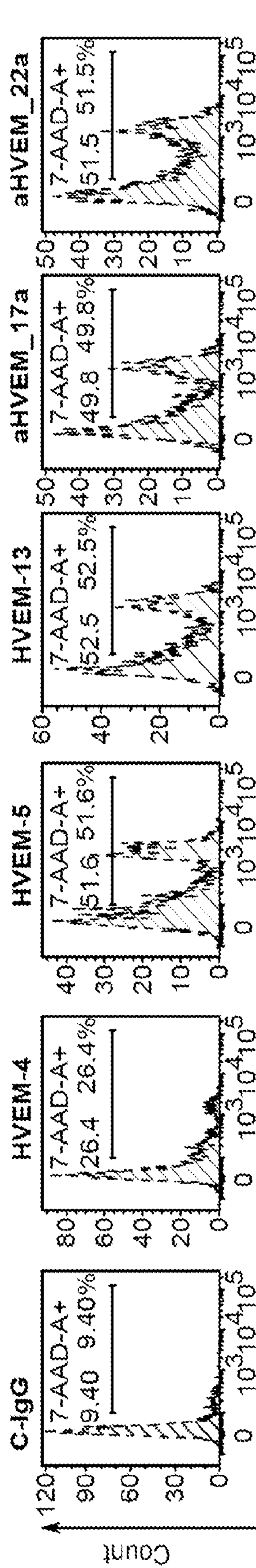
FIGS. 29A-29B present exemplary data showing that HVEM5, HVEM13, HVEM17 and HVEM22 induce ADCC in MM cells.
Figure 29A:
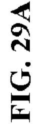
Figure 29B:
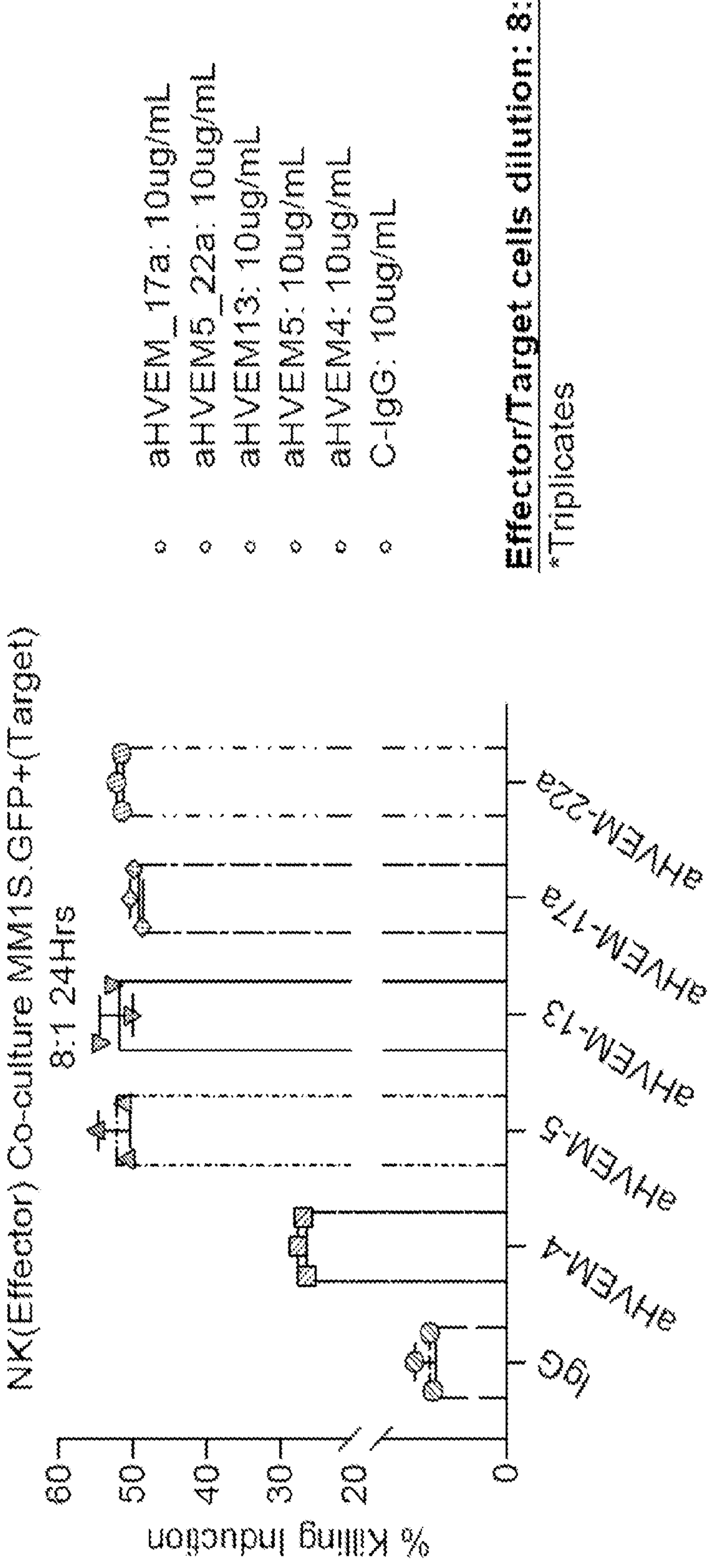
Figure 30A:
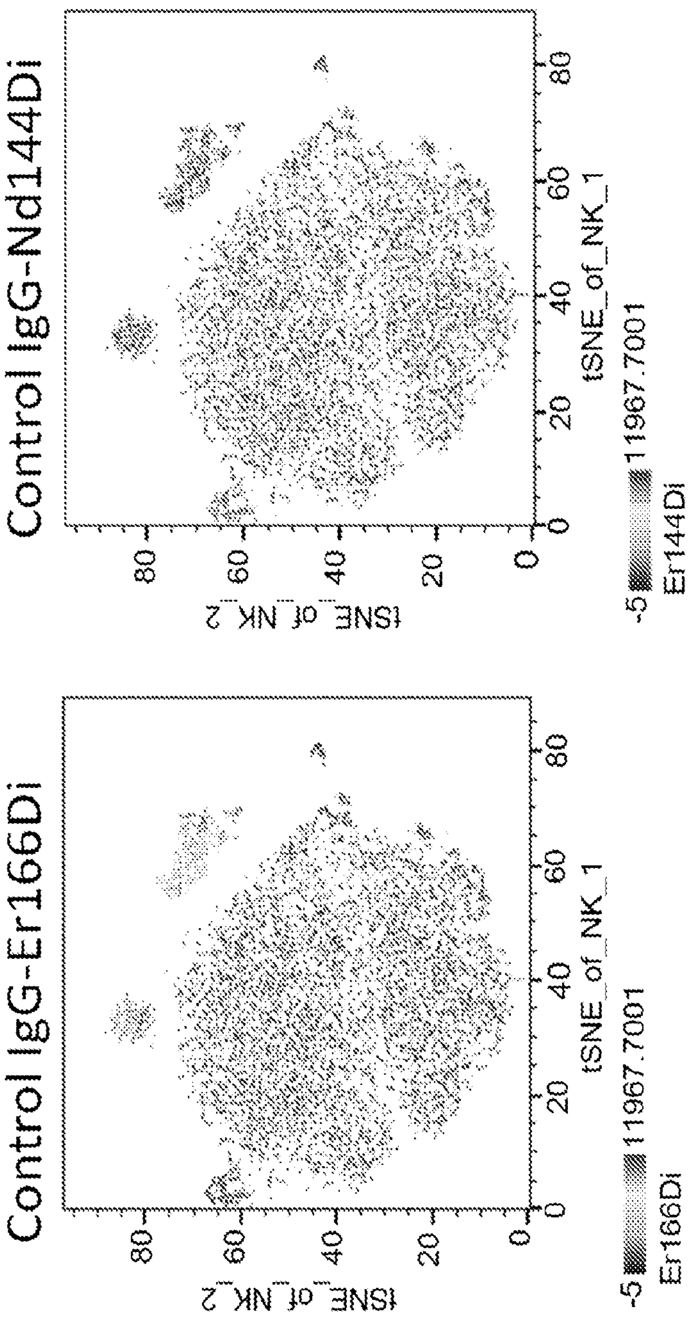
FIGS. 30A-30C present exemplary data showing that HVEM13 and HVEM5 cross-react with cynomolgus monkey PBMCs. Metal-conjugated HVEM-5 and 13 were used to assess Cynomolgus Monkey Cross Reactivity by mass cytometry (CyTOF).
Figure 30A:
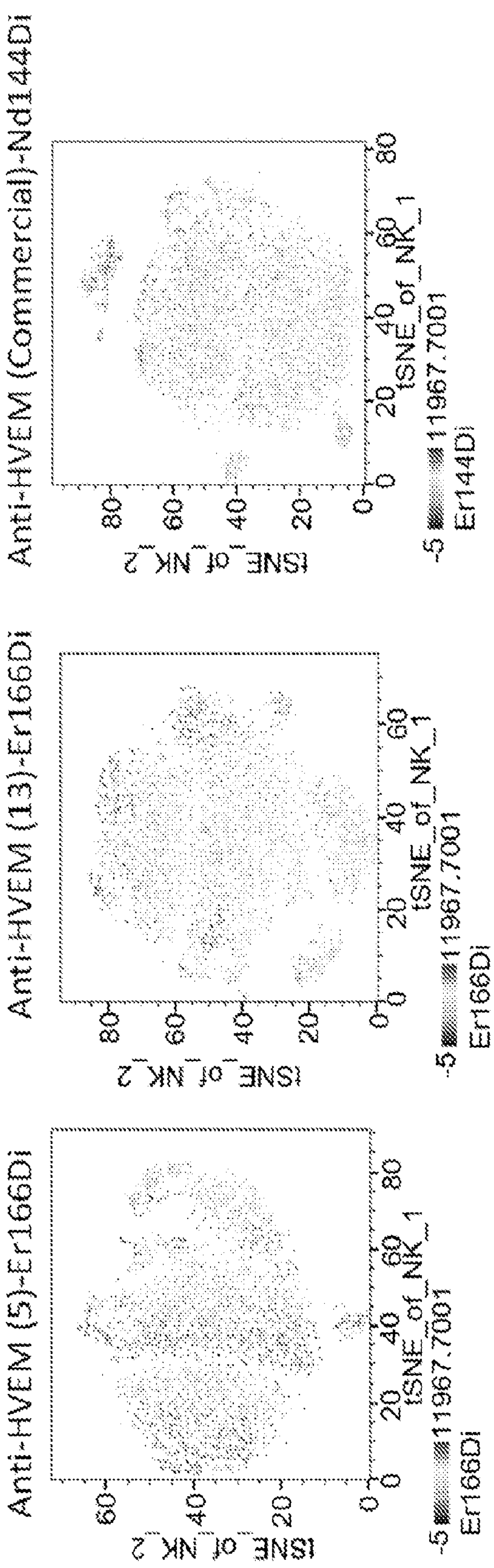
Figure 30B:
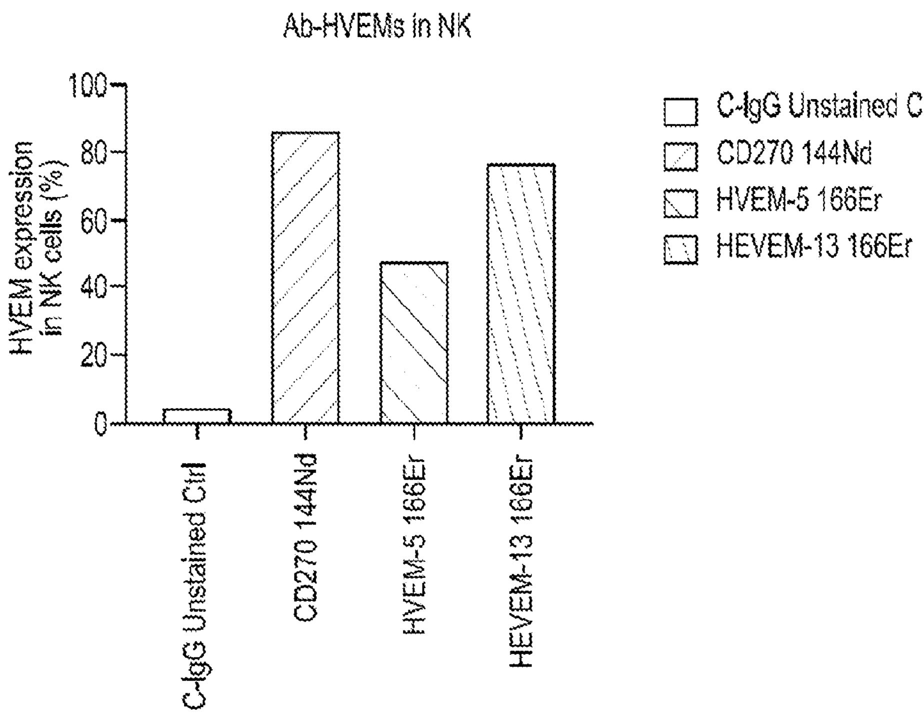
Figure 30C:
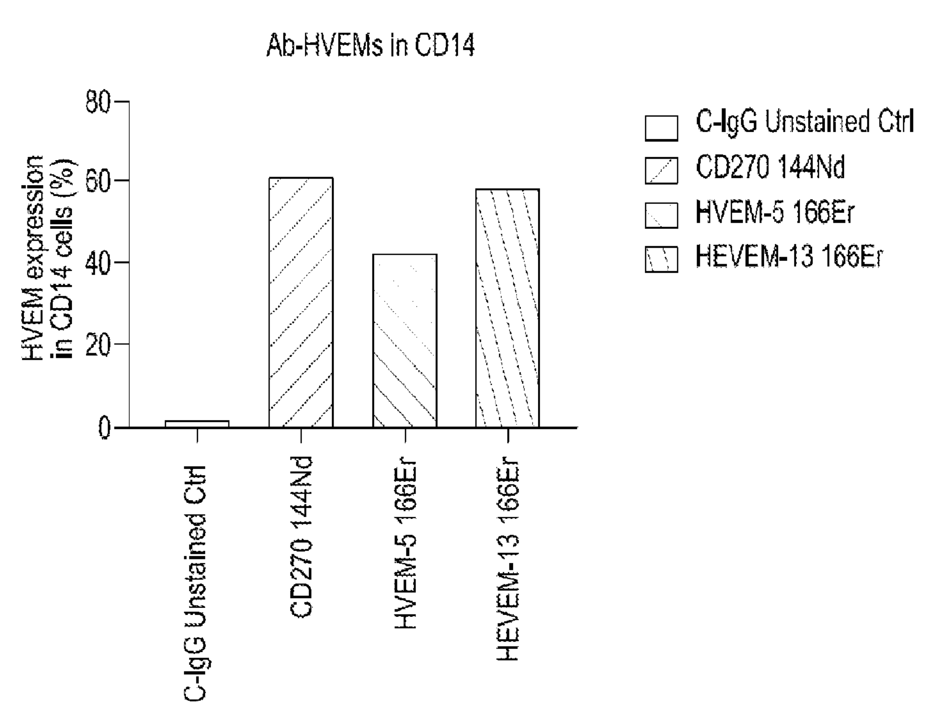
Figure 31A:
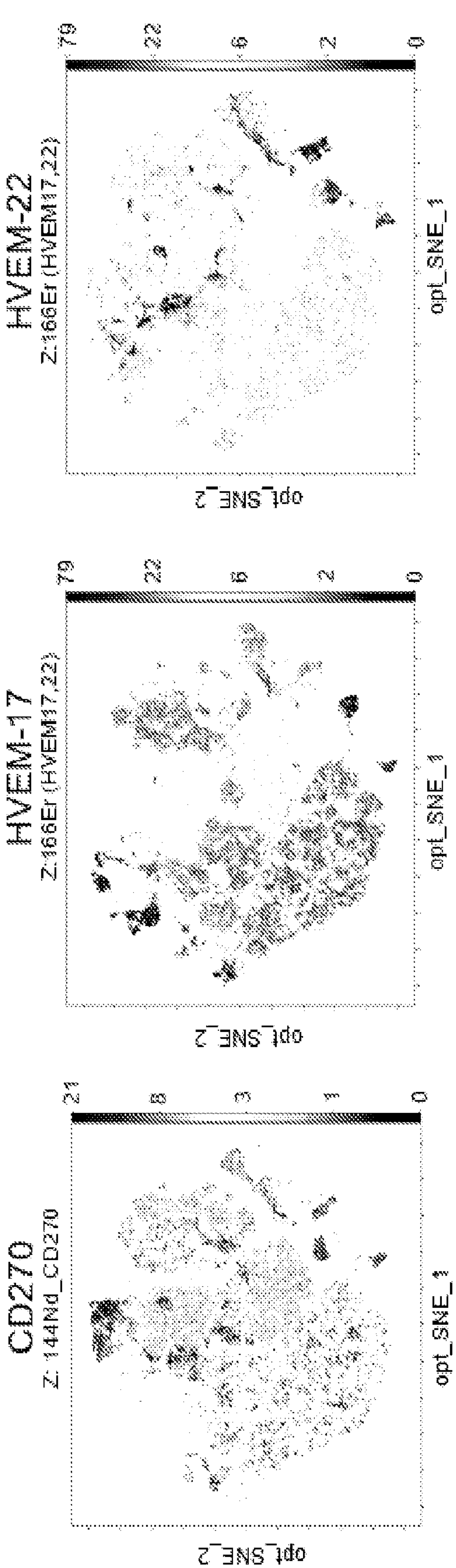
FIGS. 31A-31B present exemplary data showing that HVEM17 and HVEM22 bind PBMCs from cynomolgus monkey. Metal-conjugated HVEM-17 and 22 were used to assess the HVEM binding on Cynomolgus Monkey total PBMCs by mass cytometry (CyTOF).
Figure 31B:
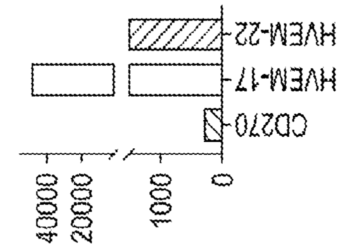
Figure 31B:
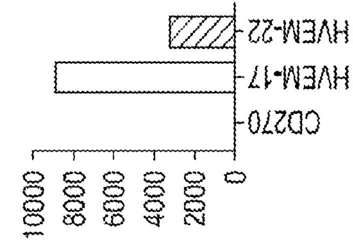
Figure 31B:
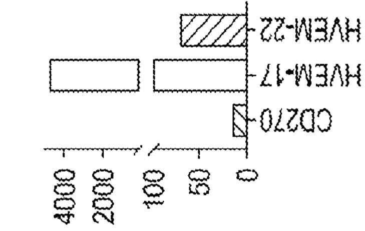
Figure 31B:
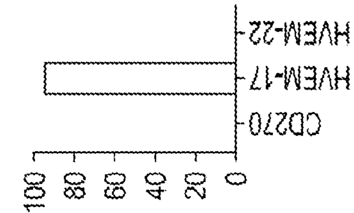
Figure 31B:
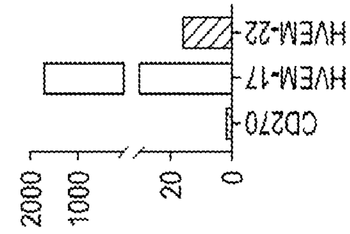
Figure 32A:
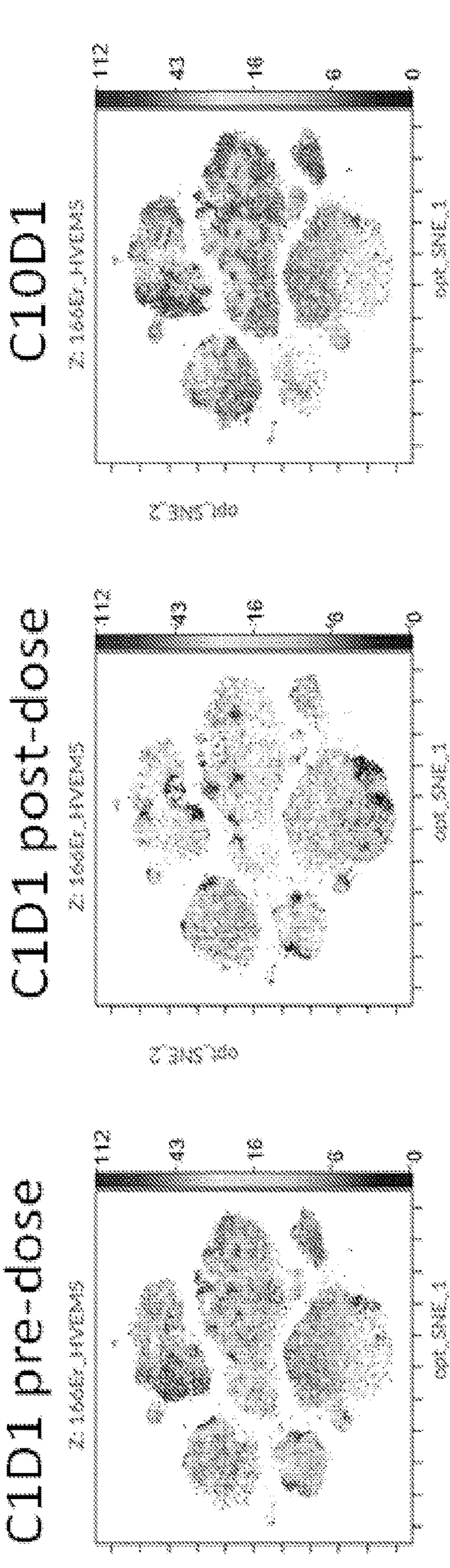
FIGS. 32A-32B present exemplary data from a longitudinal Dara-Progressing patient shows increased HVEM expression at progression following the course of treatment.
Figure 32A:
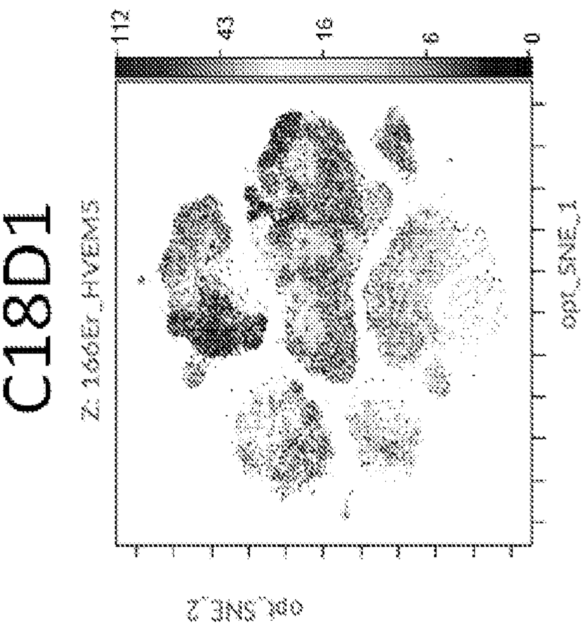
Figure 32A:
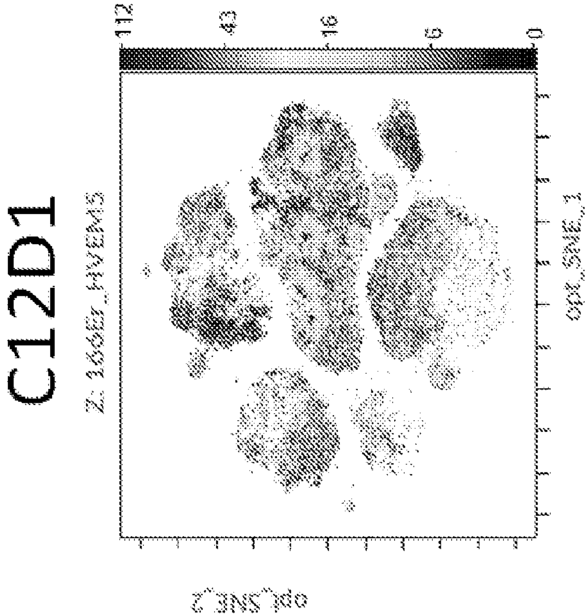
Figure 32B:
Figure 33A:
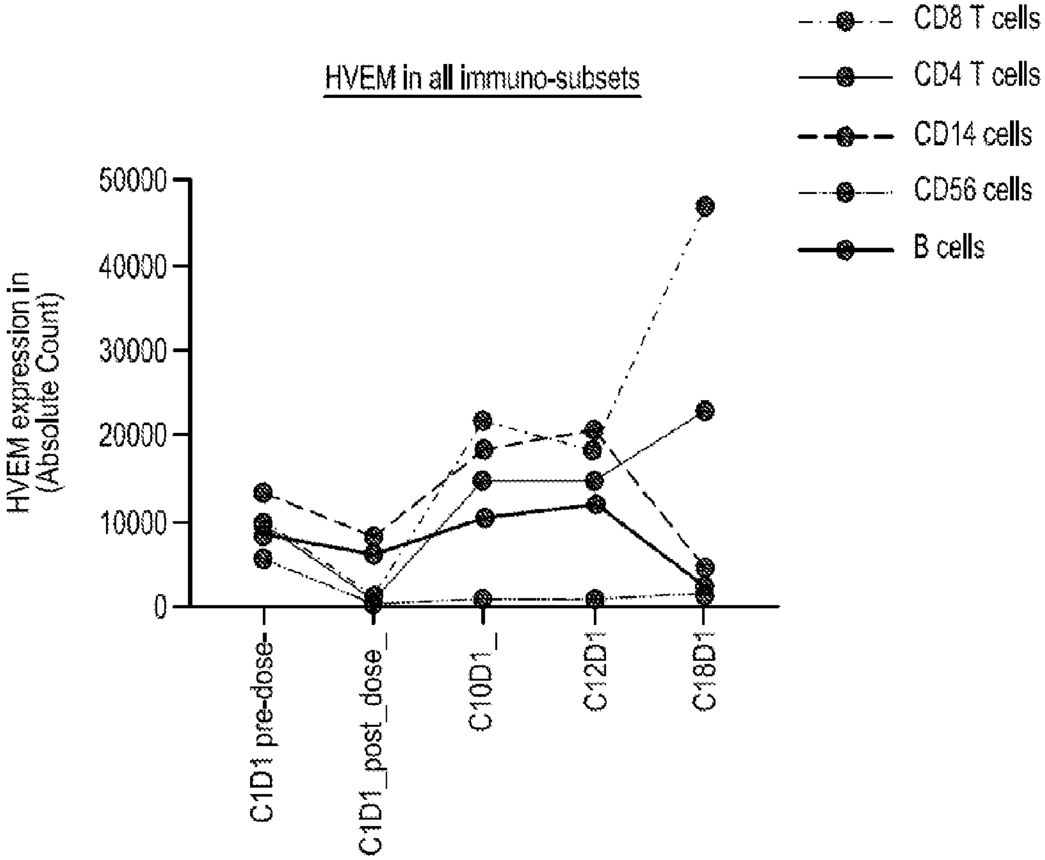
FIGS. 33A-33E present exemplary data showing increased expression of HVEM, TIGIT, TIM-3 and PD-1 in CD8+ T cells during anti-MM treatment in a longitudinal Dara-Progressing patient.
Figure 33B:
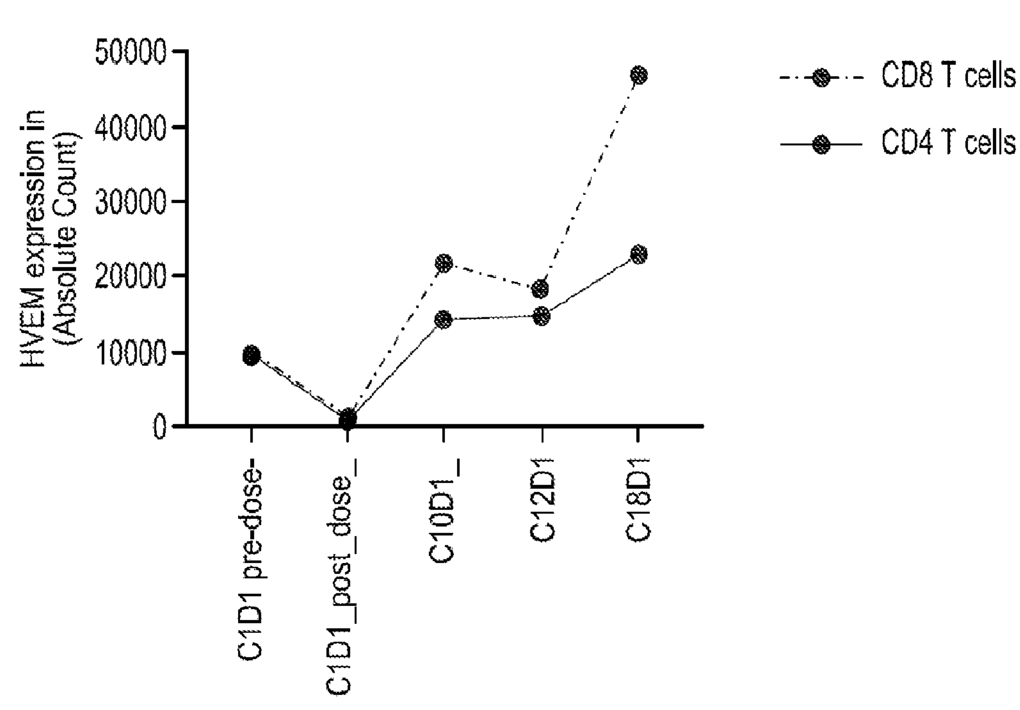
Figure 33C:
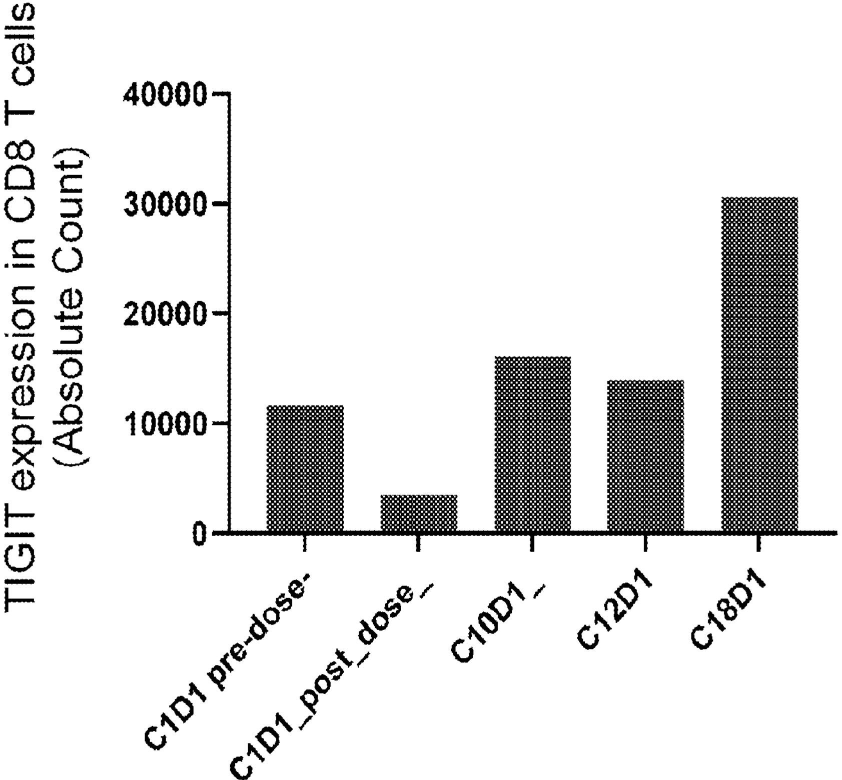
Figure 33D:
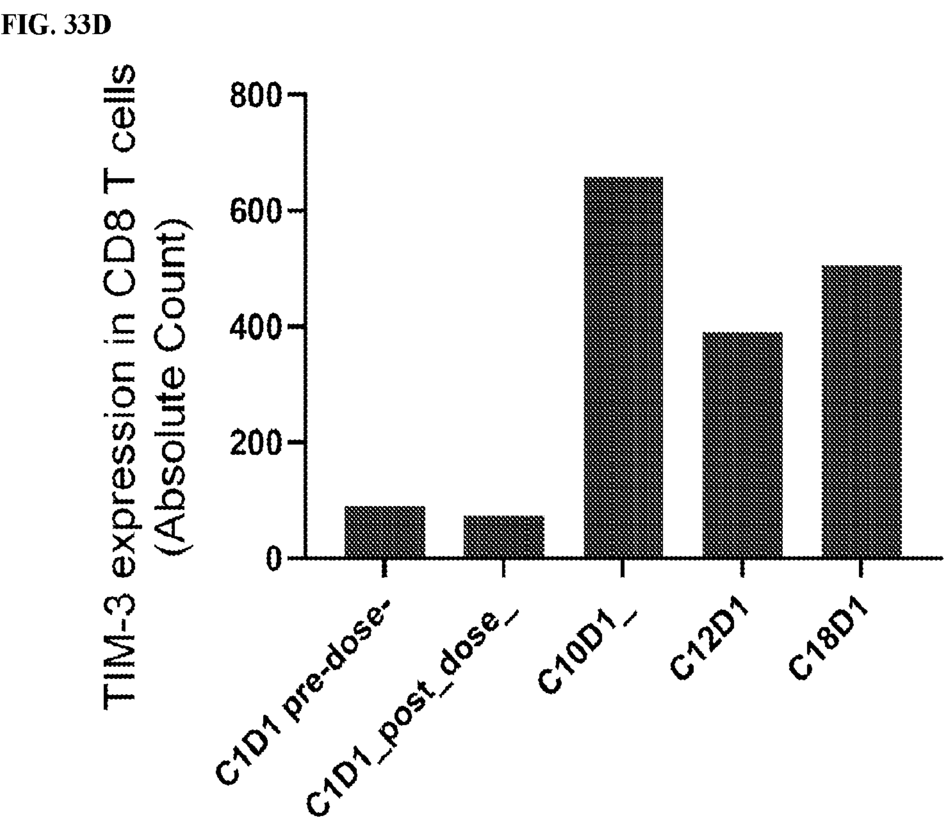
Figure 33E:
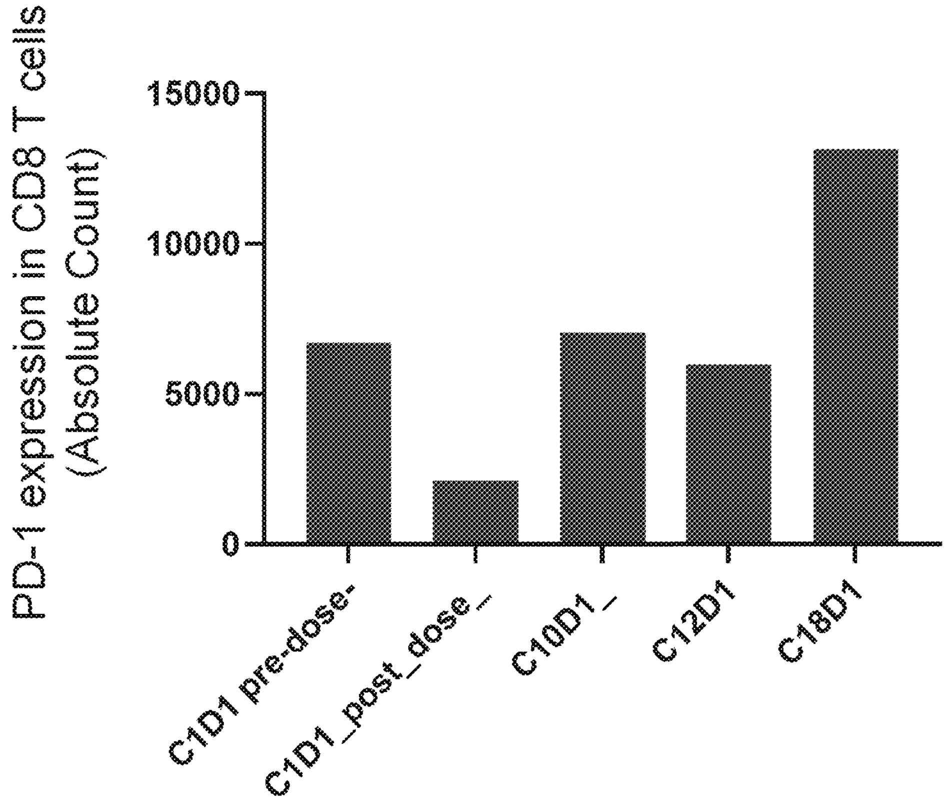

Example 9: Mouse Chimeric (Mc)HVEM13 Induced Antibody Dependent Mediated Cytotoxicity in Myeloma Cells Effector cells, fresh isolated NK cells from healthy donor (HD), and target cells, MM.1S GFP+/Luc+ cells were co-cultured at different ratios effector:target ratio (1:1, 4:1, 8:1) for 4 hours. Briefly, effector cells ($2\times10^6$ cells/well for the 8:1 ratio) were seeded at the appropriate concentration then co-cultured with the appropriate ratio of target cells, then incubated, with either human-IgG (Cat. #1-001-A) or Daratumumab (Dara-mAb) (Cat. #NCD 57894-502-05) (10 μg/mL) or aHVEM13 (10 μg/mL) for 4 hrs. After incubation, the killing induction (%) was assessed by flow cytometry using 7-aminoactinomycin D (7-AAD) (Cat. #51-68981E BD Biosciences). Data are expressed as the mean±SEM (n=3). The anti-CD38 daratumumab was used as internal positive control while the total human-IgG was used as internal negative control. See FIGS. 9-10.

In FIG. 12, HD (healthy donor) PBMCs stimulated with IL-2 o.n. (overnight) then co-cultured with MM1.S GFP+ and treated 12 hours with Dara and HVEM13 antibodies.

Example 10: Imaging Mass Cytometry of Mice and Human Bone Marrow Tissue

Mass cytometry was performed on mice bone marrow tissues engrafted with MM1.S cells. Mass cytometry staining of the bone marrow tissues was carried out with 166Er-conjugated HVEM antibodies. HVEM-4, 5, 13, 17, and 22 were used for staining and the nucleus was counterterstained with Ir-191. Imaging mass cytometry of mouse bone marrow engrafted with multiple myeloma cells revealed extensive HVEM-17 binding.

Mass cytometery was performed on bone marrow from a patient with multiple myeloma. Mass cytometry staining of bone marrow tissues from the patient was carried out with 166Er-conjugated HVEM antibodies. HVEM-4, 5, 13, 17, and 22 were used for staining and the nucleus was counterterstained with Ir-191. Imaging mass cytometry of bone marrow tissues from a patient with multiple myeloma revealed extensive HVEM-17 and HVEM-22 binding.

CyTOF imaging was performed on a healthy tissue microarray. Sample tissues probed using CyTOF imaging included: thyroid, spleen, uterus, ovary, pancreas, lung, prostate, testis, stomach, colon, liver, and kidney. Mass cytometry staining on the healthy tissue microarray was carried out using 166Er-conjugated HVEM-17 or HVEM-22 antibodies. The nucleus was counterstained with Ir-191. Results revealed that HVEM-17 does not bind any of the organs tested in the healthy tissue microarray.

EMBODIMENTS

P Embodiment 1. An anti-Herpes Virus Entry Mediator (HVEM) antibody comprising a light chain variable domain and a heavy chain variable domain, wherein said light chain variable domain comprises: a CDR L1 as set forth in SEQ ID NO:1, a CDR L2 as set forth in SEQ ID NO:2 and a CDR L3 as set forth in SEQ ID NO:3; and wherein said heavy chain variable domain comprises: a CDR H1 as set forth in SEQ ID NO:4, a CDR H2 as set forth in SEQ ID NO:5, and a CDR H3 as set forth in SEQ ID NO:6.

P Embodiment 2. The antibody of P embodiment 1, wherein said light chain variable domain comprises a FR L1 as set forth in SEQ ID NO:7, a FR L2 as set forth in SEQ ID NO:8, a FR L3 as set forth in SEQ ID NO:9 and a FR L4 as set forth in SEQ ID NO:10.

P Embodiment 3. The antibody of P embodiment 1 or 2, wherein said heavy chain variable domain comprises a FR H1 as set forth in SEQ ID NO:11, a FR H2 as set forth in SEQ ID NO:12, a FR H3 as set forth in SEQ ID NO:13 and a FR H4 as set forth in SEQ ID NO:14.

P Embodiment 4. The antibody of any one of P embodiments 1-3, wherein said light chain variable domain comprises the sequence of SEQ ID NO:15.

P Embodiment 5. The antibody of any one of P embodiments 1-4, wherein said heavy chain variable domain comprises the sequence of SEQ ID NO:16.

P Embodiment 6. The antibody of any one of P embodiments 1-5, wherein said antibody is a humanized antibody.

P Embodiment 7. The antibody of any one of P embodiments 1-5, wherein said antibody is a chimeric antibody.

P Embodiment 8. The antibody of any one of P embodiments 1-5, wherein said antibody is a Fab' fragment.

P Embodiment 9. The antibody of any one of P embodiments 1-6, wherein said antibody is a single chain antibody (scFv).

P Embodiment 10. The antibody of any one of P embodiments 1-5 or 9, wherein said light chain variable domain and said heavy chain variable domain form part of a scFv P Embodiment 11. The antibody of any one of P embodiments 1-7, wherein said antibody is an IgG.

P Embodiment 12. The antibody of any one of P embodiments 1-7, wherein said antibody is an IgG1.

P Embodiment 13. The antibody of any one of P embodiments 1-12, wherein said antibody is capable of binding a Herpes Virus Entry Mediator (HVEM) protein.

P Embodiment 14. The antibody of any one of P embodiments 1-13, wherein said antibody is bound to a Herpes Virus Entry Mediator (HVEM) protein.

P Embodiment 15. The antibody of P embodiment 14, wherein said HVEM forms part of a cell.

P Embodiment 16. The antibody of P embodiment 15, wherein said cell is a plasma cell.

P Embodiment 17. The antibody of P embodiment 15 or 16, wherein said cell is a myeloma cell.

P Embodiment 18. An isolated nucleic acid encoding an antibody of P embodiment 1.

P Embodiment 19. A pharmaceutical composition comprising a therapeutically effective amount of an antibody of any one of P embodiments 1-17 and a pharmaceutically acceptable excipient.

P Embodiment 20. A method of treating cancer in a subject in need thereof, said method comprising administering to a subject a therapeutically effective amount of an antibody of any one of P embodiments 1-17, thereby treating cancer in said subject.

P Embodiment 21. The method of treating cancer of P embodiment 20, wherein the cancer is melanoma, lymphoma, carcinoma, myeloma, leukemia, glioma, breast cancer, prostate cancer, bladder cancer, uterine cancer, gastric cancer, colorectal cancer, lung cancer, esophageal cancer, brain cancer, head and neck cancer, renal cancer, hepatic cancer, or thyroid cancer.

P Embodiment 22. A recombinant protein comprising: (i) an antibody region comprising: (a) a light chain variable domain comprising a CDR L1 as set forth in SEQ ID NO:1, a CDR L2 as set forth in SEQ ID NO:2 and a CDR L3 as set forth in SEQ ID NO:3; and (b) a heavy chain variable domain comprising a CDR H1 as set forth in SEQ ID NO:4, a CDR H2 as set forth in SEQ ID NO:5, and a CDR H3 as set forth in SEQ ID NO:6; and (ii) a transmembrane domain.

P Embodiment 23. An isolated nucleic acid encoding a recombinant protein of P embodiment 22.

P Embodiment 24. A pharmaceutical composition comprising a therapeutically effective amount of a recombinant protein of P embodiment 22 and a pharmaceutically acceptable excipient.

P Embodiment 25. A method of treating cancer in a subject in need thereof, said method comprising administering to a subject a therapeutically effective amount of a recombinant protein of P embodiment 22, thereby treating cancer in said subject.

P Embodiment 26. The method of treating cancer of P embodiment 25, wherein the cancer is melanoma, lymphoma, carcinoma, myeloma, leukemia, glioma, breast cancer, prostate cancer, bladder cancer, uterine cancer, gastric cancer, colorectal cancer, lung cancer, esophageal cancer, brain cancer, head and neck cancer, renal cancer, hepatic cancer, or thyroid cancer.

P Embodiment 27. A bispecific recombinant protein comprising: (i) a first antibody region capable of binding an effector cell ligand; and (ii) a second antibody region, comprising: (a) a light chain variable domain comprising a CDR L1 as set forth in SEQ ID NO:1, a CDR L2 as set forth in SEQ ID NO:2 and a CDR L3 as set forth in SEQ ID NO:3; and (b) a heavy chain variable domain comprising a CDR H1 as set forth in SEQ ID NO: 4, a CDR H2 as set forth in SEQ ID NO:5, and a CDR H3 as set forth in SEQ ID NO:6.

P Embodiment 28. A pharmaceutical composition comprising a therapeutically effective amount of a bispecific recombinant protein of P embodiment 27 and a pharmaceutically acceptable excipient.

P Embodiment 29. A method of treating cancer in a subject in need thereof, said method comprising administering to a subject a therapeutically effective amount of a bispecific recombinant protein of P embodiment 28, thereby treating cancer in said subject.

P Embodiment 30. The method of treating cancer of P embodiment 29, wherein the cancer is melanoma, lymphoma, carcinoma, myeloma, leukemia, glioma, breast cancer, prostate cancer, bladder cancer, uterine cancer, gastric cancer, colorectal cancer, lung cancer, esophageal cancer, brain cancer, head and neck cancer, renal cancer, hepatic cancer, or thyroid cancer.

P Embodiment 31. An anti-Herpes Virus Entry Mediator (HVEM) antibody comprising a light chain variable domain and a heavy chain variable domain, wherein said light chain variable domain comprises: a CDR L1 as set forth in SEQ ID NO: 17, a CDR L2 as set forth in SEQ ID NO: 18 and a CDR L3 as set forth in SEQ ID NO:19; and wherein said heavy chain variable domain comprises: a CDR H1 as set forth in SEQ ID NO: 20, a CDR H2 as set forth in SEQ ID NO:21, and a CDR H3 as set forth in SEQ ID NO: 22.

P Embodiment 32. The antibody of P embodiment 31, wherein said light chain variable domain comprises a FR L1 as set forth in SEQ ID NO:23, a FR L2 as set forth in SEQ ID NO:24, a FR L3 as set forth in SEQ ID NO:25 and a FR L4 as set forth in SEQ ID NO:26.

P Embodiment 33. The antibody of P embodiment 31 or 32, wherein said heavy chain variable domain comprises a FR H1 as set forth in SEQ ID NO:27, a FR H2 as set forth in SEQ ID NO:28, a FR H3 as set forth in SEQ ID NO:29 and a FR H4 as set forth in SEQ ID NO:30.

P Embodiment 34. The antibody of any one of P embodiments 31-33, wherein said light chain variable domain comprises the sequence of SEQ ID NO:31.

P Embodiment 35. The antibody of any one of P embodiments 31-34, wherein said heavy chain variable domain comprises the sequence of SEQ ID NO:32.

P Embodiment 36. The antibody of any one of P embodiments 31-35, wherein said antibody is a humanized antibody.

P Embodiment 37. The antibody of any one of P embodiments 31-35, wherein said antibody is a chimeric antibody.

P Embodiment 38. The antibody of any one of P embodiments 31-35, wherein said antibody is a Fab' fragment.

P Embodiment 39. The antibody of any one of P embodiments 31-36, wherein said antibody is a single chain antibody (scFv).

P Embodiment 40. The antibody of any one of P embodiments 31-35 or 39, wherein said light chain variable domain and said heavy chain variable domain form part of a scFv P Embodiment 41. The antibody of any one of P embodiments 31-37, wherein said antibody is an IgG.

P Embodiment 42. The antibody of any one of P embodiments 31-37, wherein said antibody is an IgG1.

P Embodiment 43. The antibody of any one of P embodiments 31-42, wherein said antibody is capable of binding a Herpes Virus Entry Mediator (HVEM) protein.

P Embodiment 44. The antibody of any one of P embodiments 31-43, wherein said antibody is bound to a Herpes Virus Entry Mediator (HVEM) protein.

P Embodiment 45. The antibody of P embodiment 44, wherein said HVEM forms part of a cell.

P Embodiment 46. The antibody of P embodiment 45, wherein said cell is a plasma cell.

P Embodiment 47. The antibody of P embodiment 45 or 46, wherein said cell is a myeloma cell.

P Embodiment 48. An isolated nucleic acid encoding an antibody of P embodiment 31.

P Embodiment 49. A pharmaceutical composition comprising a therapeutically effective amount of an antibody of any one of P embodiments 31-47 and a pharmaceutically acceptable excipient.

P Embodiment 50. A method of treating cancer in a subject in need thereof, said method comprising administering to a subject a therapeutically effective amount of an antibody of any one of P embodiments 31-47, thereby treating cancer in said subject.

P Embodiment 51. The method of treating cancer of P embodiment 50, wherein the cancer is melanoma, lymphoma, carcinoma, myeloma, leukemia, glioma, breast cancer, prostate cancer, bladder cancer, uterine cancer, gastric cancer, colorectal cancer, lung cancer, esophageal cancer, brain cancer, head and neck cancer, renal cancer, hepatic cancer, or thyroid cancer.

P Embodiment 52. A recombinant protein comprising: (i) an antibody region comprising: (a) a light chain variable domain comprising a CDR L1 as set forth in SEQ ID NO:17, a CDR L2 as set forth in SEQ ID NO:18 and a CDR L3 as set forth in SEQ ID NO:19; and (b) a heavy chain variable domain comprising a CDR H1 as set forth in SEQ ID NO: 20, a CDR H2 as set forth in SEQ ID NO:21, and a CDR H3 as set forth in SEQ ID NO: 22; and (ii) a transmembrane domain.

P Embodiment 53. An isolated nucleic acid encoding a recombinant protein of P embodiment 52.

P Embodiment 54. A pharmaceutical composition comprising a therapeutically effective amount of a recombinant protein of P embodiment 52 and a pharmaceutically acceptable excipient.

P Embodiment 55. A method of treating cancer in a subject in need thereof, said method comprising administering to a subject a therapeutically effective amount of a recombinant protein of P embodiment 52, thereby treating cancer in said subject.

P Embodiment 56. The method of treating cancer of P embodiment 55, wherein the cancer is melanoma, lymphoma, carcinoma, myeloma, leukemia, glioma, breast cancer, prostate cancer, bladder cancer, uterine cancer, gastric cancer, colorectal cancer, lung cancer, esophageal cancer, brain cancer, head and neck cancer, renal cancer, hepatic cancer, or thyroid cancer.

P Embodiment 57. A bispecific recombinant protein comprising: (i) a first antibody region capable of binding an effector cell ligand; and (ii) a second antibody region, comprising: (a) a light chain variable domain comprising a CDR L1 as set forth in SEQ ID NO:17, a CDR L2 as set forth in SEQ ID NO:18 and a CDR L3 as set forth in SEQ ID NO: 19; and (b) a heavy chain variable domain comprising a CDR H1 as set forth in SEQ ID NO:20, a CDR H2 as set forth in SEQ ID NO:21, and a CDR H3 as set forth in SEQ ID NO: 22.

P Embodiment 58. A pharmaceutical composition comprising a therapeutically effective amount of a bispecific recombinant protein of P embodiment 57 and a pharmaceutically acceptable excipient.

P Embodiment 59. A method of treating cancer in a subject in need thereof, said method comprising administering to a subject a therapeutically effective amount of a bispecific recombinant protein of P embodiment 58, thereby treating cancer in said subject.

P Embodiment 60. The method of treating cancer of P embodiment 59, wherein the cancer is melanoma, lymphoma, carcinoma, myeloma, leukemia, glioma, breast cancer, prostate cancer, bladder cancer, uterine cancer, gastric cancer, colorectal cancer, lung cancer, esophageal cancer, brain cancer, head and neck cancer, renal cancer, hepatic cancer, or thyroid cancer.

P Embodiment 61. An anti-Herpes Virus Entry Mediator (HVEM) antibody comprising a light chain variable domain and a heavy chain variable domain, wherein said light chain variable domain comprises: a CDR L1 as set forth in SEQ ID NO:33, a CDR L2 as set forth in SEQ ID NO:34 and a CDR L3 as set forth in SEQ ID NO:35; and wherein said heavy chain variable domain comprises: a CDR H1 as set forth in SEQ ID NO:36, a CDR H2 as set forth in SEQ ID NO:37, and a CDR H3 as set forth in SEQ ID NO:38.

P Embodiment 62. The antibody of P embodiment 61, wherein said light chain variable domain comprises a FR L1 as set forth in SEQ ID NO:39, a FR L2 as set forth in SEQ ID NO:40, a FR L3 as set forth in SEQ ID NO:41 and a FR L4 as set forth in SEQ ID NO:42.

P Embodiment 63. The antibody of P embodiment 61 or 62, wherein said heavy chain variable domain comprises a FR H1 as set forth in SEQ ID NO:43, a FR H2 as set forth in SEQ ID NO:44, a FR H3 as set forth in SEQ ID NO:45 and a FR H4 as set forth in SEQ ID NO:46.

P Embodiment 64. The antibody of any one of P embodiments 61-63, wherein said light chain variable domain comprises the sequence of SEQ ID NO:47.

P Embodiment 65. The antibody of any one of P embodiments 61-64, wherein said heavy chain variable domain comprises the sequence of SEQ ID NO:48.

P Embodiment 66. The antibody of any one of P embodiments 61-65, wherein said antibody is a humanized antibody.

P Embodiment 67. The antibody of any one of P embodiments 61-65, wherein said antibody is a chimeric antibody.

P Embodiment 68. The antibody of any one of P embodiments 61-65, wherein said antibody is a Fab' fragment.

P Embodiment 69. The antibody of any one of P embodiments 61-66, wherein said antibody is a single chain antibody (scFv).

P Embodiment 70. The antibody of any one of P embodiments 61-65 or 69, wherein said light chain variable domain and said heavy chain variable domain form part of a scFv P Embodiment 71. The antibody of any one of P embodiments 61-67, wherein said antibody is an IgG.

P Embodiment 72. The antibody of any one of P embodiments 61-37, wherein said antibody is an IgG1.

P Embodiment 73. The antibody of any one of P embodiments 61-72, wherein said antibody is capable of binding a Herpes Virus Entry Mediator (HVEM) protein.

P Embodiment 74. The antibody of any one of P embodiments 61-73, wherein said antibody is bound to a Herpes Virus Entry Mediator (HVEM) protein.

P Embodiment 75. The antibody of P embodiment 74, wherein said HVEM forms part of a cell.

P Embodiment 76. The antibody of P embodiment 75, wherein said cell is a plasma cell.

P Embodiment 77. The antibody of P embodiment 75 or 76, wherein said cell is a myeloma cell.

P Embodiment 78. An isolated nucleic acid encoding an antibody of P embodiment 61.

P Embodiment 79. A pharmaceutical composition comprising a therapeutically effective amount of an antibody of any one of P embodiments 61-77 and a pharmaceutically acceptable excipient.

P Embodiment 80. A method of treating cancer in a subject in need thereof, said method comprising administering to a subject a therapeutically effective amount of an antibody of any one of P embodiments 61-77, thereby treating cancer in said subject.

P Embodiment 81. The method of treating cancer of P embodiment 80, wherein the cancer is melanoma, lymphoma, carcinoma, myeloma, leukemia, glioma, breast cancer, prostate cancer, bladder cancer, uterine cancer, gastric cancer, colorectal cancer, lung cancer, esophageal cancer, brain cancer, head and neck cancer, renal cancer, hepatic cancer, or thyroid cancer.

P Embodiment 82. A recombinant protein comprising: (i) an antibody region comprising: (a) a light chain variable domain comprising a CDR L1 as set forth in SEQ ID NO:33, a CDR L2 as set forth in SEQ ID NO:34 and a CDR L3 as set forth in SEQ ID NO:35; and (b) a heavy chain variable domain comprising a CDR H1 as set forth in SEQ ID NO: 36, a CDR H2 as set forth in SEQ ID NO:37, and a CDR H3 as set forth in SEQ ID NO:38; and (ii) a transmembrane domain.

P Embodiment 83. An isolated nucleic acid encoding a recombinant protein of P embodiment 82.

P Embodiment 84. A pharmaceutical composition comprising a therapeutically effective amount of a recombinant protein of P embodiment 82 and a pharmaceutically acceptable excipient.

P Embodiment 85. A method of treating cancer in a subject in need thereof, said method comprising administering to a subject a therapeutically effective amount of a recombinant protein of P embodiment 82, thereby treating cancer in said subject.

P Embodiment 86. The method of treating cancer of P embodiment 85, wherein the cancer is melanoma, lymphoma, carcinoma, myeloma, leukemia, glioma, breast cancer, prostate cancer, bladder cancer, uterine cancer, gastric cancer, colorectal cancer, lung cancer, esophageal cancer, brain cancer, head and neck cancer, renal cancer, hepatic cancer, or thyroid cancer.

P Embodiment 87. A bispecific recombinant protein comprising: (i) a first antibody region capable of binding an effector cell ligand; and (ii) a second antibody region, comprising: (a) a light chain variable domain comprising a CDR L1 as set forth in SEQ ID NO:33, a CDR L2 as set forth in SEQ ID NO:34 and a CDR L3 as set forth in SEQ ID NO:35; and (b) a heavy chain variable domain comprising a CDR H1 as set forth in SEQ ID NO:36, a CDR H2 as set forth in SEQ ID NO:37, and a CDR H3 as set forth in SEQ ID NO:38.

P Embodiment 88. A pharmaceutical composition comprising a therapeutically effective amount of a bispecific recombinant protein of P embodiment 87 and a pharmaceutically acceptable excipient.

P Embodiment 89. A method of treating cancer in a subject in need thereof, said method comprising administering to a subject a therapeutically effective amount of a bispecific recombinant protein of P embodiment 88, thereby treating cancer in said subject.

P Embodiment 90. The method of treating cancer of P embodiment 89, wherein the cancer is melanoma, lymphoma, carcinoma, myeloma, leukemia, glioma, breast cancer, prostate cancer, bladder cancer, uterine cancer, gastric cancer, colorectal cancer, lung cancer, esophageal cancer, brain cancer, head and neck cancer, renal cancer, hepatic cancer, or thyroid cancer.

P Embodiment 91. An anti-Herpes Virus Entry Mediator (HVEM) antibody comprising a light chain variable domain and a heavy chain variable domain, wherein said light chain variable domain comprises: a CDR L1 as set forth in SEQ ID NO:49, a CDR L2 as set forth in SEQ ID NO:50 and a CDR L3 as set forth in SEQ ID NO:51; and wherein said heavy chain variable domain comprises: a CDR H1 as set forth in SEQ ID NO: 52, a CDR H2 as set forth in SEQ ID NO:53, and a CDR H3 as set forth in SEQ ID NO: 54.

P Embodiment 92. The antibody of P embodiment 91, wherein said light chain variable domain comprises a FR L1 as set forth in SEQ ID NO:55, a FR L2 as set forth in SEQ ID NO:56, a FR L3 as set forth in SEQ ID NO:57 and a FR L4 as set forth in SEQ ID NO:58.

P Embodiment 93. The antibody of P embodiment 91 or 92, wherein said heavy chain variable domain comprises a FR H1 as set forth in SEQ ID NO:59, a FR H2 as set forth in SEQ ID NO:60, a FR H3 as set forth in SEQ ID NO:61 and a FR H4 as set forth in SEQ ID NO:62.

P Embodiment 94. The antibody of any one of P embodiments 91-93, wherein said light chain variable domain comprises the sequence of SEQ ID NO:63.

P Embodiment 95. The antibody of any one of P embodiments 91-94, wherein said heavy chain variable domain comprises the sequence of SEQ ID NO:64.

P Embodiment 96. The antibody of any one of embodiments 91-95, wherein said antibody is a humanized antibody.

P Embodiment 97. The antibody of any one of P embodiments 91-95, wherein said antibody is a chimeric antibody.

P Embodiment 98. The antibody of any one of P embodiments 91-95, wherein said antibody is a Fab' fragment.

P Embodiment 99. The antibody of any one of P embodiments 91-96, wherein said antibody is a single chain antibody (scFv).

P Embodiment 100. The antibody of any one of P embodiments 91-95 or 99, wherein said light chain variable domain and said heavy chain variable domain form part of a scFv P Embodiment 101. The antibody of any one of P embodiments 91-97, wherein said antibody is an IgG.

P Embodiment 102. The antibody of any one of P embodiments 91-97, wherein said antibody is an IgG1.

P Embodiment 103. The antibody of any one of P embodiments 91-102, wherein said antibody is capable of binding a Herpes Virus Entry Mediator (HVEM) protein.

P Embodiment 104. The antibody of any one of P embodiments 91-103, wherein said antibody is bound to a Herpes Virus Entry Mediator (HVEM) protein.

P Embodiment 105. The antibody of P embodiment 104, wherein said HVEM forms part of a cell.

P Embodiment 106. The antibody of P embodiment 105, wherein said cell is a plasma cell.

P Embodiment 107. The antibody of P embodiment 105 or 106, wherein said cell is a myeloma cell.

P Embodiment 108. An isolated nucleic acid encoding an antibody of P embodiment 91.

P Embodiment 109. A pharmaceutical composition comprising a therapeutically effective amount of an antibody of any one of P embodiments 91-107 and a pharmaceutically acceptable excipient.

P Embodiment 110. A method of treating cancer in a subject in need thereof, said method comprising administering to a subject a therapeutically effective amount of an antibody of any one of P embodiments 91-107, thereby treating cancer in said subject.

P Embodiment 111. The method of treating cancer of P embodiment 110, wherein the cancer is melanoma, lymphoma, carcinoma, myeloma, leukemia, glioma, breast cancer, prostate cancer, bladder cancer, uterine cancer, gastric cancer, colorectal cancer, lung cancer, esophageal cancer, brain cancer, head and neck cancer, renal cancer, hepatic cancer, or thyroid cancer.

P Embodiment 112. A recombinant protein comprising: (i) an antibody region comprising: (a) a light chain variable domain comprising a CDR L1 as set forth in SEQ ID NO:49, a CDR L2 as set forth in SEQ ID NO:50 and a CDR L3 as set forth in SEQ ID NO:51; and (b) a heavy chain variable domain comprising a CDR H1 as set forth in SEQ ID NO: 52, a CDR H2 as set forth in SEQ ID NO:53, and a CDR H3 as set forth in SEQ ID NO: 54; and (ii) a transmembrane domain.

P Embodiment 113. An isolated nucleic acid encoding a recombinant protein of P embodiment 112.

P Embodiment 114. A pharmaceutical composition comprising a therapeutically effective amount of a recombinant protein of P embodiment 112 and a pharmaceutically acceptable excipient.

P Embodiment 115. A method of treating cancer in a subject in need thereof, said method comprising administering to a subject a therapeutically effective amount of a recombinant protein of P embodiment 112, thereby treating cancer in said subject.

P Embodiment 116. The method of treating cancer of P embodiment 115, wherein the cancer is melanoma, lymphoma, carcinoma, myeloma, leukemia, glioma, breast cancer, prostate cancer, bladder cancer, uterine cancer, gastric cancer, colorectal cancer, lung cancer, esophageal cancer, brain cancer, head and neck cancer, renal cancer, hepatic cancer, or thyroid cancer.

P Embodiment 117. A bispecific recombinant protein comprising: (i) a first antibody region capable of binding an effector cell ligand; and (ii) a second antibody region, comprising: (a) a light chain variable domain comprising a CDR L1 as set forth in SEQ ID NO:49, a CDR L2 as set forth in SEQ ID NO:50 and a CDR L3 as set forth in SEQ ID NO:51; and (b) a heavy chain variable domain comprising a CDR H1 as set forth in SEQ ID NO:52, a CDR H2 as set forth in SEQ ID NO:53, and a CDR H3 as set forth in SEQ ID NO: 54.

P Embodiment 118. A pharmaceutical composition comprising a therapeutically effective amount of a bispecific recombinant protein of P embodiment 117 and a pharmaceutically acceptable excipient.

P Embodiment 119. A method of treating cancer in a subject in need thereof, said method comprising administering to a subject a therapeutically effective amount of a bispecific recombinant protein of P embodiment 118, thereby treating cancer in said subject.

P Embodiment 120. The method of treating cancer of P embodiment 119, wherein the cancer is melanoma, lymphoma, carcinoma, myeloma, leukemia, glioma, breast cancer, prostate cancer, bladder cancer, uterine cancer, gastric cancer, colorectal cancer, lung cancer, esophageal cancer, brain cancer, head and neck cancer, renal cancer, hepatic cancer, or thyroid cancer.

EMBODIMENTS

Embodiment 1. An anti-Herpes Virus Entry Mediator (HVEM) antibody comprising a light chain variable domain and a heavy chain variable domain, wherein said light chain variable domain comprises: a CDR L1 as set forth in SEQ ID NO:1, a CDR L2 as set forth in SEQ ID NO:2 and a CDR L3 as set forth in SEQ ID NO:3; and wherein said heavy chain variable domain comprises: a CDR H1 as set forth in SEQ ID NO:4, a CDR H2 as set forth in SEQ ID NO:5, and a CDR H3 as set forth in SEQ ID NO:6.

Embodiment 2. The antibody of embodiment 1, wherein said light chain variable domain comprises a FR L1 as set forth in SEQ ID NO:7, a FR L2 as set forth in SEQ ID NO:8, a FR L3 as set forth in SEQ ID NO:9 and a FR L4 as set forth in SEQ ID NO:10.

Embodiment 3. The antibody of embodiment 1 or 2, wherein said heavy chain variable domain comprises a FR H1 as set forth in SEQ ID NO:11, a FR H2 as set forth in SEQ ID NO:12, a FR H3 as set forth in SEQ ID NO:13 and a FR H4 as set forth in SEQ ID NO:14.

Embodiment 4. The antibody of any one of embodiments 1-3, comprising a light chain comprising the sequence of SEQ ID NO:15.

Embodiment 5. The antibody of any one of embodiments 1-4, comprising a heavy chain comprising the sequence of SEQ ID NO:16.

Embodiment 6. The antibody of any one of embodiments 1-5, wherein said antibody is a humanized antibody.

Embodiment 7. The antibody of any one of embodiments 1-5, wherein said antibody is a chimeric antibody.

Embodiment 8. The antibody of any one of embodiments 1-5, wherein said antibody is a Fab' fragment.

Embodiment 9. The antibody of any one of embodiments 1-6, wherein said antibody is a single chain antibody (scFv).

Embodiment 10. The antibody of any one of embodiments 1-5 or 9, wherein said light chain variable domain and said heavy chain variable domain form part of a scFv.

Embodiment 11. The antibody of any one of embodiments 1-7, wherein said antibody is an IgG.

Embodiment 12. The antibody of any one of embodiments 1-7, wherein said antibody is an IgG1 or IgG2A.

Embodiment 13. The antibody of any one of embodiments 1-12, wherein said antibody is capable of binding a Herpes Virus Entry Mediator (HVEM) protein.

Embodiment 14. The antibody of any one of embodiments 1-13, wherein said antibody is bound to a Herpes Virus Entry Mediator (HVEM) protein.

Embodiment 15. The antibody of embodiment 14, wherein said HVEM forms part of a cell.

Embodiment 16. The antibody of embodiment 15, wherein said cell is a plasma cell.

Embodiment 17. The antibody of embodiment 15 or 16, wherein said cell is a myeloma cell.

Embodiment 18. An isolated nucleic acid encoding an antibody of embodiment 1.

Embodiment 19. A pharmaceutical composition comprising a therapeutically effective amount of an antibody of any one of embodiments 1-17 and a pharmaceutically acceptable excipient.

Embodiment 20. A method of treating cancer in a subject in need thereof, said method comprising administering to a subject a therapeutically effective amount of an antibody of any one of embodiments 1-17, thereby treating cancer in said subject.

Embodiment 21. The method of treating cancer of embodiment 20, wherein the cancer is melanoma, lymphoma, carcinoma, myeloma, leukemia, glioma, breast cancer, prostate cancer, bladder cancer, uterine cancer, gastric cancer, colorectal cancer, lung cancer, esophageal cancer, brain cancer, head and neck cancer, renal cancer, hepatic cancer, or thyroid cancer.

Embodiment 22. A recombinant protein comprising: (i) an antibody region comprising: (a) a light chain variable domain comprising a CDR L1 as set forth in SEQ ID NO:1, a CDR L2 as set forth in SEQ ID NO:2 and a CDR L3 as set forth in SEQ ID NO:3; and (b) a heavy chain variable domain comprising a CDR H1 as set forth in SEQ ID NO:4, a CDR H2 as set forth in SEQ ID NO:5, and a CDR H3 as set forth in SEQ ID NO:6; and (ii) a transmembrane domain.

Embodiment 23. An isolated nucleic acid encoding a recombinant protein of embodiment 22.

Embodiment 24. A pharmaceutical composition comprising a therapeutically effective amount of a recombinant protein of embodiment 22 and a pharmaceutically acceptable excipient.

Embodiment 25. A method of treating cancer in a subject in need thereof, said method comprising administering to a subject a therapeutically effective amount of a recombinant protein of embodiment 22, thereby treating cancer in said subject.

Embodiment 26. The method of treating cancer of embodiment 25, wherein the cancer is melanoma, lymphoma, carcinoma, myeloma, leukemia, glioma, breast cancer, prostate cancer, bladder cancer, uterine cancer, gastric cancer, colorectal cancer, lung cancer, esophageal cancer, brain cancer, head and neck cancer, renal cancer, hepatic cancer, or thyroid cancer.

Embodiment 27. A bispecific recombinant protein comprising: (i) a first antibody region capable of binding an effector cell ligand; and (ii) a second antibody region, comprising: (a) a light chain variable domain comprising a CDR L1 as set forth in SEQ ID NO:1, a CDR L2 as set forth in SEQ ID NO:2 and a CDR L3 as set forth in SEQ ID NO:3; and (b) a heavy chain variable domain comprising a CDR H1 as set forth in SEQ ID NO:4, a CDR H2 as set forth in SEQ ID NO:5, and a CDR H3 as set forth in SEQ ID NO:6.

Embodiment 28. A pharmaceutical composition comprising a therapeutically effective amount of a bispecific recombinant protein of embodiment 27 and a pharmaceutically acceptable excipient.

Embodiment 29. A method of treating cancer in a subject in need thereof, said method comprising administering to a subject a therapeutically effective amount of a bispecific recombinant protein of embodiment 28, thereby treating cancer in said subject.

Embodiment 30. The method of treating cancer of embodiment 29, wherein the cancer is melanoma, lymphoma, carcinoma, myeloma, leukemia, glioma, breast cancer, prostate cancer, bladder cancer, uterine cancer, gastric cancer, colorectal cancer, lung cancer, esophageal cancer, brain cancer, head and neck cancer, renal cancer, hepatic cancer, or thyroid cancer.

Embodiment 31. An anti-Herpes Virus Entry Mediator (HVEM) antibody comprising a light chain variable domain and a heavy chain variable domain, wherein said light chain variable domain comprises: a CDR L1 as set forth in SEQ ID NO:66, a CDR L2 as set forth in SEQ ID NO:67 and a CDR L3 as set forth in SEQ ID NO:68; and wherein said heavy chain variable domain comprises: a CDR H1 as set forth in SEQ ID NO:69, a CDR H2 as set forth in SEQ ID NO:70, and a CDR H3 as set forth in SEQ ID NO:71.

Embodiment 32. The antibody of embodiment 31, wherein said light chain variable domain comprises a FR L1 as set forth in SEQ ID NO:72, a FR L2 as set forth in SEQ ID NO:73, a FR L3 as set forth in SEQ ID NO:74 and a FR L4 as set forth in SEQ ID NO:75.

Embodiment 33. The antibody of embodiment 31 or 32, wherein said heavy chain variable domain comprises a FR H1 as set forth in SEQ ID NO:76, a FR H2 as set forth in SEQ ID NO:77, a FR H3 as set forth in SEQ ID NO:78 and a FR H4 as set forth in SEQ ID NO:79.

Embodiment 34. The antibody of any one of embodiments 31-33, wherein said light chain variable domain comprises the sequence of SEQ ID NO:80.

Embodiment 35. The antibody of any one of embodiments 31-34, wherein said heavy chain variable domain comprises the sequence of SEQ ID NO:81.

Embodiment 36. The antibody of any one of embodiments 31-35, comprising a light chain comprising the sequence of SEQ ID NO:82.

Embodiment 37. The antibody of any one of embodiments 31-36, comprising a heavy chain comprising the sequence of SEQ ID NO:83.

Embodiment 38. The antibody of any one of embodiments 31-35, wherein said antibody is a humanized antibody.

Embodiment 39. The antibody of any one of embodiments 31-35, wherein said antibody is a chimeric antibody.

Embodiment 40. The antibody of any one of embodiments 31-35, wherein said antibody is a Fab' fragment.

Embodiment 41. The antibody of any one of embodiments 31-35, wherein said antibody is a single chain antibody (scFv).

Embodiment 42. The antibody of any one of embodiments 31-35 or 41, wherein said light chain variable domain and said heavy chain variable domain form part of a scFv.

Embodiment 43. The antibody of any one of embodiments 31-39, wherein said antibody is an IgG.

Embodiment 44. The antibody of any one of embodiments 31-39, wherein said antibody is an IgG1 or an IgG2A.

Embodiment 45. The antibody of any one of embodiments 31-44, wherein said antibody is capable of binding a Herpes Virus Entry Mediator (HVEM) protein.

Embodiment 46. The antibody of any one of embodiments 31-45, wherein said antibody is bound to a Herpes Virus Entry Mediator (HVEM) protein.

Embodiment 47. The antibody of embodiment 46, wherein said HVEM forms part of a cell.

Embodiment 48. The antibody of embodiment 47, wherein said cell is a plasma cell.

Embodiment 49. The antibody of embodiment 47 or 48, wherein said cell is a myeloma cell.

Embodiment 50. An isolated nucleic acid encoding an antibody of embodiment 31.

Embodiment 51. A pharmaceutical composition comprising a therapeutically effective amount of an antibody of any one of embodiments 31-49 and a pharmaceutically acceptable excipient.

Embodiment 52. A method of treating cancer in a subject in need thereof, said method comprising administering to a subject a therapeutically effective amount of an antibody of any one of embodiments 31-49, thereby treating cancer in said subject.

Embodiment 53. The method of treating cancer of embodiment 52, wherein the cancer is melanoma, lymphoma, carcinoma, myeloma, leukemia, glioma, breast cancer, prostate cancer, bladder cancer, uterine cancer, gastric cancer, colorectal cancer, lung cancer, esophageal cancer, brain cancer, head and neck cancer, renal cancer, hepatic cancer, or thyroid cancer.

Embodiment 54. A recombinant protein comprising: (i) an antibody region comprising: (a) a light chain variable domain comprising a CDR L1 as set forth in SEQ ID NO:66, a CDR L2 as set forth in SEQ ID NO:67 and a CDR L3 as set forth in SEQ ID NO:68; and (b) a heavy chain variable domain comprising a CDR H1 as set forth in SEQ ID NO: 69, a CDR H2 as set forth in SEQ ID NO:70, and a CDR H3 as set forth in SEQ ID NO:71; and (ii) a transmembrane domain.

Embodiment 55. An isolated nucleic acid encoding a recombinant protein of embodiment 54.

Embodiment 56. A pharmaceutical composition comprising a therapeutically effective amount of a recombinant protein of embodiment 54 and a pharmaceutically acceptable excipient.

Embodiment 57. A method of treating cancer in a subject in need thereof, said method comprising administering to a subject a therapeutically effective amount of a recombinant protein of embodiment 54, thereby treating cancer in said subject.

Embodiment 58. The method of treating cancer of embodiment 57, wherein the cancer is melanoma, lymphoma, carcinoma, myeloma, leukemia, glioma, breast cancer, prostate cancer, bladder cancer, uterine cancer, gastric cancer, colorectal cancer, lung cancer, esophageal cancer, brain cancer, head and neck cancer, renal cancer, hepatic cancer, or thyroid cancer.

Embodiment 59. A bispecific recombinant protein comprising: (i) a first antibody region capable of binding an effector cell ligand; and (ii) a second antibody region, comprising: (a) a light chain variable domain comprising a CDR L1 as set forth in SEQ ID NO:66, a CDR L2 as set forth in SEQ ID NO:67 and a CDR L3 as set forth in SEQ ID NO:68; and (b) a heavy chain variable domain comprising a CDR H1 as set forth in SEQ ID NO:69, a CDR H2 as set forth in SEQ ID NO:70, and a CDR H3 as set forth in SEQ ID NO:71.

Embodiment 60. A pharmaceutical composition comprising a therapeutically effective amount of a bispecific recombinant protein of embodiment 59 and a pharmaceutically acceptable excipient.

Embodiment 61. A method of treating cancer in a subject in need thereof, said method comprising administering to a subject a therapeutically effective amount of a bispecific recombinant protein of embodiment 60, thereby treating cancer in said subject.

Embodiment 62. The method of treating cancer of embodiment 61, wherein the cancer is melanoma, lymphoma, carcinoma, myeloma, leukemia, glioma, breast cancer, prostate cancer, bladder cancer, uterine cancer, gastric cancer, colorectal cancer, lung cancer, esophageal cancer, brain cancer, head and neck cancer, renal cancer, hepatic cancer, or thyroid cancer.

Embodiment 63. An anti-Herpes Virus Entry Mediator (HVEM) antibody comprising a light chain variable domain and a heavy chain variable domain, wherein said light chain variable domain comprises: a CDR L1 as set forth in SEQ ID NO:84, a CDR L2 as set forth in SEQ ID NO:85 and a CDR L3 as set forth in SEQ ID NO:86; and wherein said heavy chain variable domain comprises: a CDR H1 as set forth in SEQ ID NO:87, a CDR H2 as set forth in SEQ ID NO:88, and a CDR H3 as set forth in SEQ ID NO:89.

Embodiment 64. The antibody of embodiment 63, wherein said light chain variable domain comprises a FR L1 as set forth in SEQ ID NO:90, a FR L2 as set forth in SEQ ID NO:91, a FR L3 as set forth in SEQ ID NO:92 and a FR L4 as set forth in SEQ ID NO:93.

Embodiment 65. The antibody of embodiment 63 or 64, wherein said heavy chain variable domain comprises a FR H1 as set forth in SEQ ID NO:94, a FR H2 as set forth in SEQ ID NO:95, a FR H3 as set forth in SEQ ID NO:96 and a FR H4 as set forth in SEQ ID NO:97.

Embodiment 66. The antibody of any one of embodiments 63-65, wherein said light chain variable domain comprises the sequence of SEQ ID NO:98.

Embodiment 67. The antibody of any one of embodiments 63-66, wherein said heavy chain variable domain comprises the sequence of SEQ ID NO:99.

Embodiment 68. The antibody of any one of embodiments 63-67, comprising a light chain comprising the sequence of SEQ ID NO:100.

Embodiment 69. The antibody of any one of embodiments 63-68, comprising a heavy chain comprising the sequence of SEQ ID NO:101.

Embodiment 70. The antibody of any one of embodiments 63-67, wherein said antibody is a humanized antibody.

Embodiment 71. The antibody of any one of embodiments 63-67, wherein said antibody is a chimeric antibody.

Embodiment 72. The antibody of any one of embodiments 63-67, wherein said antibody is a Fab' fragment.

Embodiment 73. The antibody of any one of embodiments 63-67, wherein said antibody is a single chain antibody (scFv).

Embodiment 74. The antibody of any one of embodiments 63-67 or 73, wherein said light chain variable domain and said heavy chain variable domain form part of a scFv Embodiment 75. The antibody of any one of embodiments 63-71, wherein said antibody is an IgG.

Embodiment 76. The antibody of any one of embodiments 63-75, wherein said antibody is an IgG1.

Embodiment 77. The antibody of any one of embodiments 63-76, wherein said antibody is capable of binding a Herpes Virus Entry Mediator (HVEM) protein.

Embodiment 78. The antibody of any one of embodiments 63-77, wherein said antibody is bound to a Herpes Virus Entry Mediator (HVEM) protein.

Embodiment 79. The antibody of embodiment 78, wherein said HVEM forms part of a cell.

Embodiment 80. The antibody of embodiment 79, wherein said cell is a plasma cell.

Embodiment 81. The antibody of embodiment 79 or 80, wherein said cell is a myeloma cell.

Embodiment 82. An isolated nucleic acid encoding an antibody of embodiment 63.

Embodiment 83. A pharmaceutical composition comprising a therapeutically effective amount of an antibody of any one of embodiments 63-81 and a pharmaceutically acceptable excipient.

Embodiment 84. A method of treating cancer in a subject in need thereof, said method comprising administering to a subject a therapeutically effective amount of an antibody of any one of embodiments 63-81, thereby treating cancer in said subject.

Embodiment 85. The method of treating cancer of embodiment 84, wherein the cancer is melanoma, lymphoma, carcinoma, myeloma, leukemia, glioma, breast cancer, prostate cancer, bladder cancer, uterine cancer, gastric cancer, colorectal cancer, lung cancer, esophageal cancer, brain cancer, head and neck cancer, renal cancer, hepatic cancer, or thyroid cancer.

Embodiment 86. A recombinant protein comprising: (i) an antibody region comprising: (a) a light chain variable domain comprising a CDR L1 as set forth in SEQ ID NO:84, a CDR L2 as set forth in SEQ ID NO:85 and a CDR L3 as set forth in SEQ ID NO:86; and (b) a heavy chain variable domain comprising a CDR H1 as set forth in SEQ ID NO:87, a CDR H2 as set forth in SEQ ID NO:88, and a CDR H3 as set forth in SEQ ID NO: 89; and (ii) a transmembrane domain.

Embodiment 87. An isolated nucleic acid encoding a recombinant protein of embodiment 86.

Embodiment 88. A pharmaceutical composition comprising a therapeutically effective amount of a recombinant protein of embodiment 86 and a pharmaceutically acceptable excipient.

Embodiment 89. A method of treating cancer in a subject in need thereof, said method comprising administering to a subject a therapeutically effective amount of a recombinant protein of embodiment 86, thereby treating cancer in said subject.

Embodiment 90. The method of treating cancer of embodiment 89, wherein the cancer is melanoma, lymphoma, carcinoma, myeloma, leukemia, glioma, breast cancer, prostate cancer, bladder cancer, uterine cancer, gastric cancer, colorectal cancer, lung cancer, esophageal cancer, brain cancer, head and neck cancer, renal cancer, hepatic cancer, or thyroid cancer.

Embodiment 91. A bispecific recombinant protein comprising: (i) a first antibody region capable of binding an effector cell ligand; and (ii) a second antibody region, comprising: (a) a light chain variable domain comprising a CDR L1 as set forth in SEQ ID NO:84, a CDR L2 as set forth in SEQ ID NO:85 and a CDR L3 as set forth in SEQ ID NO:86; and (b) a heavy chain variable domain comprising a CDR H1 as set forth in SEQ ID NO: 87, a CDR H2 as set forth in SEQ ID NO:88, and a CDR H3 as set forth in SEQ ID NO: 89.

Embodiment 92. A pharmaceutical composition comprising a therapeutically effective amount of a bispecific recombinant protein of embodiment 91 and a pharmaceutically acceptable excipient.

Embodiment 93. A method of treating cancer in a subject in need thereof, said method comprising administering to a subject a therapeutically effective amount of a bispecific recombinant protein of embodiment 92, thereby treating cancer in said subject.

Embodiment 94. The method of treating cancer of embodiment 93, wherein the cancer is melanoma, lymphoma, carcinoma, myeloma, leukemia, glioma, breast cancer, prostate cancer, bladder cancer, uterine cancer, gastric cancer, colorectal cancer, lung cancer, esophageal cancer, brain cancer, head and neck cancer, renal cancer, hepatic cancer, or thyroid cancer.

Embodiment 95. An anti-Herpes Virus Entry Mediator (HVEM) antibody comprising a light chain variable domain and a heavy chain variable domain, wherein said light chain variable domain comprises: a CDR L1 as set forth in SEQ ID NO:102, a CDR L2 as set forth in SEQ ID NO:103 and a CDR L3 as set forth in SEQ ID NO:104; and wherein said heavy chain variable domain comprises: a CDR H1 as set forth in SEQ ID NO: 105, a CDR H2 as set forth in SEQ ID NO:106, and a CDR H3 as set forth in SEQ ID NO:107.

Embodiment 96. The antibody of embodiment 95, wherein said light chain variable domain comprises a FR L1 as set forth in SEQ ID NO:108, a FR L2 as set forth in SEQ ID NO:109, a FR L3 as set forth in SEQ ID NO:110 and a FR L4 as set forth in SEQ ID NO:111.

Embodiment 97. The antibody of embodiment 95 or 96, wherein said heavy chain variable domain comprises a FR H1 as set forth in SEQ ID NO: 112, a FR H2 as set forth in SEQ ID NO: 113, a FR H3 as set forth in SEQ ID NO: 114 and a FR H4 as set forth in SEQ ID NO:115.

Embodiment 98. The antibody of any one of embodiments 95-97, wherein said light chain variable domain comprises the sequence of SEQ ID NO: 116.

Embodiment 99. The antibody of any one of embodiments 95-98, wherein said heavy chain variable domain comprises the sequence of SEQ ID NO: 117.

Embodiment 100. The antibody of any one of embodiments 95-99, comprising a light chain comprising the sequence of SEQ ID NO:118.

Embodiment 101. The antibody of any one of embodiments 95-100, comprising a heavy chain comprising the sequence of SEQ ID NO: 119.

Embodiment 102. The antibody of any one of embodiments 95-99, wherein said antibody is a humanized antibody.

Embodiment 103. The antibody of any one of embodiments 95-99, wherein said antibody is a chimeric antibody.

Embodiment 104. The antibody of any one of embodiments 95-99, wherein said antibody is a Fab' fragment.

Embodiment 105. The antibody of any one of embodiments 95-99, wherein said antibody is a single chain antibody (scFv).

Embodiment 106. The antibody of any one of embodiments 95-99 or 105, wherein said light chain variable domain and said heavy chain variable domain form part of a scFv.

Embodiment 107. The antibody of any one of embodiments 95-103, wherein said antibody is an IgG.

Embodiment 108. The antibody of any one of embodiments 95-103, wherein said antibody is an IgG1.

Embodiment 109. The antibody of any one of embodiments 95-108, wherein said antibody is capable of binding a Herpes Virus Entry Mediator (HVEM) protein.

Embodiment 110. The antibody of any one of embodiments 95-109, wherein said antibody is bound to a Herpes Virus Entry Mediator (HVEM) protein.

Embodiment 111. The antibody of embodiment 110, wherein said HVEM forms part of a cell.

Embodiment 112. The antibody of embodiment 111, wherein said cell is a plasma cell.

Embodiment 113. The antibody of embodiment 111 or 112, wherein said cell is a myeloma cell.

Embodiment 114. An isolated nucleic acid encoding an antibody of embodiment 95.

Embodiment 115. A pharmaceutical composition comprising a therapeutically effective amount of an antibody of any one of embodiments 95-113 and a pharmaceutically acceptable excipient.

Embodiment 116. A method of treating cancer in a subject in need thereof, said method comprising administering to a subject a therapeutically effective amount of an antibody of any one of embodiments 95-113, thereby treating cancer in said subject.

Embodiment 117. The method of treating cancer of embodiment 116, wherein the cancer is melanoma, lymphoma, carcinoma, myeloma, leukemia, glioma, breast cancer, prostate cancer, bladder cancer, uterine cancer, gastric cancer, colorectal cancer, lung cancer, esophageal cancer, brain cancer, head and neck cancer, renal cancer, hepatic cancer, or thyroid cancer.

Embodiment 118. A recombinant protein comprising: (i) an antibody region comprising: (a) a light chain variable domain comprising a CDR L1 as set forth in SEQ ID NO:102, a CDR L2 as set forth in SEQ ID NO:103 and a CDR L3 as set forth in SEQ ID NO: 104; and (b) a heavy chain variable domain comprising a CDR H1 as set forth in SEQ ID NO: 105, a CDR H2 as set forth in SEQ ID NO: 106, and a CDR H3 as set forth in SEQ ID NO: 107; and (ii) a transmembrane domain.

Embodiment 119. An isolated nucleic acid encoding a recombinant protein of embodiment 118.

Embodiment 120. A pharmaceutical composition comprising a therapeutically effective amount of a recombinant protein of embodiment 118 and a pharmaceutically acceptable excipient.

Embodiment 121. A method of treating cancer in a subject in need thereof, said method comprising administering to a subject a therapeutically effective amount of a recombinant protein of embodiment 118, thereby treating cancer in said subject.

Embodiment 122. The method of treating cancer of embodiment 121, wherein the cancer is melanoma, lymphoma, carcinoma, myeloma, leukemia, glioma, breast cancer, prostate cancer, bladder cancer, uterine cancer, gastric cancer, colorectal cancer, lung cancer, esophageal cancer, brain cancer, head and neck cancer, renal cancer, hepatic cancer, or thyroid cancer.

Embodiment 123. A bispecific recombinant protein comprising: (i) a first antibody region capable of binding an effector cell ligand; and (ii) a second antibody region, comprising: (a) a light chain variable domain comprising a CDR L1 as set forth in SEQ ID NO:102, a CDR L2 as set forth in SEQ ID NO:103 and a CDR L3 as set forth in SEQ ID NO:104; and (b) a heavy chain variable domain comprising a CDR H1 as set forth in SEQ ID NO:105, a CDR H2 as set forth in SEQ ID NO:106, and a CDR H3 as set forth in SEQ ID NO: 107.

Embodiment 124. A pharmaceutical composition comprising a therapeutically effective amount of a bispecific recombinant protein of embodiment 123 and a pharmaceutically acceptable excipient.

Embodiment 125. A method of treating cancer in a subject in need thereof, said method comprising administering to a subject a therapeutically effective amount of a bispecific recombinant protein of embodiment 124, thereby treating cancer in said subject.

Embodiment 126. The method of treating cancer of embodiment 125, wherein the cancer is melanoma, lymphoma, carcinoma, myeloma, leukemia, glioma, breast cancer, prostate cancer, bladder cancer, uterine cancer, gastric cancer, colorectal cancer, lung cancer, esophageal cancer, brain cancer, head and neck cancer, renal cancer, hepatic cancer, or thyroid cancer.

What is claimed is:

1. An anti-Herpes Virus Entry Mediator (HVEM) antibody comprising a light chain variable domain and a heavy chain variable domain, wherein (a) said light chain variable domain comprises a CDR L1 as set forth in SEQ ID NO:1, a CDR L2 as set forth in SEQ ID NO:2 and a CDR L3 as set forth in SEQ ID NO: 3; and said heavy chain variable domain comprises a CDR H1 as set forth in SEQ ID NO:4, a CDR H2 as set forth in SEQ ID NO:5, and a CDR H3 as set forth in SEQ ID NO: 6;

(b) said light chain variable domain comprises a CDR L1 as set forth in SEQ ID NO:84, a CDR L2 as set forth in SEQ ID NO:85 and a CDR L3 as set forth in SEQ ID NO: 86; and said heavy chain variable domain comprises a CDR H1 as set forth in SEQ ID NO: 87, a CDR H2 as set forth in SEQ ID NO:88, and a CDR H3 as set forth in SEQ ID NO: 89; or (c) said light chain variable domain comprises a CDR L1 as set forth in SEQ ID NO:102, a CDR L2 as set forth in SEQ ID NO:103 and a CDR L3 as set forth in SEQ ID NO:104; and said heavy chain variable domain comprises a CDR H1 as set forth in SEQ ID NO: 105, a CDR H2 as set forth in SEQ ID NO:106, and a CDR H3 as set forth in SEQ ID NO: 107.

2. A pharmaceutical composition comprising a therapeutically effective amount of an antibody of claim 1 and a pharmaceutically acceptable excipient.

3. A method of treating cancer in a subject in need thereof, said method comprising administering to a subject a therapeutically effective amount of an antibody of claim 1, thereby treating cancer in said subject.

4. A recombinant protein comprising:

(i) an antibody region comprising a light chain variable domain and a heavy chain variable domain of said antibody of claim 1; and (ii) a transmembrane domain.

5. A pharmaceutical composition comprising a therapeutically effective amount of a recombinant protein of claim 4 and a pharmaceutically acceptable excipient.

6. A method of treating cancer in a subject in need thereof, said method comprising administering to a subject a therapeutically effective amount of a recombinant protein of claim 4, thereby treating cancer in said subject.

7. A bispecific recombinant protein comprising:

(i) a first antibody region capable of binding an effector cell ligand; and (ii) a second antibody region, comprising a light chain variable domain and a heavy chain variable domain of said antibody of claim 1.

8. A pharmaceutical composition comprising a therapeutically effective amount of a bispecific recombinant protein of claim 7 and a pharmaceutically acceptable excipient.

9. A method of treating cancer in a subject in need thereof, said method comprising administering to a subject a therapeutically effective amount of a bispecific recombinant protein of claim 8, thereby treating cancer in said subject.

10. An anti-Herpes Virus Entry Mediator (HVEM) antibody comprising a light chain variable domain and a heavy chain variable domain, wherein said light chain variable domain comprises:

a CDR L1 as set forth in SEQ ID NO:66, a CDR L2 as set forth in SEQ ID NO:67 and a CDR L3 as set forth in SEQ ID NO:68; and wherein said heavy chain variable domain comprises:

a CDR H1 as set forth in SEQ ID NO:69, a CDR H2 as set forth in SEQ ID NO: 70, and a CDR H3 as set forth in SEQ ID NO:71.

11. An isolated nucleic acid encoding an antibody of claim 10.

12. A pharmaceutical composition comprising a therapeutically effective amount of an antibody of claim 10 and a pharmaceutically acceptable excipient.

13. A method of treating cancer in a subject in need thereof, said method comprising administering to a subject a therapeutically effective amount of an antibody of claim 10, thereby treating cancer in said subject.

14. A recombinant protein comprising:

(i) an antibody region comprising a light chain variable domain and a heavy chain variable domain of said antibody of claim 10; and (ii) a transmembrane domain.

15. A pharmaceutical composition comprising a therapeutically effective amount of a recombinant protein of claim 14 and a pharmaceutically acceptable excipient.

16. A method of treating cancer in a subject in need thereof, said method comprising administering to a subject a therapeutically effective amount of a recombinant protein of claim 14, thereby treating cancer in said subject.

17. A bispecific recombinant protein comprising:

(i) a first antibody region capable of binding an effector cell ligand; and (ii) a second antibody region, comprising a light chain variable domain and a heavy chain variable domain of said antibody of claim 10.

18. A pharmaceutical composition comprising a therapeutically effective amount of a bispecific recombinant protein of claim 17 and a pharmaceutically acceptable excipient.

19. A method of treating cancer in a subject in need thereof, said method comprising administering to a subject a therapeutically effective amount of a bispecific recombinant protein of claim 18, thereby treating cancer in said subject.

* * * * *

SEQUENCE LISTING

```
<160> NUMBER OF SEQ ID NOS: 123

<210> SEQ ID NO 1
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 1

Ser Ala Ser Ser Ser Val Ser Tyr Met His
1               5                   10


<210> SEQ ID NO 2
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 2

Asp Thr Ser Lys Leu Ala Ser
1               5


<210> SEQ ID NO 3
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 3

Gln Gln Trp Thr Ser Asp Pro Leu Thr
1               5


<210> SEQ ID NO 4
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 4

Gly Tyr Ile Leu Thr Asn Tyr Gly
1               5
```

```
<210> SEQ ID NO 5
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 5

Ile Asn Thr Tyr Thr Gly Glu Pro Thr Tyr
1               5                   10


<210> SEQ ID NO 6
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 6

Ala Arg Gly Tyr Gly Asn His Trp Tyr Phe Asp Tyr
1               5                   10


<210> SEQ ID NO 7
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 7

Gln Ile Val Leu Thr Gln Ser Pro Ala Ile Leu Ser Ala Ser Pro Gly
1               5                   10                  15

Glu Lys Val Thr Met Thr Cys
            20


<210> SEQ ID NO 8
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 8

Trp Tyr Gln Arg Lys Ser Gly Thr Ser Pro Lys Arg Trp Ile Tyr
1               5                   10                  15


<210> SEQ ID NO 9
<211> LENGTH: 32
<212> TYPE: PRT
<213> ORGANISM: Artificial Sequence
<220> FEATURE:
<223> OTHER INFORMATION: Synthetic polypeptide

<400> SEQUENCE: 9

Gly Val Pro Ala Arg Phe Ser Gly Ser Gly Ser Gly Thr Ser Tyr Ser
1               5                   10                  15

Leu Thr Ile Ser Ser Met Glu Ala Glu Asp Ala Ala Thr Tyr Tyr Cys
            20                  25                  30


<210> SEQ ID NO 10
<211> LENGTH: 10
<212> TYPE: PRT
<213> ORGANISM: Artificial Sequence
<220> FEATURE:
<223> OTHER INFORMATION: Synthetic polypeptide
```

<400> SEQUENCE: 10

Phe Gly Ala Gly Thr Lys Leu Glu Leu Lys
1 5 10

<210> SEQ ID NO 11
<211> LENGTH: 25
<212> TYPE: PRT
<213> ORGANISM: Artificial Sequence
<220> FEATURE:
<223> OTHER INFORMATION: Synthetic polypeptide

<400> SEQUENCE: 11

Gln Ile Gln Leu Val Gln Ser Gly Pro Glu Leu Lys Lys Pro Gly Glu
1 5 10 15

Thr Val Lys Ile Ser Cys Lys Ala Ser
20 25

<210> SEQ ID NO 12
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 12

Met Asn Trp Val Lys Gln Ala Pro Gly Lys Gly Leu Lys Trp Met Gly
1 5 10 15

Trp

<210> SEQ ID NO 13
<211> LENGTH: 36
<212> TYPE: PRT
<213> ORGANISM: Artificial Sequence
<220> FEATURE:
<223> OTHER INFORMATION: Synthetic polypeptide

<400> SEQUENCE: 13

Ala Asp Ala Phe Lys Gly Arg Phe Ala Phe Ser Leu Glu Thr Ser Ala
1 5 10 15

Ser Thr Ala Tyr Leu Gln Ile Asn Asn Leu Lys Asn Glu Asp Thr Ala
20 25 30

Thr Tyr Phe Cys
35

<210> SEQ ID NO 14
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 14

Trp Gly Gln Gly Thr Ser Val Thr Val Ser Ser
1 5 10

<210> SEQ ID NO 15
<211> LENGTH: 213
<212> TYPE: PRT
<213> ORGANISM: Artificial Sequence
<220> FEATURE:
<223> OTHER INFORMATION: Synthetic polypeptide

<400> SEQUENCE: 15

Gln Ile Val Leu Thr Gln Ser Pro Ala Ile Leu Ser Ala Ser Pro Gly

```
1               5                   10                  15

Glu Lys Val Thr Met Thr Cys Ser Ala Ser Ser Ser Val Ser Tyr Met
            20                  25                  30

His Trp Tyr Gln Arg Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Thr Ser Asp Pro Leu Thr
                85                  90                  95

Phe Gly Ala Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 16
<211> LENGTH: 222
<212> TYPE: PRT
<213> ORGANISM: Artificial Sequence
<220> FEATURE:
<223> OTHER INFORMATION: Synthetic polypeptide

<400> SEQUENCE: 16

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Ile Leu Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Ala Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Gly Tyr Gly Asn His Trp Tyr Phe Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
```

```
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys
    210                 215                 220


<210> SEQ ID NO 17
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 17

Arg Ala Ser Gln Asp Ile Asn Asn Tyr Leu Asn
1               5                   10


<210> SEQ ID NO 18
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 18

Tyr Thr Ser Arg Leu His Ser
1               5


<210> SEQ ID NO 19
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 19

Gln Gln Gly Asn Thr Leu Pro Trp Thr Phe
1               5                   10


<210> SEQ ID NO 20
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 20

Gly Phe Ala Phe Ser Arg Tyr Asp
1               5


<210> SEQ ID NO 21
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 21

Ser Ser Gly Gly Thr Tyr Asp Tyr Asn Pro
1               5                   10
```

<210> SEQ ID NO 22
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 22

```
Ala Arg Asp Gly Val Arg Gln Gly Glu Tyr Gly Met
1               5                   10
```

<210> SEQ ID NO 23
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 23

```
Asp Ile Gln Leu Thr Gln Thr Thr Ser Ser Leu Ser Ala Ser Leu Gly
1               5                   10                  15

Asp Arg Val Thr Ile Ser Cys
            20
```

<210> SEQ ID NO 24
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 24

```
Trp Tyr Gln Gln Lys Pro Asp Gly Thr Val Lys Leu Leu Ile Tyr
1               5                   10                  15
```

<210> SEQ ID NO 25
<211> LENGTH: 32
<212> TYPE: PRT
<213> ORGANISM: Artificial Sequence
<220> FEATURE:
<223> OTHER INFORMATION: Synthetic polypeptide

<400> SEQUENCE: 25

```
Gly Val Pro Ser Arg Phe Ser Gly Ser Gly Ser Gly Thr Asp Tyr Ser
1               5                   10                  15

Leu Thr Ile Ser Asn Leu Glu Gln Glu Asp Ile Ala Thr Tyr Phe Cys
            20                  25                  30
```

<210> SEQ ID NO 26
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 26

```
Gly Gly Gly Thr Lys Leu Glu Ile Lys
1               5
```

<210> SEQ ID NO 27
<211> LENGTH: 25
<212> TYPE: PRT
<213> ORGANISM: Artificial Sequence
<220> FEATURE:
<223> OTHER INFORMATION: Synthetic polypeptide

```
<400> SEQUENCE: 27

Glu Val Lys Leu Val Glu Ser Gly Gly Gly Leu Val Arg Pro Gly Gly
1               5                   10                  15

Ser Leu Lys Leu Ser Cys Ala Ala Ser
            20                  25


<210> SEQ ID NO 28
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 28

Met Ser Trp Val Leu Gln Thr Pro Glu Lys Arg Leu Glu Trp Val Ala
1               5                   10                  15

Ser Ile


<210> SEQ ID NO 29
<211> LENGTH: 35
<212> TYPE: PRT
<213> ORGANISM: Artificial Sequence
<220> FEATURE:
<223> OTHER INFORMATION: Synthetic polypeptide

<400> SEQUENCE: 29

Asp Ser Met Lys Gly Arg Phe Thr Ile Ser Arg Asp Asn Ala Arg Asn
1               5                   10                  15

Thr Leu Tyr Leu Gln Met Ser Ser Leu Arg Ser Glu Asp Thr Ala Leu
            20                  25                  30

Tyr Tyr Cys
        35


<210> SEQ ID NO 30
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 30

Asp Tyr Trp Gly Gln Gly Thr Ser Val Thr Val Ser Ser
1               5                   10


<210> SEQ ID NO 31
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 31

Asp Ile Gln Leu Thr Gln Thr Thr Ser Ser Leu Ser Ala Ser Leu Gly
1               5                   10                  15

Asp Arg Val Thr Ile Ser Cys Arg Ala Ser Gln Asp Ile Asn Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80
```

```
Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 32
<211> LENGTH: 224
<212> TYPE: PRT
<213> ORGANISM: Artificial Sequence
<220> FEATURE:
<223> OTHER INFORMATION: Synthetic polypeptide

<400> SEQUENCE: 32

Glu Val Lys Leu Val Glu Ser Gly Gly Gly Leu Val Arg Pro Gly Gly
1               5                   10                  15

Ser Leu Lys Leu Ser Cys Ala Ala Ser Gly Phe Ala Phe Ser Arg Tyr
            20                  25                  30

Asp Met Ser Trp Val Leu Gln Thr Pro Glu Lys Arg Leu Glu Trp Val
        35                  40                  45

Ala Ser Ile Ser Ser Gly Gly Thr Tyr Asp Tyr Asn Pro Asp Ser Met
    50                  55                  60

Lys Gly Arg Phe Thr Ile Ser Arg Asp Asn Ala Arg Asn Thr Leu Tyr
65                  70                  75                  80

Leu Gln Met Ser Ser Leu Arg Ser Glu Asp Thr Ala Leu Tyr Tyr Cys
                85                  90                  95

Ala Arg Asp Gly Val Arg Gln Gly Glu Tyr Gly Met Asp Tyr Trp Gly
            100                 105                 110

Gln Gly Thr Ser Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220
```

<210> SEQ ID NO 33
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 33

Lys Ala Ser Gln Asn Val Asp Thr Tyr Val Ala
1               5                   10

<210> SEQ ID NO 34
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 34

Ser Ala Ser Tyr Arg Tyr Ser
1               5

<210> SEQ ID NO 35
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 35

Gln Gln Tyr Asn Asn Tyr Pro Leu Thr Phe
1               5                   10

<210> SEQ ID NO 36
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 36

Gly Phe Thr Phe Ser Ser Ser Gly
1               5

<210> SEQ ID NO 37
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 37

Ser Ser Gly Ser Ser Thr Ile Tyr Tyr Ala
1               5                   10

<210> SEQ ID NO 38
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 38

Ala Lys Asn Arg Gly Tyr Gly Asn Tyr Ala Tyr Ala Met
1               5                   10

<210> SEQ ID NO 39
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 39

```
Asp Ile Val Met Thr Gln Ser Gln Lys Phe Met Ser Thr Ser Val Gly
1               5                   10                  15

Asp Arg Val Ser Val Thr Cys
            20
```

<210> SEQ ID NO 40
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 40

```
Trp Tyr Gln Gln Lys Pro Gly Gln Ser Pro Lys Ala Leu Ile Tyr
1               5                   10                  15
```

<210> SEQ ID NO 41
<211> LENGTH: 32
<212> TYPE: PRT
<213> ORGANISM: Artificial Sequence
<220> FEATURE:
<223> OTHER INFORMATION: Synthetic polypeptide

<400> SEQUENCE: 41

```
Gly Val Pro Asp Arg Phe Thr Gly Ser Gly Ser Gly Thr Asp Phe Thr
1               5                   10                  15

Leu Thr Ile Ser Asn Val Gln Ser Glu Asp Leu Ala Glu Tyr Phe Cys
            20                  25                  30
```

<210> SEQ ID NO 42
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 42

```
Gly Ala Gly Thr Lys Leu Asn Leu Lys
1               5
```

<210> SEQ ID NO 43
<211> LENGTH: 25
<212> TYPE: PRT
<213> ORGANISM: Artificial Sequence
<220> FEATURE:
<223> OTHER INFORMATION: Synthetic polypeptide

<400> SEQUENCE: 43

```
Asp Val Gln Leu Val Glu Ser Gly Gly Gly Leu Val Gln Pro Gly Gly
1               5                   10                  15

Ser Arg Lys Leu Ser Cys Ala Ala Ser
            20                  25
```

<210> SEQ ID NO 44
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 44

```
Met Gln Trp Val Arg Gln Ala Pro Glu Lys Gly Leu Glu Trp Val Ala
1               5                   10                  15

Tyr Ile
```

<210> SEQ ID NO 45
<211> LENGTH: 35
<212> TYPE: PRT
<213> ORGANISM: Artificial Sequence
<220> FEATURE:
<223> OTHER INFORMATION: Synthetic polypeptide

<400> SEQUENCE: 45

```
Asp Thr Val Lys Gly Arg Phe Thr Ile Ser Arg Asp Asn Pro Lys Asn
1               5                   10                  15

Thr Leu Phe Leu Gln Met Thr Ser Leu Arg Ser Glu Asp Thr Ala Met
            20                  25                  30

Tyr Tyr Cys
        35
```

<210> SEQ ID NO 46
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 46

```
Asp Tyr Trp Gly Gln Gly Thr Ser Val Thr Val Ser Ser
1               5                   10
```

<210> SEQ ID NO 47
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 47

```
Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Asp Thr Tyr
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Asn Tyr Pro Leu
                85                  90                  95

Thr Phe Gly Ala Gly Thr Lys Leu Asn Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 48
<211> LENGTH: 225
<212> TYPE: PRT
<213> ORGANISM: Artificial Sequence
<220> FEATURE:
<223> OTHER INFORMATION: Synthetic polypeptide

<400> SEQUENCE: 48

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Ser
            20                  25                  30

Gly Met Gln Trp Val Arg Gln Ala Pro Glu Lys Gly Leu Glu Trp Val
        35                  40                  45

Ala Tyr Ile Ser Ser Gly Ser Ser Thr Ile Tyr Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Ala Lys Asn Arg Gly Tyr Gly Asn Tyr Ala Tyr Ala Met Asp Tyr Trp
            100                 105                 110

Gly Gln Gly Thr Ser Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys
225


<210> SEQ ID NO 49
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 49
```

Gln Ala Ser Gln Gly Ile Ser Ile Asn Leu Asn
1 5 10

<210> SEQ ID NO 50
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 50

Gly Thr Ser Asn Leu Glu Asp
1 5

<210> SEQ ID NO 51
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 51

Leu Gln His Ser Tyr Leu Pro Tyr Thr Phe
1 5 10

<210> SEQ ID NO 52
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 52

Gly Tyr Thr Phe Thr Asp Tyr Glu
1 5

<210> SEQ ID NO 53
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 53

Asp Pro Glu Thr Gly Gly Thr Ala Tyr Asn
1 5 10

<210> SEQ ID NO 54
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 54

Thr Arg Asp Tyr Arg Leu Phe
1 5

<210> SEQ ID NO 55
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 55

```
Asp Val Gln Met Ile Gln Ser Pro Ser Ser Leu Ser Ala Ser Leu Gly
1               5                   10                  15

Asp Ile Val Thr Met Thr Cys
            20


<210> SEQ ID NO 56
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 56

Trp Leu Gln Gln Lys Pro Gly Lys Ala Pro Thr Leu Leu Ile Tyr
1               5                   10                  15


<210> SEQ ID NO 57
<211> LENGTH: 32
<212> TYPE: PRT
<213> ORGANISM: Artificial Sequence
<220> FEATURE:
<223> OTHER INFORMATION: Synthetic polypeptide

<400> SEQUENCE: 57

Gly Val Pro Ser Arg Phe Ser Gly Ser Arg Tyr Gly Thr Asp Phe Thr
1               5                   10                  15

Leu Thr Ile Ser Ser Leu Glu Asp Glu Asp Met Ala Thr Tyr Phe Phe
            20                  25                  30


<210> SEQ ID NO 58
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 58

Gly Gly Gly Thr Lys Leu Glu Ile Lys
1               5


<210> SEQ ID NO 59
<211> LENGTH: 25
<212> TYPE: PRT
<213> ORGANISM: Artificial Sequence
<220> FEATURE:
<223> OTHER INFORMATION: Synthetic polypeptide

<400> SEQUENCE: 59

Gln Val Gln Leu Gln Gln Ser Gly Ala Glu Leu Val Arg Pro Gly Ala
1               5                   10                  15

Ser Val Thr Leu Ser Cys Lys Ala Ser
            20                  25


<210> SEQ ID NO 60
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 60

Met His Trp Val Lys Gln Thr Pro Val His Gly Leu Glu Trp Ile Gly
1               5                   10                  15

Gly Ile
```

<210> SEQ ID NO 61
<211> LENGTH: 35
<212> TYPE: PRT
<213> ORGANISM: Artificial Sequence
<220> FEATURE:
<223> OTHER INFORMATION: Synthetic polypeptide

<400> SEQUENCE: 61

```
Gln Lys Phe Lys Ala Lys Ala Thr Leu Thr Ala Asp Lys Ser Ser Ser
1               5                   10                  15

Thr Ala Asp Met Glu Leu Arg Ser Leu Thr Ser Glu Asp Ser Ala Val
            20                  25                  30

Tyr Tyr Cys
        35
```

<210> SEQ ID NO 62
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 62

```
Asp Tyr Trp Gly Gln Gly Thr Ser Val Thr Val Ser Ser
1               5                   10
```

<210> SEQ ID NO 63
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 63

```
Asp Val Gln Met Ile Gln Ser Pro Ser Ser Leu Ser Ala Ser Leu Gly
1               5                   10                  15

Asp Ile Val Thr Met Thr Cys Gln Ala Ser Gln Gly Ile Ser Ile Asn
            20                  25                  30

Leu Asn Trp Leu Gln Gln Lys Pro Gly Lys Ala Pro Thr Leu Leu Ile
        35                  40                  45

Tyr Gly Thr Ser Asn Leu Glu Asp Gly Val Pro Ser Arg Phe Ser Gly
    50                  55                  60

Ser Arg Tyr Gly Thr Asp Phe Thr Leu Thr Ile Ser Ser Leu Glu Asp
65                  70                  75                  80

Glu Asp Met Ala Thr Tyr Phe Phe Leu Gln His Ser Tyr Leu Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
```

```
        195                 200                 205

Phe Asn Arg Gly Glu Cys
    210


<210> SEQ ID NO 64
<211> LENGTH: 219
<212> TYPE: PRT
<213> ORGANISM: Artificial Sequence
<220> FEATURE:
<223> OTHER INFORMATION: Synthetic polypeptide

<400> SEQUENCE: 64

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Glu Met His Trp Val Lys Gln Thr Pro Val His Gly Leu Glu Trp Ile
        35                  40                  45

Gly Gly Ile Asp Pro Glu Thr Gly Gly Thr Ala Tyr Asn Gln Lys Phe
    50                  55                  60

Lys Ala Lys Ala Thr Leu Thr Ala Asp Lys Ser Ser Ser Thr Ala Asp
65                  70                  75                  80

Met Glu Leu Arg Ser Leu Thr Ser Glu Asp Ser Ala Val Tyr Tyr Cys
                85                  90                  95

Thr Arg Asp Tyr Arg Leu Phe Asp Tyr Trp Gly Gln Gly Thr Ser Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys
    210                 215


<210> SEQ ID NO 65
<211> LENGTH: 394
<212> TYPE: PRT
<213> ORGANISM: Artificial Sequence
<220> FEATURE:
<223> OTHER INFORMATION: Synthetic polypeptide

<400> SEQUENCE: 65

Leu Pro Ser Cys Lys Glu Asp Glu Tyr Pro Val Gly Ser Glu Cys Cys
1               5                   10                  15

Pro Lys Cys Ser Pro Gly Tyr Arg Val Lys Glu Ala Cys Gly Glu Leu
            20                  25                  30

Thr Gly Thr Val Cys Glu Pro Cys Pro Pro Gly Thr Tyr Ile Ala His
        35                  40                  45

Leu Asn Gly Leu Ser Lys Cys Leu Gln Cys Gln Met Cys Asp Pro Ala
    50                  55                  60
```

```
Met Gly Leu Arg Ala Ser Arg Asn Cys Ser Arg Thr Glu Asn Ala Val
65                  70                  75                  80

Cys Gly Cys Ser Pro Gly His Phe Cys Ile Val Gln Asp Gly Asp His
                85                  90                  95

Cys Ala Ala Cys Arg Ala Tyr Ala Thr Ser Ser Pro Gly Gln Arg Val
            100                 105                 110

Gln Lys Gly Gly Thr Glu Ser Gln Asp Thr Leu Cys Gln Asn Cys Pro
        115                 120                 125

Pro Gly Thr Phe Ser Pro Asn Gly Thr Leu Glu Glu Cys Gln His Gln
    130                 135                 140

Thr Lys Cys Ser Trp Leu Val Thr Lys Ala Gly Ala Gly Thr Ser Ser
145                 150                 155                 160

Ser His Trp Val Gly Gly Gly Ser Lys Pro Cys Pro Pro Cys Lys Cys
                165                 170                 175

Pro Ala Pro Asn Leu Leu Gly Gly Pro Ser Val Phe Ile Phe Pro Pro
            180                 185                 190

Lys Ile Lys Asp Val Leu Met Ile Ser Leu Ser Pro Ile Val Thr Cys
        195                 200                 205

Val Val Val Asp Val Ser Glu Asp Asp Pro Asp Val Gln Ile Ser Trp
    210                 215                 220

Phe Val Asn Asn Val Glu Val His Thr Ala Gln Thr Gln Thr His Arg
225                 230                 235                 240

Glu Asp Tyr Asn Ser Thr Leu Arg Val Val Ser Ala Leu Pro Ile Gln
                245                 250                 255

His Gln Asp Trp Met Ser Gly Lys Glu Phe Lys Cys Lys Val Asn Asn
            260                 265                 270

Lys Asp Leu Pro Ala Pro Ile Glu Arg Thr Ile Ser Lys Pro Lys Gly
        275                 280                 285

Ser Val Arg Ala Pro Gln Val Tyr Val Leu Pro Pro Pro Glu Glu Glu
    290                 295                 300

Met Thr Lys Lys Gln Val Thr Leu Thr Cys Met Val Thr Asp Phe Met
305                 310                 315                 320

Pro Glu Asp Ile Tyr Val Glu Trp Thr Asn Asn Gly Lys Thr Glu Leu
                325                 330                 335

Asn Tyr Lys Asn Thr Glu Pro Val Leu Asp Ser Asp Gly Ser Tyr Phe
            340                 345                 350

Met Tyr Ser Lys Leu Arg Val Glu Lys Lys Asn Trp Val Glu Arg Asn
        355                 360                 365

Ser Tyr Ser Cys Ser Val Val His Glu Gly Leu His Asn His His Thr
    370                 375                 380

Thr Lys Ser Phe Ser Arg Thr Pro Gly Lys
385                 390


<210> SEQ ID NO 66
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 66

Ser Ala Ser Ser Ser Val Ser Ser Ser Tyr Leu Phe
1               5                   10


<210> SEQ ID NO 67
<211> LENGTH: 7
```

<212> TYPE: PRT
<213> ORGANISM: Artificial Sequence
<220> FEATURE:
<223> OTHER INFORMATION: Synthetic polypeptide

<400> SEQUENCE: 67

Ser Thr Ser Asn Leu Ala Ser
1               5

<210> SEQ ID NO 68
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 68

His Gln Trp Ser Ser Tyr Pro Tyr Thr
1               5

<210> SEQ ID NO 69
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 69

Gly Tyr Thr Leu Thr Asn Phe
1               5

<210> SEQ ID NO 70
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 70

Asn Thr Tyr Thr Gly Glu
1               5

<210> SEQ ID NO 71
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 71

Ser Phe Tyr Gly Asn Glu His Tyr
1               5

<210> SEQ ID NO 72
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 72

Gln Ile Val Leu Thr Gln Ser Pro Ala Ile Met Ser Ala Ser Pro Gly
1               5                   10                  15

Glu Lys Val Thr Leu Thr Cys
            20

<210> SEQ ID NO 73
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 73

Trp Tyr Gln Gln Lys Pro Gly Ser Ser Pro Lys Leu Trp Ile Tyr
1 5 10 15

<210> SEQ ID NO 74
<211> LENGTH: 32
<212> TYPE: PRT
<213> ORGANISM: Artificial Sequence
<220> FEATURE:
<223> OTHER INFORMATION: Synthetic polypeptide

<400> SEQUENCE: 74

Gly Val Pro Ala Arg Phe Ser Gly His Gly Ser Gly Thr Ser Tyr Ser
1 5 10 15

Leu Thr Ile Ser Ser Met Glu Ala Glu Asp Ala Ala Ser Tyr Phe Cys
20 25 30

<210> SEQ ID NO 75
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 75

Phe Gly Gly Gly Thr Lys Leu Glu Ile Lys
1 5 10

<210> SEQ ID NO 76
<211> LENGTH: 25
<212> TYPE: PRT
<213> ORGANISM: Artificial Sequence
<220> FEATURE:
<223> OTHER INFORMATION: Synthetic polypeptide

<400> SEQUENCE: 76

Gln Ile Gln Leu Val Gln Ser Gly Pro Glu Leu Lys Lys Pro Gly Glu
1 5 10 15

Pro Val Lys Ile Ser Cys Arg Ala Ser
20 25

<210> SEQ ID NO 77
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 77

Gly Met Asn Trp Val Lys Gln Ala Pro Gly Lys Gly Leu Lys Trp Met
1 5 10 15

Gly Trp Ile

<210> SEQ ID NO 78
<211> LENGTH: 41
<212> TYPE: PRT
<213> ORGANISM: Artificial Sequence
<220> FEATURE:
<223> OTHER INFORMATION: Synthetic polypeptide

<400> SEQUENCE: 78

```
Pro Thr Tyr Ala Asp Asp Phe Lys Gly Arg Phe Ala Phe Ser Leu Glu
1               5                   10                  15

Thr Ser Ala Ser Thr Ala Tyr Leu Gln Ile Asn Asn Leu Lys Asn Glu
            20                  25                  30

Asp Thr Ala Thr Tyr Phe Cys Ala Arg
        35                  40
```

<210> SEQ ID NO 79
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 79

```
Trp Gly Gln Gly Thr Ser Val Thr Val Ser Ser
1               5                   10
```

<210> SEQ ID NO 80
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 80

```
Gln Ile Val Leu Thr Gln Ser Pro Ala Ile Met Ser Ala Ser Pro Gly
1               5                   10                  15

Glu Lys Val Thr Leu Thr Cys Ser Ala Ser Ser Ser Val Ser Ser Ser
            20                  25                  30

Tyr Leu Phe Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly His Gly Ser Gly Thr Ser Tyr Ser Leu Thr Ile Ser Ser Met Glu
65                  70                  75                  80

Ala Glu Asp Ala Ala Ser Tyr Phe Cys His Gln Trp Ser Ser Tyr Pro
                85                  90                  95

Tyr Thr Phe Gly Gly Gly Thr Lys Leu Glu Ile Lys
            100                 105
```

<210> SEQ ID NO 81
<211> LENGTH: 117
<212> TYPE: PRT
<213> ORGANISM: Artificial Sequence
<220> FEATURE:
<223> OTHER INFORMATION: Synthetic polypeptide

<400> SEQUENCE: 81

```
Gln Ile Gln Leu Val Gln Ser Gly Pro Glu Leu Lys Lys Pro Gly Glu
1               5                   10                  15

Pro Val Lys Ile Ser Cys Arg Ala Ser Gly Tyr Thr Leu Thr Asn Phe
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
```

```
65                  70                  75                  80

Leu Gln Ile Asn Asn Leu Lys Asn Glu Asp Thr Ala Thr Tyr Phe Cys
                85                  90                  95

Ala Arg Ser Phe Tyr Gly Asn Glu His Tyr Trp Gly Gln Gly Thr Ser
            100                 105                 110

Val Thr Val Ser Ser
        115


<210> SEQ ID NO 82
<211> LENGTH: 215
<212> TYPE: PRT
<213> ORGANISM: Artificial Sequence
<220> FEATURE:
<223> OTHER INFORMATION: Synthetic polypeptide

<400> SEQUENCE: 82

Gln Ile Val Leu Thr Gln Ser Pro Ala Ile Met Ser Ala Ser Pro Gly
1               5                   10                  15

Glu Lys Val Thr Leu Thr Cys Ser Ala Ser Ser Ser Val Ser Ser Ser
            20                  25                  30

Tyr Leu Phe Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly His Gly Ser Gly Thr Ser Tyr Ser Leu Thr Ile Ser Ser Met Glu
65                  70                  75                  80

Ala Glu Asp Ala Ala Ser Tyr Phe Cys His Gln Trp Ser Ser Tyr Pro
                85                  90                  95

Tyr Thr Phe Gly Gly Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 83
<211> LENGTH: 447
<212> TYPE: PRT
<213> ORGANISM: Artificial Sequence
<220> FEATURE:
<223> OTHER INFORMATION: Synthetic polypeptide

<400> SEQUENCE: 83

Gln Ile Gln Leu Val Gln Ser Gly Pro Glu Leu Lys Lys Pro Gly Glu
1               5                   10                  15

Pro Val Lys Ile Ser Cys Arg Ala Ser Gly Tyr Thr Leu Thr Asn Phe
            20                  25                  30
```

```
Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Ser Phe Tyr Gly Asn Glu His Tyr Trp Gly Gln Gly Thr Ser
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

<210> SEQ ID NO 84
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 84

Arg Ser Ser Gln Ser Pro Leu His Ser Asn Gly Asn Thr Tyr Leu Asp
1 5 10 15

<210> SEQ ID NO 85
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 85

Lys Val Ser Asn Arg Phe Ser
1 5

<210> SEQ ID NO 86
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 86

Ser Gln Thr Thr His Val Pro Pro Thr
1 5

<210> SEQ ID NO 87
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 87

Gly Tyr Thr Phe Ile His Tyr
1 5

<210> SEQ ID NO 88
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 88

Asp Pro Glu Thr Gly Gly
1 5

<210> SEQ ID NO 89
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 89

Gly Asp Trp Val Phe Ala Tyr
1 5

<210> SEQ ID NO 90

<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 90

```
Asp Val Val Met Thr Gln Thr Pro Leu Ser Leu Pro Val Ser Leu Gly
1               5                   10                  15

Asp Gln Ala Ser Ile Ser Cys
            20
```

<210> SEQ ID NO 91
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 91

```
Trp Tyr Leu Gln Lys Pro Gly Gln Ser Pro Lys Leu Leu Ile Tyr
1               5                   10                  15
```

<210> SEQ ID NO 92
<211> LENGTH: 32
<212> TYPE: PRT
<213> ORGANISM: Artificial Sequence
<220> FEATURE:
<223> OTHER INFORMATION: Synthetic polypeptide

<400> SEQUENCE: 92

```
Gly Val Pro Asp Arg Phe Ser Gly Ser Gly Ser Gly Thr Asp Phe Thr
1               5                   10                  15

Leu Lys Ile Ser Arg Val Glu Ala Glu Asp Leu Gly Ile Tyr Phe Cys
            20                  25                  30
```

<210> SEQ ID NO 93
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 93

```
Phe Gly Gly Gly Thr Lys Leu Glu Ile Lys
1               5                   10
```

<210> SEQ ID NO 94
<211> LENGTH: 25
<212> TYPE: PRT
<213> ORGANISM: Artificial Sequence
<220> FEATURE:
<223> OTHER INFORMATION: Synthetic polypeptide

<400> SEQUENCE: 94

```
Gln Val Gln Leu Gln Gln Ser Gly Ala Glu Leu Val Arg Pro Gly Ala
1               5                   10                  15

Ser Val Thr Leu Ser Cys Lys Thr Ser
            20                  25
```

<210> SEQ ID NO 95
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 95

Glu Ile His Trp Val Lys Gln Ser Pro Val His Gly Leu Glu Trp Ile
1               5                   10                  15

Gly Ala Ile

<210> SEQ ID NO 96
<211> LENGTH: 41
<212> TYPE: PRT
<213> ORGANISM: Artificial Sequence
<220> FEATURE:
<223> OTHER INFORMATION: Synthetic polypeptide

<400> SEQUENCE: 96

Thr Ala Asp Asn Gln Lys Phe Lys Asp Lys Val Thr Leu Thr Ala Asp
1               5                   10                  15

Lys Ser Ser Asn Thr Ala Tyr Met Asp Leu Arg Ser Leu Thr Ser Glu
            20                  25                  30

Asp Ser Ala Val Tyr Tyr Cys Thr Arg
        35                  40

<210> SEQ ID NO 97
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 97

Trp Gly Gln Gly Thr Leu Val Thr Val Ser Ala
1               5                   10

<210> SEQ ID NO 98
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 98

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Pro Leu His Ser
            20                  25                  30

Asn Gly Asn Thr Tyr Leu Asp Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Phe Cys Ser Gln Thr
                85                  90                  95

Thr His Val Pro Pro Thr Phe Gly Gly Gly Thr Lys Leu Glu Ile Lys
            100                 105                 110

<210> SEQ ID NO 99
<211> LENGTH: 116
<212> TYPE: PRT
<213> ORGANISM: Artificial Sequence
<220> FEATURE:
<223> OTHER INFORMATION: Synthetic polypeptide

<400> SEQUENCE: 99

Gln Val Gln Leu Gln Gln Ser Gly Ala Glu Leu Val Arg Pro Gly Ala
1               5                   10                  15

Ser Val Thr Leu Ser Cys Lys Thr Ser Gly Tyr Thr Phe Ile His Tyr
            20                  25                  30

Glu Ile His Trp Val Lys Gln Ser Pro Val His Gly Leu Glu Trp Ile
        35                  40                  45

Gly Ala Ile Asp Pro Glu Thr Gly Gly Thr Ala Asp Asn Gln Lys Phe
    50                  55                  60

Lys Asp Lys Val Thr Leu Thr Ala Asp Lys Ser Ser Asn Thr Ala Tyr
65                  70                  75                  80

Met Asp Leu Arg Ser Leu Thr Ser Glu Asp Ser Ala Val Tyr Tyr Cys
                85                  90                  95

Thr Arg Gly Asp Trp Val Phe Ala Tyr Trp Gly Gln Gly Thr Leu Val
            100                 105                 110

Thr Val Ser Ala
        115

<210> SEQ ID NO 100
<211> LENGTH: 219
<212> TYPE: PRT
<213> ORGANISM: Artificial Sequence
<220> FEATURE:
<223> OTHER INFORMATION: Synthetic polypeptide

<400> SEQUENCE: 100

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Pro Leu His Ser
            20                  25                  30

Asn Gly Asn Thr Tyr Leu Asp Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Phe Cys Ser Gln Thr
                85                  90                  95

Thr His Val Pro Pro Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

```
<210> SEQ ID NO 101
<211> LENGTH: 446
<212> TYPE: PRT
<213> ORGANISM: Artificial Sequence
<220> FEATURE:
<223> OTHER INFORMATION: Synthetic polypeptide

<400> SEQUENCE: 101

Gln Val Gln Leu Gln Gln Ser Gly Ala Glu Leu Val Arg Pro Gly Ala
1               5                   10                  15

Ser Val Thr Leu Ser Cys Lys Thr Ser Gly Tyr Thr Phe Ile His Tyr
            20                  25                  30

Glu Ile His Trp Val Lys Gln Ser Pro Val His Gly Leu Glu Trp Ile
        35                  40                  45

Gly Ala Ile Asp Pro Glu Thr Gly Gly Thr Ala Asp Asn Gln Lys Phe
    50                  55                  60

Lys Asp Lys Val Thr Leu Thr Ala Asp Lys Ser Ser Asn Thr Ala Tyr
65                  70                  75                  80

Met Asp Leu Arg Ser Leu Thr Ser Glu Asp Ser Ala Val Tyr Tyr Cys
                85                  90                  95

Thr Arg Gly Asp Trp Val Phe Ala Tyr Trp Gly Gln Gly Thr Leu Val
            100                 105                 110

Thr Val Ser Ala Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
```

```
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445


<210> SEQ ID NO 102
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 102

Thr Ala Arg Ser Ser Val Ser Ser Ser Tyr Leu His
1               5                   10


<210> SEQ ID NO 103
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 103

Ser Thr Ser Asn Leu Ala Ser
1               5


<210> SEQ ID NO 104
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 104

His Gln Tyr His Arg Ser Thr Trp Thr
1               5


<210> SEQ ID NO 105
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 105

Gly Tyr Thr Phe Thr Asn Phe
1               5


<210> SEQ ID NO 106
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 106

Asn Thr Tyr Thr Gly Glu
1               5
```

<210> SEQ ID NO 107
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 107

Ser Tyr Tyr Phe Val Thr Ser Glu Asp Tyr
1               5                   10

<210> SEQ ID NO 108
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 108

Gln Ile Val Leu Thr Gln Ser Pro Ala Ile Met Ser Ala Ser Pro Gly
1               5                   10                  15

Glu Arg Val Thr Met Thr Cys
            20

<210> SEQ ID NO 109
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 109

Trp Tyr Gln Gln Lys Pro Gly Ser Ser Pro Lys Leu Trp Ile Tyr
1               5                   10                  15

<210> SEQ ID NO 110
<211> LENGTH: 32
<212> TYPE: PRT
<213> ORGANISM: Artificial Sequence
<220> FEATURE:
<223> OTHER INFORMATION: Synthetic polypeptide

<400> SEQUENCE: 110

Gly Val Pro Ala Arg Phe Ser Gly Ser Gly Ser Gly Ala Ser Tyr Ser
1               5                   10                  15

Leu Thr Asn Ser Ser Met Glu Ala Glu Asp Ala Ala Thr Tyr Tyr Cys
            20                  25                  30

<210> SEQ ID NO 111
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 111

Phe Gly Gly Gly Thr Lys Leu Glu Ile Lys
1               5                   10

<210> SEQ ID NO 112
<211> LENGTH: 25
<212> TYPE: PRT
<213> ORGANISM: Artificial Sequence
<220> FEATURE:
<223> OTHER INFORMATION: Synthetic polypeptide

<400> SEQUENCE: 112

Gln Ile Gln Leu Val Gln Ser Gly Pro Glu Leu Lys Lys Pro Gly Glu
1               5                   10                  15

Thr Val Lys Ile Ser Cys Lys Ala Ser
            20                  25

<210> SEQ ID NO 113
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 113

Gly Met Asn Trp Val Lys Gln Ala Pro Gly Lys Ala Leu Lys Trp Val
1               5                   10                  15

Gly Trp Ile

<210> SEQ ID NO 114
<211> LENGTH: 41
<212> TYPE: PRT
<213> ORGANISM: Artificial Sequence
<220> FEATURE:
<223> OTHER INFORMATION: Synthetic polypeptide

<400> SEQUENCE: 114

Pro Thr Tyr Ala Asp Asp Phe Lys Gly Arg Phe Ala Phe Ser Leu Glu
1               5                   10                  15

Thr Ser Ala Thr Thr Ala Tyr Leu Gln Ile Ser Asn Leu Lys Asn Glu
            20                  25                  30

Asp Thr Ala Thr Tyr Phe Cys Ala Arg
        35                  40

<210> SEQ ID NO 115
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 115

Trp Gly Gln Gly Thr Ser Val Thr Val Ser Ser
1               5                   10

<210> SEQ ID NO 116
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 116

Gln Ile Val Leu Thr Gln Ser Pro Ala Ile Met Ser Ala Ser Pro Gly
1               5                   10                  15

Glu Arg Val Thr Met Thr Cys Thr Ala Arg Ser Ser Val Ser Ser Ser
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Ala Ser Tyr Ser Leu Thr Asn Ser Ser Met Glu
65                  70                  75                  80

```
Ala Glu Asp Ala Ala Thr Tyr Tyr Cys His Gln Tyr His Arg Ser Thr
                85                  90                  95

Trp Thr Phe Gly Gly Gly Thr Lys Leu Glu Ile Lys
            100                 105


<210> SEQ ID NO 117
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 117

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Phe
            20                  25                  30

Gly Met Asn Trp Val Lys Gln Ala Pro Gly Lys Ala Leu Lys Trp Val
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Thr Thr Ala Tyr
65                  70                  75                  80

Leu Gln Ile Ser Asn Leu Lys Asn Glu Asp Thr Ala Thr Tyr Phe Cys
                85                  90                  95

Ala Arg Ser Tyr Tyr Phe Val Thr Ser Glu Asp Tyr Trp Gly Gln Gly
            100                 105                 110

Thr Ser Val Thr Val Ser Ser
        115


<210> SEQ ID NO 118
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 118

Gln Ile Val Leu Thr Gln Ser Pro Ala Ile Met Ser Ala Ser Pro Gly
1               5                   10                  15

Glu Arg Val Thr Met Thr Cys Thr Ala Arg Ser Ser Val Ser Ser Ser
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Ala Ser Tyr Ser Leu Thr Asn Ser Ser Met Glu
65                  70                  75                  80

Ala Glu Asp Ala Ala Thr Tyr Tyr Cys His Gln Tyr His Arg Ser Thr
                85                  90                  95

Trp Thr Phe Gly Gly Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
```

```
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu
    210


<210> SEQ ID NO 119
<211> LENGTH: 449
<212> TYPE: PRT
<213> ORGANISM: Artificial Sequence
<220> FEATURE:
<223> OTHER INFORMATION: Synthetic polypeptide

<400> SEQUENCE: 119

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Phe
            20                  25                  30

Gly Met Asn Trp Val Lys Gln Ala Pro Gly Lys Ala Leu Lys Trp Val
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Thr Thr Ala Tyr
65                  70                  75                  80

Leu Gln Ile Ser Asn Leu Lys Asn Glu Asp Thr Ala Thr Tyr Phe Cys
                85                  90                  95

Ala Arg Ser Tyr Tyr Phe Val Thr Ser Glu Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
```

```
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 120
<211> LENGTH: 215
<212> TYPE: PRT
<213> ORGANISM: Artificial Sequence
<220> FEATURE:
<223> OTHER INFORMATION: Synthetic polypeptide

<400> SEQUENCE: 120

Gln Ile Val Leu Thr Gln Ser Pro Ala Ile Met Ser Ala Ser Pro Gly
1               5                   10                  15

Glu Lys Val Thr Leu Thr Cys Ser Ala Ser Ser Ser Val Ser Ser Ser
            20                  25                  30

Tyr Leu Phe Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly His Gly Ser Gly Thr Ser Tyr Ser Leu Thr Ile Ser Ser Met Glu
65                  70                  75                  80

Ala Glu Asp Ala Ala Ser Tyr Phe Cys His Gln Trp Ser Ser Tyr Pro
                85                  90                  95

Tyr Thr Phe Gly Gly Gly Thr Lys Leu Glu Ile Lys Arg Ala Asp Ala
            100                 105                 110

Ala Pro Thr Val Ser Ile Phe Pro Pro Ser Ser Glu Gln Leu Thr Ser
        115                 120                 125

Gly Gly Ala Ser Val Val Cys Phe Leu Asn Asn Phe Tyr Pro Lys Asp
    130                 135                 140

Ile Asn Val Lys Trp Lys Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
                165                 170                 175

Ser Ser Thr Leu Thr Leu Thr Lys Asp Glu Tyr Glu Arg His Asn Ser
            180                 185                 190

Tyr Thr Cys Glu Ala Thr His Lys Thr Ser Thr Ser Pro Ile Val Lys
        195                 200                 205
```

```
Ser Phe Asn Arg Asn Glu Cys
    210                 215


<210> SEQ ID NO 121
<211> LENGTH: 441
<212> TYPE: PRT
<213> ORGANISM: Artificial Sequence
<220> FEATURE:
<223> OTHER INFORMATION: Synthetic polypeptide

<400> SEQUENCE: 121

Gln Ile Gln Leu Val Gln Ser Gly Pro Glu Leu Lys Lys Pro Gly Glu
1               5                   10                  15

Pro Val Lys Ile Ser Cys Arg Ala Ser Gly Tyr Thr Leu Thr Asn Phe
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Ser Phe Tyr Gly Asn Glu His Tyr Trp Gly Gln Gly Thr Ser
            100                 105                 110

Val Thr Val Ser Ser Ala Lys Thr Thr Pro Pro Ser Val Tyr Pro Leu
        115                 120                 125

Ala Pro Gly Ser Ala Ala Gln Thr Asn Ser Met Val Thr Leu Gly Cys
    130                 135                 140

Leu Val Lys Gly Tyr Phe Pro Glu Pro Val Thr Val Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Pro Ser Ser Pro Arg
            180                 185                 190

Pro Ser Glu Thr Val Thr Cys Asn Val Ala His Pro Ala Ser Ser Thr
        195                 200                 205

Lys Val Asp Lys Lys Ile Val Pro Arg Asp Cys Gly Cys Lys Pro Cys
    210                 215                 220

Ile Cys Thr Val Pro Glu Val Ser Ser Val Phe Ile Phe Pro Pro Lys
225                 230                 235                 240

Pro Lys Asp Val Leu Thr Ile Thr Leu Thr Pro Lys Val Thr Cys Val
                245                 250                 255

Val Val Asp Ile Ser Lys Asp Asp Pro Glu Val Gln Phe Ser Trp Phe
            260                 265                 270

Val Asp Asp Val Glu Val His Thr Ala Gln Thr Gln Pro Arg Glu Glu
        275                 280                 285

Gln Phe Asn Ser Thr Phe Arg Ser Val Ser Glu Leu Pro Ile Met His
    290                 295                 300

Gln Asp Trp Leu Asn Gly Lys Glu Phe Lys Cys Arg Val Asn Ser Ala
305                 310                 315                 320

Ala Phe Pro Ala Pro Ile Glu Lys Thr Ile Ser Lys Thr Lys Gly Arg
                325                 330                 335

Pro Lys Ala Pro Gln Val Tyr Thr Ile Pro Pro Pro Lys Glu Gln Met
            340                 345                 350
```

```
Ala Lys Asp Lys Val Ser Leu Thr Cys Met Ile Thr Asp Phe Phe Pro
        355                 360                 365

Glu Asp Ile Thr Val Glu Trp Gln Trp Asn Gly Gln Pro Ala Glu Asn
    370                 375                 380

Tyr Lys Asn Thr Gln Pro Ile Met Asn Thr Asn Gly Ser Tyr Phe Val
385                 390                 395                 400

Tyr Ser Lys Leu Asn Val Gln Lys Ser Asn Trp Glu Ala Gly Asn Thr
                405                 410                 415

Phe Thr Cys Ser Val Leu His Glu Gly Leu His Asn His His Thr Glu
            420                 425                 430

Lys Ser Leu Ser His Ser Pro Gly Lys
        435                 440


<210> SEQ ID NO 122
<211> LENGTH: 215
<212> TYPE: PRT
<213> ORGANISM: Artificial Sequence
<220> FEATURE:
<223> OTHER INFORMATION: Synthetic polypeptide

<400> SEQUENCE: 122

Gln Ile Val Leu Thr Gln Ser Pro Ala Ile Met Ser Ala Ser Pro Gly
1               5                   10                  15

Glu Lys Val Thr Leu Thr Cys Ser Ala Ser Ser Ser Val Ser Ser Ser
            20                  25                  30

Tyr Leu Phe Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly His Gly Ser Gly Thr Ser Tyr Ser Leu Thr Ile Ser Ser Met Glu
65                  70                  75                  80

Ala Glu Asp Ala Ala Ser Tyr Phe Cys His Gln Trp Ser Ser Tyr Pro
                85                  90                  95

Tyr Thr Phe Gly Gly Gly Thr Lys Leu Glu Ile Lys Arg Ala Asp Ala
            100                 105                 110

Ala Pro Thr Val Ser Ile Phe Pro Pro Ser Ser Glu Gln Leu Thr Ser
        115                 120                 125

Gly Gly Ala Ser Val Val Cys Phe Leu Asn Asn Phe Tyr Pro Lys Asp
    130                 135                 140

Ile Asn Val Lys Trp Lys Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
                165                 170                 175

Ser Ser Thr Leu Thr Leu Thr Lys Asp Glu Tyr Glu Arg His Asn Ser
            180                 185                 190

Tyr Thr Cys Glu Ala Thr His Lys Thr Ser Thr Ser Pro Ile Val Lys
        195                 200                 205

Ser Phe Asn Arg Asn Glu Cys
    210                 215


<210> SEQ ID NO 123
<211> LENGTH: 447
<212> TYPE: PRT
<213> ORGANISM: Artificial Sequence
<220> FEATURE:
<223> OTHER INFORMATION: Synthetic polypeptide
```

<400> SEQUENCE: 123

```
Gln Ile Gln Leu Val Gln Ser Gly Pro Glu Leu Lys Lys Pro Gly Glu
1               5                   10                  15

Pro Val Lys Ile Ser Cys Arg Ala Ser Gly Tyr Thr Leu Thr Asn Phe
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Ser Phe Tyr Gly Asn Glu His Tyr Trp Gly Gln Gly Thr Ser
            100                 105                 110

Val Thr Val Ser Ser Ala Lys Thr Thr Ala Pro Ser Val Tyr Pro Leu
        115                 120                 125

Ala Pro Val Cys Gly Asp Thr Thr Gly Ser Ser Val Thr Leu Gly Cys
    130                 135                 140

Leu Val Lys Gly Tyr Phe Pro Glu Pro Val Thr Leu Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Thr Ser Ser Thr Trp
            180                 185                 190

Pro Ser Gln Ser Ile Thr Cys Asn Val Ala His Pro Ala Ser Ser Thr
        195                 200                 205

Lys Val Asp Lys Lys Ile Glu Pro Arg Gly Pro Thr Ile Lys Pro Cys
    210                 215                 220

Pro Pro Cys Lys Cys Pro Ala Pro Asn Leu Leu Gly Gly Pro Ser Val
225                 230                 235                 240

Phe Ile Phe Pro Pro Lys Ile Lys Asp Val Leu Met Ile Ser Leu Ser
                245                 250                 255

Pro Ile Val Thr Cys Val Val Val Asp Val Ser Glu Asp Asp Pro Asp
            260                 265                 270

Val Gln Ile Ser Trp Phe Val Asn Asn Val Glu Val His Thr Ala Gln
        275                 280                 285

Thr Gln Thr His Arg Glu Asp Tyr Asn Ser Thr Leu Arg Val Val Ser
    290                 295                 300

Ala Leu Pro Ile Gln His Gln Asp Trp Met Ser Gly Lys Glu Phe Lys
305                 310                 315                 320

Cys Lys Val Asn Asn Lys Asp Leu Pro Ala Pro Ile Glu Arg Thr Ile
                325                 330                 335

Ser Lys Pro Lys Gly Ser Val Arg Ala Pro Gln Val Tyr Val Leu Pro
            340                 345                 350

Pro Pro Glu Glu Glu Met Thr Lys Lys Gln Val Thr Leu Thr Cys Met
        355                 360                 365

Val Thr Asp Phe Met Pro Glu Asp Ile Tyr Val Glu Trp Thr Asn Asn
    370                 375                 380

Gly Lys Thr Glu Leu Asn Tyr Lys Asn Thr Glu Pro Val Leu Asp Ser
385                 390                 395                 400

Asp Gly Ser Tyr Phe Met Tyr Ser Lys Leu Arg Val Glu Lys Lys Asn
                405                 410                 415
```

-continued

```
Trp Val Glu Arg Asn Ser Tyr Ser Cys Ser Val Val His Glu Gly Leu
            420                 425                 430

His Asn His His Thr Thr Lys Ser Phe Ser Arg Thr Pro Gly Lys
        435                 440                 445
```